United States Patent
Fuchiwaki et al.

(10) Patent No.: US 9,780,317 B2
(45) Date of Patent: Oct. 3, 2017

(54) AMINE DERIVATIVE, ORGANIC LUMINESCENT MATERIAL AND ORGANIC ELECTROLUMINESCENT DEVICE USING THE AMINE DERIVATIVE OR THE ORGANIC LUMINESCENT MATERIAL

(71) Applicant: SAMSUNG DISPLAY CO., LTD., Yongin, Gyeonggi-Do (KR)

(72) Inventors: Junta Fuchiwaki, Yokohama (JP); Hiromi Oyama, Yokohama (JP); Yasuo Miyata, Yokohama (JP); Naoya Sakamoto, Yokohama (JP); Masatsugu Ueno, Yokohama (JP); Ichinori Takada, Yokohama (JP)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 69 days.

(21) Appl. No.: 14/731,180

(22) Filed: Jun. 4, 2015

(65) Prior Publication Data
US 2015/0270502 A1    Sep. 24, 2015

(30) Foreign Application Priority Data

Dec. 5, 2012  (JP) ................................ 2012-266773
Nov. 29, 2013  (JP) ................................ 2013-247442
(Continued)

(51) Int. Cl.
*H01L 51/50* (2006.01)
*H01L 51/00* (2006.01)
(Continued)

(52) U.S. Cl.
CPC ........ *H01L 51/0094* (2013.01); *C07F 7/0812* (2013.01); *C07F 7/0814* (2013.01);
(Continued)

(58) Field of Classification Search
None
See application file for complete search history.

(56) References Cited

U.S. PATENT DOCUMENTS 7,740,958 B2    6/2010  Saitoh et al.
7,927,719 B2    4/2011  Hwang et al.
(Continued)

FOREIGN PATENT DOCUMENTS

CN    102190627 A    9/2011
EP    2 042 481 A1    4/2009
(Continued)

OTHER PUBLICATIONS

USPTO Action mailed Apr. 12, 2017, in U.S. Appl. No. 14/832,292, wherein claims were provisionally rejected on the ground of nonstatutory double patenting over claims of the captioned application.

*Primary Examiner* — Gregory Clark
(74) *Attorney, Agent, or Firm* — Lee & Morse, P.C.

(57) ABSTRACT

An amine derivative represented by the following General Formula (1) is provided.

[Formula 1]

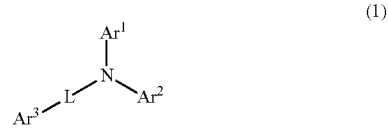

(1)

In the above General Formula (1), Ar1, Ar2 and Ar3 are independently a substituted or unsubstituted aryl group or a substituted or unsubstituted heteroaryl group, at least one of Ar1, Ar2 and Ar3 is substituted with a substituted or
(Continued)

unsubstituted silyl group, and L is a single bond, a substituted or unsubstituted arylene group, or a substituted or unsubstituted heteroarylene group.

38 Claims, 2 Drawing Sheets

(30) Foreign Application Priority Data

| | | | |
|---|---|---|---|
| Nov. 29, 2013 | (JP) | ................ | 2013-247699 |
| Nov. 29, 2013 | (JP) | ................ | 2013-247741 |
| Nov. 29, 2013 | (JP) | ................ | 2013-247787 |
| Nov. 29, 2013 | (JP) | ................ | 2013-247909 |
| Nov. 29, 2013 | (JP) | ................ | 2013-247962 |
| Nov. 29, 2013 | (JP) | ................ | 2013-248003 |

(51) Int. Cl.
  *C07F 9/6568* (2006.01)
  *C07F 7/08* (2006.01)
  *C09K 11/06* (2006.01)
  *H01L 51/52* (2006.01)

(52) U.S. Cl.
  CPC .......... *C07F 7/0816* (2013.01); *C07F 7/0818* (2013.01); *C07F 9/65685* (2013.01); *C09K 11/06* (2013.01); *H01L 51/006* (2013.01); *H01L 51/0059* (2013.01); *H01L 51/0061* (2013.01); *H01L 51/0072* (2013.01); *H01L 51/0074* (2013.01); *C09K 2211/1007* (2013.01); *C09K 2211/1011* (2013.01); *C09K 2211/1025* (2013.01); *C09K 2211/1029* (2013.01); *C09K 2211/1033* (2013.01); *C09K 2211/1088* (2013.01); *C09K 2211/1092* (2013.01); *H01L 51/0052* (2013.01); *H01L 51/0054* (2013.01); *H01L 51/0058* (2013.01); *H01L 51/0067* (2013.01); *H01L 51/0068* (2013.01); *H01L 51/0073* (2013.01); *H01L 51/5012* (2013.01); *H01L 51/5056* (2013.01); *H01L 51/5206* (2013.01)

(56) References Cited

U.S. PATENT DOCUMENTS

| | | | |
|---|---|---|---|
| 8,057,918 B2 | 11/2011 | Marks et al. | |
| 8,188,315 B2 | 5/2012 | Hwang et al. | |
| 8,304,095 B2 | 11/2012 | Heil et al. | |
| 2005/0067951 A1 | 3/2005 | Richter et al. | |
| 2007/0205715 A1* | 9/2007 | Saitoh | C07F 7/0812 313/504 |
| 2008/0106188 A1* | 5/2008 | Hwang | C07F 7/0818 313/504 |
| 2011/0297923 A1 | 12/2011 | Mizuki et al. | |
| 2012/0112174 A1 | 5/2012 | Lee et al. | |
| 2013/0153878 A1 | 6/2013 | Mizuki et al. | |
| 2013/0328027 A1 | 12/2013 | Sotoyama et al. | |

FOREIGN PATENT DOCUMENTS

| | | |
|---|---|---|
| EP | 2 348 017 A1 | 7/2011 |
| EP | 2 351 760 A1 | 8/2011 |
| EP | 2 421 064 A2 | 2/2012 |
| EP | 2 423 206 B1 | 1/2014 |
| JP | 05-323634 A | 12/1993 |
| JP | H08179526 A | 7/1996 |
| JP | 20000 86595 A | 3/2000 |
| JP | 3278252 B2 | 4/2002 |
| JP | 2005-516059 A | 6/2005 |
| JP | 2007-230951 A | 9/2007 |
| JP | 2009-185024 A | 8/2009 |
| JP | 2009-194042 A | 8/2009 |
| JP | 2010-143841 A | 7/2010 |
| JP | 2010-195708 A | 9/2010 |
| JP | 4538752 B2 | 9/2010 |
| JP | 2012-049518 A | 3/2012 |
| JP | 2012049518 A | 3/2012 |
| JP | 2013-093432 A | 5/2013 |
| JP | 2013-107853 A | 6/2013 |
| JP | 5242917 B2 | 7/2013 |
| JP | 5323634 B2 | 10/2013 |
| JP | 5405630 B2 | 2/2014 |
| JP | 5443501 B2 | 3/2014 |
| JP | 5460894 B2 | 4/2014 |
| JP | 5617398 B2 | 11/2014 |
| KR | 10-2009-0058063 | 6/2009 |
| KR | 10-2009-0058063 A | 6/2009 |
| KR | 10-2009-0073925 | 7/2009 |
| KR | 10-2009-0073925 A | 7/2009 |
| KR | 10-2010-0039393 | 4/2010 |
| KR | 10-2011-0056728 A | 5/2011 |
| KR | 10-2011-0068239 | 6/2011 |
| KR | 10-2011-0069077 | 6/2011 |
| KR | 10-2011-0069077 A | 6/2011 |
| KR | 10-2012-0024624 | 3/2012 |
| KR | 10-2012-0024624 A | 3/2012 |
| KR | 10-2012-0066149 A | 6/2012 |
| KR | 10-2014-0074228 | 6/2014 |
| WO | WO 2004/020387 A1 | 3/2004 |
| WO | WO 2006/073059 A1 | 7/2006 |
| WO | WO 2007/070778 A2 | 6/2007 |
| WO | WO 2007/148660 A1 | 12/2007 |
| WO | WO 2008/015963 A1 | 2/2008 |
| WO | WO 2008/132085 A1 | 11/2008 |
| WO | WO 2010/044130 A1 | 4/2010 |
| WO | WO 2010/052932 A1 | 5/2010 |
| WO | WO 2010/110553 A2 | 9/2010 |
| WO | WO 2010/122810 A1 | 10/2010 |
| WO | WO 2011/040607 A1 | 4/2011 |
| WO | WO 2011/059099 A1 | 5/2011 |
| WO | WO 2011/077691 A1 | 6/2011 |
| WO | WO 2012/056674 A1 | 5/2012 |
| WO | WO 2012/070227 A1 | 5/2012 |
| WO | WO 2012/091471 A2 | 7/2012 |
| WO | WO 2013/039184 A1 | 3/2013 |

* cited by examiner

AMINE DERIVATIVE, ORGANIC LUMINESCENT MATERIAL AND ORGANIC ELECTROLUMINESCENT DEVICE USING THE AMINE DERIVATIVE OR THE ORGANIC LUMINESCENT MATERIAL

CROSS-REFERENCE TO RELATED APPLICATIONS

This application is a continuation of pending International Application No. PCT/JP2013/082647, entitled "Amine Derivative, Organic Luminescent Material and Organic Electroluminescent Device Using the Amine Derivative or the Organic Luminescent Material," which was filed on Dec. 4, 2013, the entire contents of which are hereby incorporated by reference.

Japanese Patent Application No. 2012-266773, filed on Dec. 5, 2012, in the Japanese Patent Office, and Japanese Patent Application Nos. 2013-248003, 2013-247962, 2013-247909, 2013-247787, 2013-247741, 2013-247699, and 2013-247442, filed on Nov. 29, 2013, in the Japanese Patent Office, and entitled: "Amine Derivative, Organic Luminescent Material and Organic Electroluminescent Device Using the Amine Derivative or the Organic Luminescent Material," are incorporated by reference herein in their entirety.

BACKGROUND

1. Field

Embodiments relate to an amine derivative for use as an organic luminescent material such as a hole transport material, etc., and an organic electroluminescent device using the organic luminescent material or the amine derivative.

2. Description of the Related Art

Recently, the development of an organic electroluminescent display device in which a luminescent material is used in a luminescent display device has been actively conducted. The organic electroluminescent display device is different from a liquid crystal display device and is a so-called self-luminescent display device realizing display by recombining holes and electrons injected from an anode and a cathode in an emission layer and emitting light by a luminescent material including an organic compound in the emission layer.

DISCLOSURE OF THE INVENTION

Embodiments are directed to an amine derivative represented by the following General Formula (1).

[Formula 1]

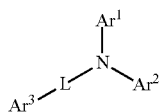

(1)

In the above General Formula (1), $Ar^1$, $Ar^2$ and $Ar^3$ are independently a substituted or unsubstituted aryl group or a substituted or unsubstituted heteroaryl group, at least one of $Ar^1$, $Ar^2$ and $Ar^3$ is substituted with a substituted or unsubstituted silyl group, and L is a single bond, a substituted or unsubstituted arylene group or a substituted or unsubstituted heteroarylene group.

In some embodiments, at least one of $Ar^1$, $Ar^2$ and $Ar^3$ may be the substituted or unsubstituted heteroaryl group in the above General Formula (1).

In other embodiments, $Ar^1$ and $Ar^2$ may be independently the substituted or unsubstituted aryl group in the above General Formula (1).

In still other embodiments, $Ar^1$ and $Ar^2$ may be independently a substituted or unsubstituted aryl group having 6 to 18 carbon atoms for forming a ring, and $Ar^3$ may be a substituted or unsubstituted dibenzoheterole group.

In even other embodiments, the silyl group substituted for at least one of $Ar^1$, $Ar^2$ and $Ar^3$ may be a triarylsilyl group where an aryl substituent at the silyl group has 6 to 18 carbon atoms for forming a ring or a trialkylsilyl group where an alkyl substituent at the silyl group has 1 to 6 carbon atoms in the above Formula (1).

In yet other embodiments, each of $Ar^1$ and $Ar^2$ may be substituted with a silyl group in the above Formula (1).

In further embodiments, each of $Ar^1$, $Ar^2$ and $Ar^3$ may be substituted with a silyl group in the above General Formula (1).

In still further embodiments, L may be a single bond or an arylene group having 6 to 14 carbon atoms for forming a ring in the above General Formula (1).

In even further embodiments, $Ar^3$ may be a substituted or unsubstituted dibenzofuryl group in the above General Formula (1).

In yet further embodiments, L is not the single bond in the above General Formula (1).

In much further embodiments, L may be a phenylene group, and the dibenzofuryl group for $Ar^3$ may be combined with L at position 3 in the above General Formula (1).

In still much further embodiments, the amine derivative represented by the above General Formula (1) may be a compound represented by the following General Formula (2).

[Formula 2]

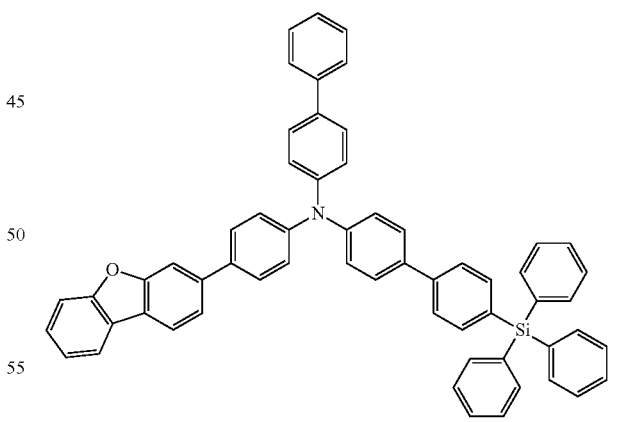

(2)

In other embodiments according to an embodiment, organic electroluminescent devices include one of the above-described amine derivatives in an emission layer.

In still other embodiments according to an embodiment, organic electroluminescent devices include one of the above-described amine derivatives in one layer of laminated layers between an emission layer and an anode.

In some embodiment, $Ar^1$ and $Ar^2$ may be independently a substituted or unsubstituted aryl group or a substituted or unsubstituted heteroaryl group, at least one of $Ar^1$ and $Ar^2$ is substituted with a substituted or unsubstituted silyl group, $Ar^3$ is a substituted or unsubstituted dibenzofuryl group, and L is a single bond in the above General Formula (1).

In other embodiments, the dibenzofuryl group may be combined with L at position 3 in the above General Formula (1).

In even other embodiments according to an embodiment, electroluminescent devices include the above-described amine derivative in an emission layer.

In yet other embodiments according to an embodiment, electroluminescent devices include the above-described amine derivative in one layer of laminated layers between an emission layer and an anode.

In some embodiments, $Ar^1$ and $Ar^2$ may be independently a substituted or unsubstituted aryl group or a substituted or unsubstituted heteroaryl group, at least one of $Ar^1$ and $Ar^2$ may be substituted with a substituted or unsubstituted silyl group, $Ar^3$ may be a substituted or unsubstituted fluorenyl group, and L may be a substituted or unsubstituted arylene group or a substituted or unsubstituted heteroarylene group in the above General Formula (1).

In further embodiments according to an embodiment, organic electroluminescent devices include the above-described amine derivative in an emission layer.

In still further embodiments according to an embodiment, organic electroluminescent devices include the above-described amine derivative in one layer of laminated layers between an emission layer and an anode.

In some embodiments, $Ar^3$ may be a substituted or unsubstituted fluorenyl group, and L may be a single bond in the above General Formula (1), and the amine derivative may be represented by the following General Formula (3).

[Formula 3]

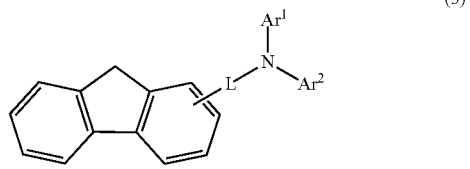

(3)

In other embodiments, a substituent of the fluorenyl group may be independently a hydrogen atom, a substituted or unsubstituted alkyl group, a substituted or unsubstituted aryl group or a substituted or unsubstituted heteroaryl group in the above General Formula (3).

In still other embodiments, the fluorenyl group may be combined with L at position 2.

In even other embodiments, $Ar^1$ and $Ar^2$ may be independently a substituted or unsubstituted aryl group in the above General Formula (3).

In yet other embodiments, $Ar^1$ may be a substituted or unsubstituted aryl group and $Ar^2$ may be a substituted or unsubstituted dibenzoheterole group in the above General Formula (3).

In further embodiments, one of $Ar^1$ and $Ar^2$ may be substituted with a substituted or unsubstituted silyl group.

In still further embodiments, the silyl group substituted for at least one of $Ar^1$ and $Ar^2$ may be a triarylsilyl group where an aryl substituent at the silyl group has 6 to 18 carbon atoms for forming a ring or a trialkylsilyl group where an alkyl substituent at the silyl group has 1 to 6 carbon atoms.

In even further embodiments according to an embodiment, materials for an organic electroluminescent device include the above-described amine derivative.

In some embodiments, the material for an organic electroluminescent device may be a hole transport material.

In yet further embodiments according to an embodiment, organic electroluminescent devices include an emission layer and a hole transport layer disposed between a cathode and an anode, and the hole transport layer includes the above-described amine derivative.

In some embodiments, $Ar^1$ and $Ar^2$ may be independently a substituted or unsubstituted aryl group or a substituted or unsubstituted heteroaryl group, at least one of $Ar^1$ and $Ar^2$ may be substituted with a substituted or unsubstituted silyl group, $Ar^3$ may be a substituted or unsubstituted carbazolyl group, and L may be a substituted or unsubstituted arylene group or a substituted or unsubstituted heteroarylene group in the above General Formula (1).

In other embodiments, the substituted or unsubstituted carbazolyl group may be combined with L at position 2 or position 3.

In much further embodiments according to an embodiment, organic electroluminescent devices include the above-described amine derivative in an emission layer.

In still much further embodiments according to an embodiment, organic electroluminescent devices include the above-described amine derivative in one layer of laminated layers between an emission layer and an anode.

In some embodiments, $Ar^1$ and $Ar^2$ may be independently a substituted or unsubstituted aryl group or a substituted or unsubstituted heteroaryl group, at least one of $Ar^1$ and $Ar^2$ may be substituted with a substituted or unsubstituted silyl group, $Ar^3$ may be a substituted or unsubstituted carbazolyl group, and L may be a substituted or unsubstituted arylene group or a substituted or unsubstituted heteroarylene group in the above General Formula (1), and the amine derivative may be represented by the following General Formula (4).

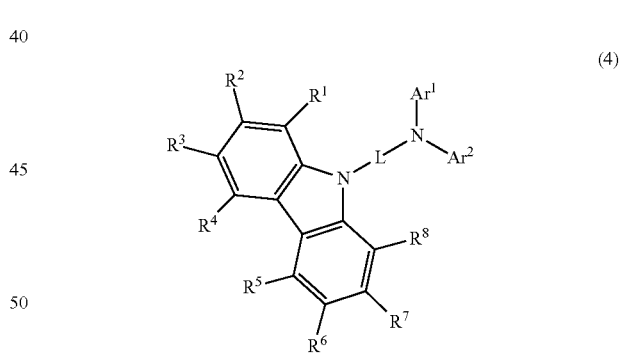

(4)

In the above General Formula (4), $R^1$ to $R^8$ are a hydrogen atom, a substituted or unsubstituted aryl group having 6 to 30 carbon atoms for forming a ring, a substituted or unsubstituted heteroaryl group having 5 to 30 carbon atoms for forming a ring, a substituted or unsubstituted alkyl group having 1 to 15 carbon atoms, a substituted or unsubstituted silyl group, a cyano group, a halogen atom or a deuterium atom.

In other embodiments, $R^1$ to $R^8$ may be combined to each other to form a saturated or unsaturated ring in the above General Formula (4).

In still other embodiments, L may be a phenylene group, a biphenylene group or a fluorenylene group in the above General Formula (4).

In even other embodiments, $Ar^1$ and $Ar^2$ may be an aryl group having 6 to 12 carbon atoms for forming a ring when L is the fluorenylene group in the above General Formula (4).

In even much further embodiments according to an embodiment, organic electroluminescent devices include the above-described amine derivative in an emission layer.

In yet much further embodiments according to an embodiment, organic electroluminescent devices include the above-described amine derivative in a layer of laminated layers between an emission layer and an anode.

In some embodiments, $Ar^1$ may be an aryl group substituted with a silyl group and represented by the following General Formula (5), $Ar^2$ may be a substituted or unsubstituted aryl group having 6 to 30 carbon atoms for forming a ring, $Ar^3$ may be an aryl group represented by the following General Formula (6), and L is an arylene group represented by the following General Formula (7).

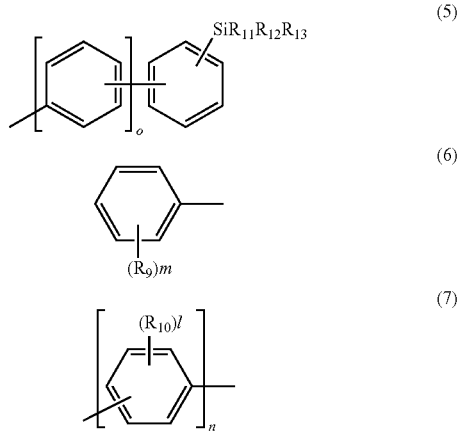

In the above General Formula (5), o is an integer satisfying the relation of $0 \leq o \leq 2$, $R_{11}$, $R_{12}$ and $R_{13}$ are independently an alkyl group having 1 to 15 carbon atoms, a substituted or unsubstituted aryl group having 6 to 30 carbon atoms for forming a ring or a heteroaryl group having 1 to 30 carbon atoms for forming a ring, in the above General Formula (6), each $R_9$ is independently a hydrogen atom, a halogen atom, an alkyl group having 1 to 15 carbon atoms, a substituted or unsubstituted aryl group having 6 to 30 carbon atoms for forming a ring, and m is an integer satisfying the relation of $0 \leq m \leq 5$, and in the above General Formula (7), each $R_{10}$ is independently a hydrogen atom, a halogen atom, an alkyl group having 1 to 15 carbon atoms, a substituted or unsubstituted aryl group having 6 to 30 carbon atoms for forming a ring, l is an integer satisfying the relation of $0 \leq l \leq 4$, and n is an integer satisfying the relation of $2 \leq n \leq 5$.

In other embodiments, $R_{11}$, $R_{12}$ and $R_{13}$ may be independently a phenyl group in the above General Formula (5).

In still other embodiments, o may be 0 or 1 in the above General Formula (5).

In even other embodiments, n may be 2 in the above General Formula (7).

In much still further embodiments according to an embodiment, materials for an organic electroluminescent device include one of the above-described amine derivatives.

In even still further embodiments according to an embodiment, organic electroluminescent devices include the above-described material for an organic electroluminescent device in a layer of laminated layers disposed between an emission layer and an anode.

BRIEF DESCRIPTION OF THE DRAWINGS

Features will become apparent to those of skill in the art by describing in detail example embodiments with reference to the attached drawings in which.

DETAILED DESCRIPTION

Figure 1:
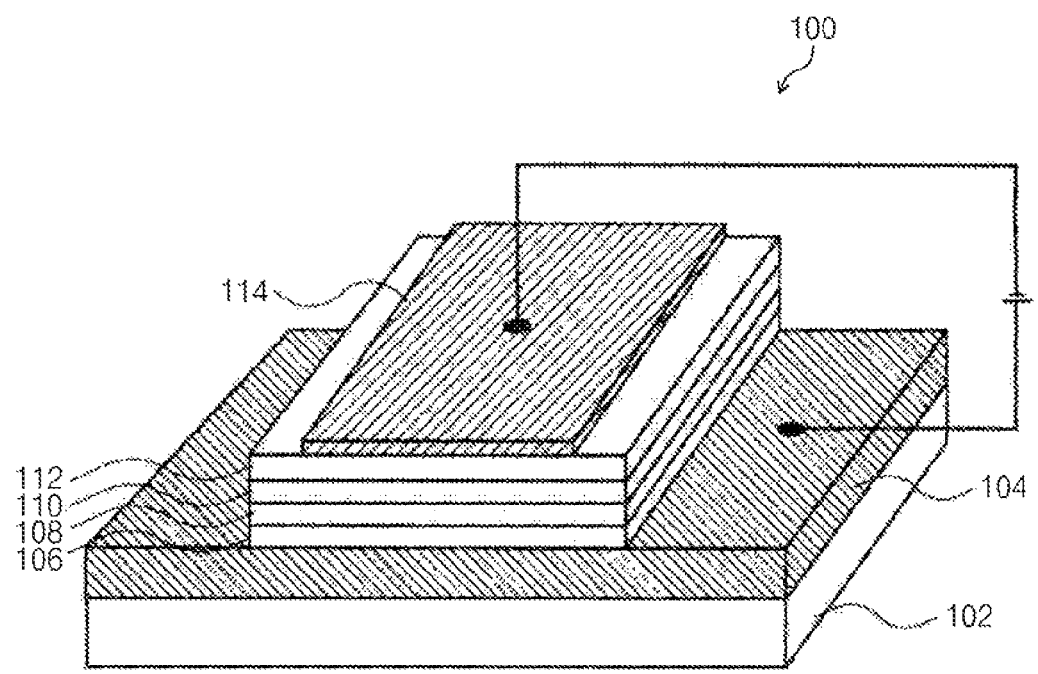
FIG. 1 illustrates a schematic cross-sectional diagram illustrating an embodiment of the structure of an organic electroluminescent device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art.

In the drawing figures, the dimensions of layers and regions may be exaggerated for clarity of illustration. Like reference numerals refer to like elements throughout.

Hereinafter, the amine derivative having a silyl group according to an embodiment will be explained. However, the organic electroluminescent material according to an embodiment and the organic electroluminescent device using thereof will be used in various other embodiments and will not be limited to the interpretation of the following description on embodiments.

An organic electroluminescent material according to an embodiment is an amine derivative having a silyl group represented by the following General Formula (1).

[Formula 6]

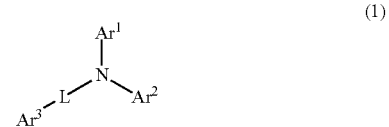

In the above General Formula (1), $Ar^1$, $Ar^2$ and $Ar^3$ are independently a substituted or unsubstituted aryl group or a substituted or unsubstituted heteroaryl group, at least one of $Ar^1$, $Ar^2$ and $Ar^3$ is substituted with a substituted or unsubstituted silyl group, and L is a single bond, a substituted or unsubstituted arylene group or a substituted or unsubstituted heteroarylene group.

As the aryl group and the heteroaryl group of "the substituted or unsubstituted aryl group" or "the substituted or unsubstituted heteroaryl group" of $Ar^1$, $Ar^2$ and $Ar^3$, a phenyl group, a naphthyl group, an anthracenyl group, a phenanthryl group, a biphenyl group, a terphenyl group, a fluorenyl group, a triphenylene group, a biphenylene group, a pyrenyl group, a benzothiazolyl group, a thiophenyl group, a thienothiophenyl group, a thienothienothiophenyl group, a benzothiophenyl group, a dibenzothiophenyl group, a dibenzofuryl group, a N-arylcarbazolyl group, a N-heteroarylcarbazolyl group, a N-alkylcarbazolyl group, a phenoxazyl group, a phenothiazyl group, a pyridyl group, a pyrimidyl group, a triazinyl group, a quinolinyl group and a quinoxalyl group are examples. The aryl group or the heteroaryl group of $Ar^1$, $Ar^2$ and $Ar^3$ may be the phenyl group, the naphthyl group, the biphenyl group, the terphenyl group, the fluorenyl group, the triphenylene group, the dibenzothiophenyl group, the dibenzofuryl group and the N-phenylcarbazolyl group, and may particularly be the phenyl group, the biphenyl group, the fluorenyl group, the triphenylene group, the dibenzothiophenyl group, the dibenzofuryl group and the N-phenylcarbazolyl group. Here, as described above, at least one of the aryl group and the heteroaryl group of $Ar^1$, $Ar^2$ and $Ar^3$ may be substituted with a silyl group. In addition, one silyl group may be substituted for at least one of $Ar^1$ and $Ar^2$ and may be substituted for at least one of $Ar^1$, $Ar^2$ and $Ar^3$.

In an implementation, at least one of $Ar^1$, $Ar^2$ and $Ar^3$ is the substituted or unsubstituted heteroaryl group, and, for example, is a substituted or unsubstituted dibenzoheterole group such as the carbazolyl group, the dibenzothiophenyl group and the dibenzofuryl group. $Ar^3$ may be the substituted or unsubstituted heteroaryl group, and $Ar^3$ may be the dibenzoheterole group. In the case that $Ar^3$ is the substituted or unsubstituted heteroaryl group, $Ar^1$ and $Ar^2$ may be the substituted or unsubstituted aryl group, and for example, $Ar^3$ is the dibenzoheterole group and $Ar^1$ and $Ar^2$ are an aryl group having 6 to 18 carbon atoms for forming a ring.

"The substituted or unsubstituted arylene group" or "the substituted or unsubstituted heteroarylene group" of L may be the same as the aryl group and the heteroaryl group of "the substituted or unsubstituted aryl group" or "the substituted or unsubstituted heteroaryl group" for $Ar^1$, $Ar^2$ and $Ar^3$ illustrated above. The arylene group and the heteroarylene group of "the substituted or unsubstituted arylene group" or "the substituted or unsubstituted heteroarylene group" of L may be a phenylene group, a naphthalene group, a biphenylene group, a thienothiophenylene group and a pyridylene group. For example, an arylene group having 6 to 14 carbon atoms for forming a ring may be used, and the phenylene group and the biphenylene group may be used. In addition, "the single bond" of L means that the nitrogen atom (N) of the amine part is directly connected to $Ar^3$ in the amine derivative having a silyl group represented by General Formula (1) according to an embodiment.

As the substituent of the aryl group or the heteroaryl group of $Ar^1$, $Ar^2$ and $Ar^3$, an alkyl group, an alkoxy group, an aryl group and a heteroaryl group may be included. Examples of the aryl group and the heteroaryl group may be the same as the aryl group and the heteroaryl group of the above-described $Ar^1$, $Ar^2$ and $Ar^3$.

The alkyl group of the substituent of the aryl group or the heteroaryl group of $Ar^1$, $Ar^2$ and $Ar^3$ is not specifically limited, and includes a methyl group, an ethyl group, a propyl group, an isopropyl group, a cyclopropyl group, a butyl group, an isobutyl group, a t-butyl group, a cyclobutyl group, a pentyl group, an isopentyl group, a neopentyl group, a cyclopentyl group, a hexyl group, a cyclohexyl group, a heptyl group, a cycloheptyl group, an octyl group, a nonyl group, a decyl group, etc.

The alkoxy group of the substituent of the aryl group or the heteroaryl group of $Ar^1$, $Ar^2$ and $Ar^3$ is not specifically limited, and includes a methoxy group, an ethoxy group, a n-propoxy group, an isopropoxy group, a n-butoxy group, an isobutoxy group, a t-butoxy group, a n-pentyloxy group, a neopentyloxy group, a n-hexyloxy group, a n-heptyloxy group, a n-octyloxy group, a 2-ethylhexyloxy group, a nonyloxy group, a decyloxy group, a 3,7-dimethyloctyloxy group, etc.

As the substituent of the arylene group or the heteroarylene group of L, an alkyl group, an alkoxy group, an aryl group and a heteroaryl group may be included. Examples are the same as the alkyl group, the alkoxy group, the aryl group and the heteroaryl group explained as the substituent of the aryl group or the heteroaryl group of $Ar^1$, $Ar^2$ and $Ar^3$.

The substituent of the silyl group substituted for at least one of $Ar^1$, $Ar^2$ and $Ar^3$ may include an alkyl group, an alkoxy group and a heteroaryl group. Examples are the same as the alkyl group, the alkoxy group, the aryl group and the heteroaryl group explained as the substituent of the aryl group or the heteroaryl group of $Ar^1$, $Ar^2$ and $Ar^3$, and the alkyl group and the aryl group are examples, and the methyl group and the phenyl group are particular examples. In addition, the silyl group substituted for at least one of $Ar^1$, $Ar^2$ and $Ar^3$ may be a trialkylsilyl group where an alkyl substituent at the silyl group has 1 to 6 carbon atoms or a triarylsilyl group where an aryl substituent at the silyl group has 6 to 18 carbon atoms for forming a ring.

Examples of the amine derivative having a silyl group according to an embodiment, represented by General Formula (1) may be the following compounds, without limitation.

[Formula 7]

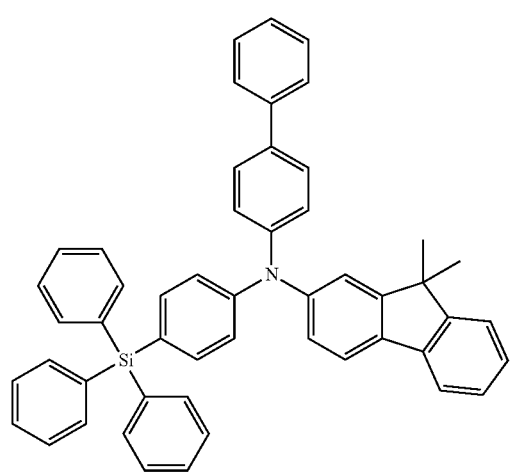

No. 1

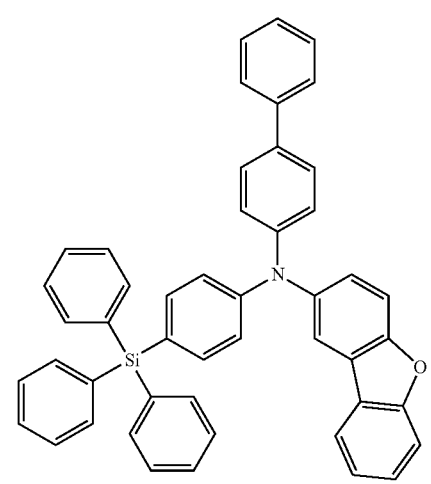

No. 2

-continued
No. 3
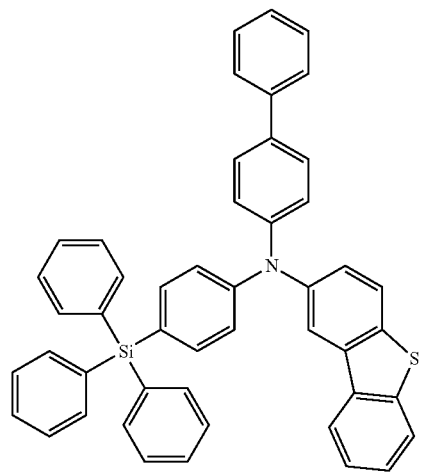
No. 4
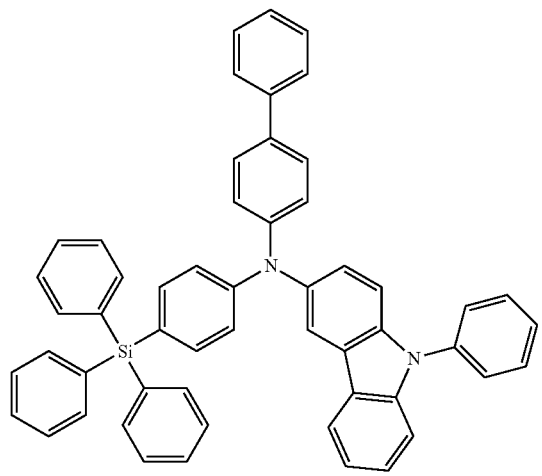
[Formula 8]
No. 5
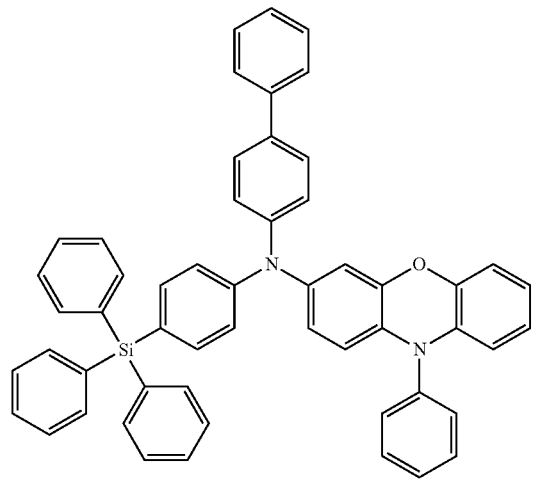
No. 6
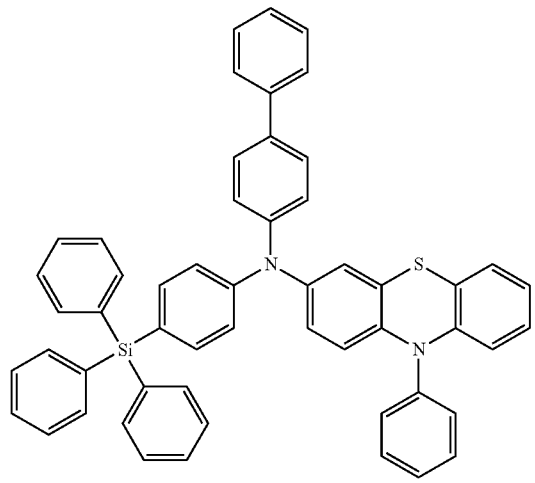
No. 7
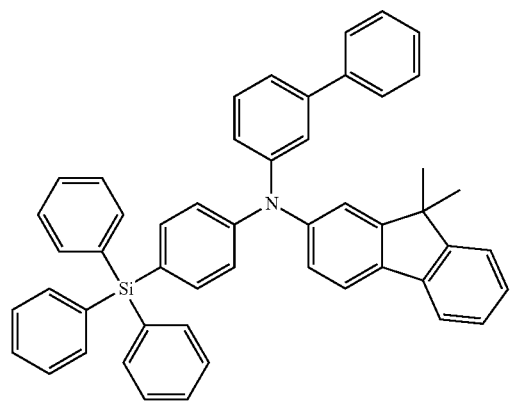
No. 8
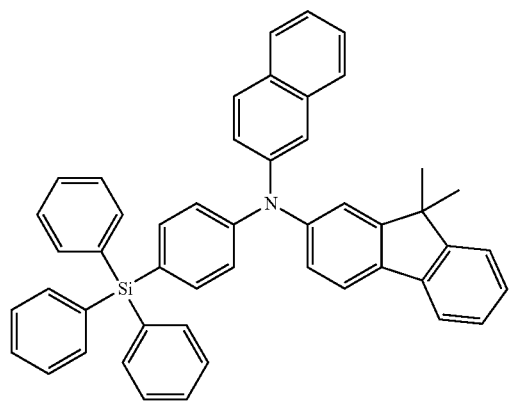

[Formula 9]
No. 9
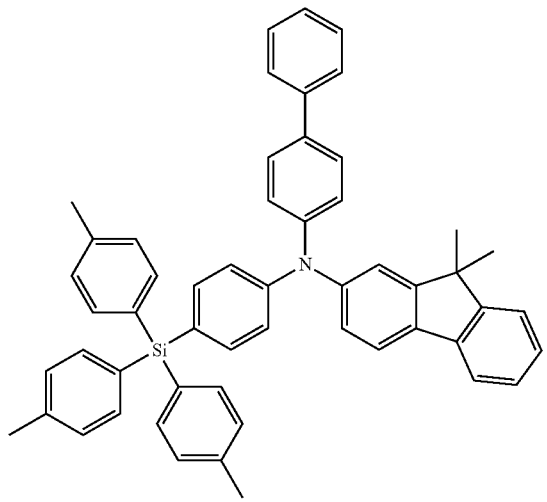
No. 10
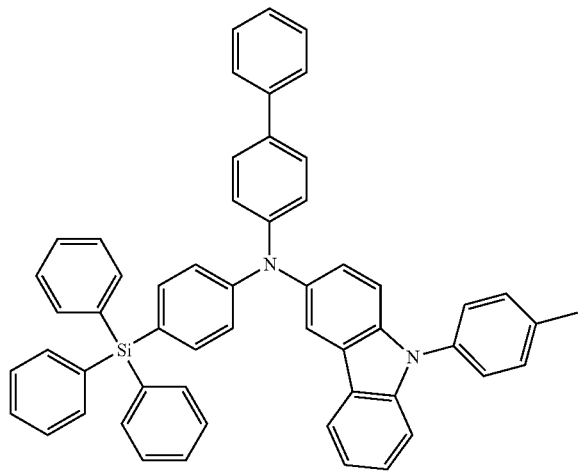
No. 11
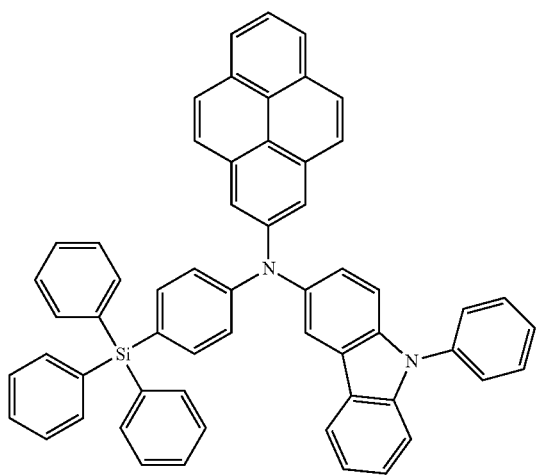
No. 12
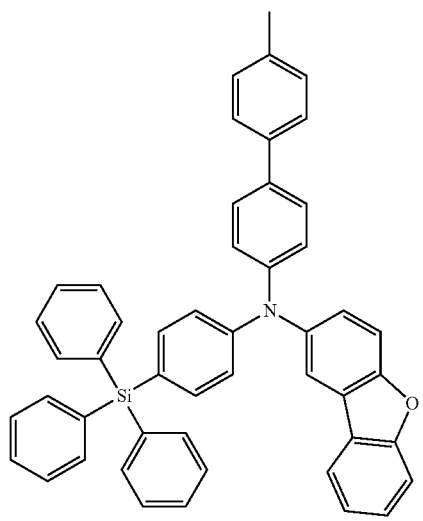
[Formula 10]
No. 13
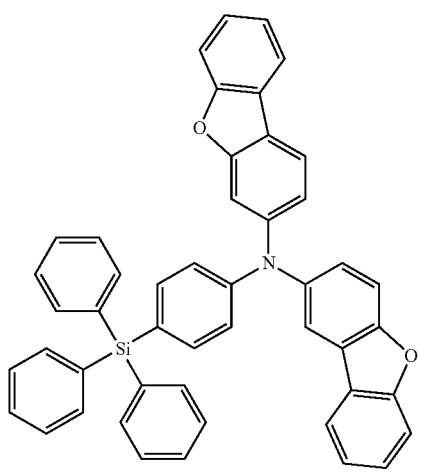
No. 14
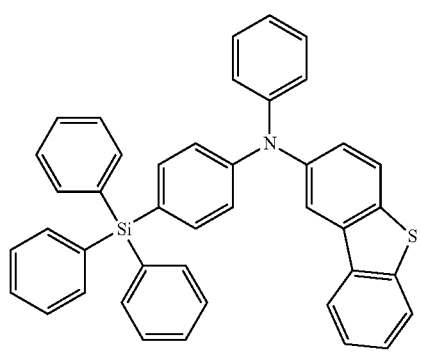

[Formula 11]
No. 15
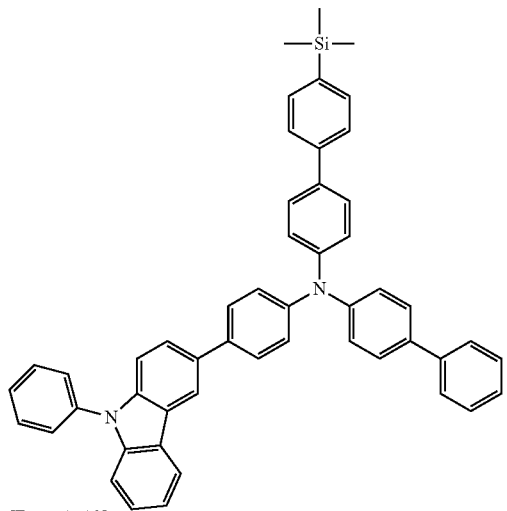
No. 16
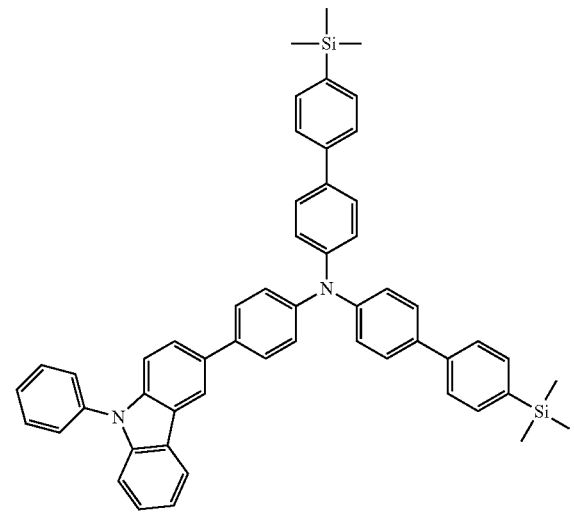
[Formula 12]
No. 17
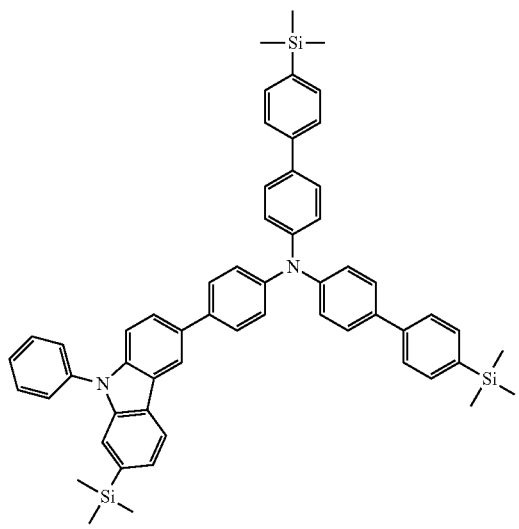
No. 18
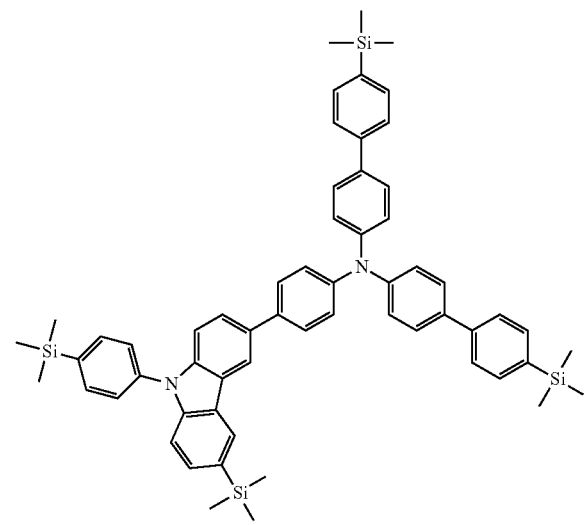
[Formula 13]
No. 19
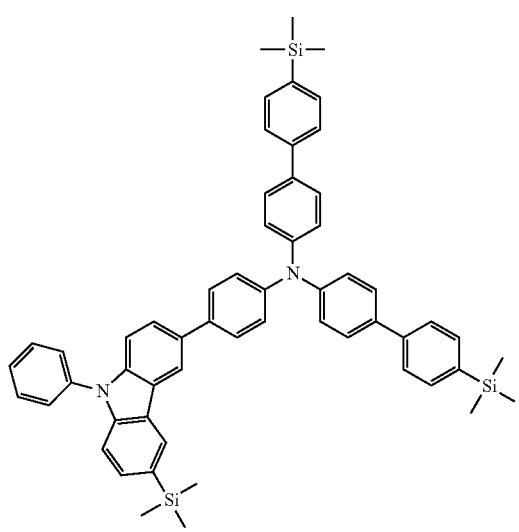
No. 20
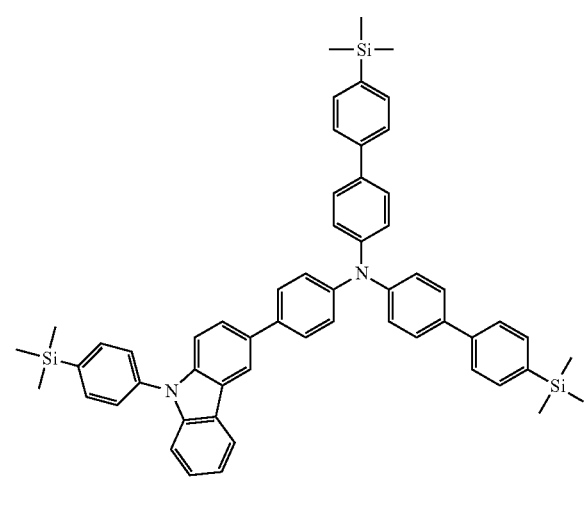

[Formula 14]
No. 21
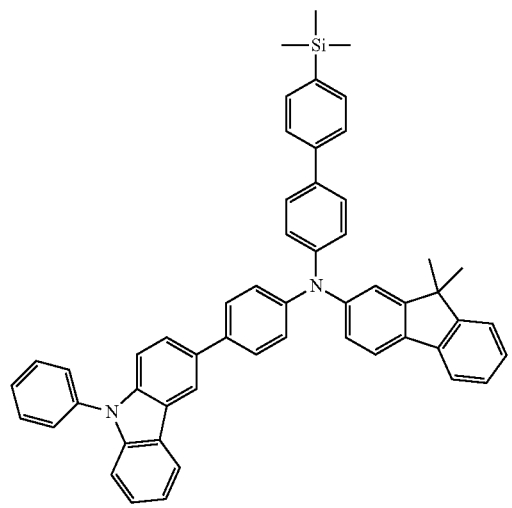
No. 22
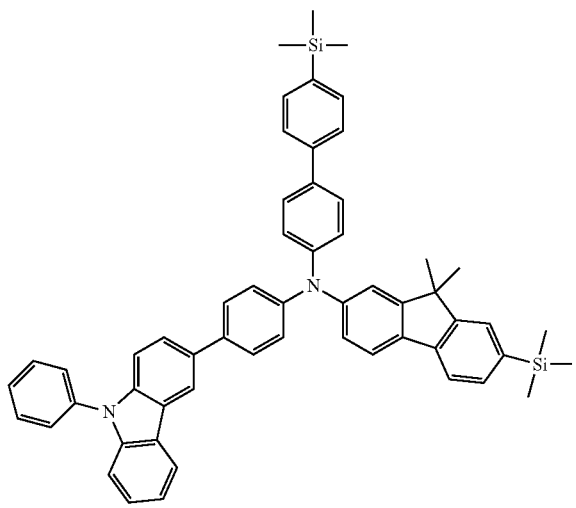
[Formula 15]
No. 23
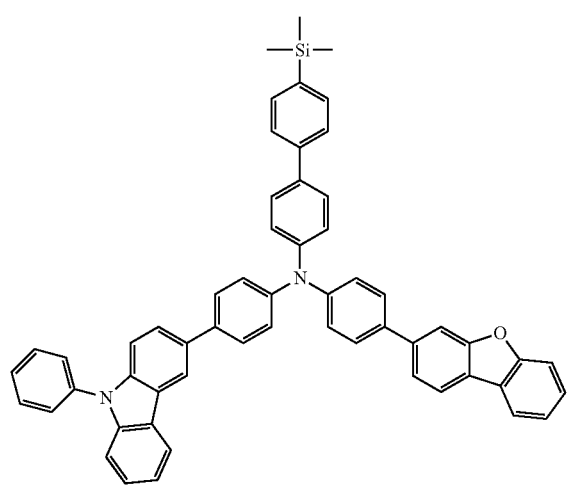
No. 24
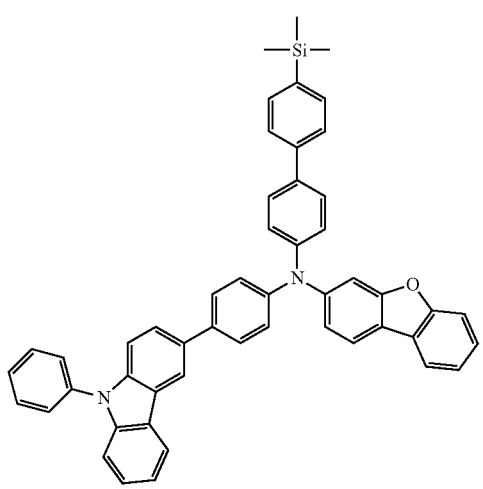
[Formula 16]
No. 25
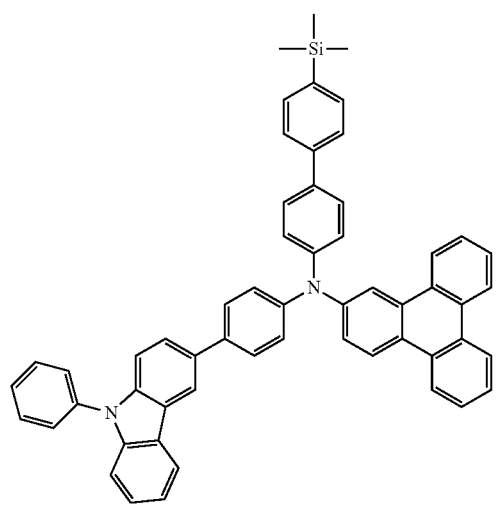
No. 26
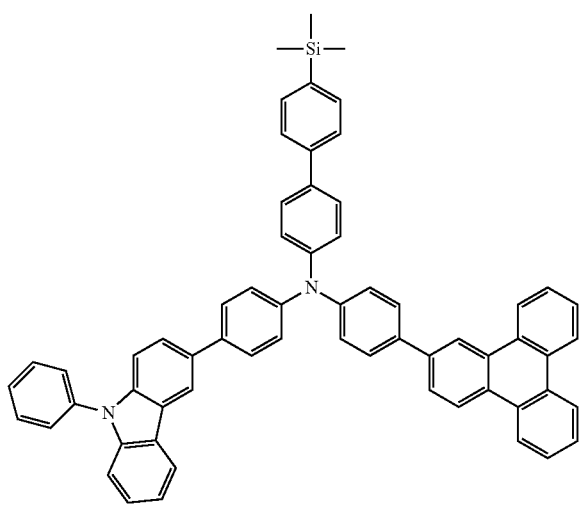

[Formula 17]
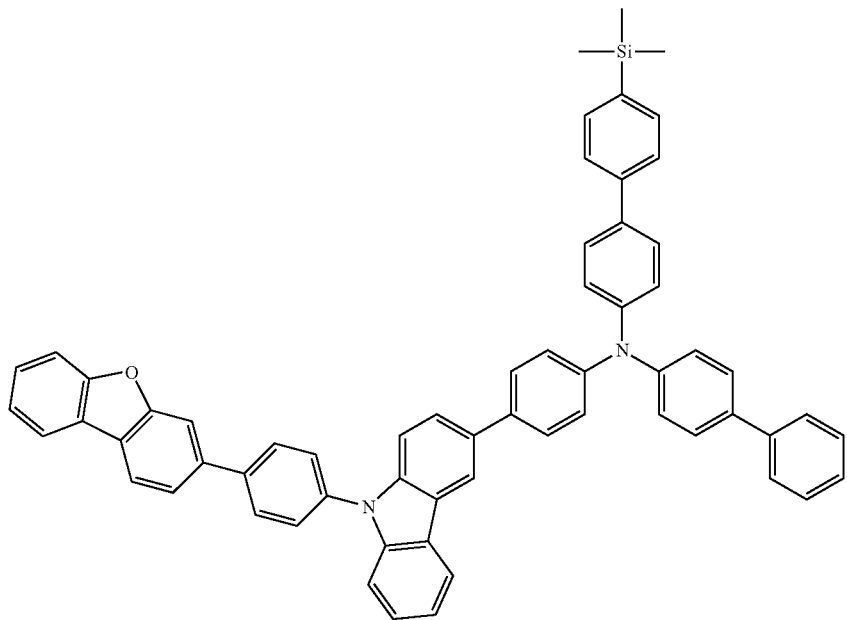
No. 27
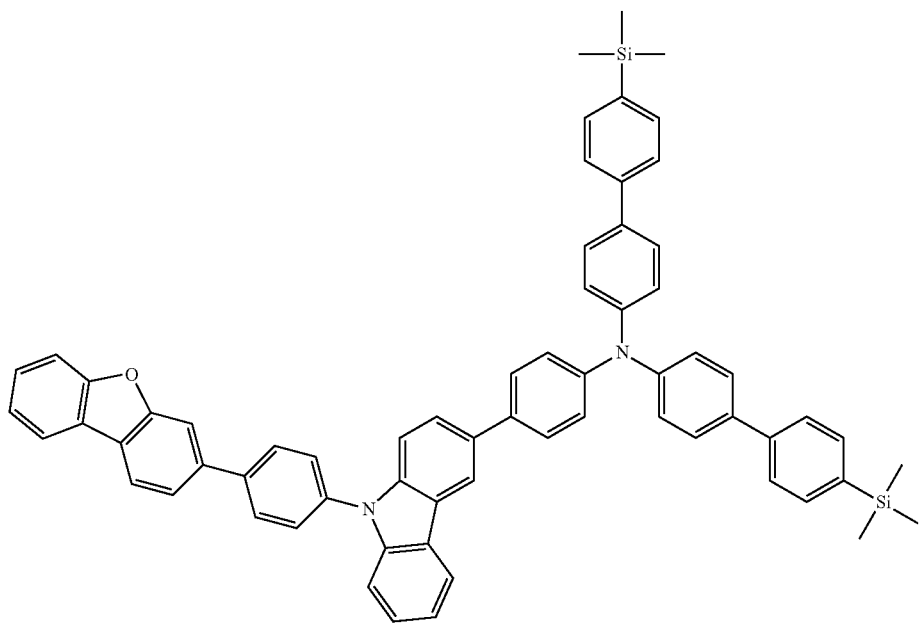
No. 28

[Formula 18]
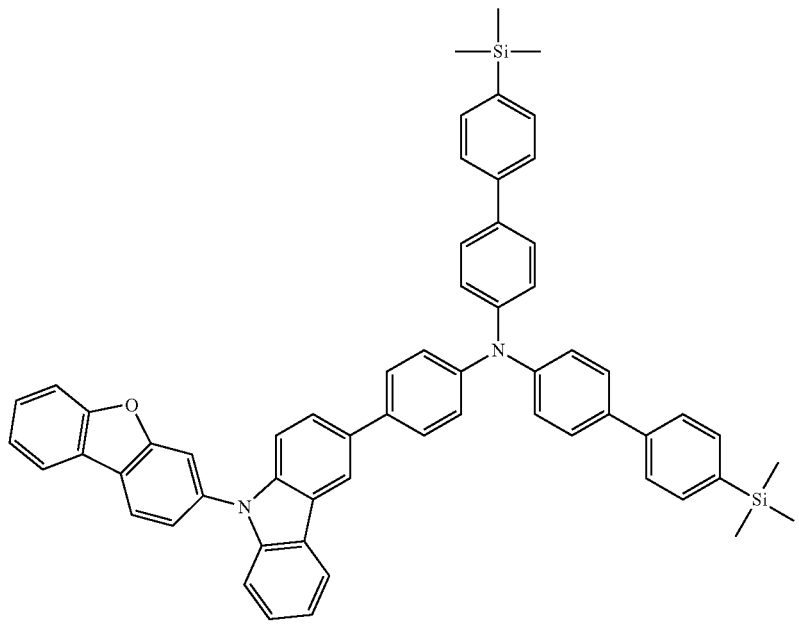
No. 29
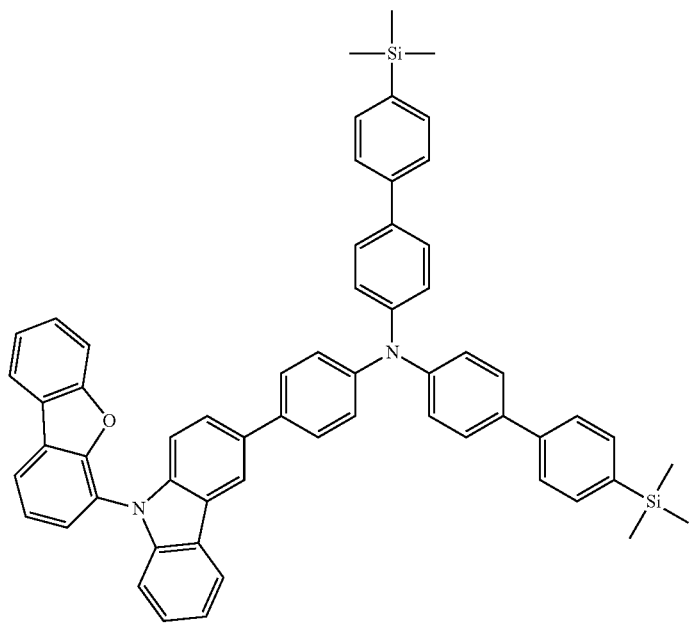
No. 30

[Formula 19]
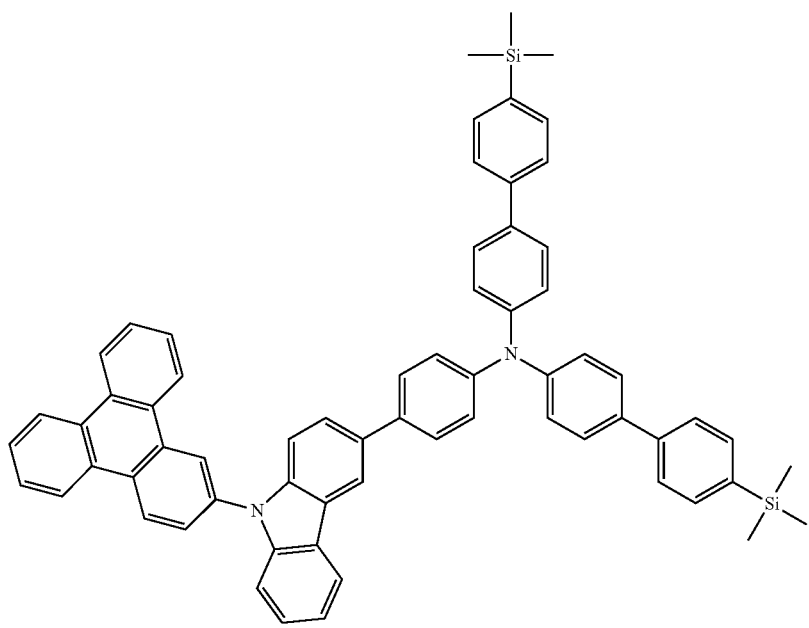
No. 31
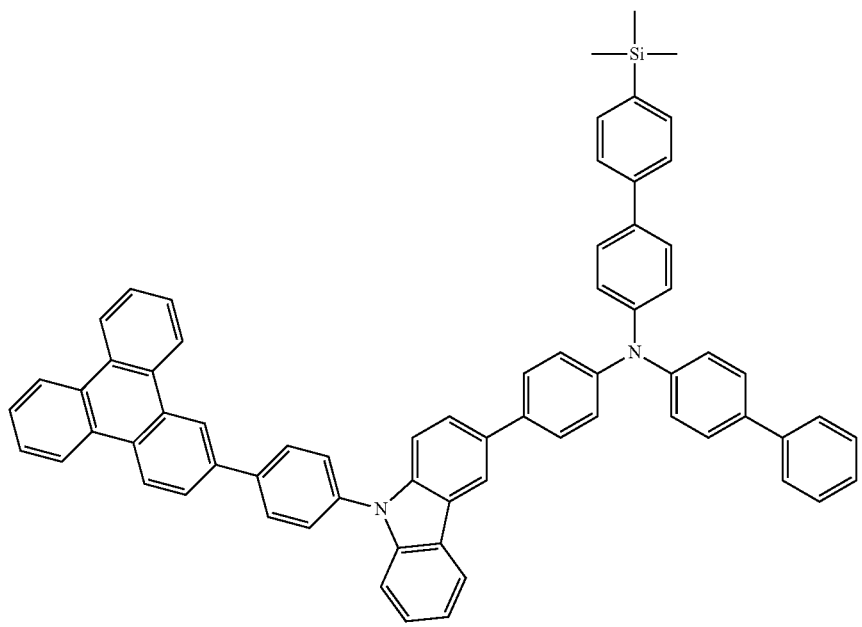
No. 32

[Formula 20]
No. 33
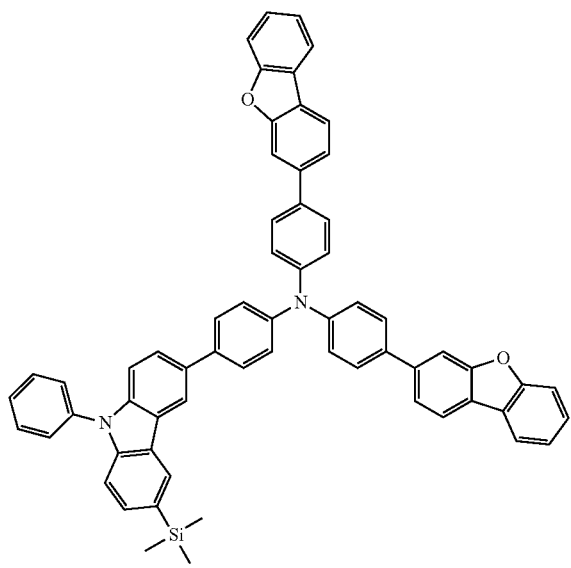
No. 34
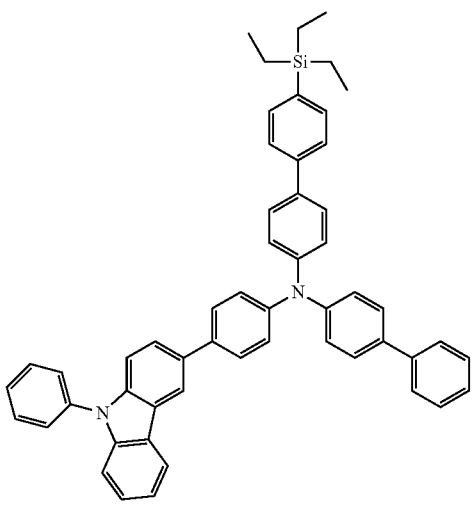
No. 35
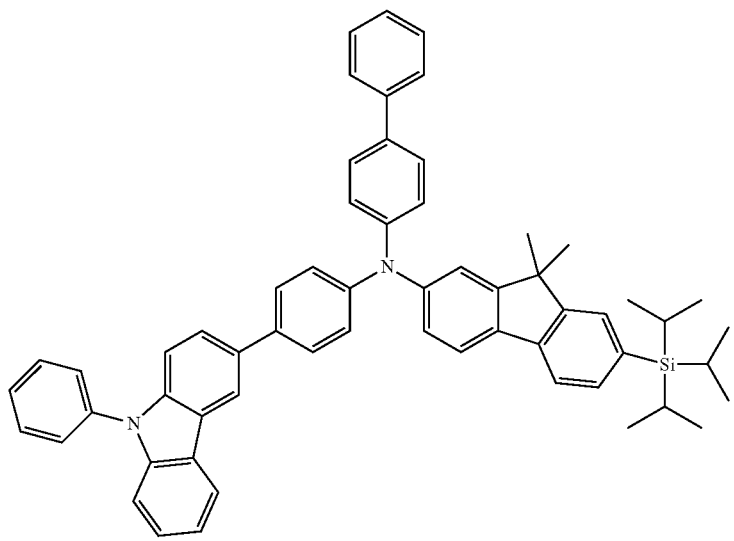

[Formula 21]
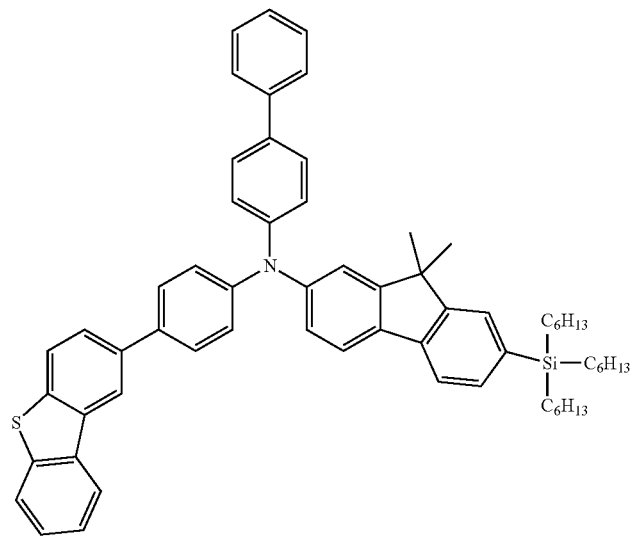
No. 36
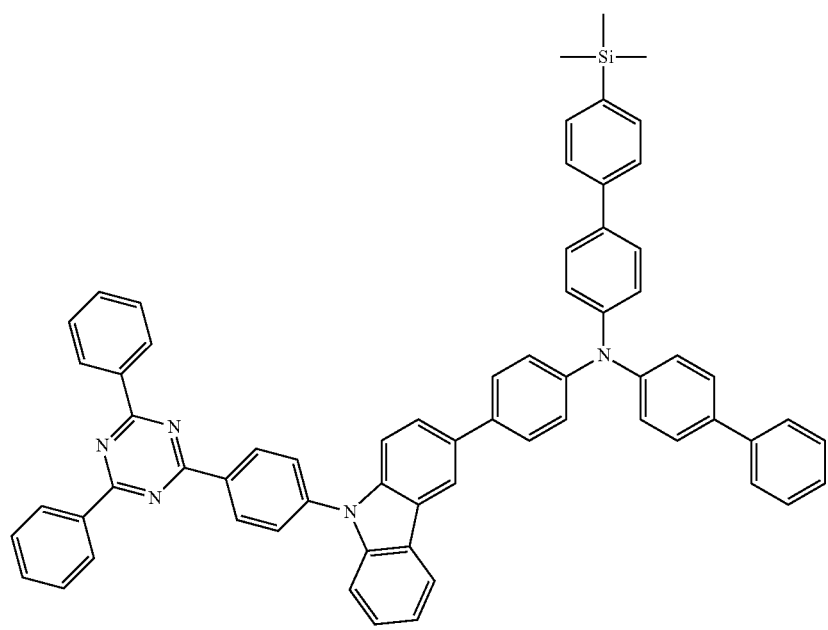
No. 37

[Formula 22]
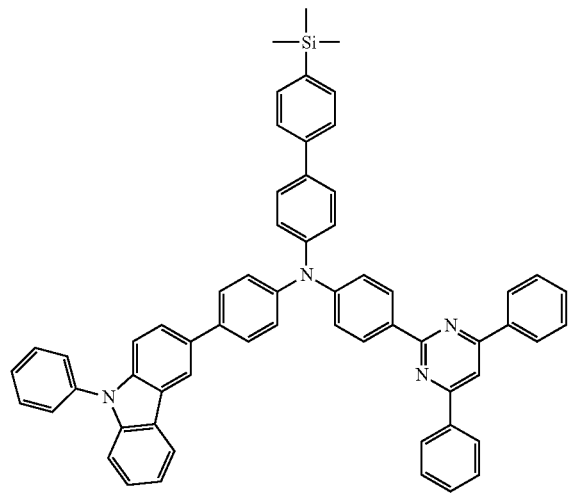
No. 38
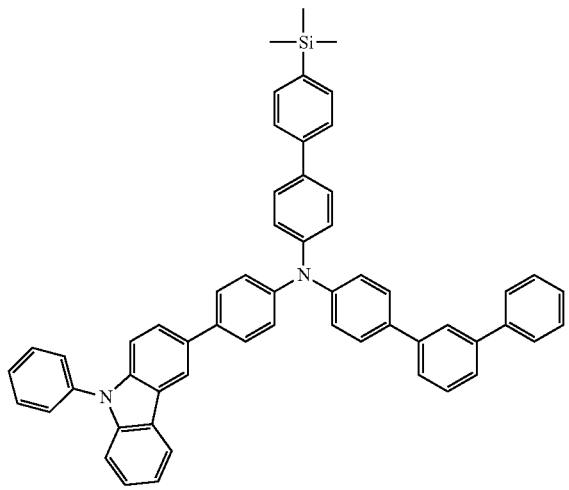
No. 39
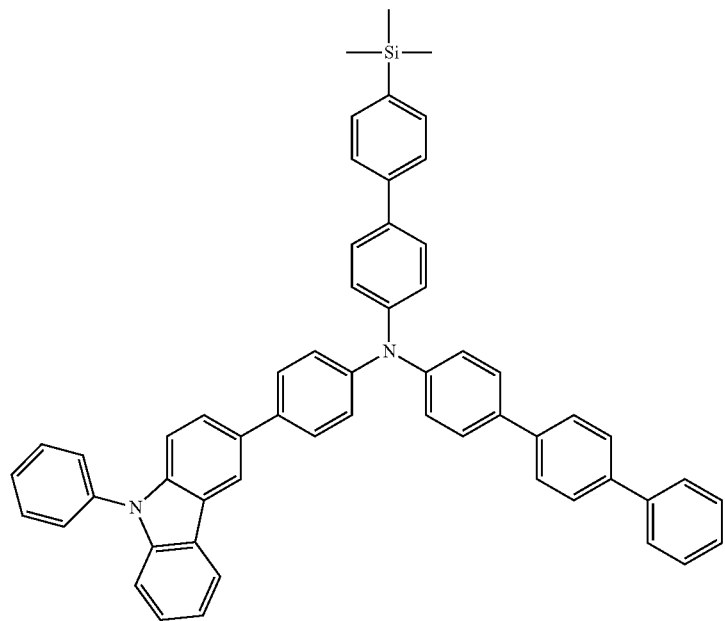
No. 40

[Formula 23]
No. 41
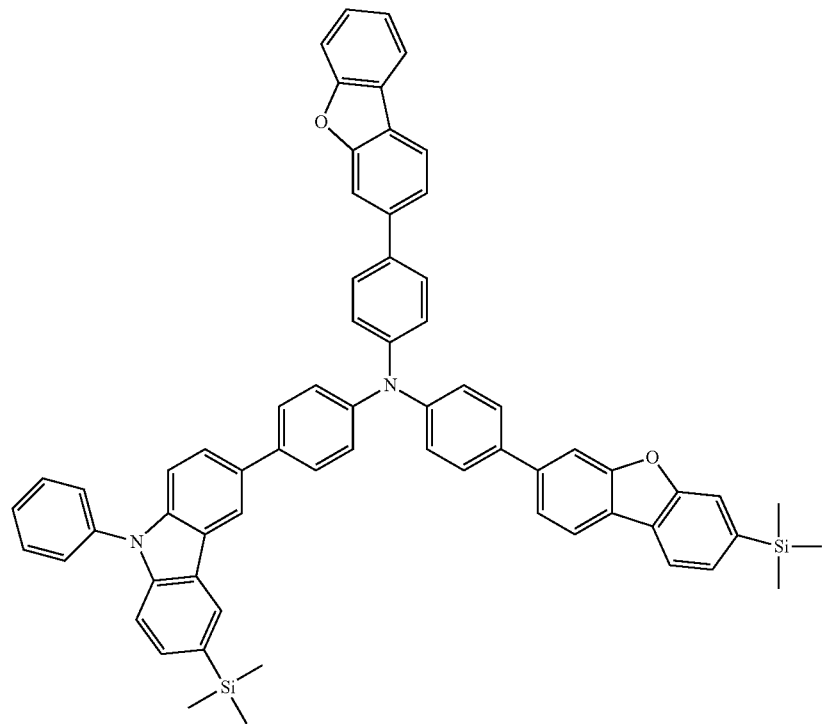
No. 42
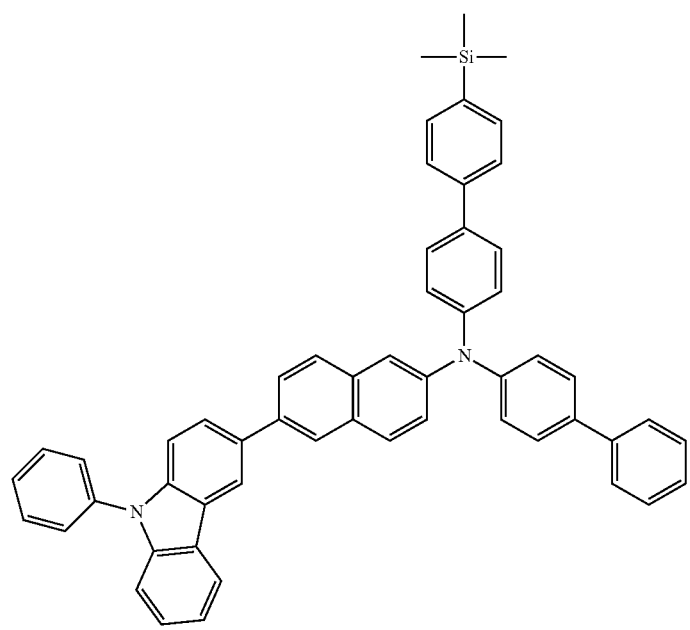

[Formula 24]
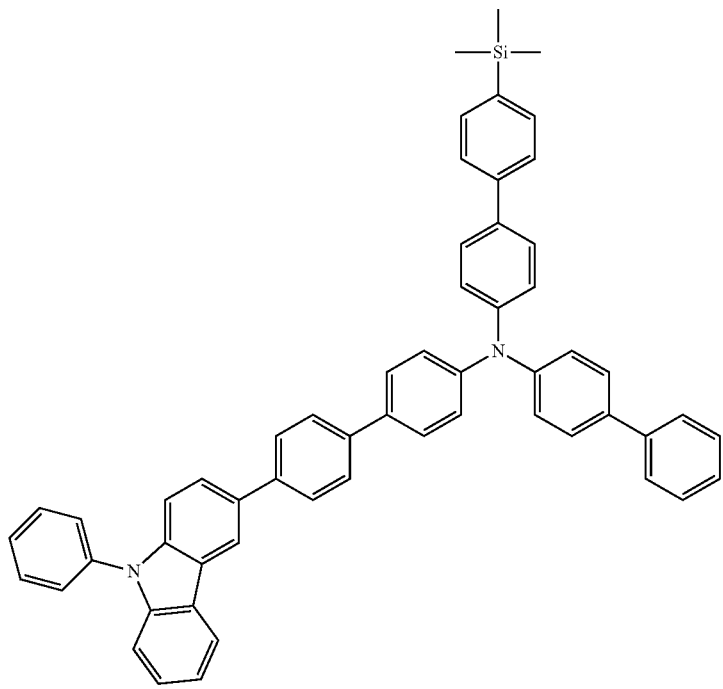
No. 43
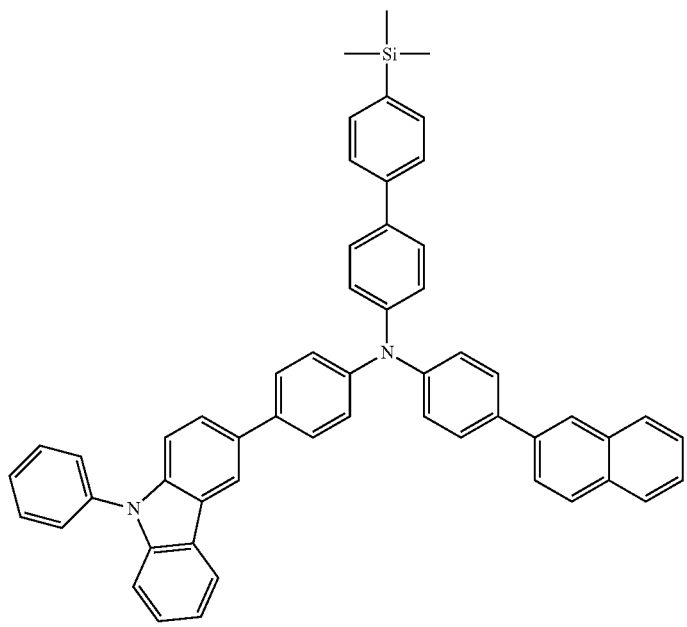
No. 44

[Formula 25]
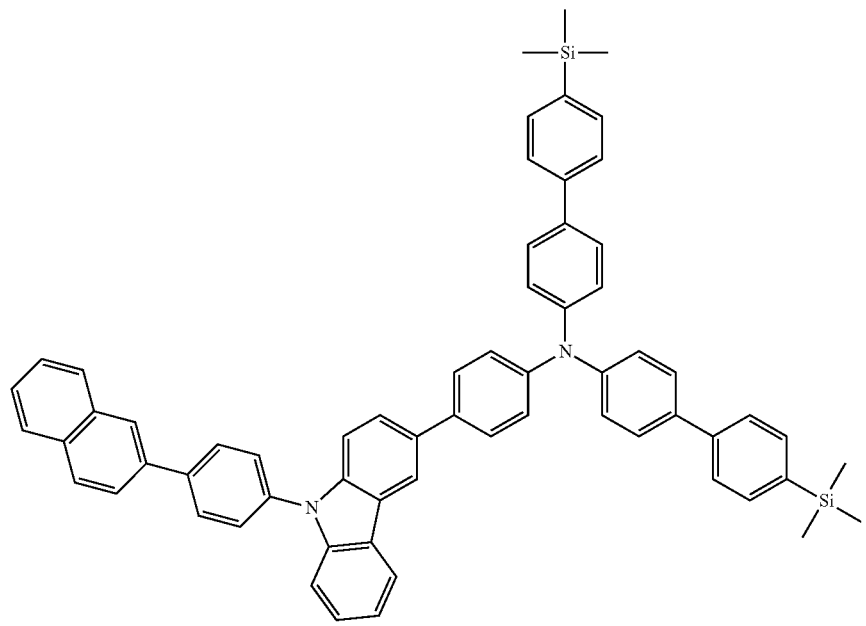
No. 45
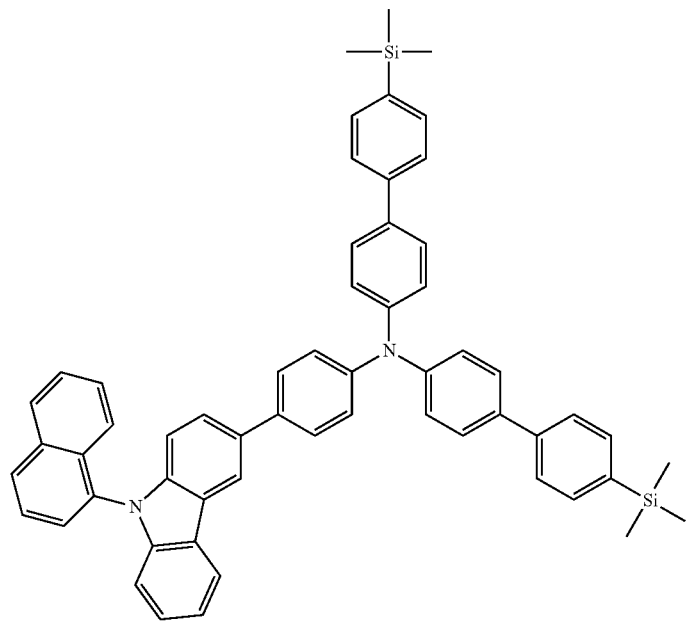
No. 46

[Formula 26]
No. 47
No. 48
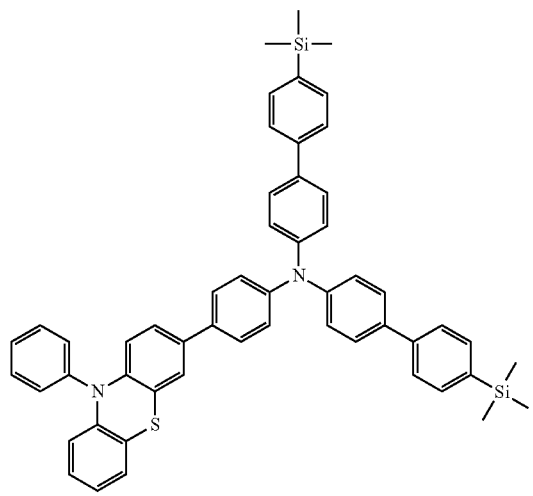
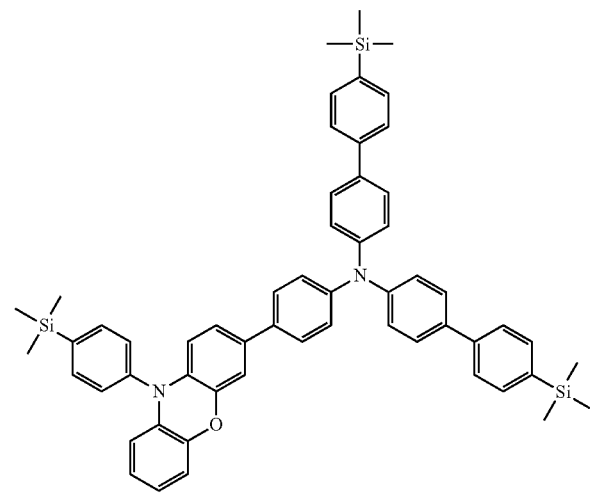
[Formula 27]
No. 49
No. 50
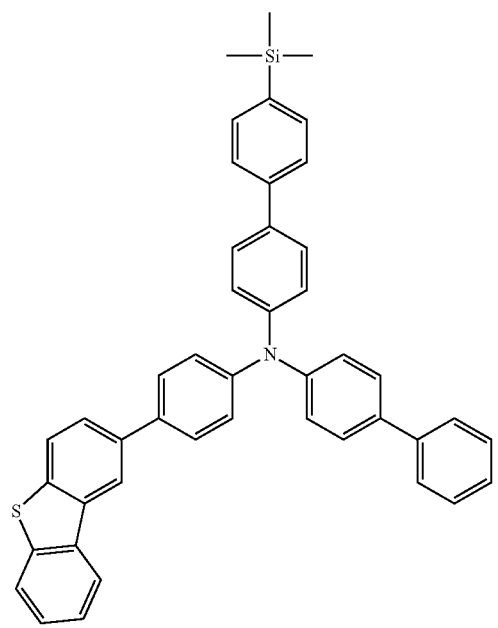
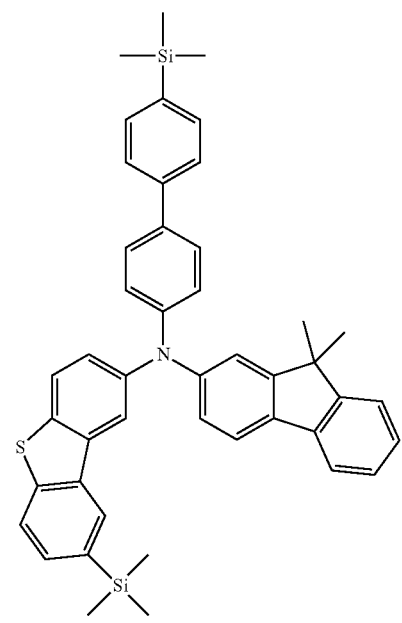

No. 51
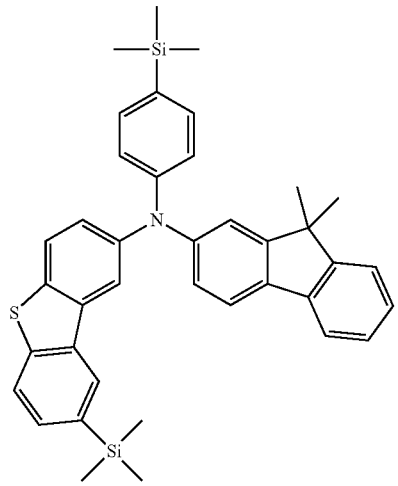
[Formula 28]
No. 52
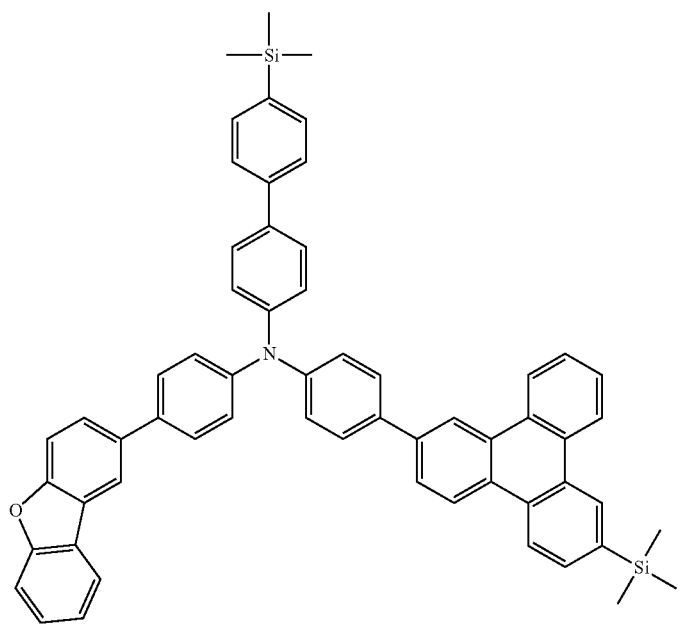

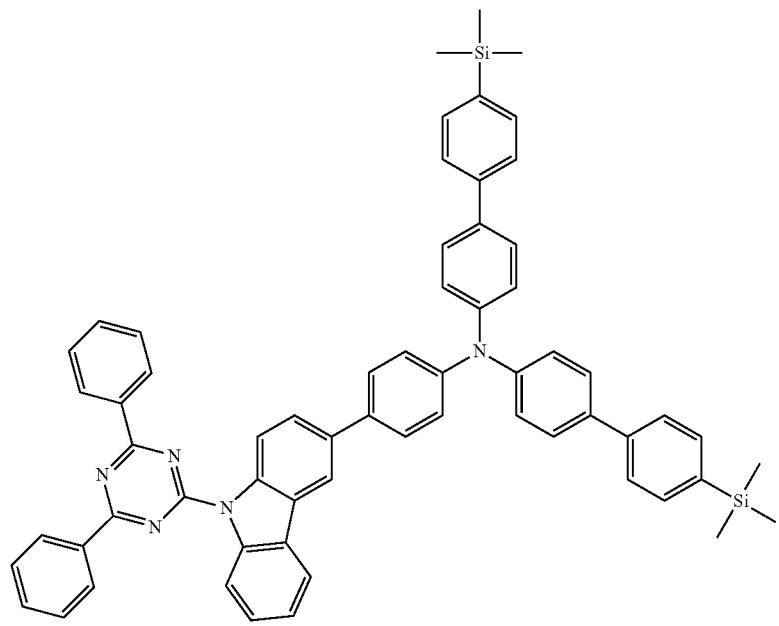
No. 53
[Formula 29]
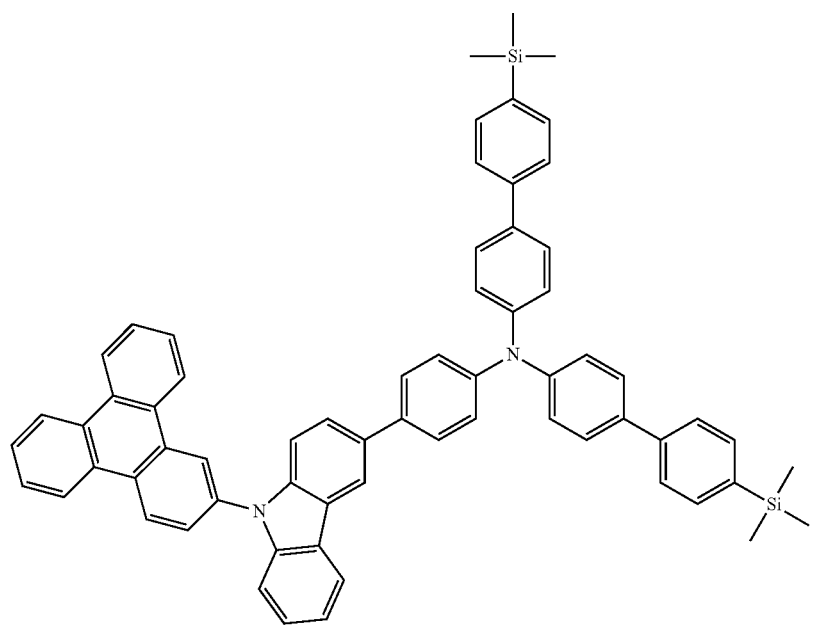
No. 54

No. 55
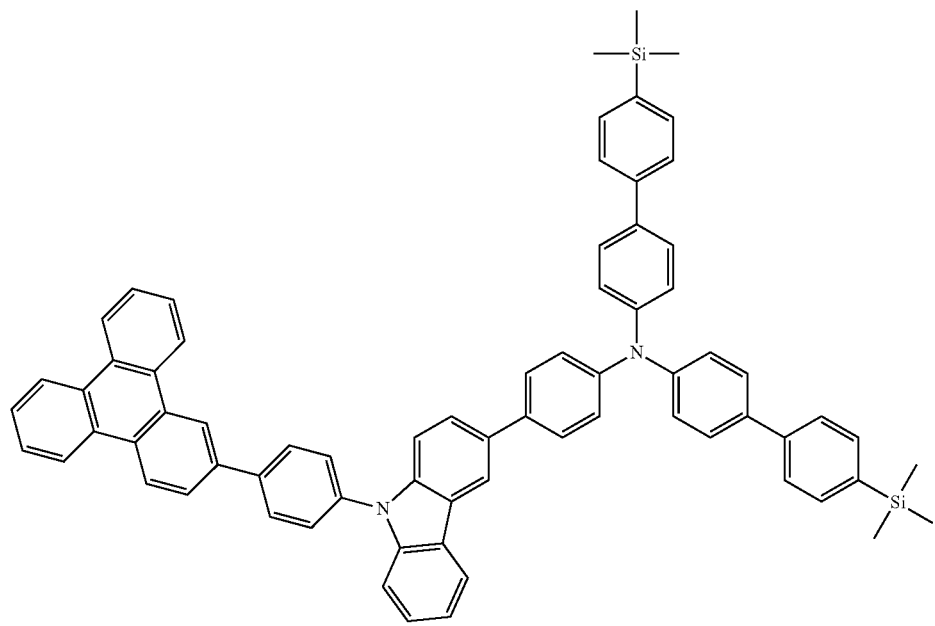
[Formula 30]
No. 56 No. 57
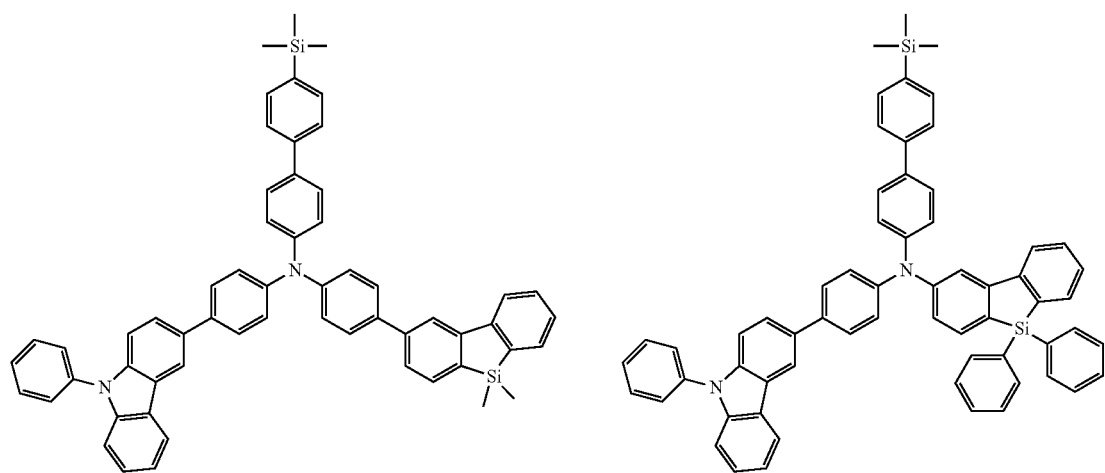

[Formula 31]
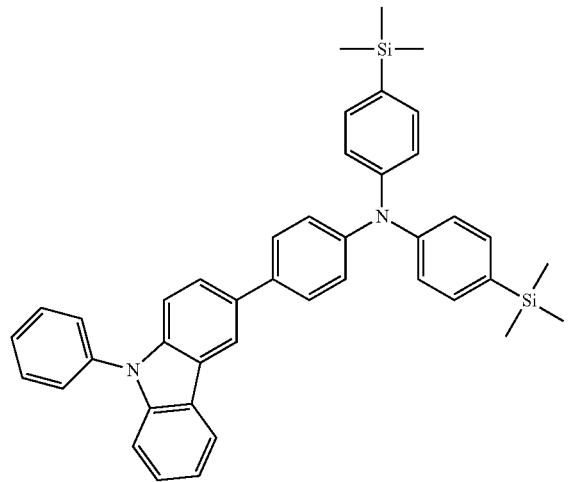
No. 58
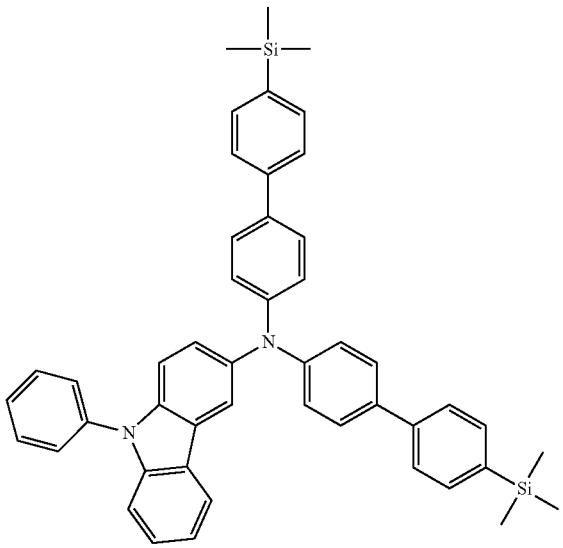
No. 59
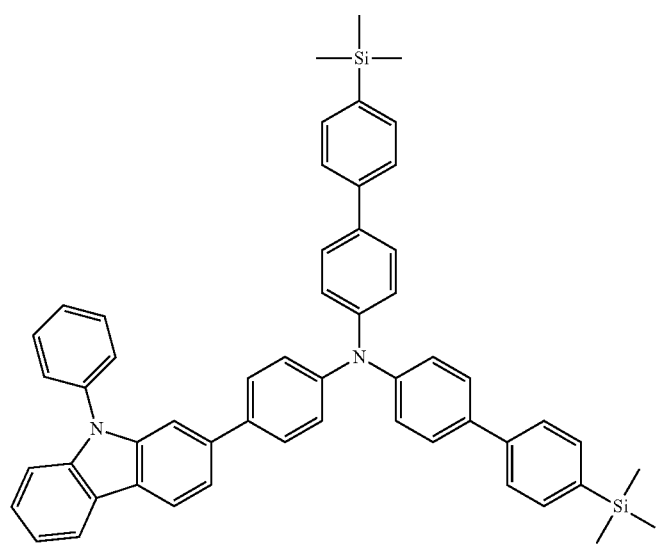
No. 60

[Formula 32]
No. 61
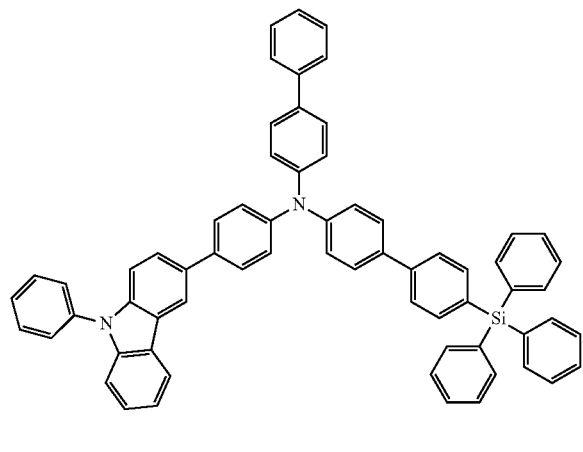
No. 62
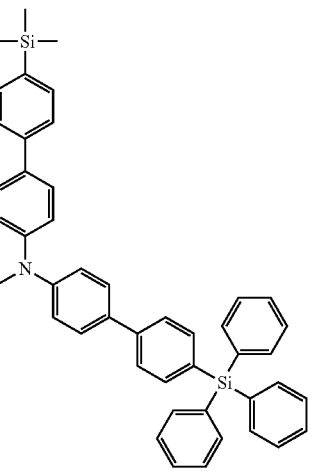
[Formula 33]
No. 63
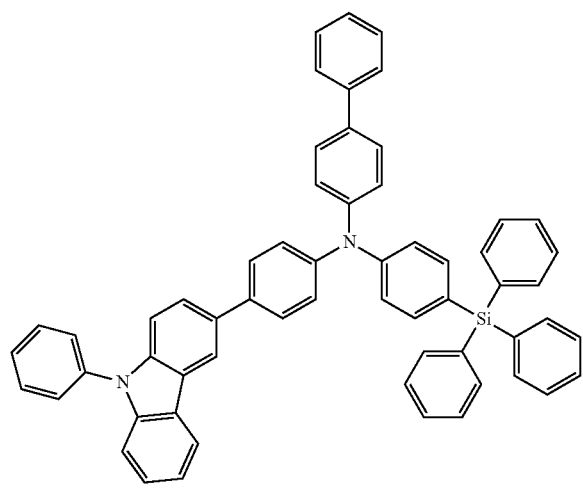
No. 64
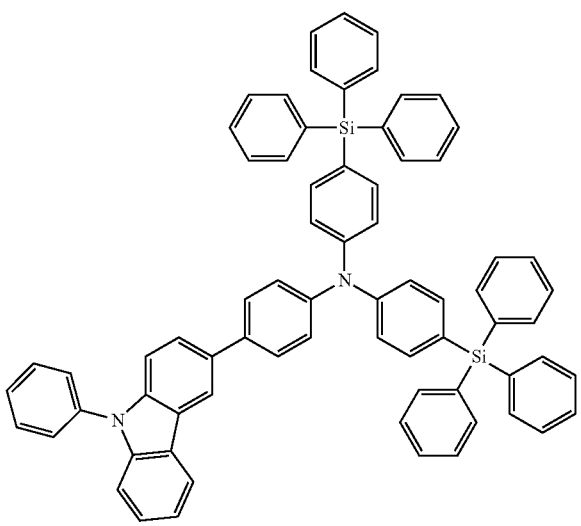
[Formula 34]
No. 65
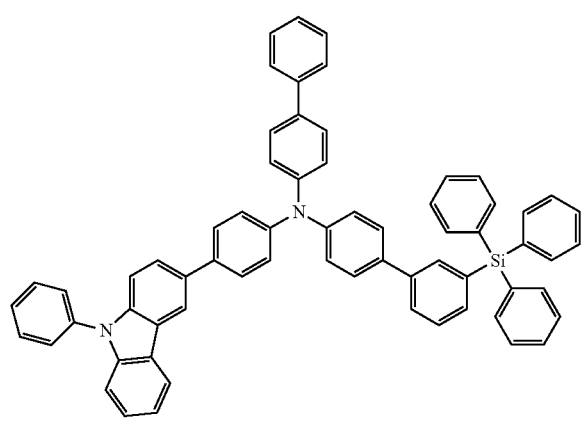
No. 66
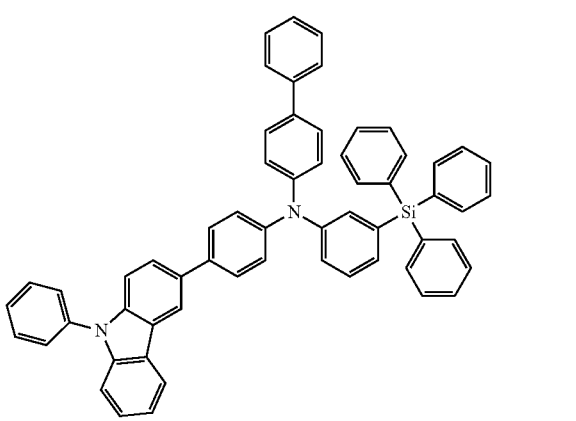

No. 67
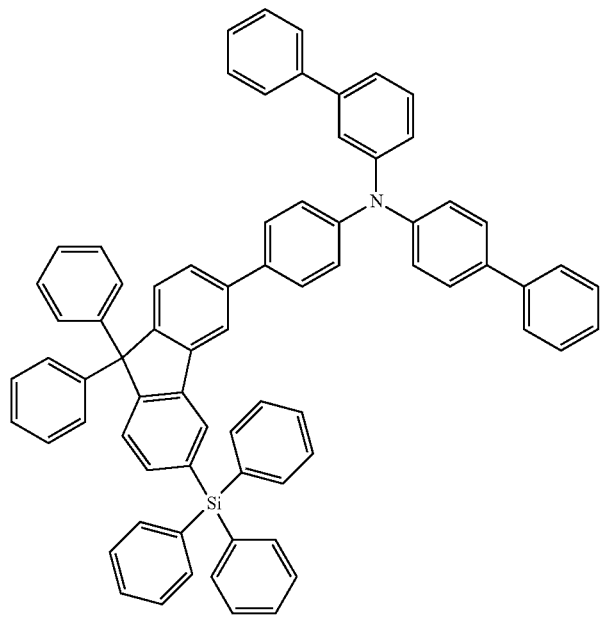
[Formula 35]
No. 68
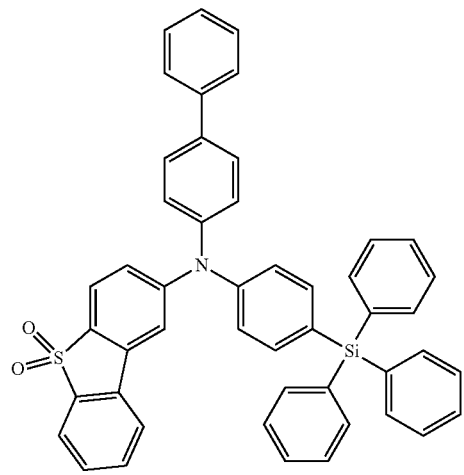
No. 69
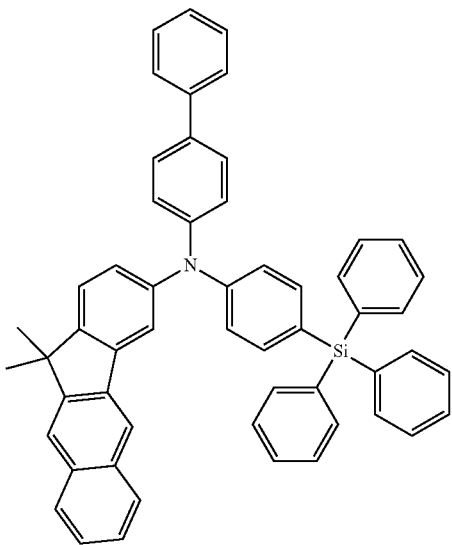

-continued
No. 70
No. 71
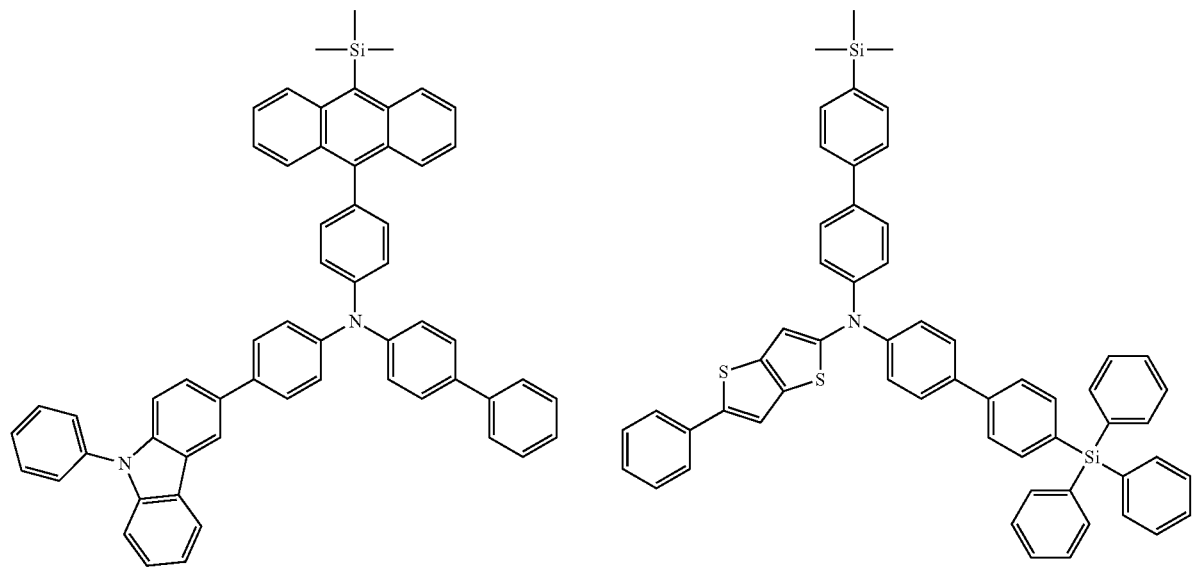
[Formula 36]
No. 72
No. 73
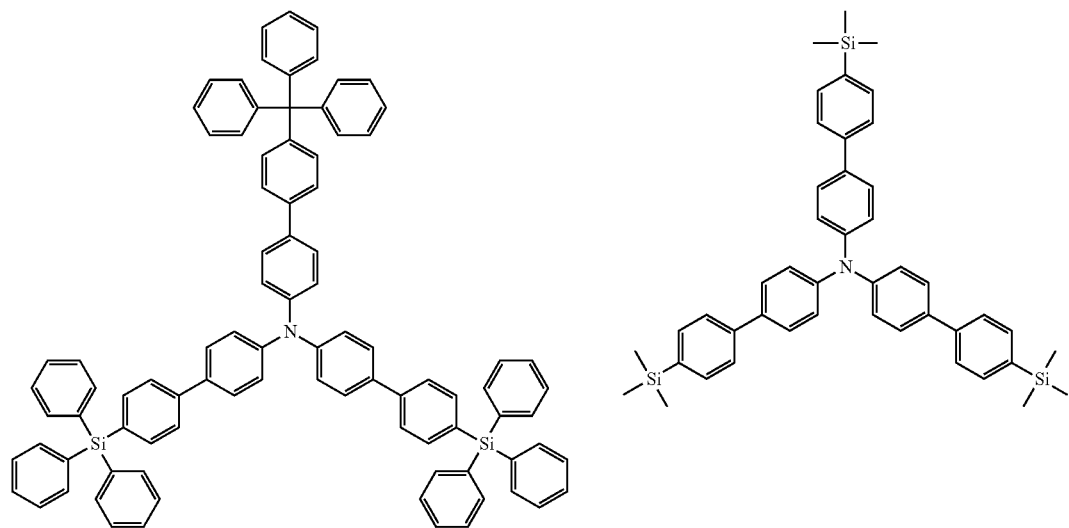

[Formula 37]
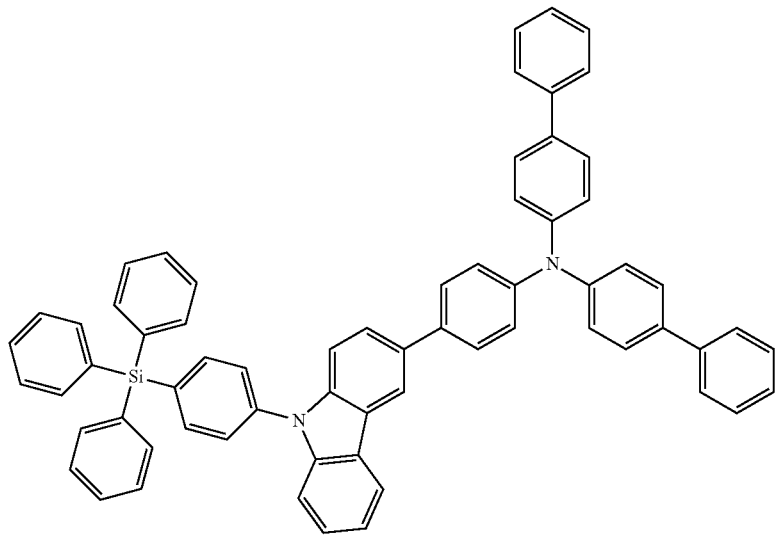
No. 74
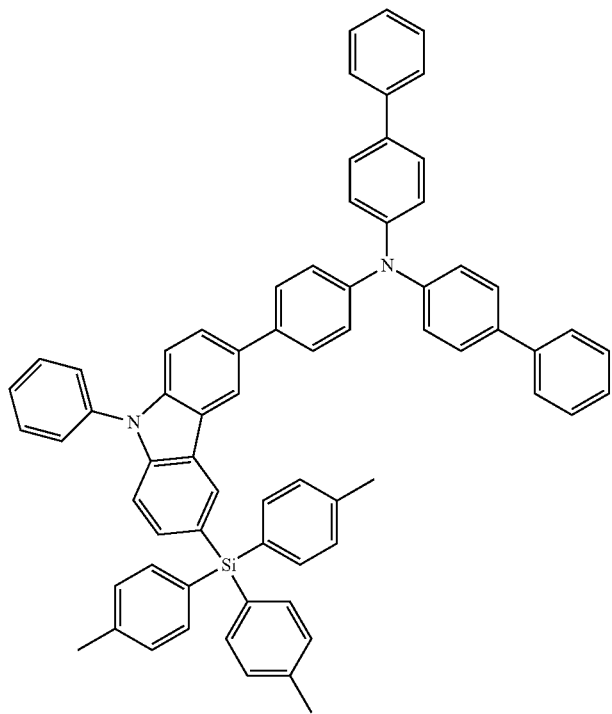
No. 75

[Formula 38]
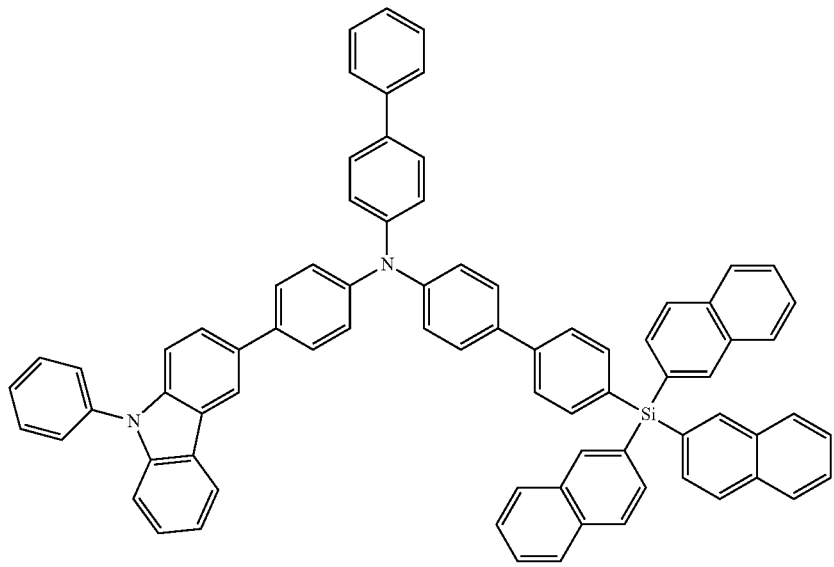
No. 76
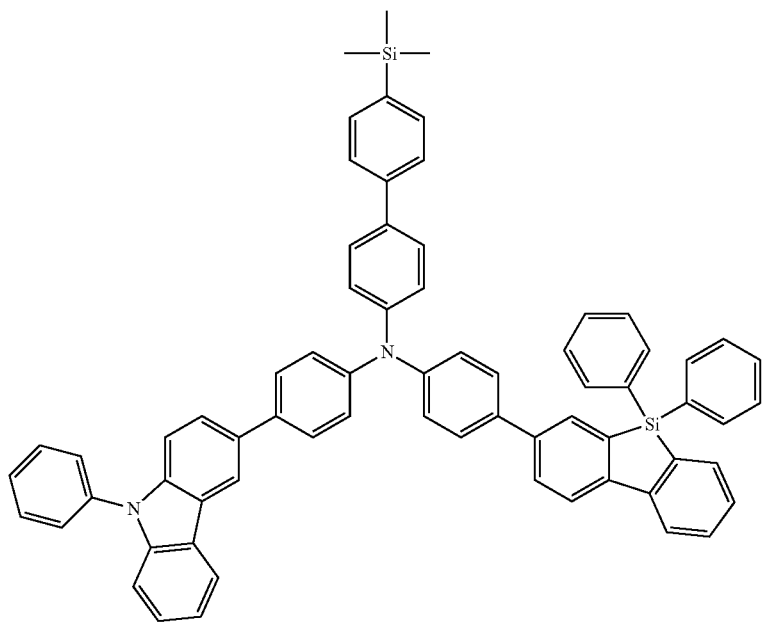
No. 77

[Formula 39]
No. 78
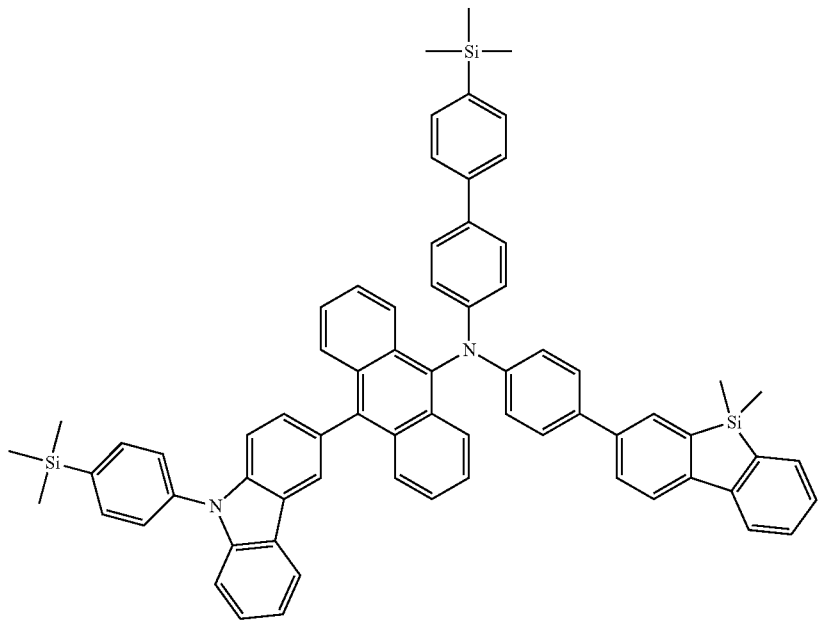
No. 79
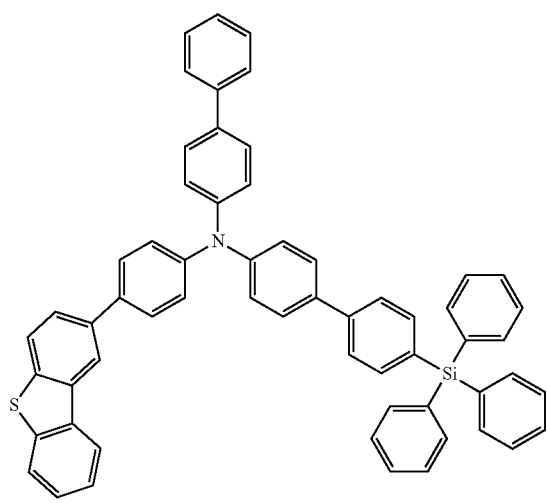
No. 80
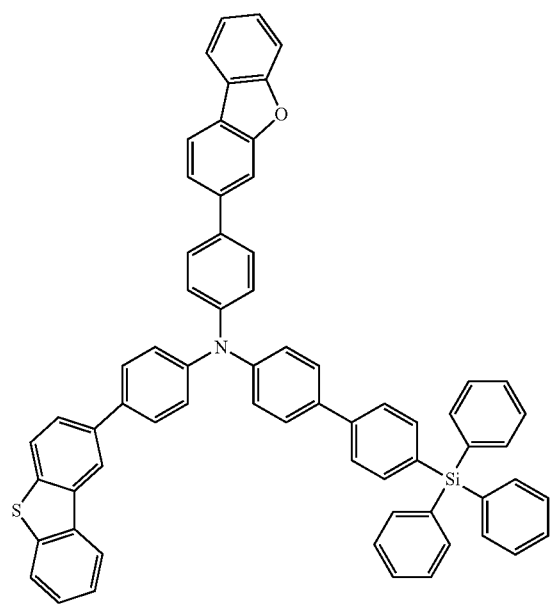

[Formula 40]
No. 81
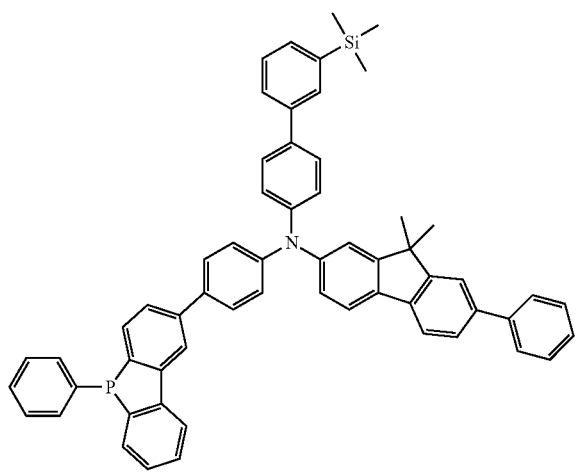
No. 82
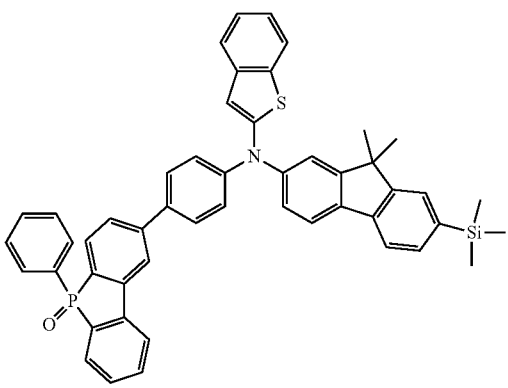
[Formula 41]
No. 83
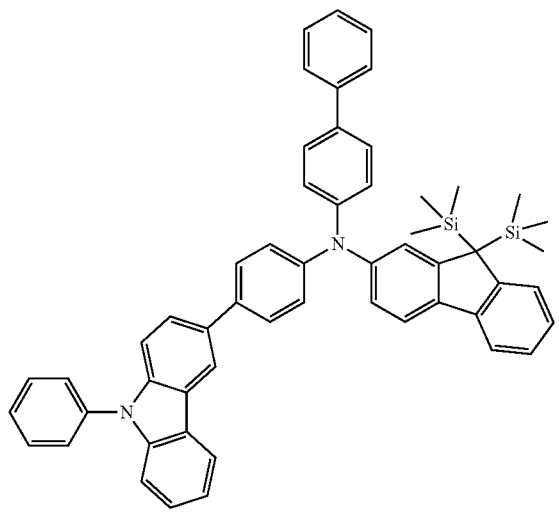
No. 84
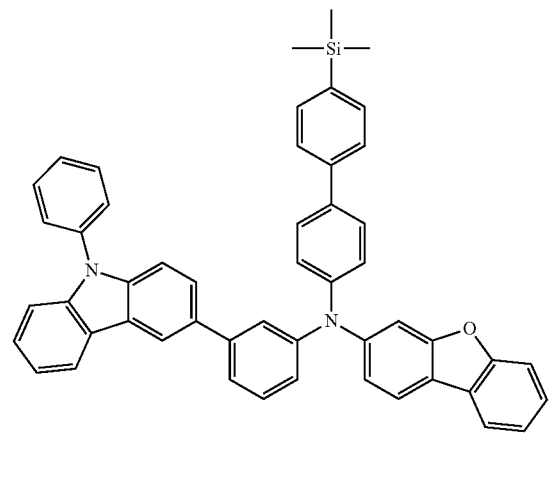
No. 85
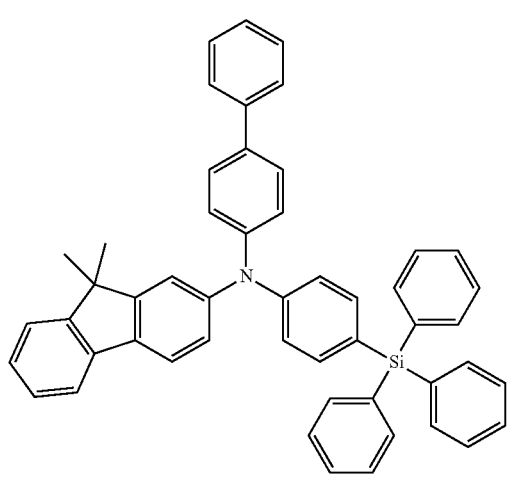
No. 86
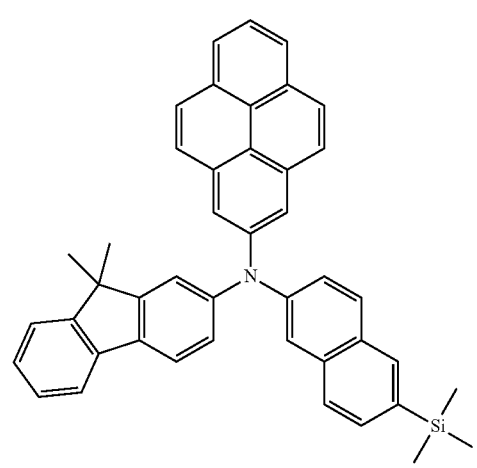

[Formula 42]
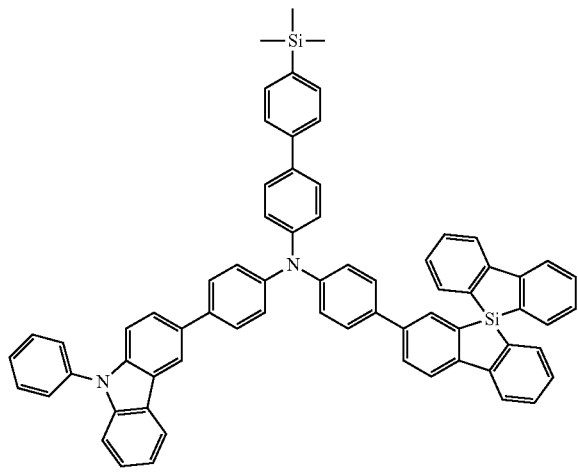
No. 87
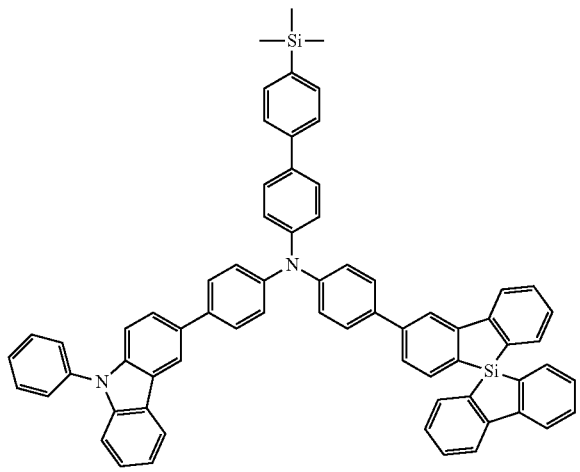
No. 88
[Formula 43]
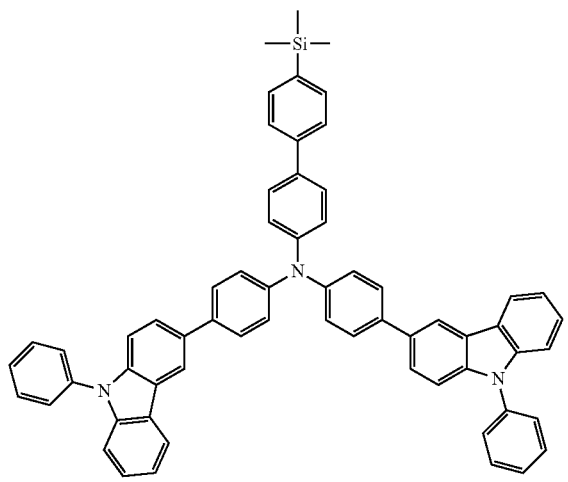
No. 89
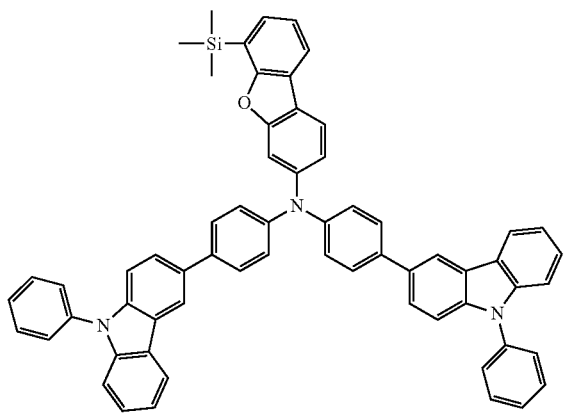
No. 90

[Formula 44]
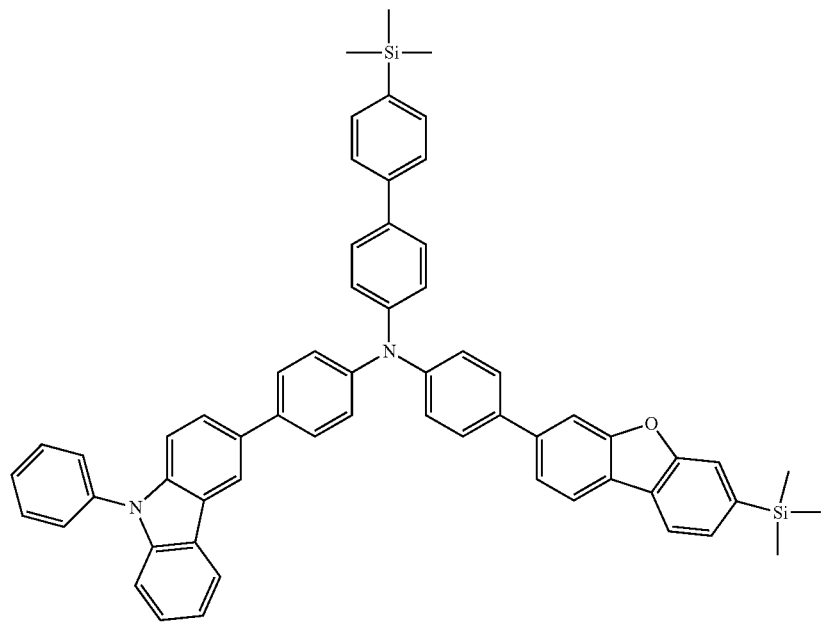
No. 91
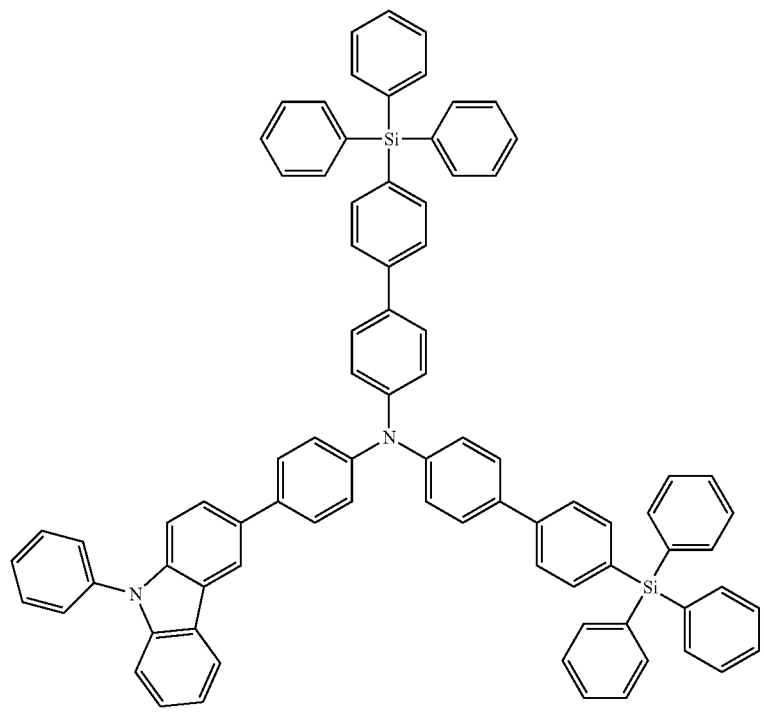
No. 92

[Formula 45]
No. 93
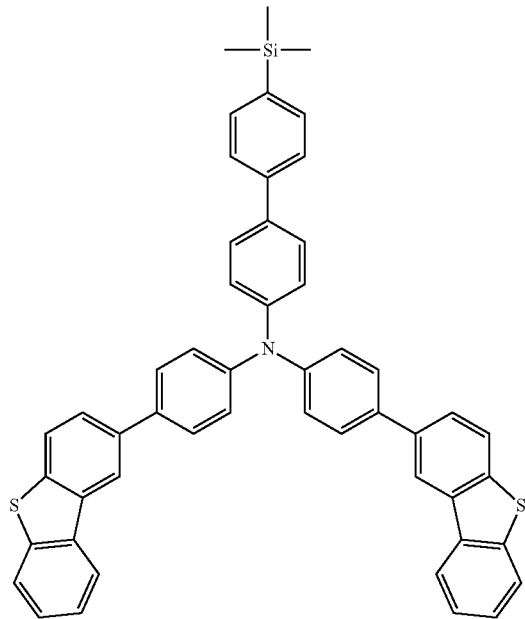
No. 94
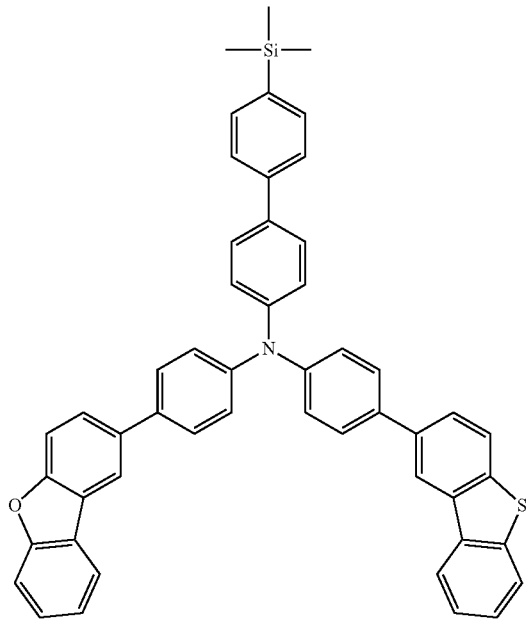
No. 95
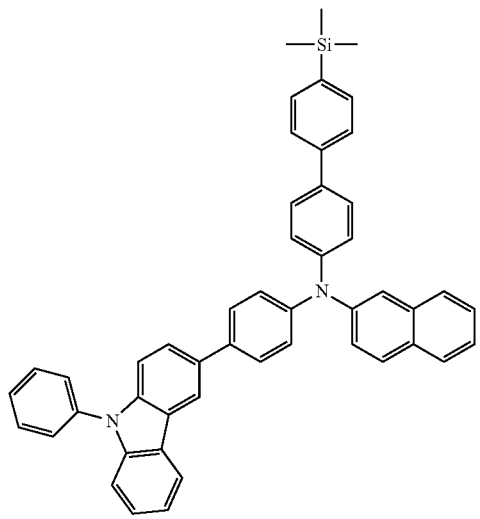
No. 96
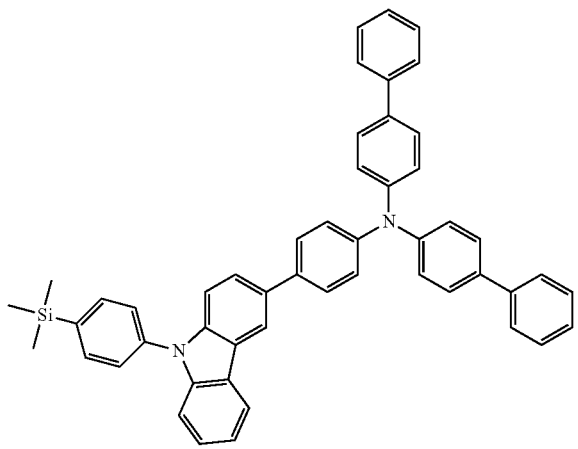

[Formula 46]
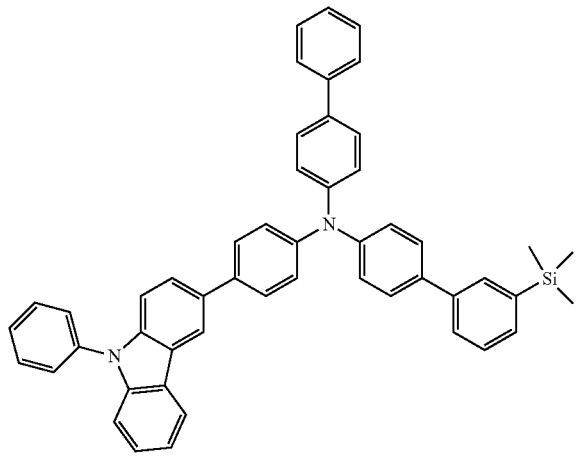
No. 97
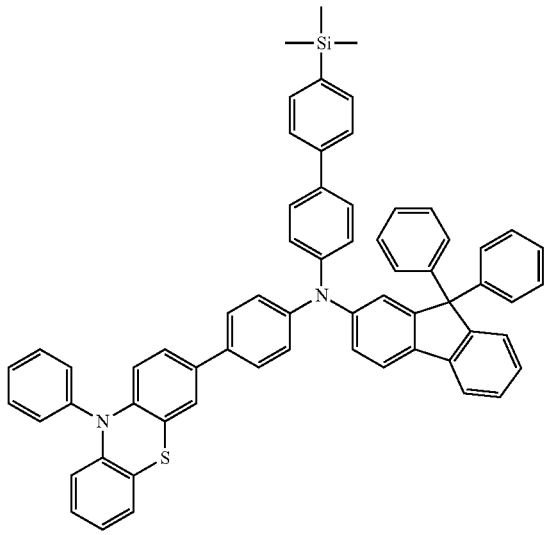
No. 98
[Formula 47]
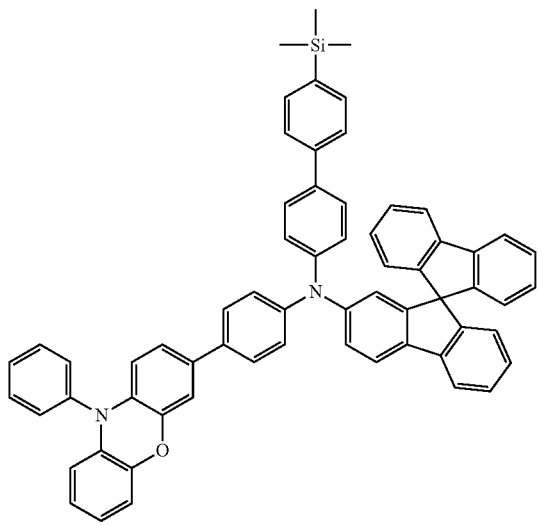
No. 99
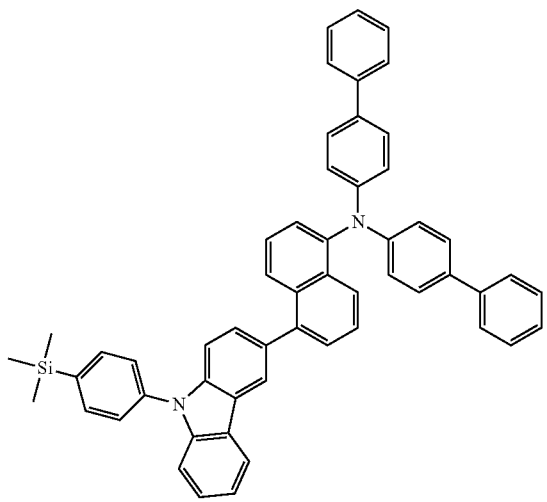
No. 100

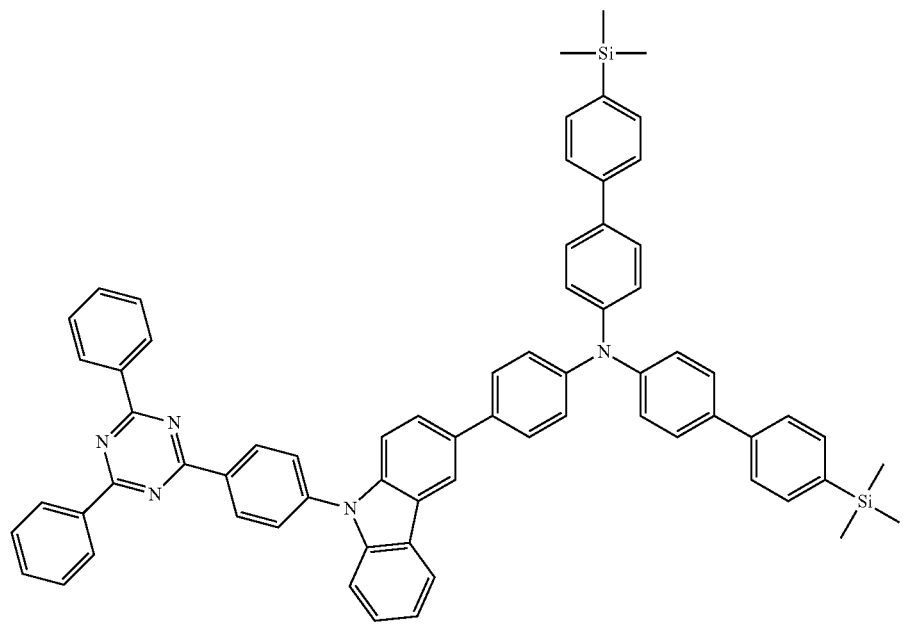
No. 101
[Formula 48]
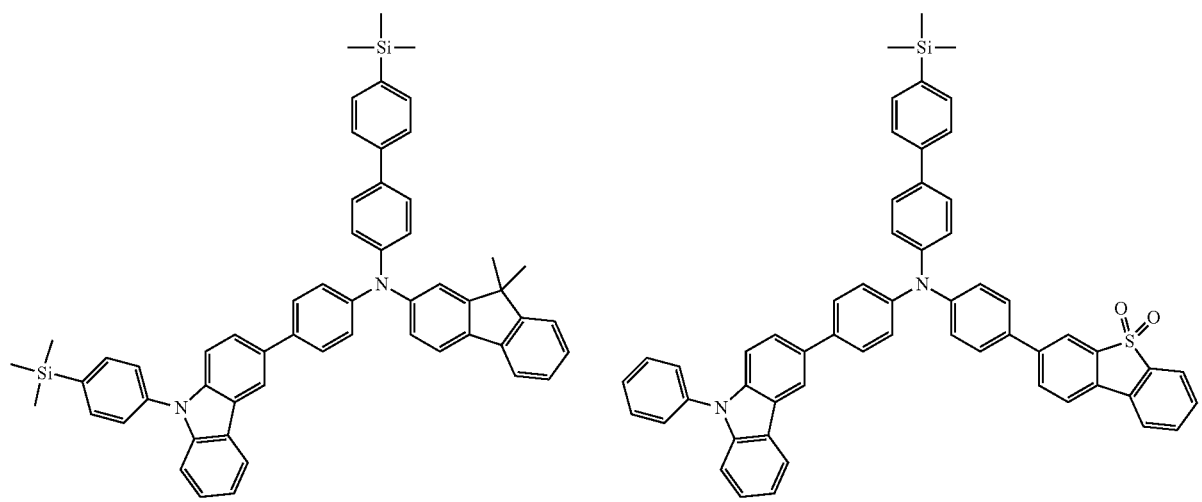
No. 102　　　　　　　　　　　　　　　No. 103

[Formula 49]
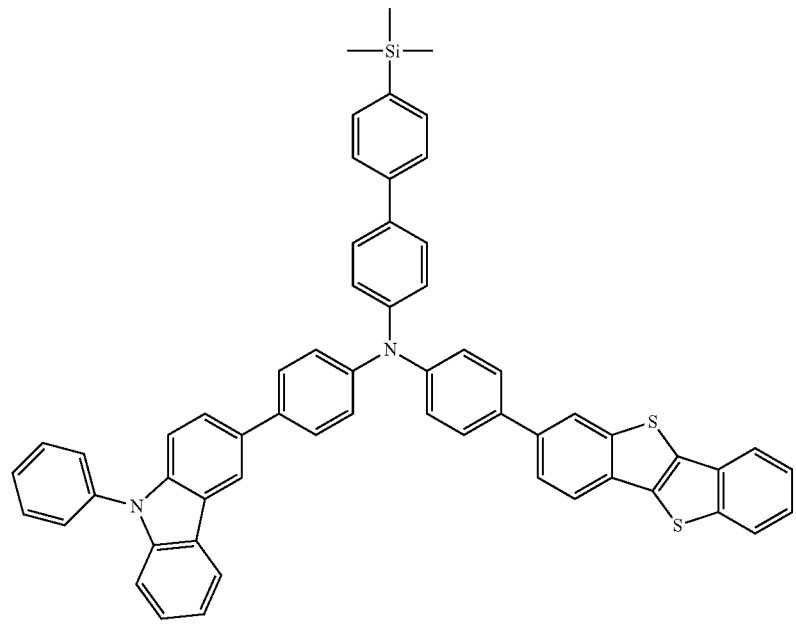
No. 104
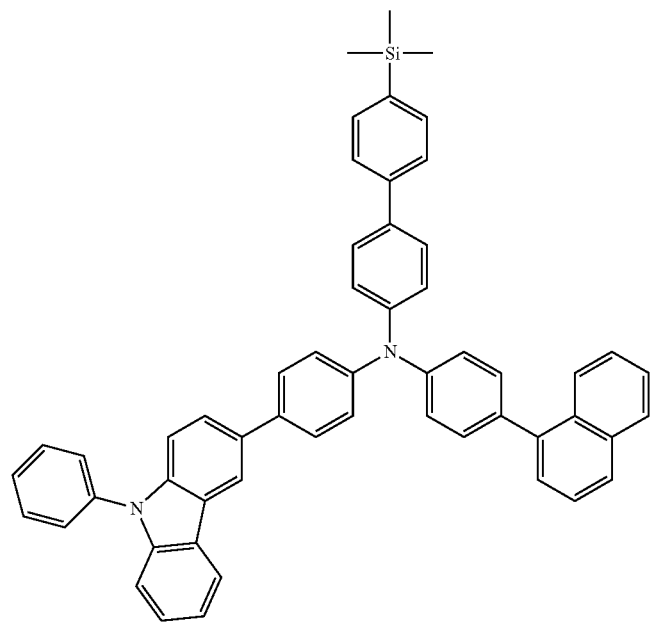
No. 105

[Formula 50]
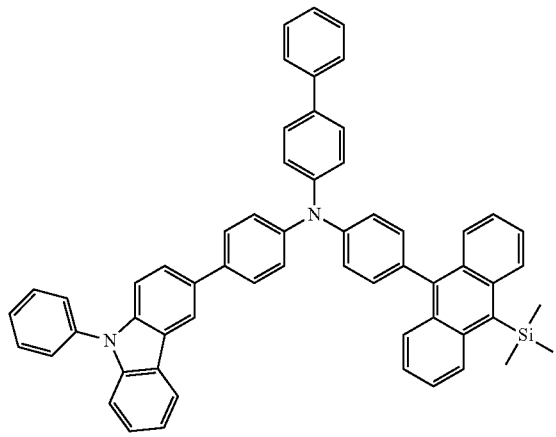
No. 106
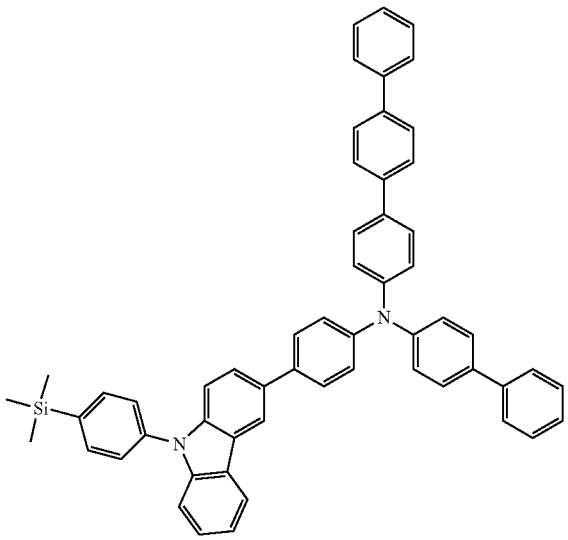
No. 107
[Formula 51]
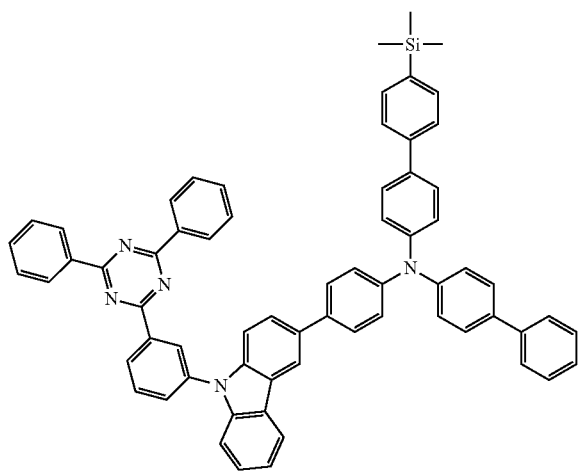
No. 108
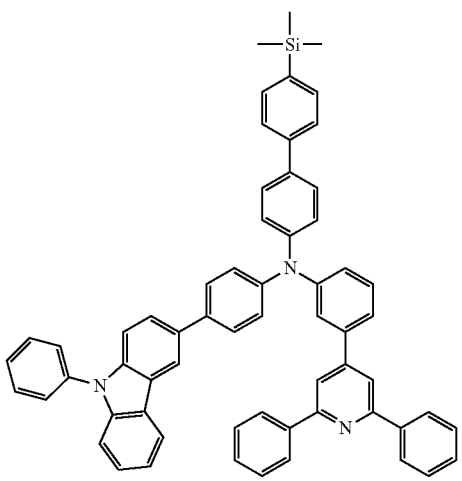
No. 109

[Formula 52]

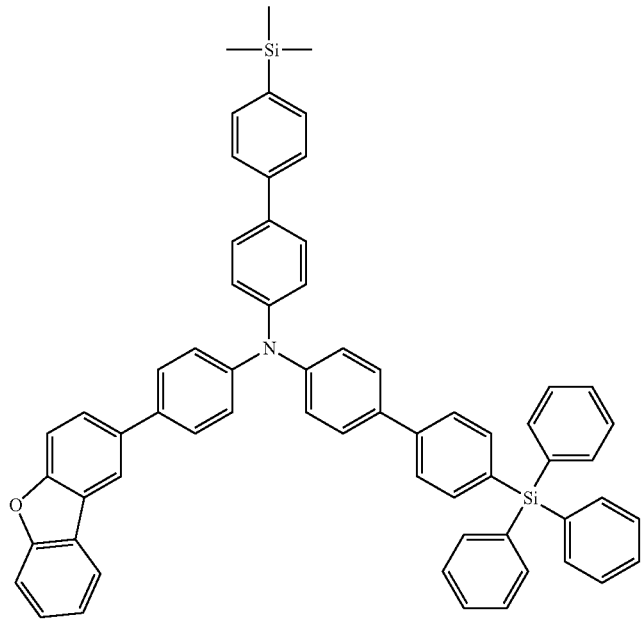

No. 110

The amine derivative having a silyl group according to an embodiment, represented by General Formula (1) may for example include the above Compounds 1, 2, 3, 4, 5, 6, 8, 15, 16, 17, 18, 19, 20, 21, 22, 23, 24, 25, 26, 27, 28, 29, 30, 31, 32, 37, 38, 40, 42, 44, 45, 46, 49, 50, 53, 54, 55, 56, 57, 59, 60, 61, 62, 63, 64, 74, 77, 79, 85, 87, 88, 89, 92, 96, 98, 101, 102, 107, and 110, and may for example include Compounds 1, 2, 3, 4, 6, 15, 16, 17, 18, 19, 20, 21, 22, 23, 24, 25, 26, 27, 28, 29, 30, 31, 32, 37, 40, 44, 45, 46, 49, 53, 54, 55, 56, 57, 59, 60, 61, 62, 63, 77, 85, 87, 88, 89, 96, 101, 107 and 110.

All the amine derivatives having a silyl group according to an embodiment may be used as the material for an organic electroluminescent device. In the amine derivative having a silyl group according to an embodiment, at least one or the substituted or unsubstituted aryl group or the substituted or unsubstituted heteroaryl group of $Ar^1$, $Ar^2$ and $Ar^a$, connected to the nitrogen atom (N) of the amine or the connecting group L is substituted with the substituted or unsubstituted silyl group exhibiting high electron tolerance. Thus, the amine derivative having a silyl group according to an embodiment is stable with respect to electrons and may be used as a material of an organic electroluminescent device, particularly as a material of a hole transport layer adjacent to an emission layer. By using the amine derivative having a silyl group according to an embodiment as the material of the hole transport layer, the electron tolerance of the hole transport layer may be improved, the deterioration of a hole transport material due to electrons intruded into the hole transport layer may be restrained, and the long life of the organic electroluminescent device may be realized.

In addition, the use of the amine derivative having a silyl group according to an embodiment is not limited to the hole transport material of the organic electroluminescent device. For example, the amine derivative may be used as a material of a hole injection layer. In the case that the amine derivative having a silyl group is used as the material of the hole injection layer, the deterioration of the hole injection layer due to electrons may be restrained, and the long life of the organic electroluminescent device may be realized as in the case of using the amine derivative as the material of the hole transport layer.

[Organic Electroluminescent Device]

An organic electroluminescent device may have, for example, the structure shown in FIG. 1; however, embodiments are not limited thereto.

An organic electroluminescent device 100 shown in FIG. 1 may include, in the schematic cross-sectional view according to an embodiment using the amine derivative according to an embodiment as a material for an organic electroluminescent device, a glass substrate 102, an anode 104 disposed on the glass substrate 102, a hole injection layer 106 disposed on the anode 104, a hole transport layer 108 disposed on the hole injection layer 106, an emission layer 110 disposed on the hole transport layer 108, an electron transport layer 112 disposed on the emission layer 110 and a cathode 114 disposed on the electron transport layer 112. Here, the electron transport layer 112 may also function as an electron injection layer.

The anode 104 may be formed using indium tin oxide (ITO) or indium zinc oxide (IZO).

The hole injection layer 106 may include 4,4',4''-tris(N-1-naphthyl-N-phenylamino)triphenylamine (1-TNATA) or 4,4',4''-tris(N-(2-naphthyl)-N-phenylamino)-triphenylamine (2-TNATA), 4,4-bis(N,N-di(3-tolyl)amino)-3,3-dimethylbiphenyl (HMTPD), etc.

[Formula 53]

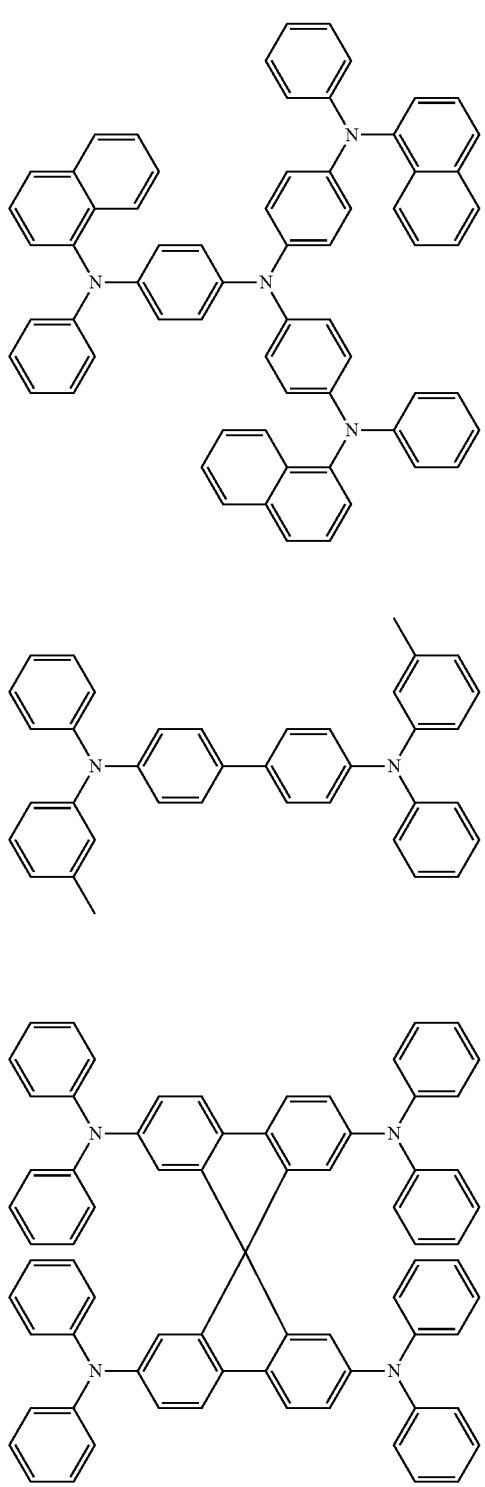

The hole transport layer 108 may be formed using the amine derivative having a silyl group according to an embodiment, represented by General Formula (1).

The emission layer 110 may include, for example, the following compounds as a host material.

[Formula 54]

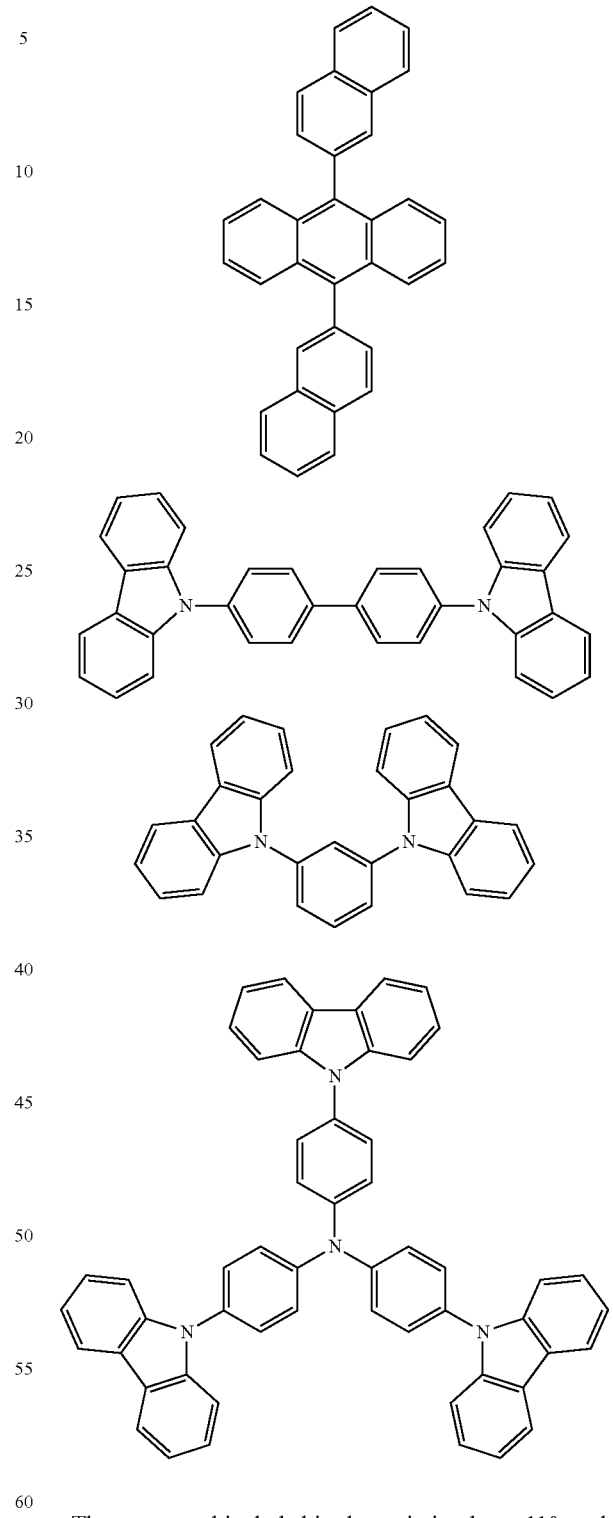

The compound included in the emission layer 110 as the host material is not limited to the above-described compounds; however, general materials may be used as the host material.

In addition, in the emission layer 110, for example, the following compounds may be included as a dopant.

[Formula 55]

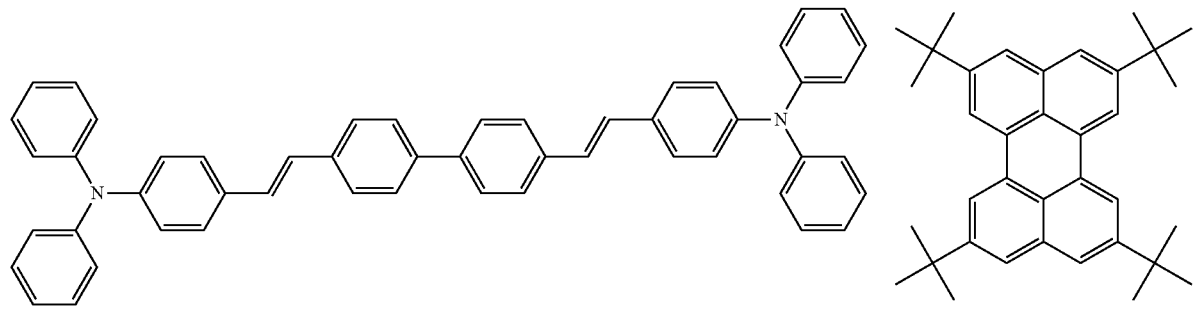

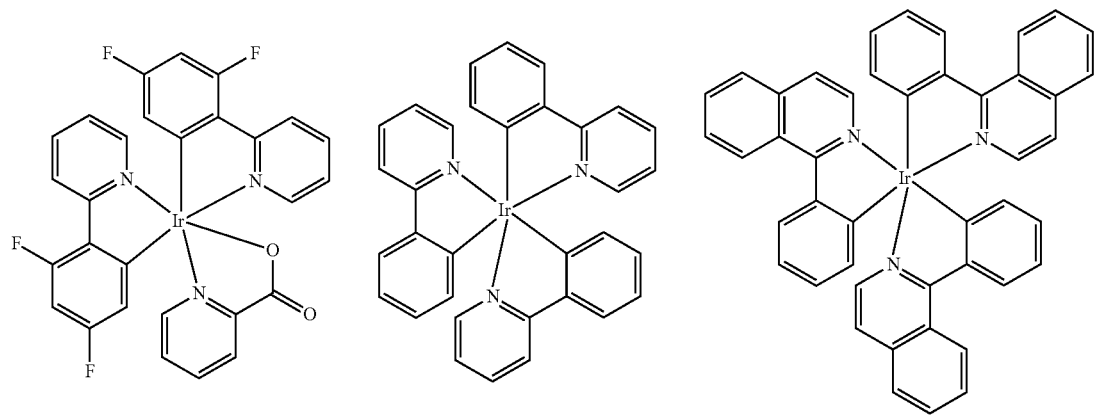

The compound doped in the emission layer 110 as the dopant is not limited to the above-described compounds; however, general materials may be used as the dopant according to a desired color range. The dopant may be doped in the material constituting the emission layer 110 by about 0.1-50%.

The electron transport layer 112 may include, for example, tris(8-hydroxyquinolinato)aluminum (Alq$_3$), etc. In addition, the following compounds may be included.

[Formula 56]

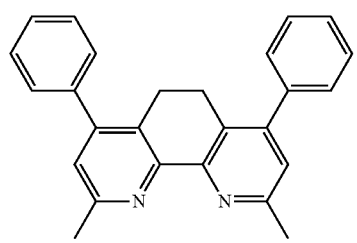

-continued

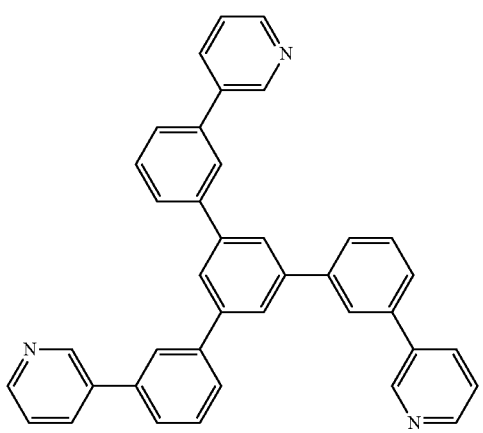

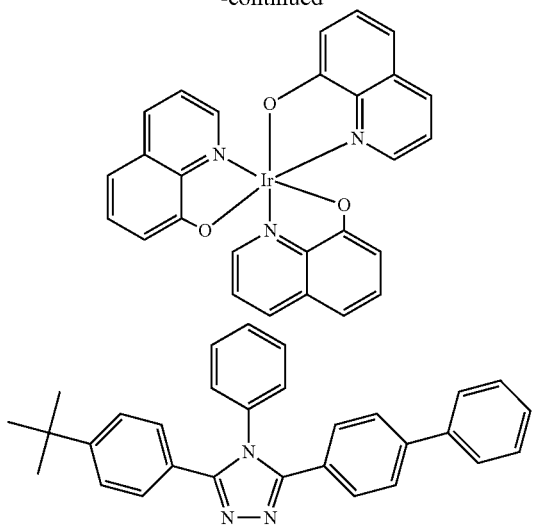

The cathode 114 may be formed using a metal such as Al, Ag, Ca, etc. or a transparent material such as ITO, IZO, etc.

In the organic electroluminescent device 100 shown in FIG. 1, a base is omitted. However, the organic electroluminescent device 100 may include an electron injection layer between the cathode 114 and the electron transport layer 112. The electron injection layer may include, for example, lithium fluoride (LiF), lithium 8-quinolinato, etc.

As described above, the amine derivative having a silyl group according to an embodiment, represented by General Formula (1) may be used as the material of the hole transport layer of the organic electroluminescent device. However, the use of the amine derivative having a silyl group according to an embodiment is not limited to the hole transport material of the organic electroluminescent device; for example it may be included in the hole injection layer as a hole injection material.

The long life of the organic electroluminescent device may be realized by using the amine derivative according to an embodiment as at least one material of the hole injection layer and the hole transport layer in the hole injection layer 106 and the hole transport layer 108 constituting the organic electroluminescent device.

As described above, the amine derivative having a silyl group according to an embodiment has electron tolerance, and may be used as the hole transport material or the hole injection material of the organic electroluminescent device; however, embodiments are not limited thereto. For example, the amine derivative may be used as a host material in an emission layer.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Example I

With respect to the amine derivative having a silyl group according to an embodiment, represented by General Formula (1), examples of synthesizing Compounds 1, 3, 61 and 63 will be explained hereinafter. The following synthetic methods are only examples, and embodiments are not limited thereto.

(Synthesis of Compound 1)

The following chemical reaction is a synthetic process of Compound 1, which is an amine derivative having a silyl group according to an embodiment, represented by General Formula (1).

[Formula 57]

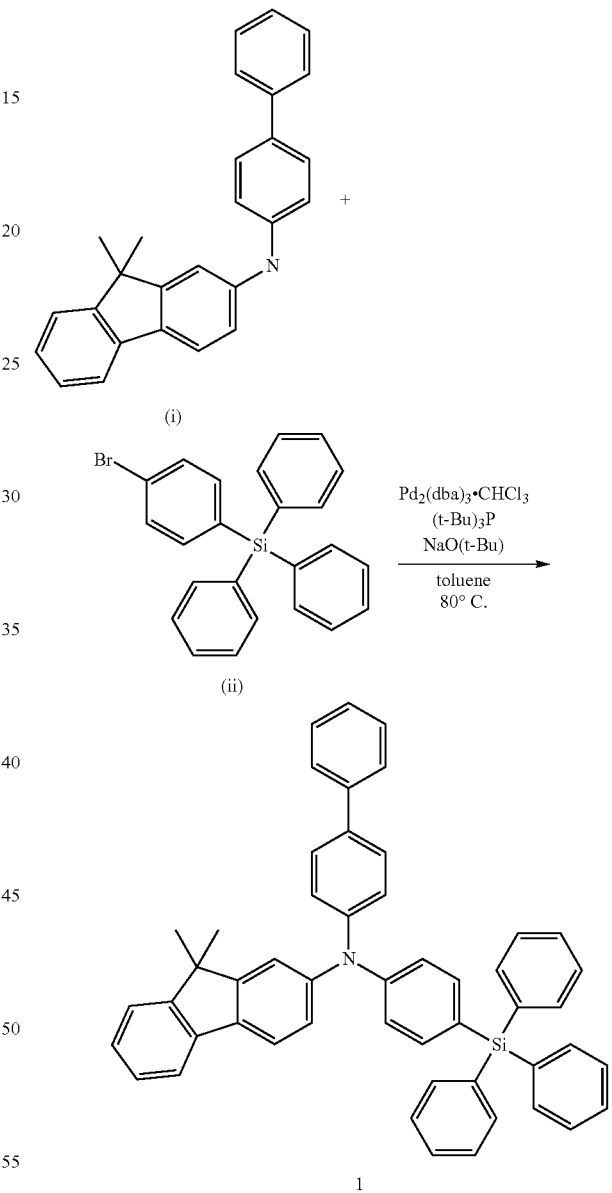

The above Compound 1 was synthesized by the following process.

Compound (i) (1.57 g, 4.33 mmol), Compound (ii) (1.50 g, 3.61 mmol), Pd$_2$(dba)$_3$.CHCl$_3$ (0.37 g, 0.36 mmol) and toluene (36 mL) were added to a reaction vessel. Then, tri(t-butyl)phosphine (0.93 mL, 1.44 mmol, 1.56 M) and sodium t-butoxide (1.04 g, 10.8 mmol) were added thereto, and the inner part of the vessel was purged with a nitrogen gas, followed by stirring at about 80° C. for about 4 hours. After cooling in the air, water was added to the reaction mixture, and an organic layer was extracted. The organic layer thus obtained was dried with anhydrous magnesium sulfate and filtered. The filtrate was concentrated by a rotary evaporator. The crude product thus obtained was separated by silica gel column chromatography (developing solvent: dichloromethane/hexane), and the solid thus obtained was recrystallized using toluene/hexane to produce 2.26 g of a target product, Compound 1, as a white powder solid with the yield of 90% (FAB-MS: C51H41NSi, measured value 695).

(Synthesis of Compound 3)

The following chemical reaction is a synthetic process of Compound 3, which is an amine derivative having a silyl group according to an embodiment.

[Formula 58]

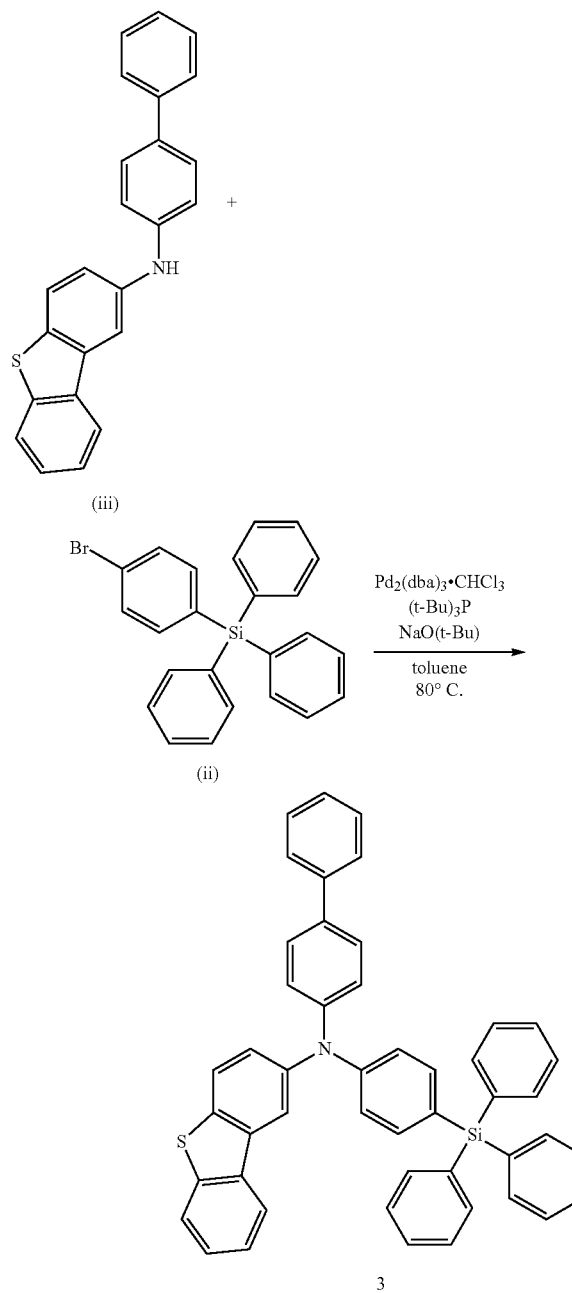

Compound 3 according to an embodiment was synthesized by the following process.

Compound (iii) (1.52 g, 4.33 mmol), Compound (ii) (1.50 g, 3.61 mmol), Pd$_2$(dba)$_3$·CHCl$_3$ (0.37 g, 0.36 mmol) and toluene (36 mL) were added to a reaction vessel. Then, tri(t-butyl)phosphine (0.93 mL, 1.44 mmol, 1.56 M) and sodium t-butoxide (1.04 g, 10.8 mmol) were added thereto, and the inner part of the vessel was purged with a nitrogen gas, followed by stirring at about 80° C. for about 4 hours. After cooling in the air, water was added to the reaction mixture, and an organic layer was extracted. The organic layer thus obtained was dried with anhydrous magnesium sulfate and filtered. The filtrate was concentrated by a rotary evaporator. The crude product thus obtained was separated by silica gel column chromatography (developing solvent: dichloromethane/hexane), and the solid thus obtained was recrystallized using toluene/hexane to produce 1.00 g of a target product, Compound 3, as a white powder solid with the yield of 40% (FAB-MS: C48H35NSSi, measured value 685).

(Synthesis of Compound 61)

The following chemical reaction is a synthetic process of Compound 61, which is an amine derivative having a silyl group according to an embodiment.

[Formula 59]

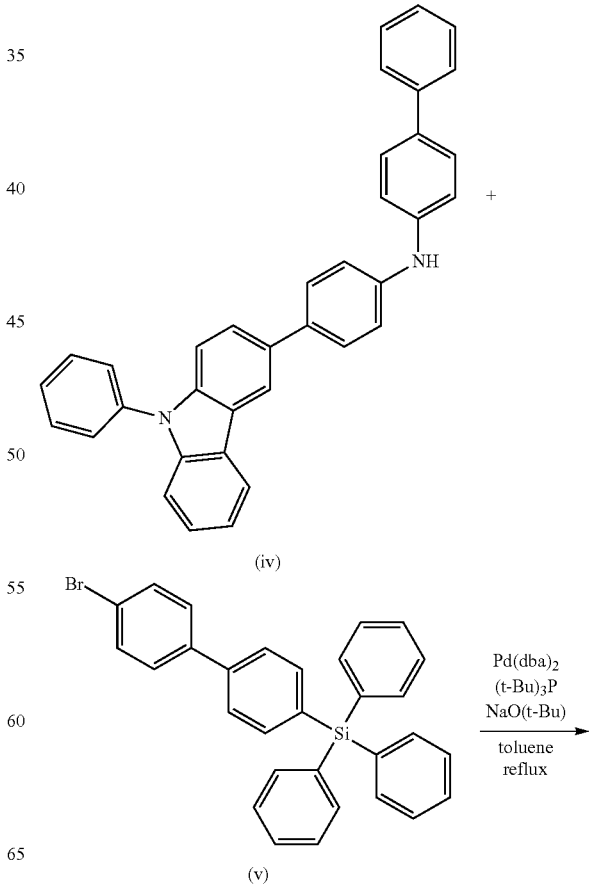

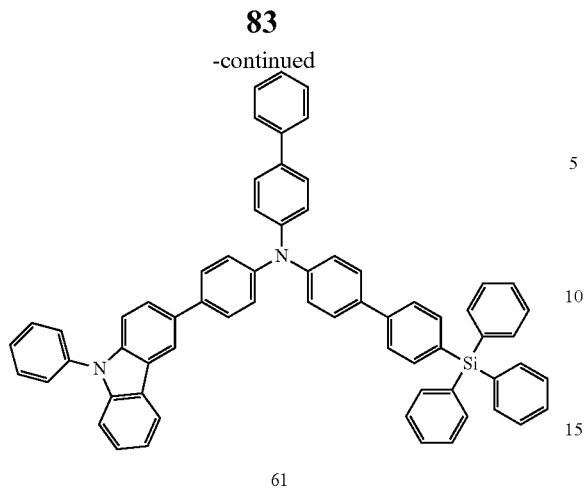

61

Compound 61 according to an embodiment was synthesized by the following process.

Compound (iv) (0.70 g, 1.44 mmol), Compound (v) (0.71 g, 1.44 mmol), Pd(dba)₂ (0.04 g, 0.07 mmol) and toluene (30 mL) were added to a reaction vessel. Then, tri(t-butyl) phosphine (0.14 mL, 0.28 mmol, 2.00 M) and sodium t-butoxide (0.21 g, 2.16 mmol) were added thereto, and the inner part of the vessel was purged with a nitrogen gas, followed by refluxing for about 6 hours. After cooling in the air, water was added to the reaction mixture, and an organic layer was extracted. The organic layer thus obtained was dried with anhydrous magnesium sulfate and filtered. The filtrate was concentrated by a rotary evaporator. The crude product thus obtained was separated by silica gel column chromatography (developing solvent: toluene/hexane), and the solid thus obtained was recrystallized using dichloromethane/hexane to produce 1.15 g of a target product, Compound 61, as a white powder solid with the yield of 89% (FAB-MS: C66H48N2Si, measured value 897).

(Synthesis of Compound 63)

The following chemical reaction is a synthetic process of Compound 63, which is an amine derivative having a silyl group according to an embodiment.

[Formula 60]

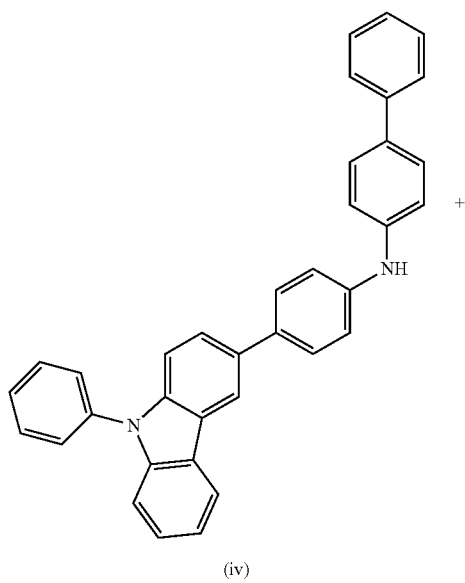

(iv)

+

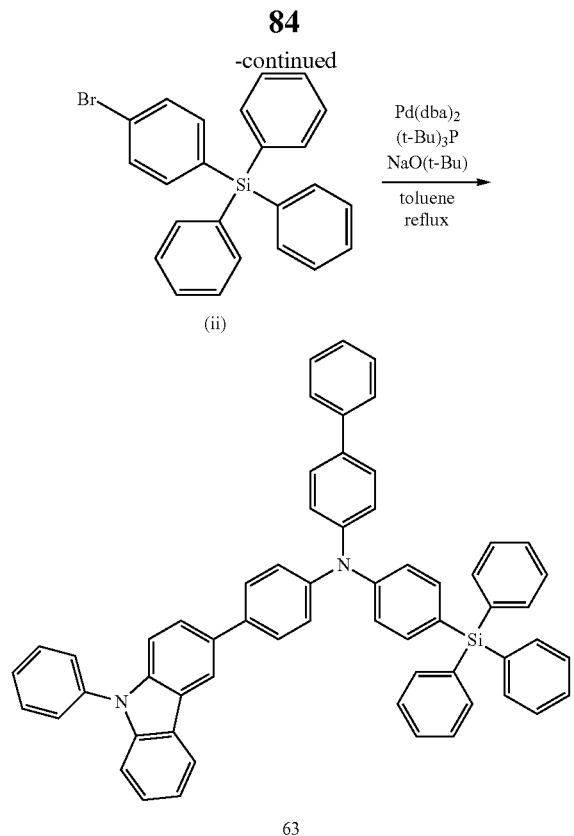

(ii)

63

Compound 63 according to an embodiment was synthesized by the following process.

Compound (iv) (1.00 g, 2.06 mmol), Compound (ii) (0.85 g, 2.06 mmol), Pd(dba)₂ (0.06 g, 0.10 mmol) and toluene (10 mL) were added to a reaction vessel. Then, tri(t-butyl) phosphine (0.03 mL, 0.06 mmol, 2.00 M) and sodium t-butoxide (0.30 g, 3.08 mmol) were added thereto, and the inner part of the vessel was purged with a nitrogen gas, followed by stirring while refluxing for about 4 hours. After cooling in the air, water was added to the reaction mixture, and an organic layer was extracted. The organic layer thus obtained was dried with anhydrous magnesium sulfate and filtered. The filtrate was concentrated by a rotary evaporator. The crude product thus obtained was separated by silica gel column chromatography (developing solvent: toluene/hexane), and the solid thus obtained was recrystallized using dichloromethane/hexane to produce 1.59 g of a target product, Compound 63, as a white powder solid with the yield of 94% (FAB-MS: C60H44N2Si, measured value 821).

Hereinafter, Example 1 of the organic electroluminescent device using the above Compound 1 in a hole transport layer as a material of an organic electroluminescent device according to an embodiment will be explained.

The manufacture of the organic electroluminescent device according to Example 1 according to an embodiment was conducted by a vacuum deposition and the following procedure. First, with respect to an ITO-glass substrate patterned and washed in advance, surface treatment using ozone was conducted. In addition, the layer thickness of an ITO layer was about 150 nm. Immediately after the ozone treatment, a layer was formed using 2-TNATA as a hole injection material (thickness of about 60 nm) on the ITO layer.

Then, a layer was formed using Compound 1 according to an embodiment as a hole transport material (about 30 nm), and a layer of 9,10-di(2-naphthyl)anthracene (ADN) doped with 2,5,8,11-tetra-t-butylperylene (TBP) in a ratio of about 3% was formed by a co-deposition (about 25 nm).

Figure 2:
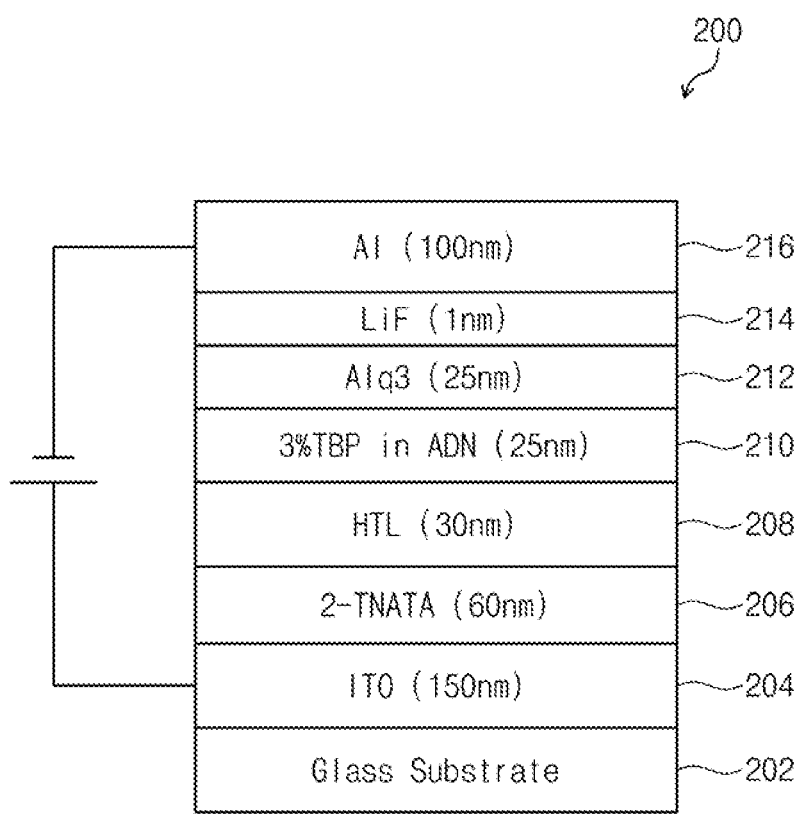
FIG. 2 illustrates a schematic diagram of an organic electroluminescent device manufactured by using an organic electroluminescent material according to an embodiment.

In addition, a layer was formed using $Alq_3$ as an electron transport material (about 25 nm), and LiF (about 1.0 nm) as an electron injection layer and aluminum (about 100 nm) as a cathode were laminated one by one to manufacture the organic electroluminescent device 200 shown in FIG. 2.

As Example 2, an organic electroluminescent device was manufactured by performing the same procedure described in Example 1 except for using Compound 3 instead of Compound 1 used in Example 1.

As Example 3, an organic electroluminescent device was manufactured by performing the same procedure described in Example 1 except for using Compound 61 instead of Compound 1 used in Example 1.

As Example 4, an organic electroluminescent device was manufactured by performing the same procedure described in Example 1 except for using Compound 63 instead of Compound 1 used in Example 1.

As Comparative Example 1 and Comparative Example 2, organic electroluminescent devices were manufactured by performing the same procedure described in Example 1 except for using Comparative Compounds 1 or 2 represented in the following as a compound constituting a hole transport material of an organic electroluminescent device. In addition, the compounds used in Comparative Examples 1 and 2 are different from the amine derivative according to an embodiment in having a structure not including a silyl group.

[Formula 61]

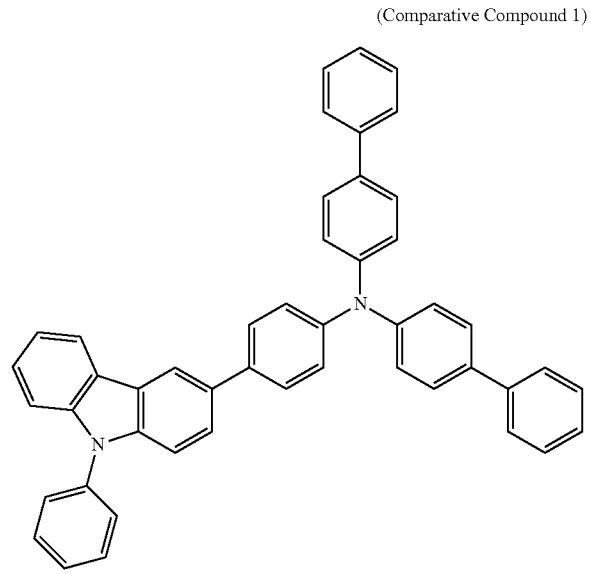

(Comparative Compound 1)

(Comparative Compound 2)

The schematic diagram of the organic electroluminescent device 200 manufactured in Examples 1 to 4 and Comparative Examples 1 and 2 is shown in FIG. 2. The organic electroluminescent device 200 thus manufactured includes an anode 204, a hole injection layer 206 disposed on the anode 204, a hole transport layer 208 disposed on the hole injection layer 206, an emission layer 210 disposed on the hole transport layer 208, an electron transport layer 212 and an electron injection layer 214 disposed on the emission layer 210 and a cathode 216 disposed on the electron injection layer 214.

The device performance of the organic electroluminescent devices 200 manufactured in Examples 1 to 4 and Comparative Examples 1 and 2 is illustrated in the following Table 1. In addition, current efficiency means values at about 10 $mA/cm^2$, and half life means luminance decrease time to half from an initial luminance of about 1,000 $cd/m^2$.

TABLE 1

| | Hole transport material | Voltage (V) | Current efficiency (cd/A) (@10 $mA/cm^2$) | Life (hr) (@1,000 $cd/m^2$) |
|---|---|---|---|---|
| Example 1 | Compound 1 | 7.1 | 6.4 | 1,700 |
| Example 2 | Compound 3 | 7.0 | 6.3 | 1,800 |
| Example 3 | Compound 61 | 6.7 | 6.9 | 2.000 |
| Example 4 | Compound 63 | 6.8 | 6.7 | 1,900 |
| Comparative Example 1 | Comparative Compound 1 | 7.5 | 6.2 | 1,500 |
| Comparative Example 2 | Comparative Compound 2 | 8.1 | 5.3 | 1,200 |

In addition, for the evaluation of the electroluminescent properties of the organic electroluminescent device 200 thus manufactured, a brightness light distribution characteristics measurement system of Hamamatsu Photonics Co. was used.

According to Table 1, it may be found that the life of the organic electroluminescent devices of Examples 1 to 4 according to an embodiment was longer than the organic electroluminescent devices of Comparative Examples 1 and 2.

The amine derivative having a silyl group according to an embodiment, represented by General Formula (1) is provided with a silyl group having electron tolerance and is a material for performing stable hole transportation with respect to electrons. Thus, the deterioration of a device due to electrons intruded into a hole transport layer may be restrained, and the long life of the device may be realized by using the amine derivative having a silyl group according to an embodiment.

In the above described Examples 1 to 4, the amine derivative having a silyl group according to an embodiment, represented by General Formula (1) was used as the hole transport material of the organic electroluminescent device; however, the use of the amine derivative having a silyl group according to an embodiment is not limited to the organic electroluminescent device, and is expanded to other luminescent devices or luminescent apparatuses. In addition, though the organic electroluminescent devices shown in FIGS. 1 and 2 are used in an organic electroluminescent display of a passive-matrix driving type, they may be also used in an organic electroluminescent display of an active-matrix driving type.

Remarkable improvement of the emission efficiency, the driving voltage and the life of an organic electroluminescent device may be obtained by disposing the amine derivative represented by General Formula (1), for example, an amine derivative having the following structure, as a material for an organic electroluminescent device between an emission layer and an anode.

In an example structure of the amine derivative represented by the above General Formula (1), $Ar^1$ and $Ar^2$ are independently a substituted or unsubstituted aryl group or a substituted or unsubstituted heteroaryl group, at least one of $Ar^1$ and $Ar^2$ is substituted with a substituted or unsubstituted silyl group, $Ar^3$ is a substituted or unsubstituted dibenzofuryl group, and L is divalent connecting group not including a single bond.

Here, as the aryl group and the heteroaryl group of "the substituted or unsubstituted aryl group" or "the substituted or unsubstituted heteroaryl group" of $Ar^1$ and $Ar^2$, a phenyl group, a naphthyl group, an anthracenyl group, a phenanthryl group, a biphenyl group, a terphenyl group, a fluorenyl group, a triphenylene group, a biphenylene group, a pyrenyl group, a benzothiazolyl group, a thiophenyl group, a thienothiophenyl group, a thienothienothiophenyl group, a benzothiophenyl group, a dibenzothiophenyl group, a dibenzofuryl group, a N-arylcarbazolyl group, a N-heteroarylcarbazolyl group, a N-alkylcarbazolyl group, a phenoxazyl group, a phenothiazyl group, a pyridyl group, a pyrimidyl group, a triazinyl group, a quinolinyl group and a quinoxalyl group are examples, as described above. The phenyl group, the naphthyl group, the biphenyl group, the terphenyl group, the fluorenyl group, the triphenylene group, the dibenzothiophenyl group, the dibenzofuryl group and the N-phenylcarbazolyl group may be used, and the phenyl group, the biphenyl group, the fluorenyl group, the triphenylene group, the dibenzothiophenyl group, the dibenzofuryl group and the N-phenylcarbazolyl group are examples. As the aryl group of $Ar^1$ and $Ar^2$, an aryl group having 6 to 18 carbon atoms for forming a ring may be used, and as the heteroaryl group of $Ar^1$ and $Ar^2$, a heteroaryl group having 5 to 18 carbon atoms for forming a ring may be used.

As the substituent of the aryl group or the heteroaryl group of $Ar^1$ and $Ar^2$, an alkyl group, an alkoxy group, an aryl group and a heteroaryl group may be used. Examples of the aryl group and the heteroaryl group are the same as the above exemplified aryl group and the heteroaryl group of $Ar^1$ and $Ar^2$.

In an example structure of the amine derivative according to an embodiment, $Ar^3$ in General Formula (1) is a substituted or unsubstituted dibenzofuryl group. Each substituent of the substituted dibenzofuryl group is independently a substituted or unsubstituted aryl group having 6 to 30 carbon atoms for forming a ring, a substituted or unsubstituted heteroaryl group having 5 to 20 carbon atoms for forming a ring or a substituted or unsubstituted alkyl group having 1 to 8 carbon atoms.

In addition, in an example structure of the amine derivative, L is a divalent connecting group in General Formula (1) or may be a substituted or unsubstituted arylene group or a substituted or unsubstituted heteroarylene group. For example, L may be the divalent group of the exemplified groups as $Ar^1$ and $Ar^2$. As L, an arylene group having 6 to 18 carbon atoms for forming a ring may be used, and a phenylene group is an example. In an example structure of the amine derivative represented by General Formula (1), L is not the single bond. By combining the substituted or unsubstituted dibenzofuryl group for $Ar^3$ with an amine part via the divalent connecting group, particularly, via the phenyl group, the conjugation system of the π electrons of a whole molecule may be enlarged. Thus, hole transport properties may be improved, and the driving at a low voltage, the increase of the life and the improvement of the emission efficiency of the organic electroluminescent device may be attained. In addition, since the stability of the molecule is improved, the deterioration of the organic electroluminescent device may be restrained, and the increase of the device life may be attained.

As the substituent of the arylene group or the heteroarylene group of L, an alkyl group, an alkoxy group, an aryl group and a heteroaryl group may be included. For example, the above-described alkyl group, alkoxy group, aryl group and heteroaryl group as the substituent of the aryl group or the heteroaryl group of $Ar^1$ and $Ar^2$, may be included.

As the substituent of the silyl group substituted in at least one of $Ar^1$ and $Ar^2$, an alkyl group, an alkoxy group, an aryl group and a heteroaryl group may be exemplified. For example, the above-described alkyl group, alkoxy group, aryl group and heteroaryl group as the substituent of the aryl group or the heteroaryl group of $Ar^1$ and $Ar^2$, may be exemplified, and the phenyl group may be used for example. In addition, the silyl group substituted for at least one of $Ar^1$ and $Ar^2$ may be a triarylsilyl group where an aryl substituent at the silyl group has 6 to 18 carbon atoms for forming a ring.

As the amine derivative in which the dibenzofuryl group for $Ar^3$ is combined with the divalent connecting group L in General Formula (1), the following compounds are examples, without limitation.

[Formula 62]

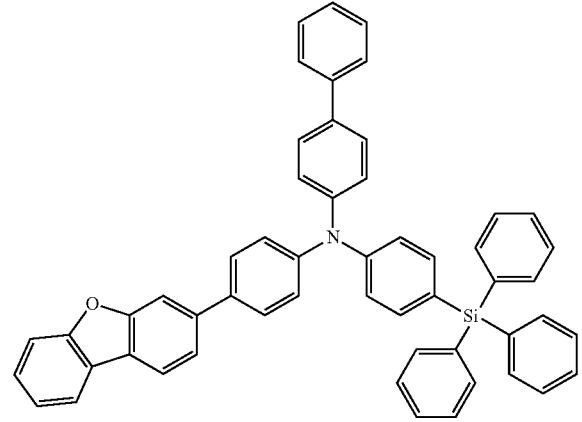

A-1

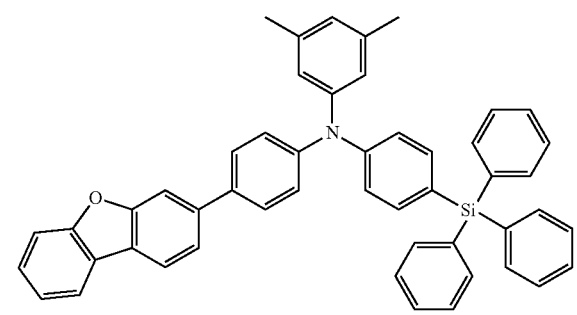

A-2

A-3
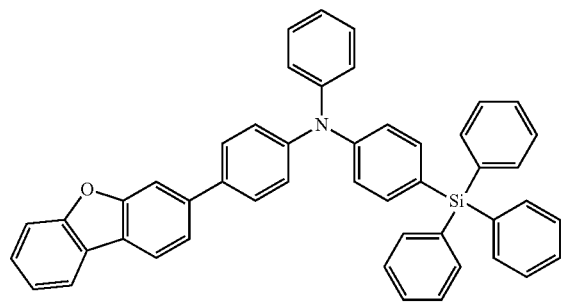
A-4
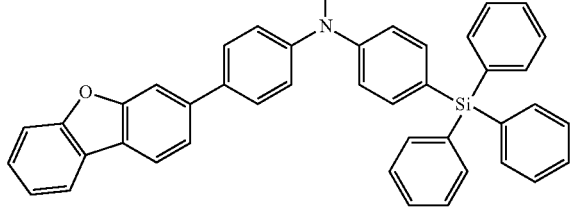
[Formula 63]
A-5
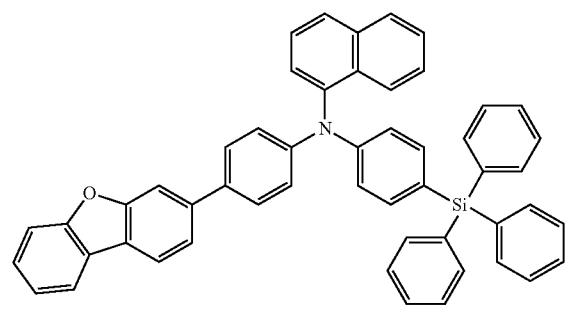
A-6
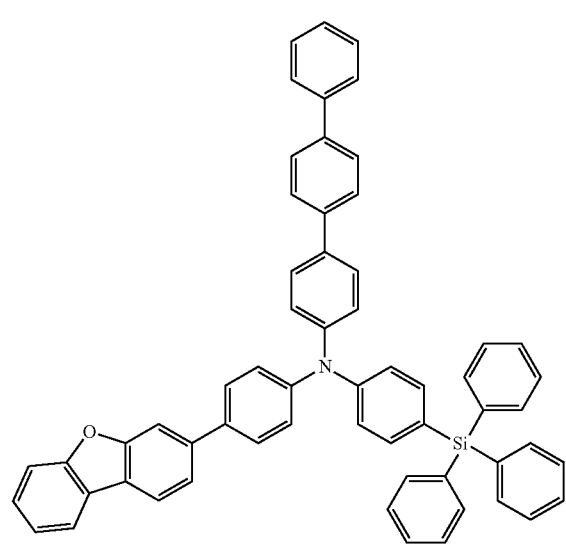
A-7
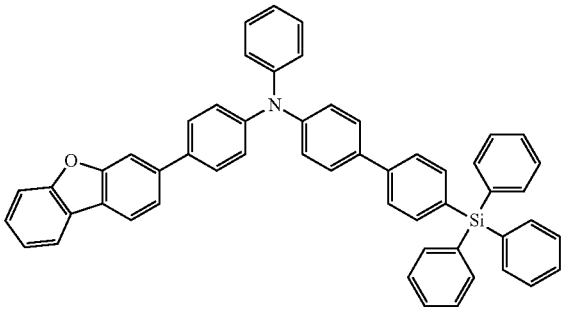
A-8
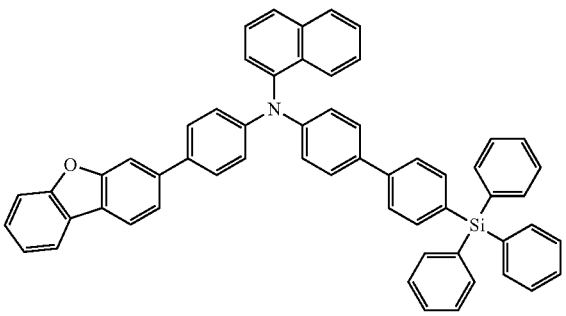
[Formula 64]
A-9
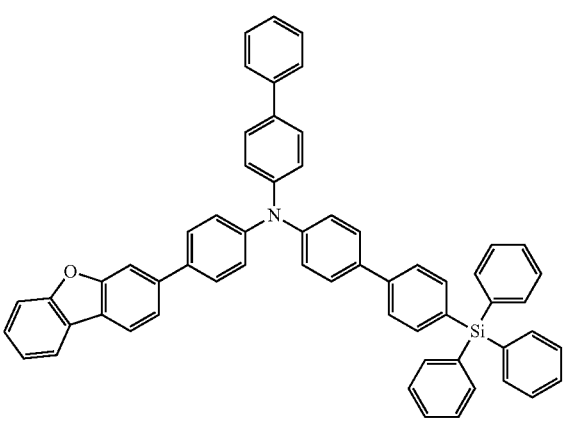
A-10

A-11
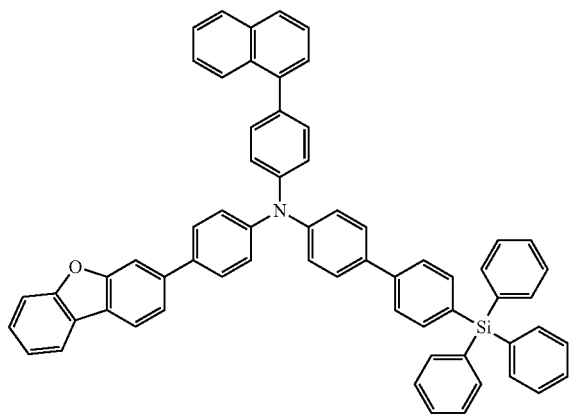
[Formula 65]
A-12
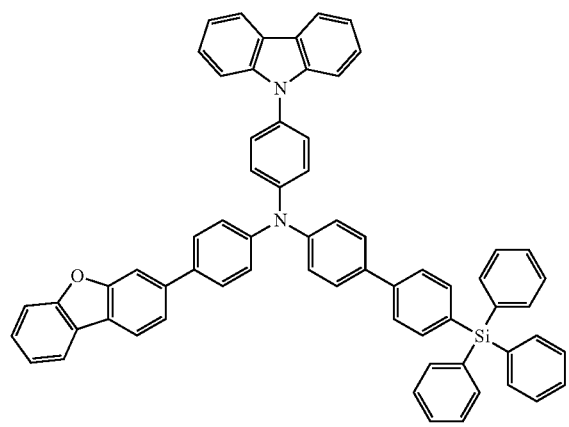
A-13
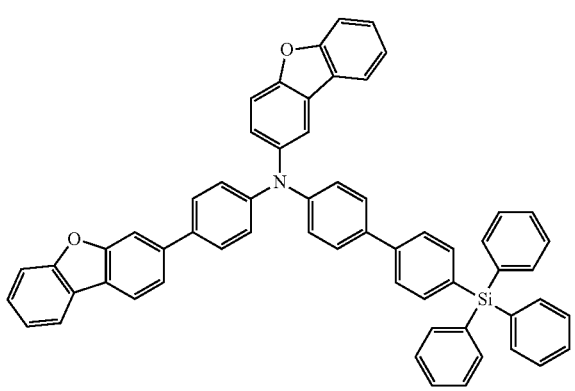
A-14
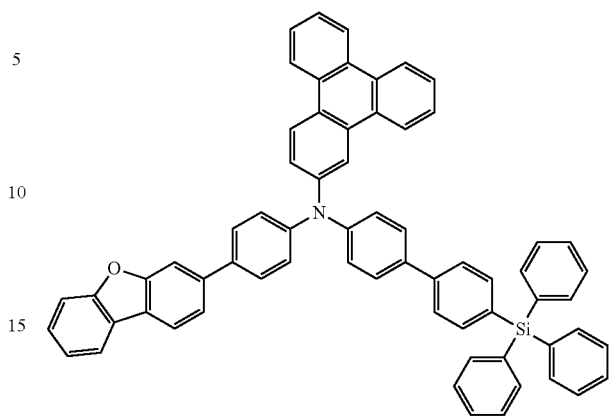
[Formula 66]
A-15
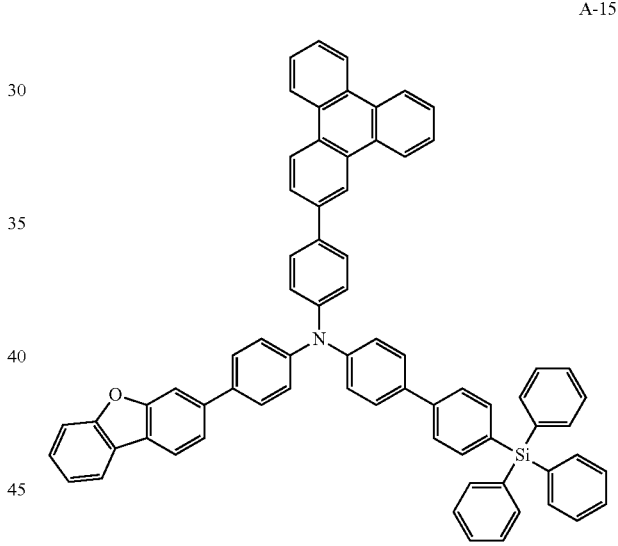
A-16
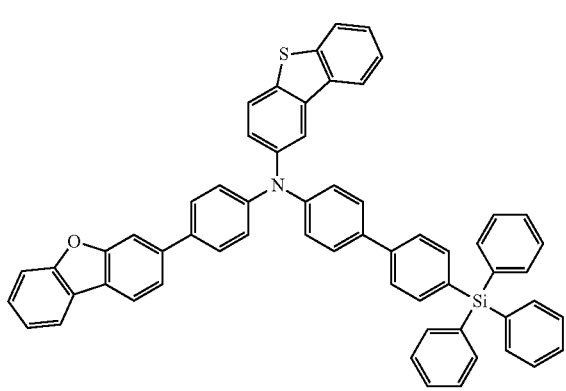

A-17
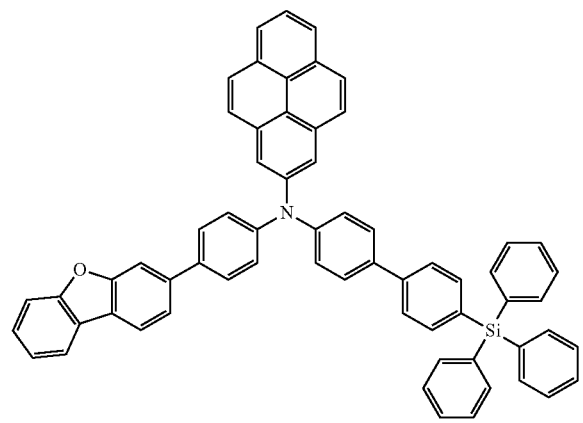
[Formula 67]
A-18
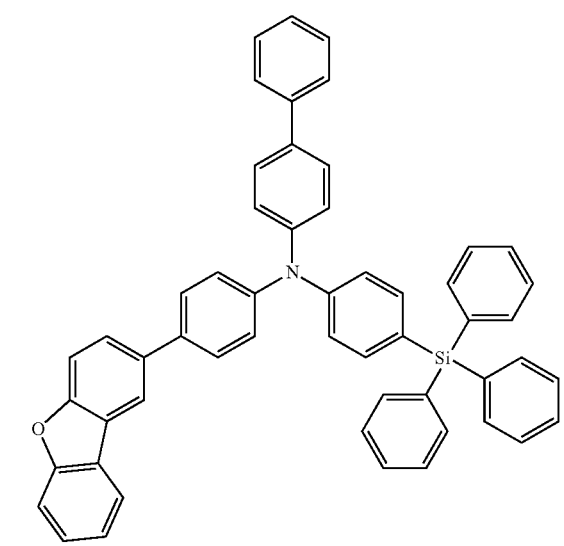
A-19
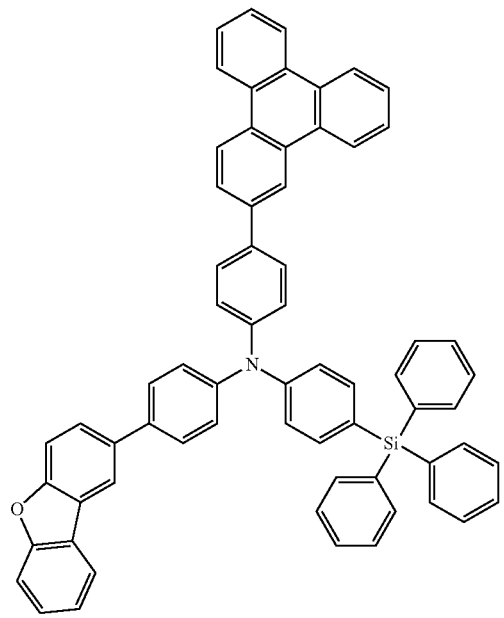
A-20
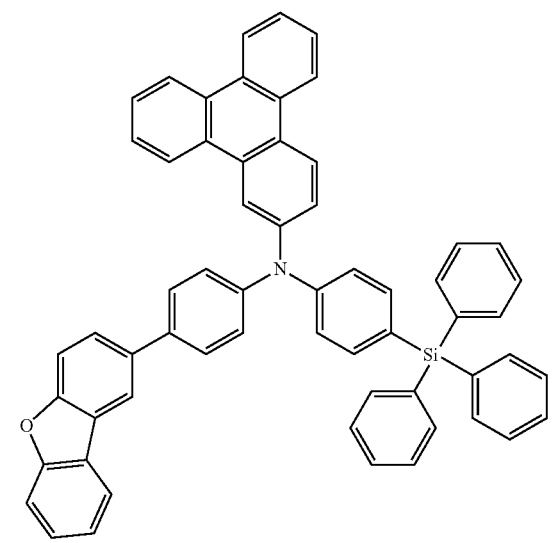
A-21
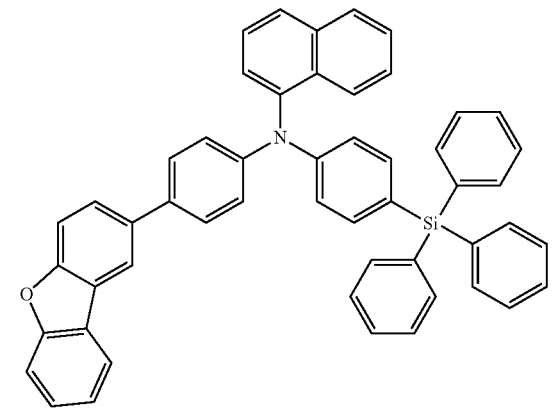
[Formula 68]
A-22
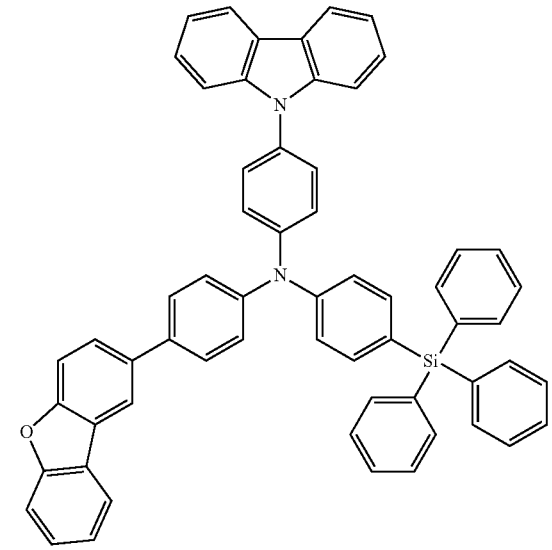

A-23 [Formula 69]
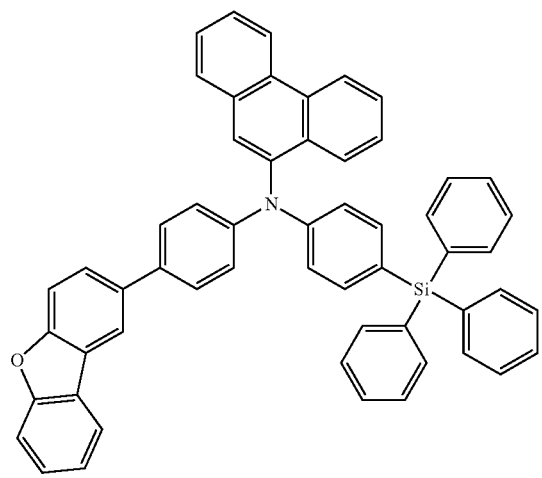
A-24
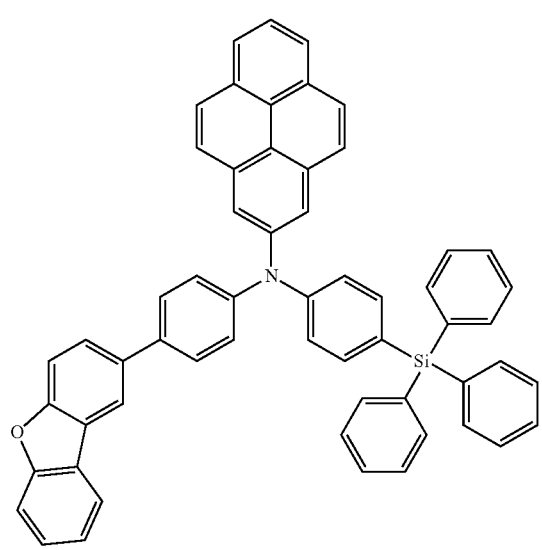
A-25
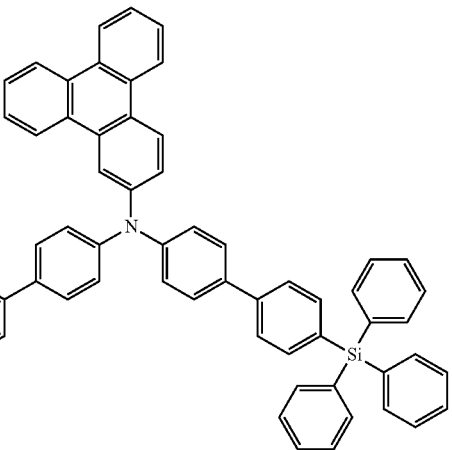
A-26
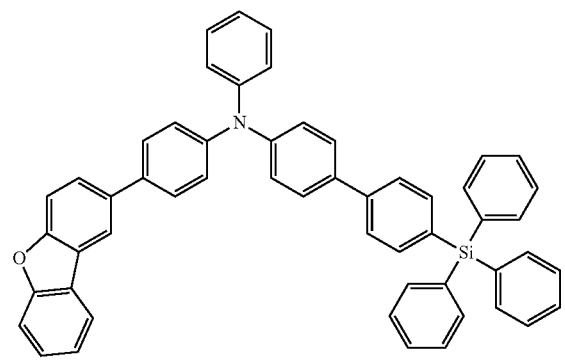
A-27
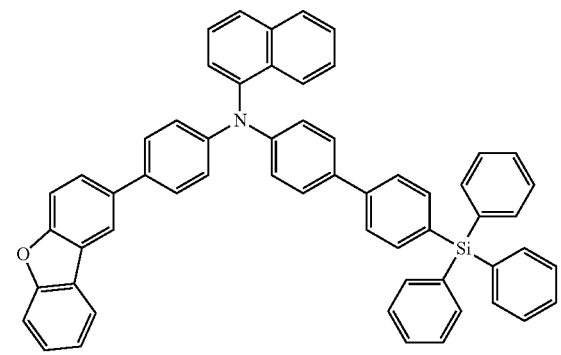
A-28

[Formula 70]
A-29
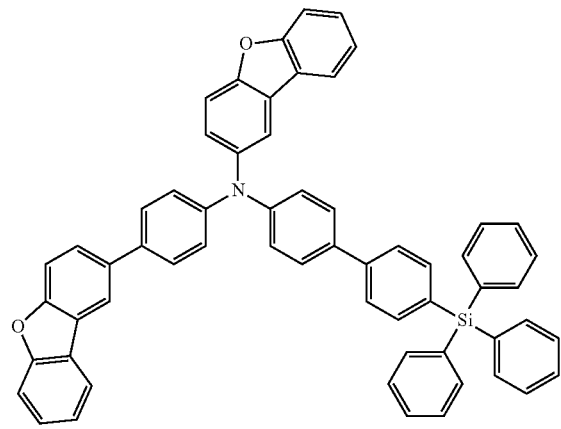
A-30
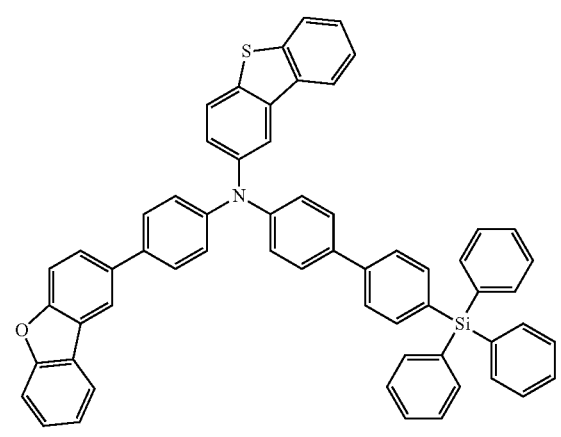
A-31
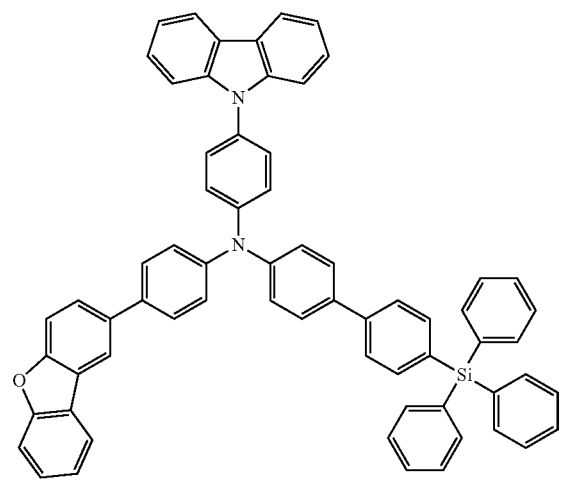
[Formula 71]
A-32
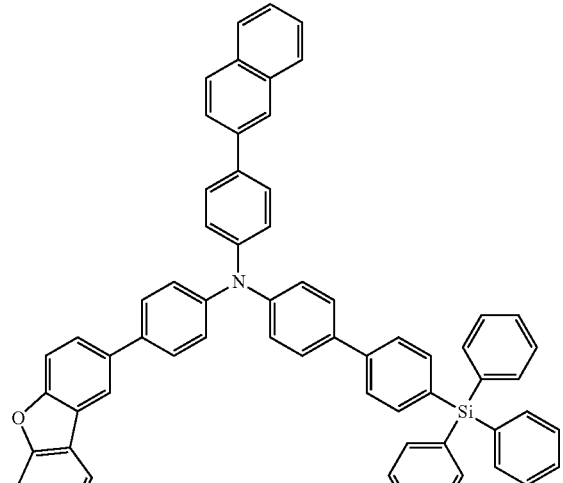
A-33
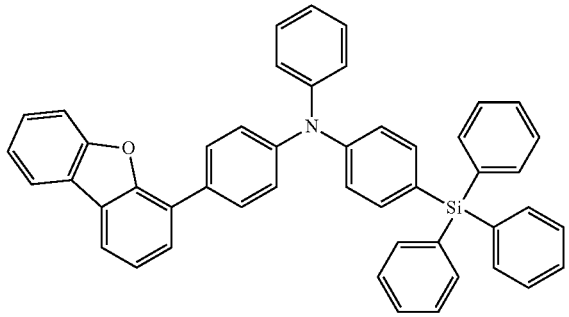
A-34
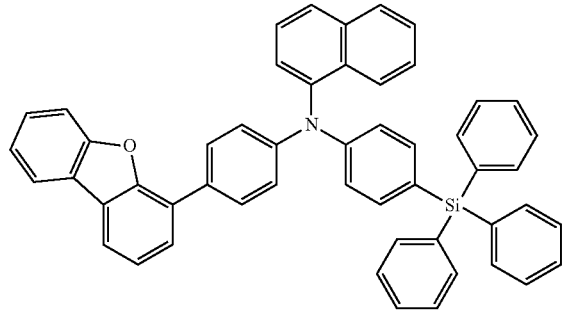

-continued
A-35
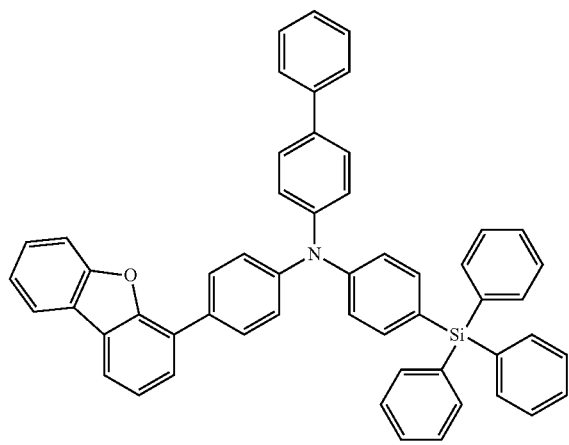
[Formula 72]
A-36
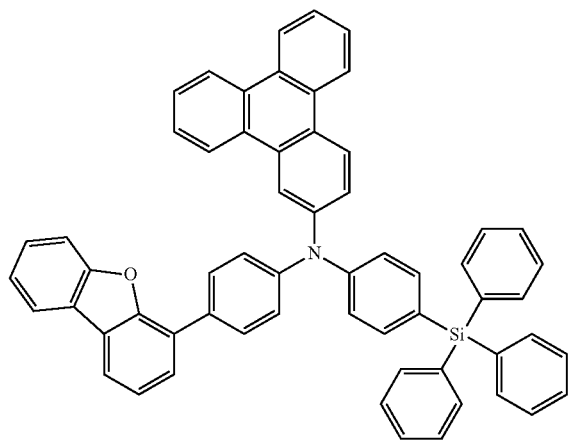
A-37
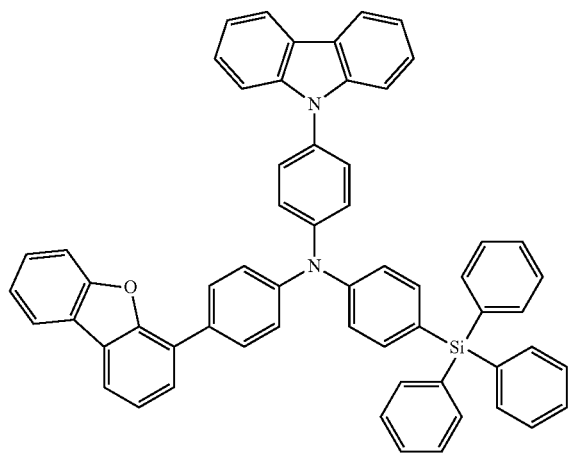
-continued
A-38
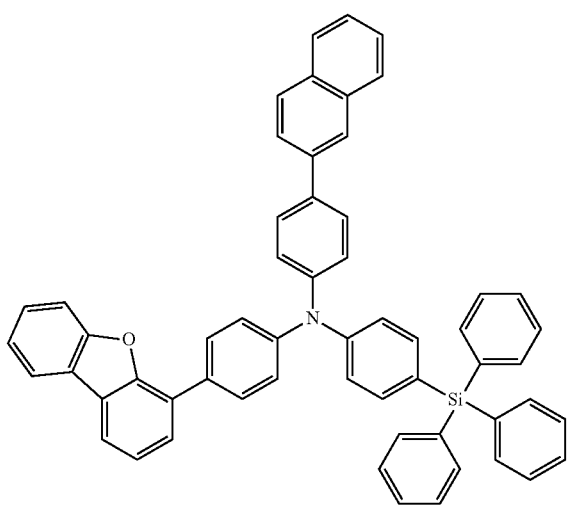
A-39
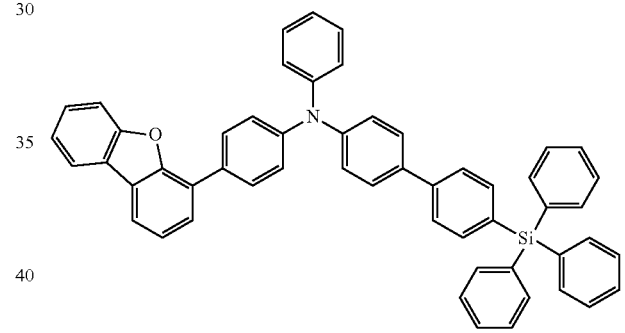
[Formula 73]
A-40
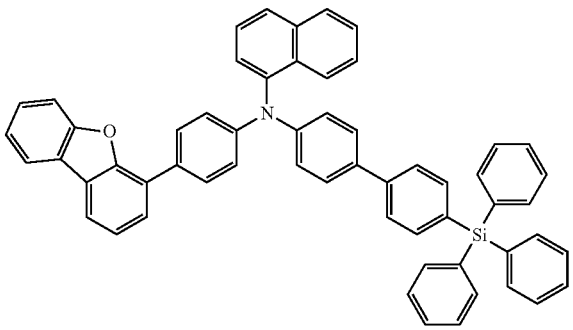

-continued

A-41

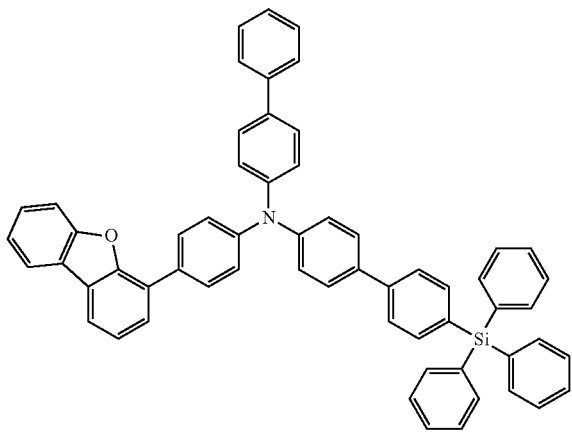

[Formula 74]

A-42

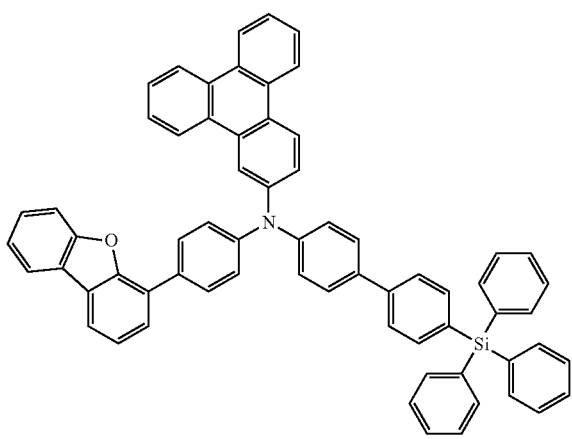

A-43

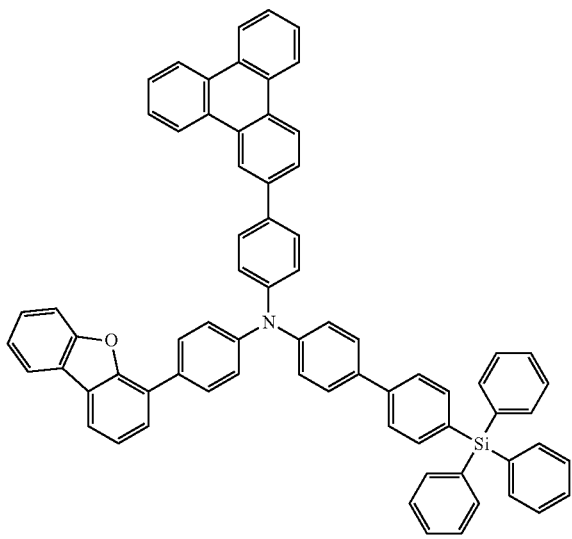

-continued

A-44

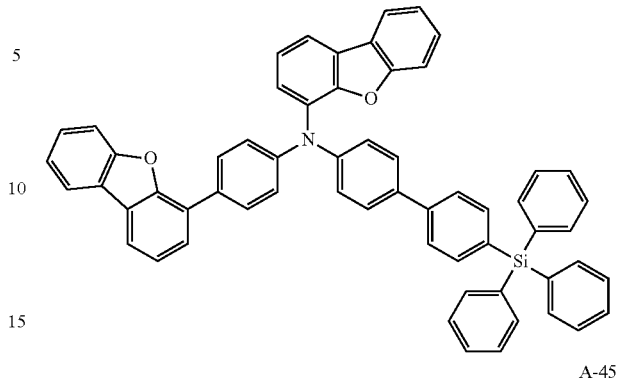

A-45

A-46

[Formula 75]

As described above, in an example amine derivative according to an embodiment in accordance with General Formula (1), $Ar^3$ is a substituted or unsubstituted dibenzofuryl group, and the dibenzofuryl group is combined with a divalent connecting group L. The dibenzofuryl group has strong electron tolerance. Thus, the electron tolerance of a hole transport layer may be improved, and the deterioration of a hole transport material due to electrons intruded in the hole transport layer may be restrained by using the amine derivative in which $Ar^3$ is the substituted or unsubstituted dibenzofuryl group in General Formula (1) as the hole transport material. In addition, by introducing the dibenzofuryl group, the planarity of the amine derivative may be increased, and the glass transition temperature thereof may be elevated. Thus, the improvement of the emission efficiency, the lowering of the driving voltage and the increase of the life of the organic electroluminescent device may be realized. In addition, the conjugation system of the π electrons of a whole molecule may be enlarged by combining the dibenzofuryl group and the amine part via the divalent connecting group L. Since hole transport properties may be improved, and the stability of the molecule may be improved, the decrease of the driving voltage, the increase of the life and the improvement of the emission efficiency of the organic electroluminescent device may be realized. The amine derivative according to an embodiment may realize the improvement of the emission efficiency, the decrease of the driving voltage and the increase of the life of the organic electroluminescent device particularly in blue-bluish green region.

In addition, in an example structure of the amine derivative represented by General Formula (1), the substituted or unsubstituted dibenzofuryl group for Ar³ is combined with L at position 2, position 3 or position 4, and may be combined with the connecting group L at position 3. In addition, the substituted or unsubstituted dibenzofuryl group for Ar³ may be combined with respect to the nitrogen atom (N) of the amine part at the para position of the divalent connecting group. By combining the dibenzofuryl group at the para position of the divalent connecting group, the conjugation length of the π electrons of a whole molecule may be the longest, and the increase of the life of the organic electroluminescent device may be attained.

The amine derivative according to an embodiment represented by General Formula (1), in which the dibenzofuryl group for Ar³ is combined with the divalent connecting group L may be used as the material of the hole transport layer of the organic electroluminescent device 100 shown in FIG. 1. In addition, the configuration of the organic electroluminescent device 100 shown in FIG. 1 is an embodiment of the organic electroluminescent device according to an embodiment, but embodiments are not limited thereto and may be variously modified.

In addition, the use of the amine derivative according to an embodiment represented by General Formula (1), in which the dibenzofuryl group for Ar³ is combined with the divalent connecting group L is not limited to the hole transport material of the organic electroluminescent device; for example it may be used as the material of a hole injection layer or the material of an emission layer. In the case that the amine derivative is used as the material of the hole injection layer or the material of the emission layer, the emission efficiency of the organic electroluminescent device may be improved, and the driving at a low voltage and the increase of the life of the organic electroluminescent device may be realized as in the case using the amine derivative as the material of the hole transport layer.

Example II

With respect to the amine derivative according to an embodiment represented by General Formula (1), in which the dibenzofuryl group for Ar³ is combined with the divalent connecting group L, examples of synthesizing Compounds A-10, A-18, A-25, A-35 and A-41 will be explained hereinafter.

The following synthetic methods are only examples, and embodiments are not limited thereto.

(Synthesis of Compound A-10)

Compound A-10 according to an embodiment was synthesized by the following process.

Under an argon atmosphere, 1.50 g of Compound (vi), 1.90 g of Compound (vii), 0.11 g of bis(dibenzylideneacetone)palladium(0) (Pd(dba)₂), 0.15 g of tri-t-butylphosphine ((t-Bu)₃P), 0.54 g of sodium t-butoxide were added to a 100 mL three-necked flask, followed by heating and refluxing in 45 mL of a toluene solvent for about 6 hours. After cooling in the air, water was added to the reaction mixture, an organic layer was separated, and solvents were distilled. The crude product thus obtained was separated by silica gel column chromatography (using a mixture solvent of dichloromethane and hexane) and recrystallized using a mixture solvent of toluene/hexane to produce 1.86 g (yield 86%) of Compound A-10 as a white solid.

[Formula 76]

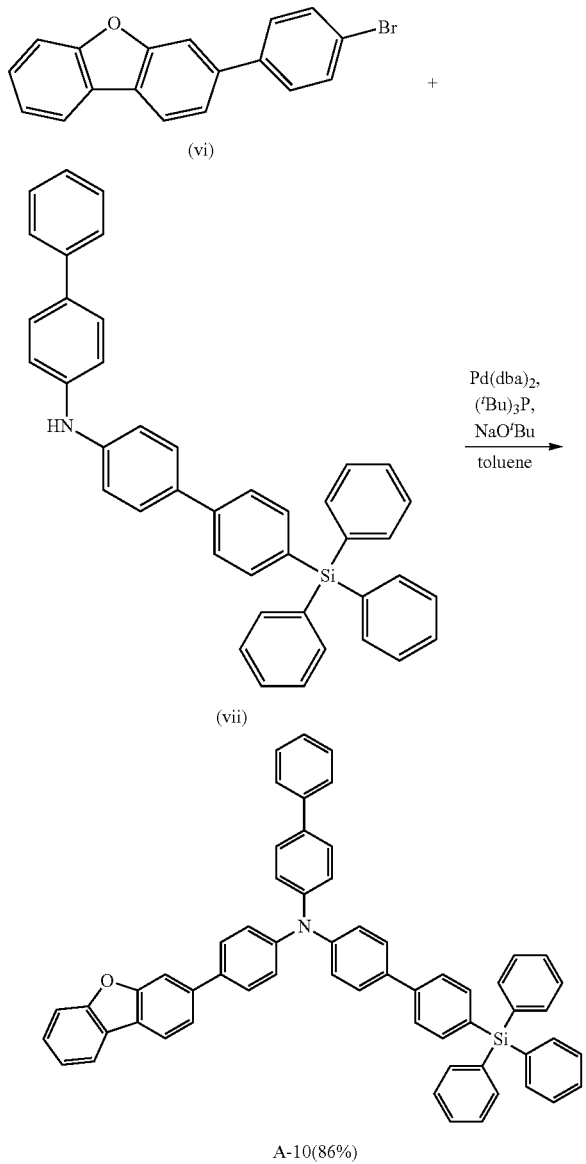

The chemical shift values of Compound A-10 measured by ¹H NMR were 8.00 (d, 1H), 7.96 (d, 1H), 7.78 (d, 1H), 7.64-7.53 (m, 20H), 7.48-7.33 (m, 14H), 7.29-7.25 (m, 6H). In addition, the molecular weight of Compound A-10 measured by FAB-MS was 822.

(Synthesis of Compound A-18)

Under an argon atmosphere, 2.50 g of Compound (viii), 2.52 g of Compound (ii), 0.25 g of $Pd_2(dba)_2$, 0.10 g of $(t-Bu)_3P$, 1.85 g of sodium t-butoxide were added to a 100 mL three-necked flask, followed by heating and refluxing in 60 mL of a toluene solvent for about 8 hours. After cooling in the air, water was added to the reaction mixture, an organic layer was extracted, and solvents were distilled. The crude product thus obtained was separated by silica gel column chromatography (using a mixture solvent of dichloromethane and hexane) and recrystallized using a mixture solvent of toluene/hexane to produce 3.31 g (yield 73%) of Compound A-18 as a white solid.

[Formula 77]

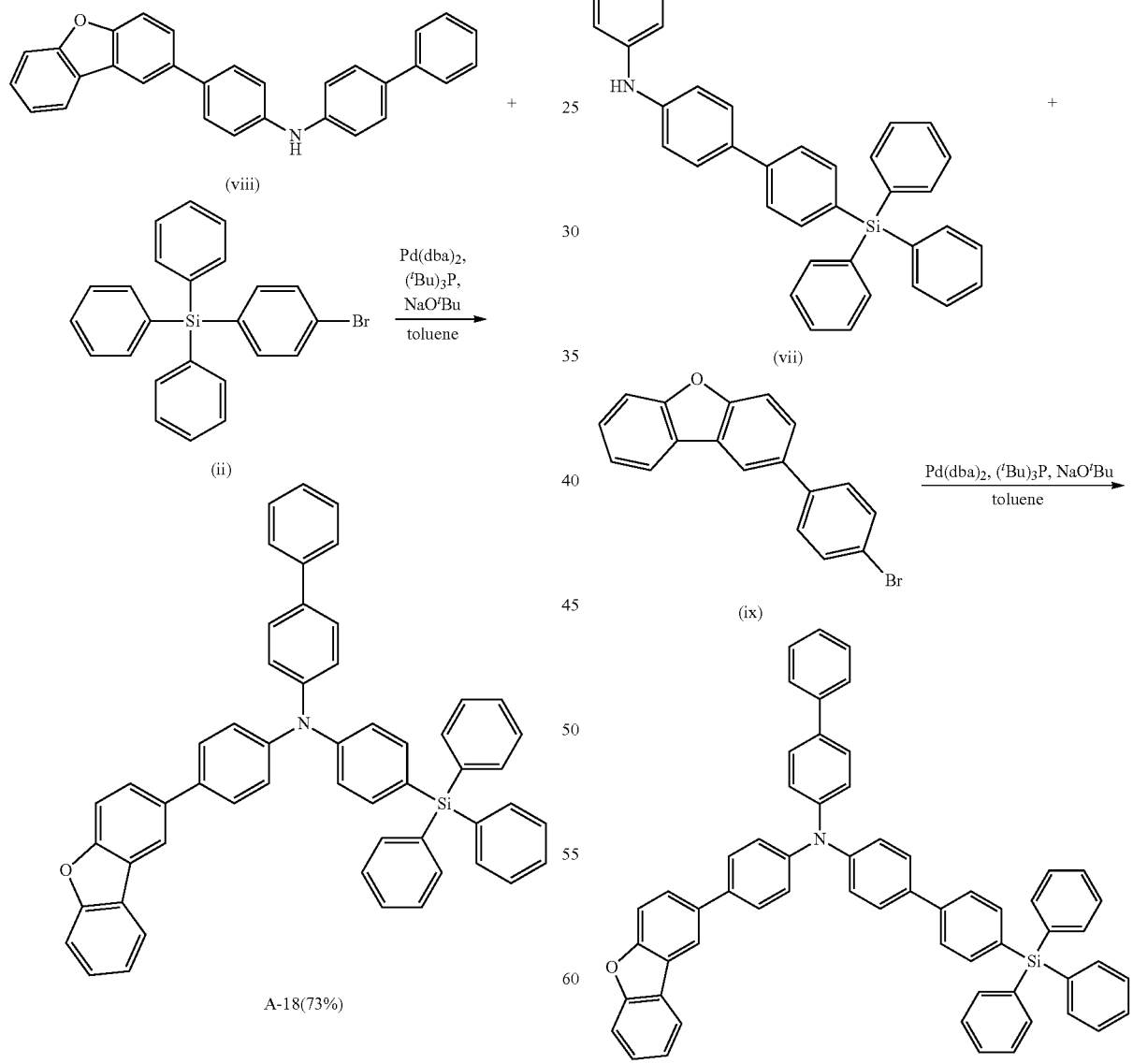

The chemical shift values of Compound A-18 measured by $^1H$ NMR were 8.13 (d, 1H), 7.98 (d, 1H), 7.69-7.24 (m, 35H), 7.16 (d, 2H). In addition, the molecular weight of Compound A-18 measured by FAB-MS was 745.

(Synthesis of Compound A-25)

Under an argon atmosphere, 1.22 g of Compound (vii), 0.80 g of Compound (ix), 88 mg of $Pd(dba)_2$, 0.12 g of $(t-Bu)_3P$, 0.43 g of sodium t-butoxide were added to a 100 mL three-necked flask, followed by heating and refluxing in 38 mL of a toluene solvent for about 7 hours. After cooling in the air, water was added to the reaction mixture, organic layer was separated, and solvents were distilled. The crude product thus obtained was separated by silica gel column chromatography (using a mixture solvent of dichloromethane and hexane) and recrystallized using a mixture solvent of toluene/hexane to produce 1.49 g (yield 79%) of Compound A-25 as a white solid.

[Formula 78]

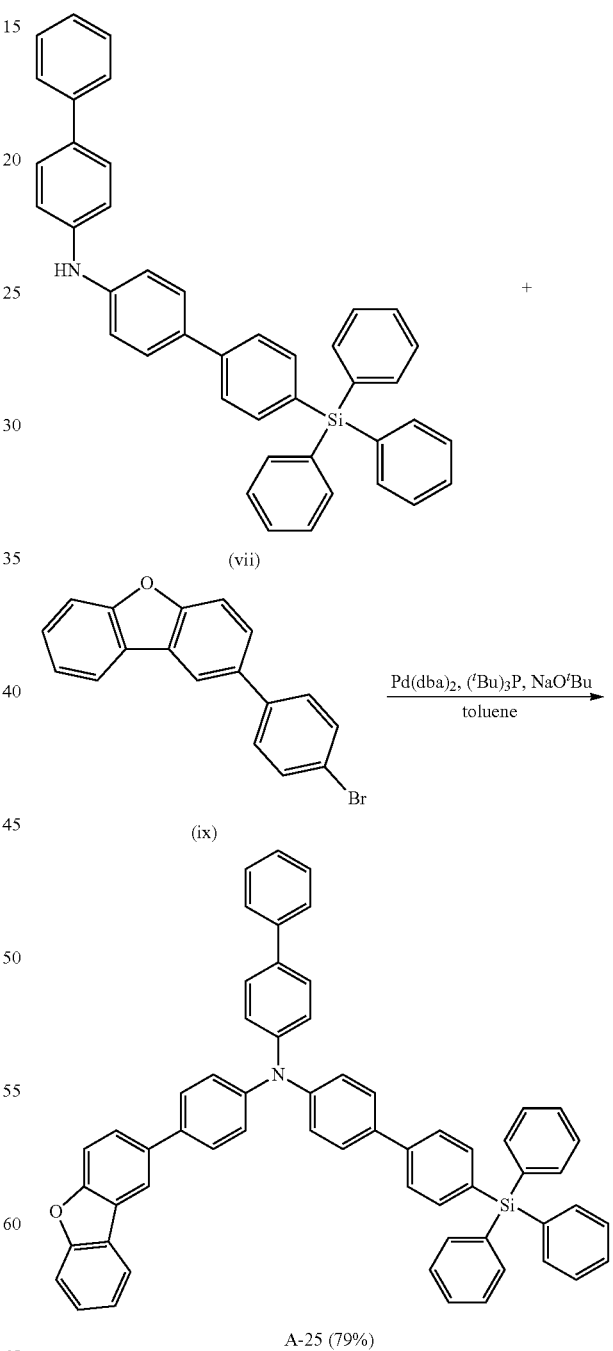

The chemical shift values of Compound A-25 measured by $^1H$ NMR were 8.01 (d, 1H), 7.93-7.86 (m, 3H), 7.76-7.53

(m, 17H), 7.50-7.28 (m, 22H). In addition, the molecular weight of Compound A-25 measured by FAB-MS was 822.

(Synthesis of Compound A-35)

Under an argon atmosphere, 0.8 g of Compound (x), 0.54 g of Compound (xi), 0.06 g of Pd(dba)$_2$, 0.12 g of (t-Bu)$_3$P, 0.3 g of sodium t-butoxide were added to a 100 mL three-necked flask, followed by heating and refluxing in 38 mL of a toluene solvent for about 7 hours. After cooling in the air, water was added to the reaction mixture, an organic layer was separated, and solvents were distilled. The crude product thus obtained was separated by silica gel column chromatography (using a mixture solvent of dichloromethane and hexane) and recrystallized using a mixture solvent of toluene/hexane to produce 0.95 g (yield 80%) of Compound A-35 as a white solid.

[Formula 79]

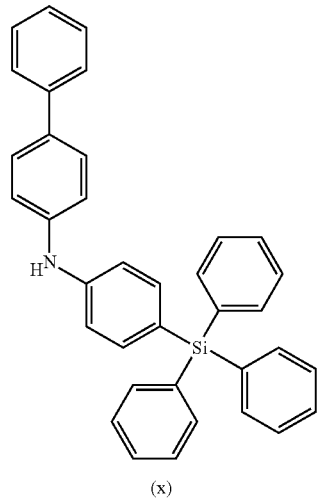
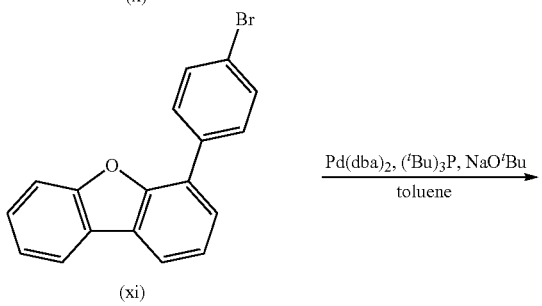
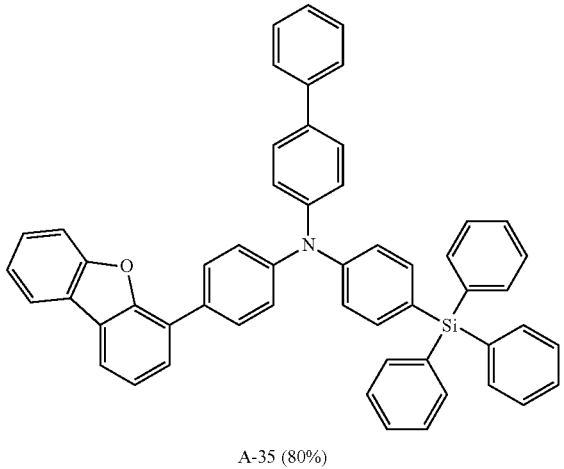

The chemical shift values of Compound A-35 measured by $^1$H NMR were 7.99 (d, 1H), 7.91 (d, 1H), 7.87 (d, 2H), 7.62-7.28 (m, 33H), 7.20 (d, 2H). In addition, the molecular weight of Compound A-35 measured by FAB-MS was 745.

(Synthesis of Compound A-41)

Under an argon atmosphere, 1.50 g of Compound (vii), 0.87 g of Compound (xi), 0.11 g of Pd(dba)$_2$, 0.15 g of (t-Bu)$_3$P, 0.54 g of sodium t-butoxide were added to a 100 mL three-necked flask, followed by heating and refluxing in 45 mL of a toluene solvent for about 7 hours. After cooling in the air, water was added to the reaction mixture, an organic layer was separated, and solvents were distilled. The crude product thus obtained was separated by silica gel column chromatography (using a mixture solvent of dichloromethane and hexane) and recrystallized using a mixture solvent of toluene/hexane to produce 1.86 g (yield 89%) of Compound A-41 as a white solid.

[Formula 80]

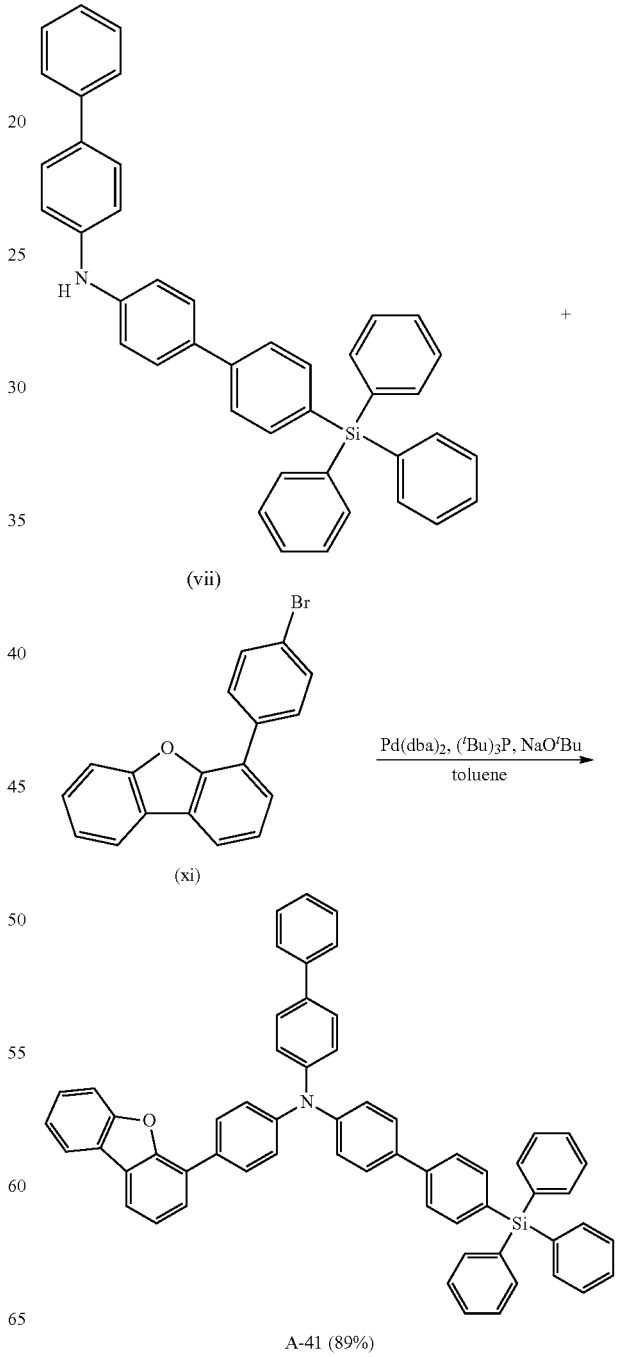

The chemical shift values of Compound A-41 measured by ¹H NMR were 8.00 (d, 1H), 7.93-7.87 (m, 3H), 7.66-7.53 (m, 17H), 7.50-7.28 (m, 22H). In addition, the molecular weight of Compound A-41 measured by FAB-MS was 822.

Hereinafter, organic electroluminescent devices using the above described Compounds A-10, A-18, A-25, A-35 and A-41 as the materials for the organic electroluminescent devices according to an embodiment in a hole transport layer will be explained. An organic electroluminescent device using Compound A-10 in the hole transport layer corresponds to Example 5, an organic electroluminescent device using Compound A-18 in the hole transport layer corresponds to Example 6, an organic electroluminescent device using Compound A-25 in the hole transport layer corresponds to Example 7, an organic electroluminescent device using Compound A-35 in the hole transport layer corresponds to Example 8 and an organic electroluminescent device using Compound A-41 in the hole transport layer corresponds to Example 9.

The manufacture of the organic electroluminescent device according to Example 5 according to an embodiment was conducted by a vacuum deposition as for the organic electroluminescent device of Example 1 and the following procedure. First, with respect to an ITO-glass substrate patterned and washed in advance, surface treatment using ozone was conducted. In addition, the layer thickness of an ITO layer was about 150 nm. Immediately after the ozone treatment, a layer was formed using 2-TNATA as a hole injection material (thickness of about 60 nm) on the ITO layer.

Then, a layer was formed using Compound A-10 according to an embodiment as a hole transport material (about 30 nm), and a layer of ADN doped with TBP in a ratio of about 3% was formed by a co-deposition (about 25 nm).

After that, a layer was formed using Alq₃ as an electron transport material (about 25 nm), and LiF (about 1.0 nm) as an electron injection layer and aluminum (about 100 nm) as a cathode were laminated one by one to manufacture the organic electroluminescent device 200 shown in FIG. 2.

As Examples 6, 7, 8 and 9, organic electroluminescent devices were manufactured by performing the same procedure described in Example 5 except for using Compounds A-18, A-25, A-35 and A-41 instead of Compound A-10 used in Example 5.

As Comparative Examples 3, 4 and 5, organic electroluminescent devices were manufactured by performing the same procedure described in Example 5 except for using Comparative Compounds 3, 4 and 5 represented in the following as compound constituting a hole transport materials of organic electroluminescent devices.

[Formula 81]

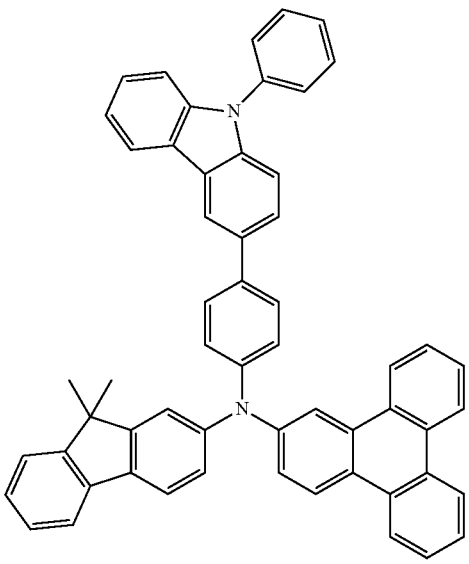

Comparative Compound 3

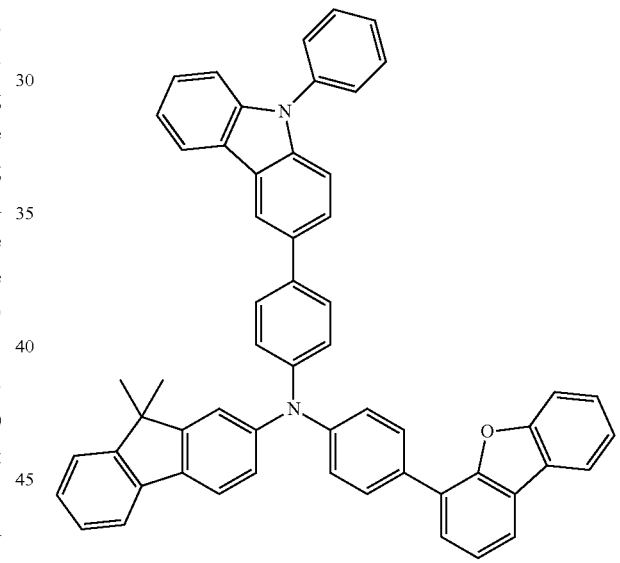

Comparative Compound 4

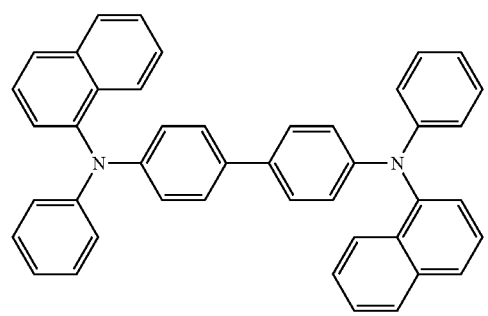

Comparative Compound 5

The driving voltage, the emission efficiency and the half life of the organic electroluminescent devices 200 manufactured in Examples 5 to 9 and Comparative Examples 3 to 5 were evaluated. In addition, emission efficiency means values at about 10 mA/cm², and half life means luminance decrease time to half from an initial luminance of about 1,000 cd/m². The evaluation results are shown in Table 2.

TABLE 2

|  | Hole transport material | Voltage (V) | Current efficiency (cd/A) | Half life (hr) |
| --- | --- | --- | --- | --- |
| Example 5 | Compound A-10 | 5.9 | 8.4 | 4,700 |
| Example 6 | Compound A-18 | 6.3 | 8.2 | 4,500 |
| Example 7 | Compound A-25 | 6.0 | 8.0 | 3,500 |
| Example 8 | Compound A-35 | 6.0 | 7.9 | 3,000 |
| Example 9 | Compound A-39 | 6.0 | 8.2 | 4,500 |
| Comparative Example 3 | Comparative Compound 3 | 6.2 | 6.0 | 1,500 |
| Comparative Example 4 | Comparative Compound 4 | 6.1 | 5.9 | 1,700 |
| Comparative Example 5 | Comparative Compound 5 | 8.1 | 5.3 | 1,200 |

According to Table 2, the organic electroluminescent devices of Examples 5 to 9 had improved emission efficiency and longer life than the organic electroluminescent devices of Comparative Examples 3 to 5. For example, in the amine derivative represented by General Formula (1), it can be seen that the emission efficiency and the life of Example 5 using Compound A-10 having the configuration of combining the dibenzofuryl group for $Ar^3$ with the divalent connecting group L at position 3, as a hole transport material was markedly improved. It thus appears that the π electrons of a whole molecule were enlarged, hole transport properties and the stability of the molecule were improved, and the increase of the emission efficiency, the decrease of the driving voltage and the long life of the organic electroluminescent device were realized by the combination of the dibenzofuryl group exhibiting strong electron tolerance with the connecting group L at position 3.

In the above-described Examples 5 to 9, the example amine derivative according to an embodiment, in which $Ar^3$ is the substituted or unsubstituted dibenzofuryl group, and L is the divalent connecting group other than a single bond in General Formula (1) was used as the hole transport material of the organic electroluminescent device; however, the use of the amine derivative according to an embodiment is not limited to the organic electroluminescent device, and is expanded to other luminescent devices or luminescent apparatus. In addition, the organic electroluminescent device using the amine derivative according to an embodiment, in which $Ar^3$ is the substituted or unsubstituted dibenzofuryl group, and L is the divalent connecting group other than the single bond in General Formula (1) may be used in an organic electroluminescent display of a passive-matrix driving type, and they may be also used in an organic electroluminescent display of an active-matrix driving type.

Remarkable improvement of the emission efficiency, the driving voltage and the life of an organic electroluminescent device may be obtained by disposing the amine derivative represented by General Formula (1), for example, an amine derivative having the following structure as a material for an organic electroluminescent device between an emission layer and an anode.

In an example structure of the amine derivative represented by General Formula (1), $Ar^1$ and $Ar^2$ are independently a substituted or unsubstituted aryl group or a substituted or unsubstituted heteroaryl group, at least one of $Ar^1$ and $Ar^2$ is substituted with a substituted or unsubstituted silyl group, $Ar^3$ is a substituted or unsubstituted dibenzofuryl group, and L is a single bond.

Here, as the aryl group and the heteroaryl group of "the substituted or unsubstituted aryl group" or "the substituted or unsubstituted heteroaryl group" of $Ar^1$ and $Ar^2$, as described above, a phenyl group, a naphthyl group, an anthracenyl group, a phenanthryl group, a biphenyl group, a terphenyl group, a fluorenyl group, a triphenylene group, a biphenylene group, a pyrenyl group, a benzothiazolyl group, a thiophenyl group, a thienothiophenyl group, a thienothienothiophenyl group, a benzothiophenyl group, a dibenzothiophenyl group, a dibenzofuryl group, a N-arylcarbazolyl group, a N-heteroarylcarbazolyl group, a N-alkylcarbazolyl group, a phenoxazyl group, a phenothiazyl group, a pyridyl group, a pyrimidyl group, a triazinyl group, a quinolinyl group and a quinoxalyl group are examples. The phenyl group, the naphthyl group, the biphenyl group, the terphenyl group, the fluorenyl group, the triphenylene group, the dibenzothiophenyl group, the dibenzofuryl group and the N-phenylcarbazolyl group may be used. As the aryl group, an aryl group having 6 to 18 carbon atoms for forming a ring may be used, and as the heteroaryl group, a heteroaryl group having 5 to 18 carbon atoms for forming a ring may be used.

As the substituent of the aryl group or the heteroaryl group of $Ar^1$ and $Ar^2$, an alkyl group, an alkoxy group, an aryl group and a heteroaryl group are examples. Examples of the aryl group and the heteroaryl group are the same as the above exemplified aryl group and the heteroaryl group of $Ar^1$ and $Ar^2$.

As the substituent of the silyl group substituted for at least one of $Ar^1$ and $Ar^2$ may include an alkyl group, an alkoxy group, an aryl group and a heteroaryl group. For example, the same alkyl group, alkoxy group, aryl group and heteroaryl group explained as the substituent of the aryl group or the heteroaryl group of $Ar^1$ and $Ar^2$ may be used, and, for example, a phenyl group may be used. In addition, as the silyl group substituted for at least one of $Ar^1$ and $Ar^2$ may be a triarylsilyl group where an aryl substituent at the silyl group has 6 to 18 carbon atoms for forming a ring.

In addition, in an example amine derivative according to an embodiment, one of $Ar^1$ and $Ar^2$ may be substituted with the substituted or unsubstituted silyl group. As described above, since the silyl group exhibits strong electron tolerance, the amine derivative introducing the silyl group may contribute to the improvement of the electron tolerance of the hole transport layer by being used as the hole transport material.

In an example structure of the amine derivative according to an embodiment, $Ar^3$ is a substituted or unsubstituted dibenzofuryl group. In the substituted dibenzofuryl group, each substituent of the dibenzofuryl group may independently be a substituted or unsubstituted aryl group having 6 to 18 carbon atoms for forming a ring. The substituents of the dibenzofuryl group may be combined to each other to form a saturated or unsaturated ring. In an implementation, the substituents at position 1 and position 9 of the dibenzofuryl group are not combined to each other.

In an example structure of the amine derivative, L is a single bond. Here, the combining position of the substituted or unsubstituted dibenzofuryl group for Ar³ with L is not specifically limited; it may be position 2, position 3 or position 4, and for example, position 3. That is, as described above, in an example structure of the amine derivative according to an embodiment, L is the single bond, and the substituted or unsubstituted dibenzofuryl group for Ar³ may be combined with the nitrogen atom (N) of the amine part at position 2, position 3 or position 4, and is for example combined with the nitrogen atom (N) at position 3. Through the combination of the dibenzofuryl group with the nitrogen atom (N) at the amine part at position 3, the conjugation system of the π electrons of a whole molecule may be enlarged. Thus, the improvement of hole transport properties may be enhanced, and the improvement of the emission efficiency and the increase of the life of the organic electroluminescent device may be enhanced. In addition, since L is the single bond, the deterioration of film forming properties due to the increase of molecular weight may be prevented.

In an example structure of the amine derivative according to an embodiment, the dibenzofuryl group for Ar³ exhibits strong electron tolerance like the silyl group substituted for at least one of Ar¹ and Ar². Thus, the amine derivative according to an embodiment having the dibenzofuryl group is more stable with respect to electrons and restrains the deterioration of a material due to electrons intruded into a laminated layer by using thereof as a material for an organic electroluminescent device, particularly as a material of a laminated layer between an emission layer and an anode. In addition, due to the high planarity, the dibenzofuryl group has high glass transition temperature. As a result, the emission efficiency of the organic electroluminescent device may be improved, and the driving at a low voltage and the long life thereof may be realized. For example, an example amine derivative according to an embodiment, which is an amine derivative in which the dibenzofuryl group for Ar³ is combined with the single bond of L in General Formula (1), may improve the emission efficiency of the organic electroluminescent device further and realize the driving at a low voltage and the long life thereof in a blue-bluish green region.

As the amine derivative in which the dibenzofuryl group for Ar³ is combined with L of the single bond in General Formula (1), the following compounds are examples, without limitation.

[Formula 82]

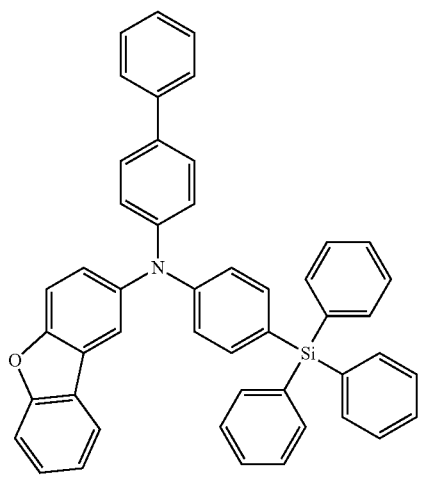

B-1

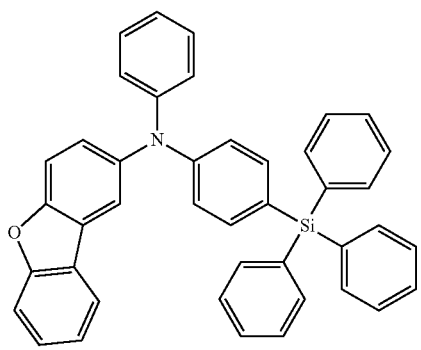

B-2

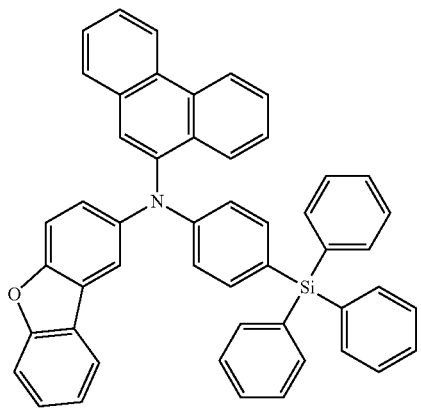

B-3

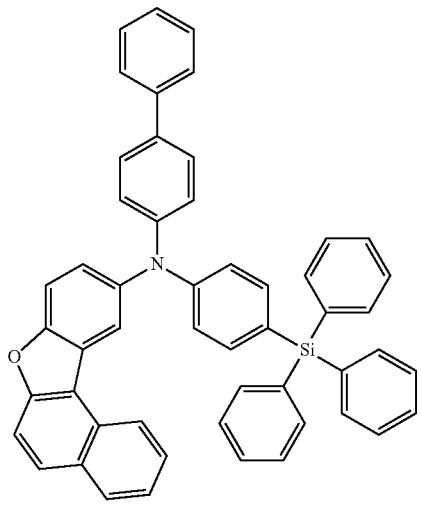

B-4

[Formula 83]
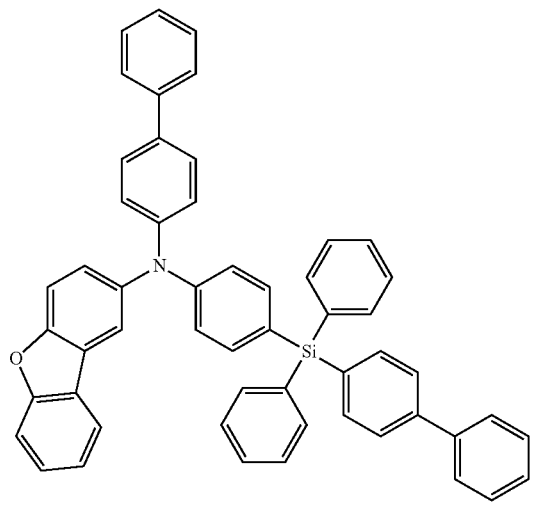
B-5
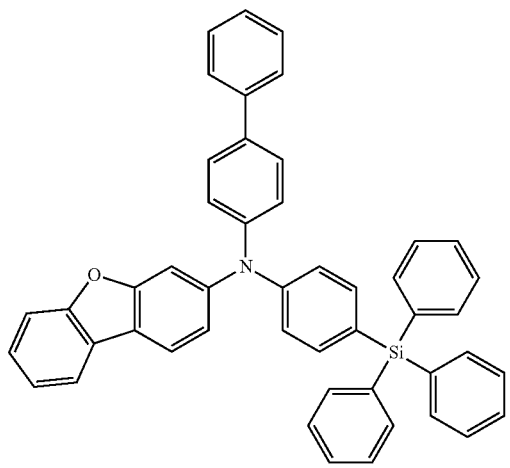
B-6
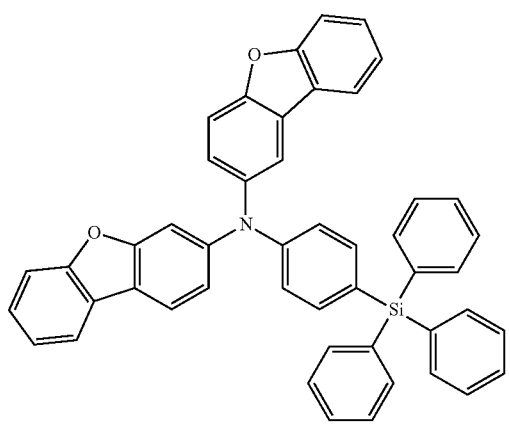
B-7
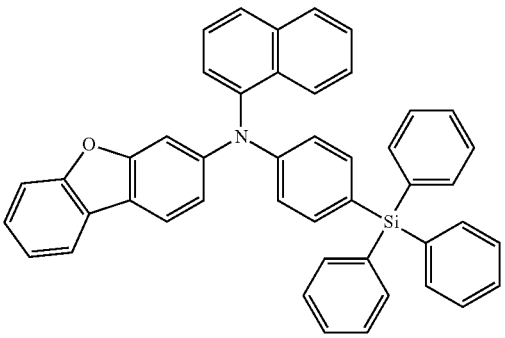
B-8
[Formula 84]
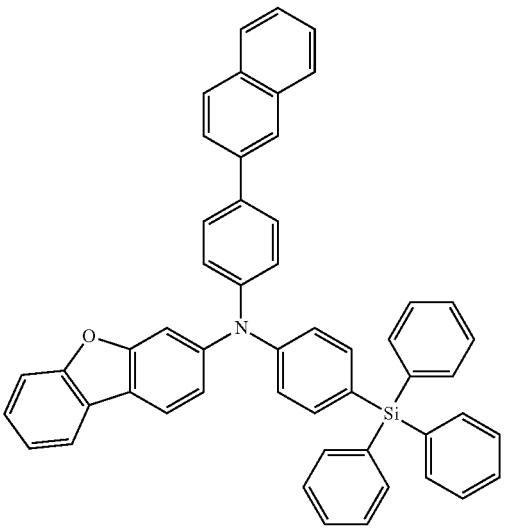
B-9
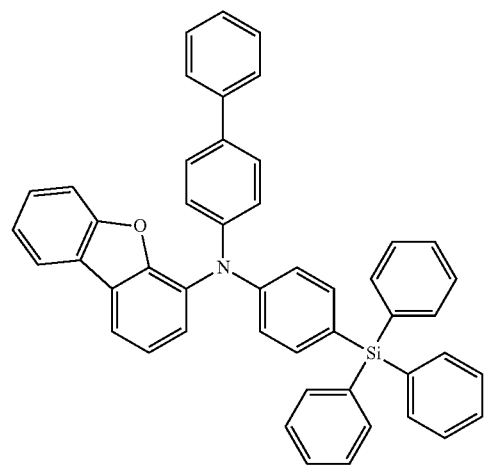
B-10

B-11
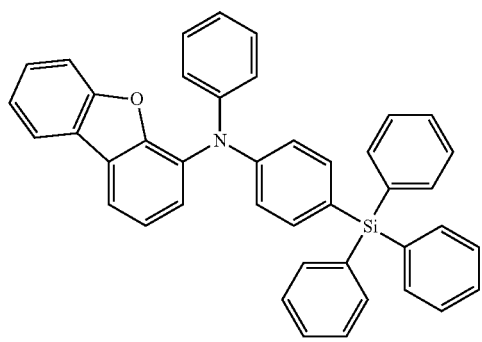
B-12
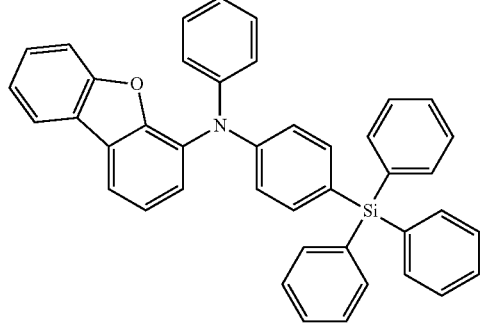
[Formula 85]
B-13
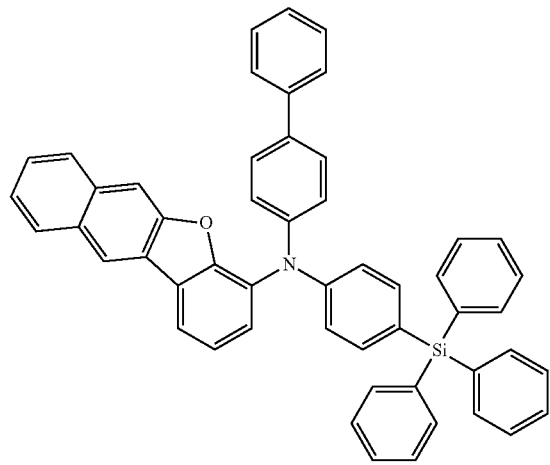
B-14
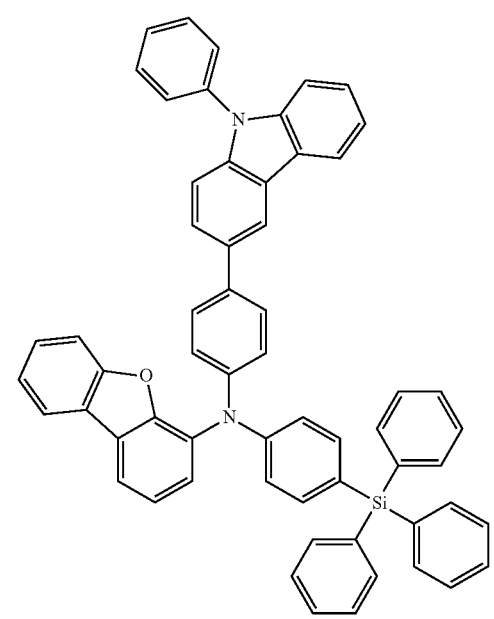
B-15
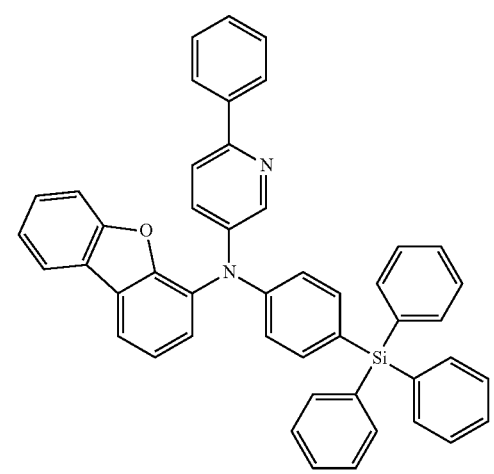
B-16
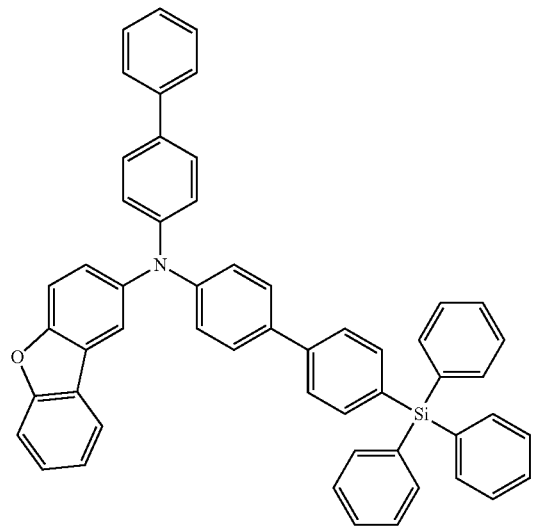

[Formula 86]
B-17
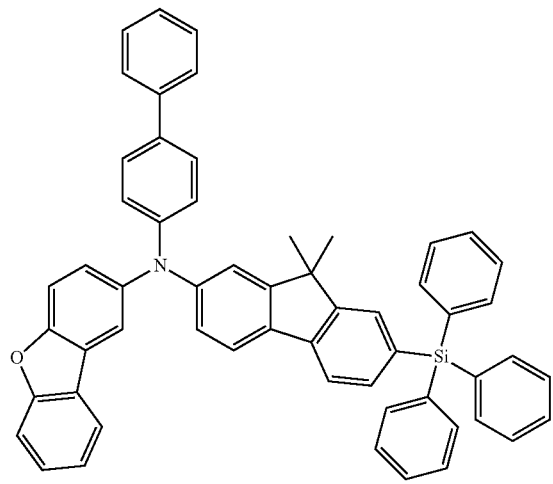
B-18
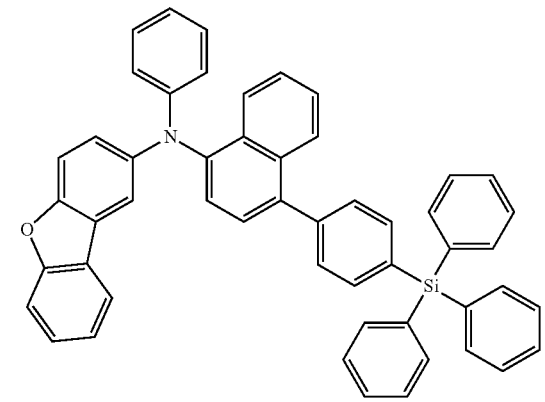
B-19
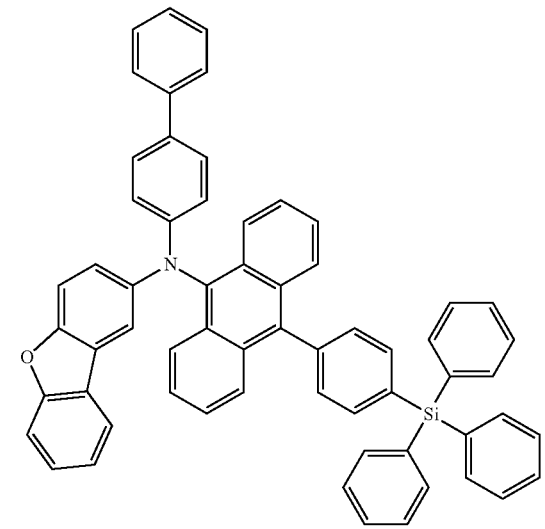
B-20
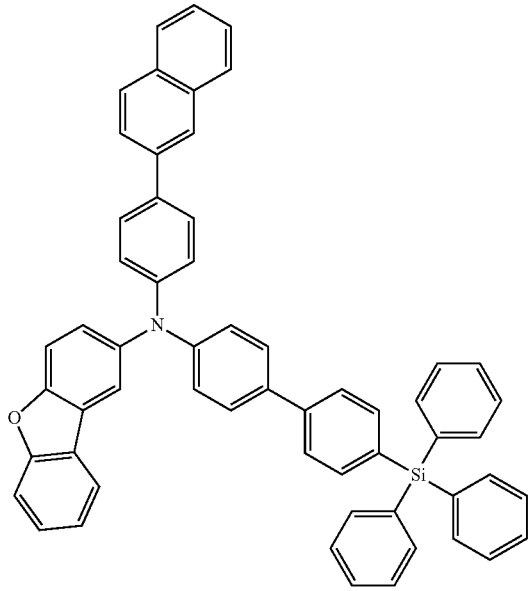
[Formula 87]
B-21
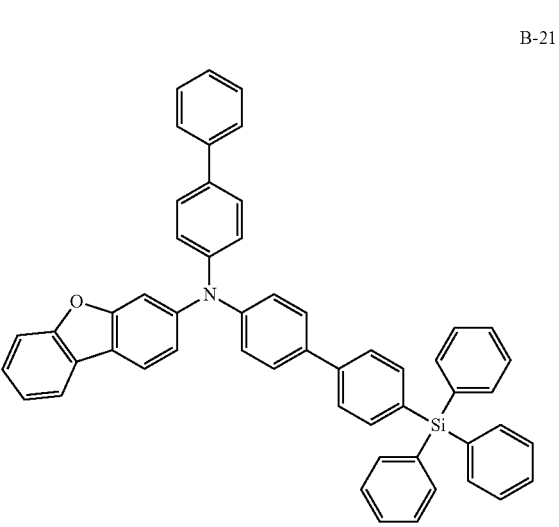

B-22
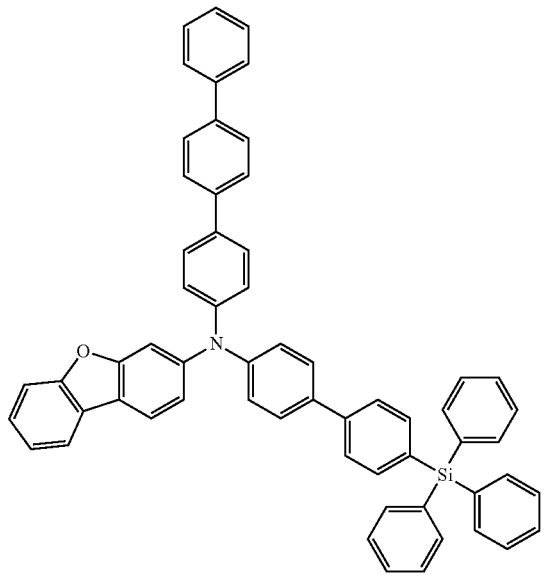
B-23
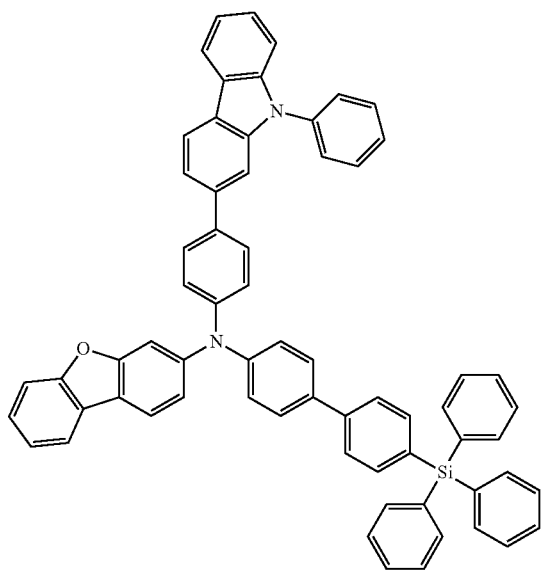
B-24
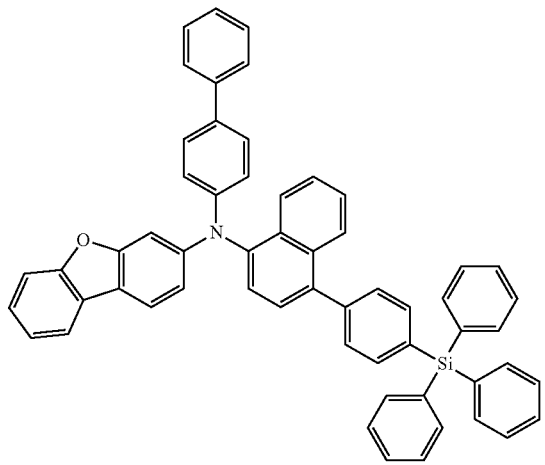
[Formula 88]
B-25
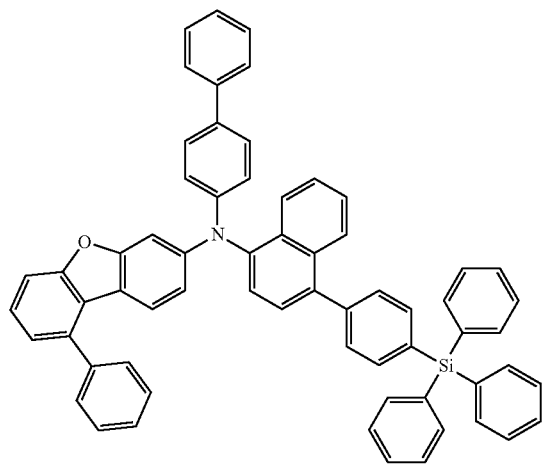
B-26
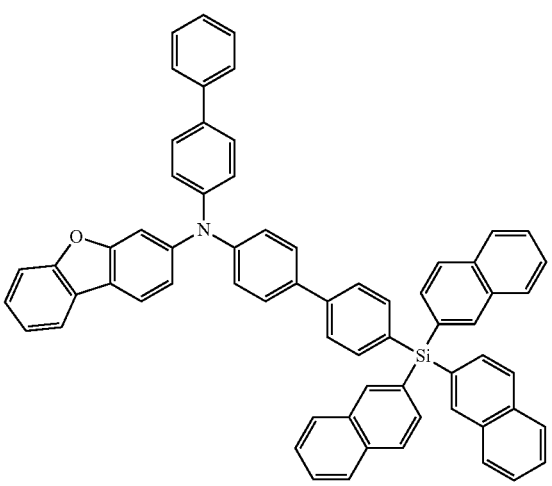
B-27
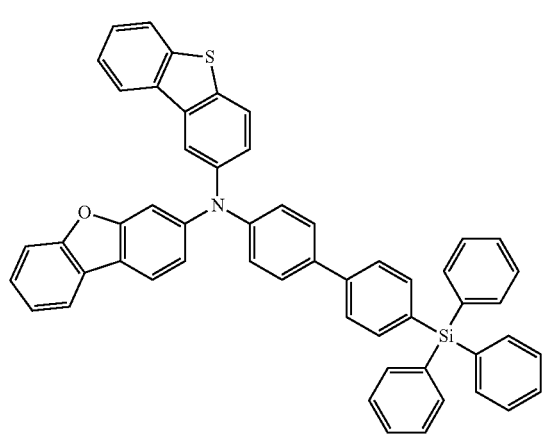

B-28
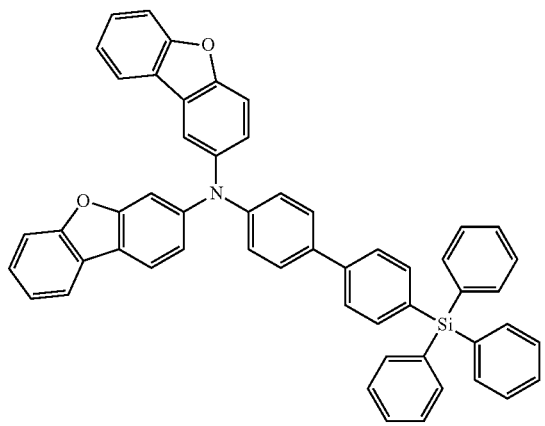
[Formula 89]
B-29
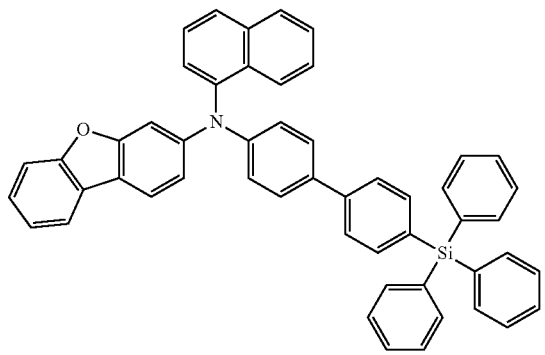
B-30
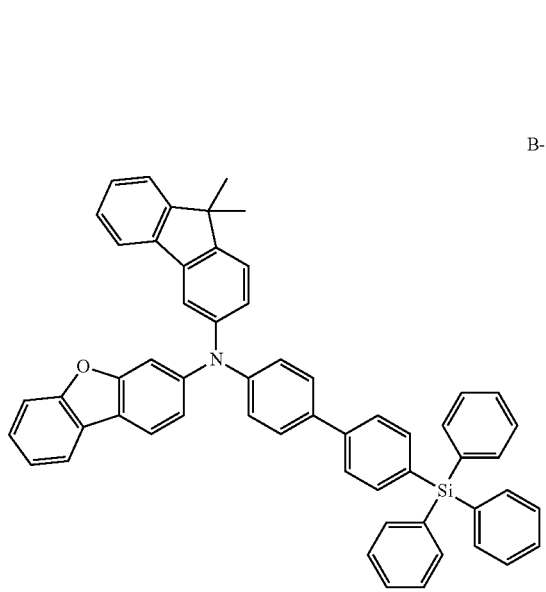
B-31
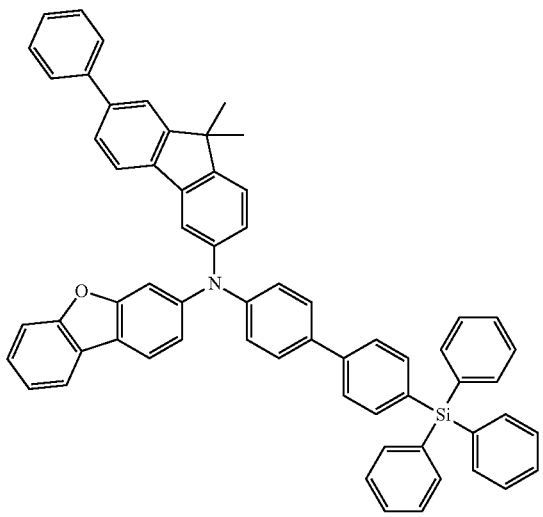
B-32
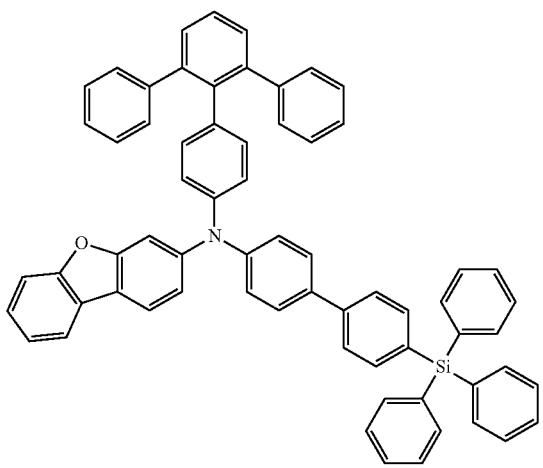
[Formula 90]
B-33
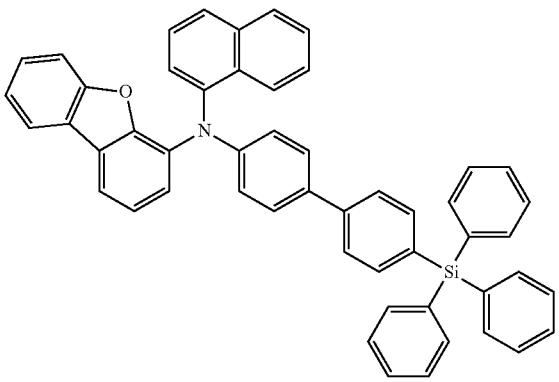

B-34
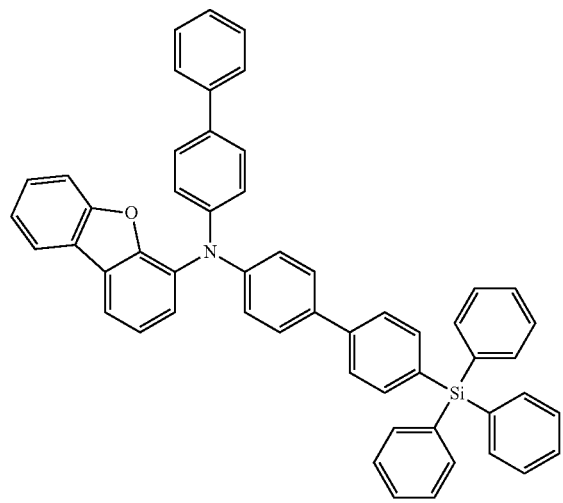
B-35
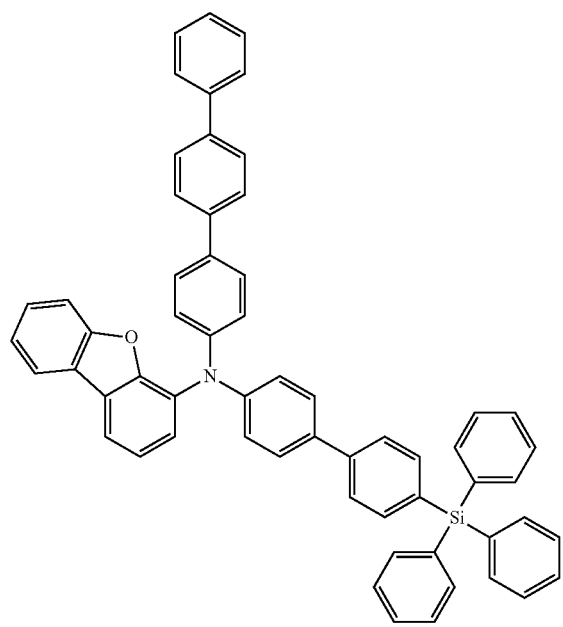
B-36
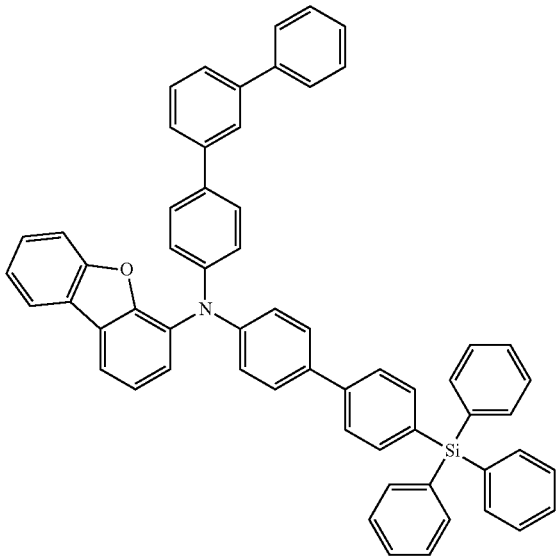
[Formula 91]
B-37
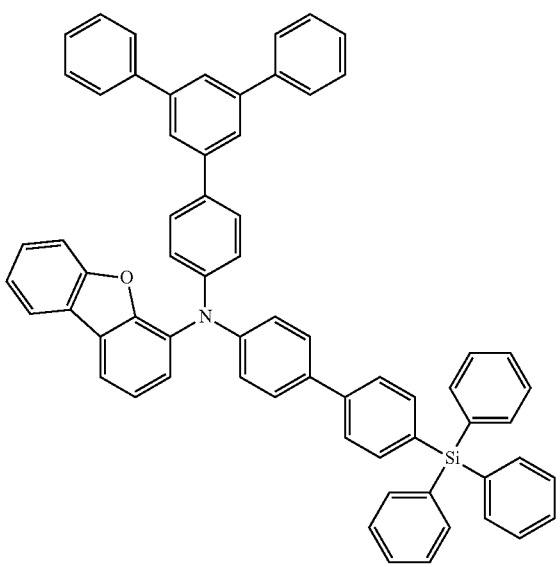

B-38

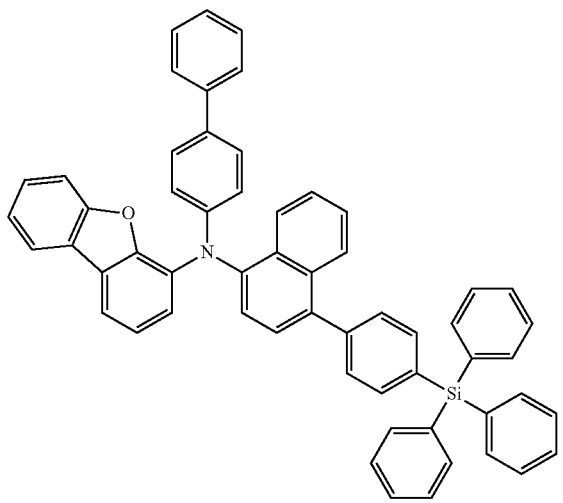

B-39

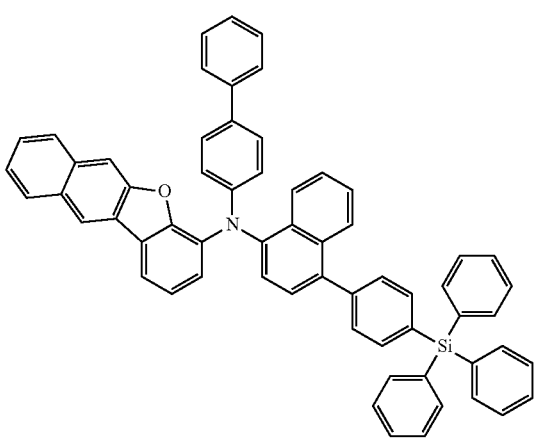

B-40

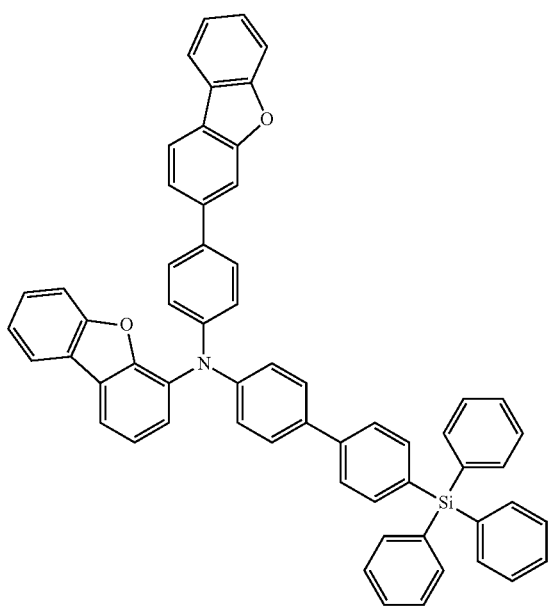

An example amine derivative according to an embodiment, which is an amine derivative in which the dibenzofuryl group for $Ar^3$ is combined with the single bond of L in General Formula (1), may be used as the material of the hole transport layer of the organic electroluminescent device 100 shown in FIG. 1. In addition, the configuration of the organic electroluminescent device 100 shown in FIG. 1 is an illustration of the organic electroluminescent device according to an embodiment without limitation, and may be variously modified.

In addition, the use of an example amine derivative according to an embodiment, which is an amine derivative in which the dibenzofuryl group for $Ar^3$ is combined with the single bond of L in General Formula (1), is not limited to the hole transport material of the organic electroluminescent device; it may be used as the material of the hole injection layer or the material of the emission layer. In the case that the amine derivative is used as the material of the hole injection layer or the material of the emission layer, the emission efficiency of the organic electroluminescent device may be improved, and the long life of the organic electroluminescent device may be realized as the case using the amine derivative as the material of the hole transport layer.

Example III

With respect to an example amine derivative according to an embodiment, represented by General Formula (1), in which the dibenzofuryl group for $Ar^3$ is combined with the single bond of L, examples of synthesizing Compounds B-1, B-16, B-21, B-34 and B-39 will be explained hereinafter. However, the following synthetic methods are only examples, and embodiments are not limited thereto.

(Synthesis of Compound B-1)

Under an argon atmosphere, 1.50 g of Compound (xi), 1.90 g of Compound (x), 0.11 g of Pd(dba)$_2$, 0.15 g of (t-Bu)$_3$P and 0.54 g of sodium t-butoxide were added to a 100 mL three-necked flask, followed by heating and refluxing in 45 mL of a toluene solvent at about 80° C. for about 6 hours. After cooling in the air, water was added to the reaction mixture, an organic layer was separated, and solvents were distilled. The crude product thus obtained was separated by silica gel column chromatography (using a mixture solvent of dichloromethane and hexane) and recrystallized using a mixture solvent of toluene/hexane to produce 2.50 g (yield 88%) of Compound B-1 as a white solid.

[Formula 92]

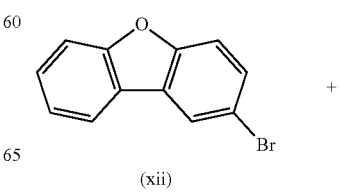

(xii)

-continued

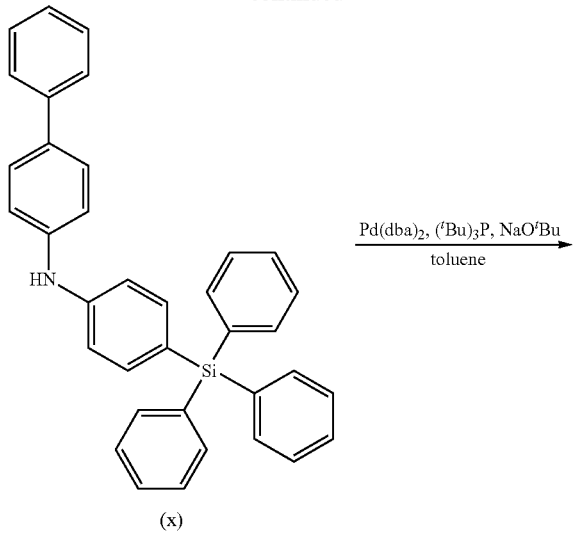

(x)

[Formula 93]

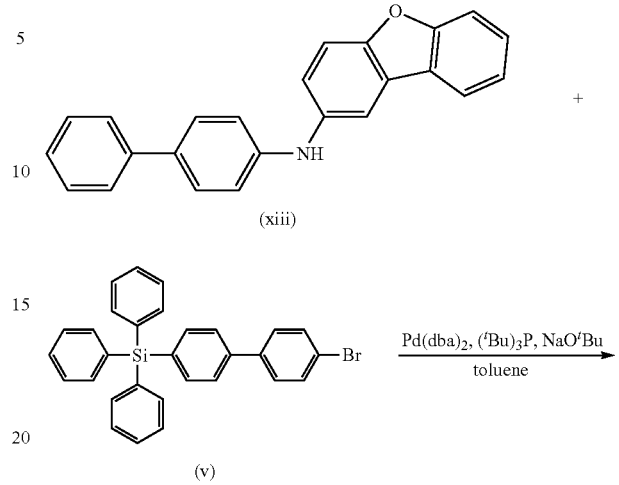

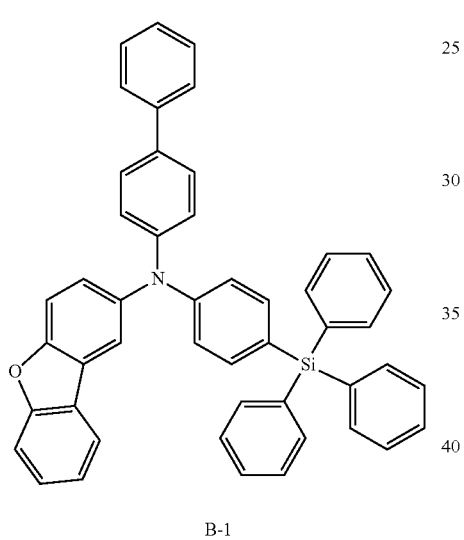

B-1

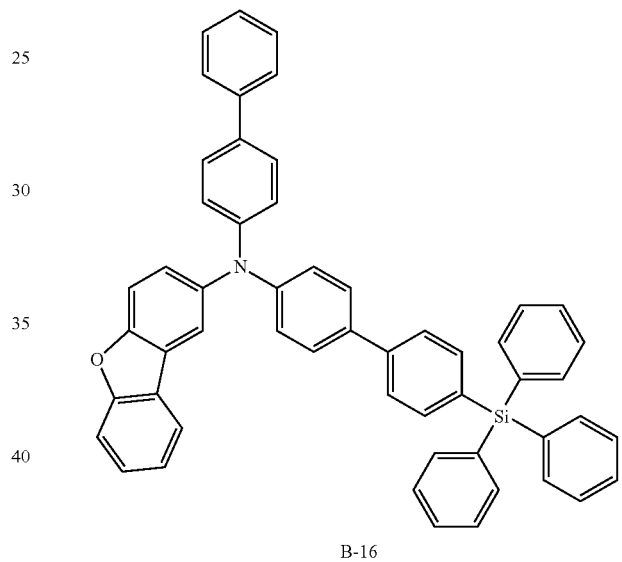

B-16

The chemical shift values of Compound B-1 measured by $^1$H NMR were 7.89 (d, 2H), 7.80 (d, 2H), 7.66-7.51 (m, 14H), 7.50-7.31 (m, 13H), 7.22 (d, 2H), 7.19 (d, 2H). In addition, the molecular weight of Compound B-1 measured by FAB-MS was 669.

(Synthesis of Compound B-16)

Under an argon atmosphere, 2.00 g of Compound (xiii), 3.08 g of Compound (v), 0.31 g of Pd(dba)$_2$, 0.13 g of (t-Bu)$_3$P and 1.15 g of sodium t-butoxide were added to a 100 mL three-necked flask, followed by heating and refluxing in 110 mL of a toluene solvent at about 80° C. for about 8 hours. After cooling in the air, water was added to the reaction mixture, an organic layer was separated, and solvents were distilled. The crude product thus obtained was separated by silica gel column chromatography (using a mixture solvent of dichloromethane and hexane) and recrystallized using a mixture solvent of toluene/hexane to produce 1.42 g (yield 68%) of Compound B-16 as a white solid.

The chemical shift values of Compound B-16 measured by $^1$H NMR were 7.88 (d, 1H), 7.80 (d, 1H), 7.67-7.59 (m, 12H), 7.58-7.51 (m, 6H), 7.50-7.39 (m, 11H), 7.39-7.31 (m, 4H), 7.22-7.19 (m, 4H). In addition, the molecular weight of Compound B-16 measured by FAB-MS was 745.

(Synthesis of Compound B-21)

Under an argon atmosphere, 2.09 g of Compound (vii), 0.94 g of Compound (xiv), 0.18 g of Pd(dba)$_2$, 0.38 g of (t-Bu)$_3$P and 0.74 g of sodium t-butoxide were added to a 100 mL three-necked flask, followed by heating and refluxing in 120 mL of a toluene solvent at about 80° C. for about 7 hours. After cooling in the air, water was added to the reaction mixture, an organic layer was separated, and solvents were distilled. The crude product thus obtained was separated by silica gel column chromatography (using a mixture solvent of dichloromethane and hexane) and recrystallized using a mixture solvent of toluene/hexane to produce 2.29 g (yield 85%) of Compound B-21 as a white solid.

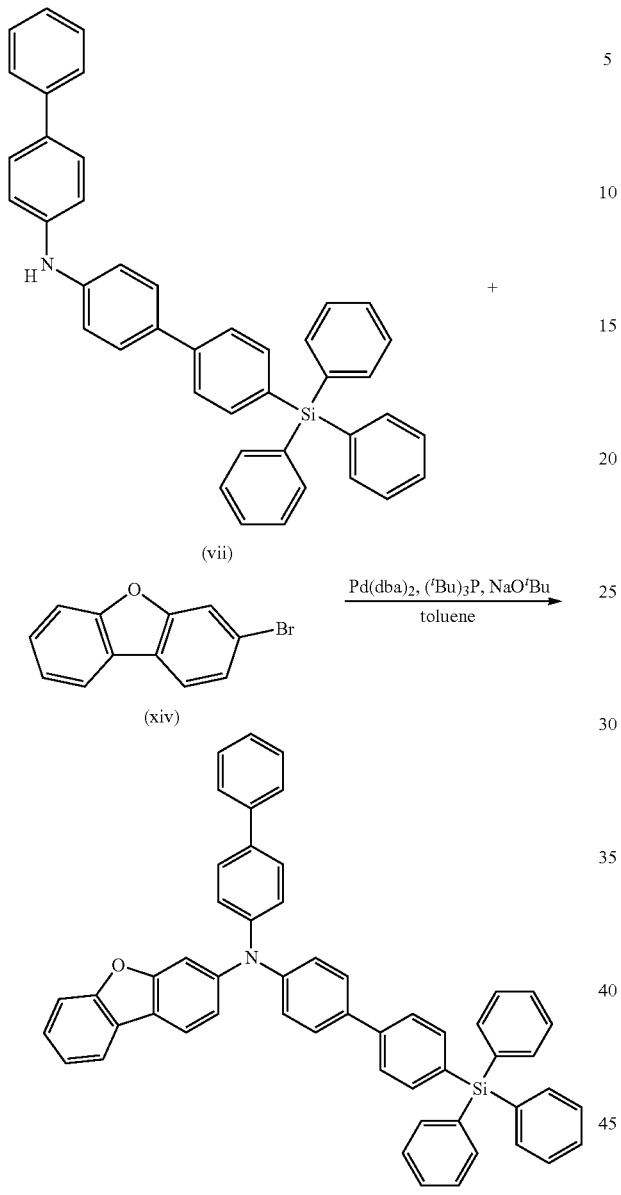

The chemical shift values of Compound B-21 measured by ¹H NMR were 7.88-7.81 (m, 2H), 7.61-7.52 (m, 12H), 7.58-7.51 (m, 6H), 7.50-7.39 (m, 11H), 7.39-7.31 (m, 4H), 7.22-7.19 (m, 4H). In addition, the molecular weight of Compound B-21 measured by FAB-MS was 745.

(Synthesis of Compound B-34)

Under an argon atmosphere, 1.11 g of Compound (vii), 0.47 g of Compound (xv), 0.10 g of Pd(dba)$_2$, 0.19 g of (t-Bu)$_3$P and 0.37 g of sodium t-butoxide were added to a 100 mL three-necked flask, followed by heating and refluxing in 60 mL of a toluene solvent at about 80° C. for about 7 hours. After cooling in the air, water was added to the reaction mixture, an organic layer was separated, and solvents were distilled. The crude product thus obtained was separated by silica gel column chromatography (using a mixture solvent of dichloromethane and hexane) and recrystallized using a mixture solvent of toluene/hexane to produce 0.98 g (yield 69%) of Compound B-34 as a white solid.

The chemical shift values of Compound B-34 measured by ¹H NMR were 7.88-7.81 (m, 2H), 7.61-7.52 (m, 12H), 7.58-7.51 (m, 6H), 7.50-7.39 (m, 11H), 7.39-7.31 (m, 4H), 7.22-7.19 (m, 4H). In addition, the molecular weight of Compound B-34 measured by FAB-MS was 745.

(Synthesis of Compound B-39)

Under an argon atmosphere, 1.50 g of Compound (xvi), 0.59 g of Compound (xv), 0.11 g of Pd(dba)$_2$, 0.15 g of (t-Bu)$_3$P and 0.54 g of sodium t-butoxide were added to a 100 mL three-necked flask, followed by heating and refluxing in 45 mL of a toluene solvent at about 80° C. for about 7 hours. After cooling in the air, water was added to the reaction mixture, an organic layer was separated, and solvents were distilled. The crude product thus obtained was separated by silica gel column chromatography (using a mixture solvent of dichloromethane and hexane) and recrystallized using a mixture solvent of toluene/hexane to produce 1.36 g (yield 72%) of Compound B-39 as a white solid.

[Formula 96]

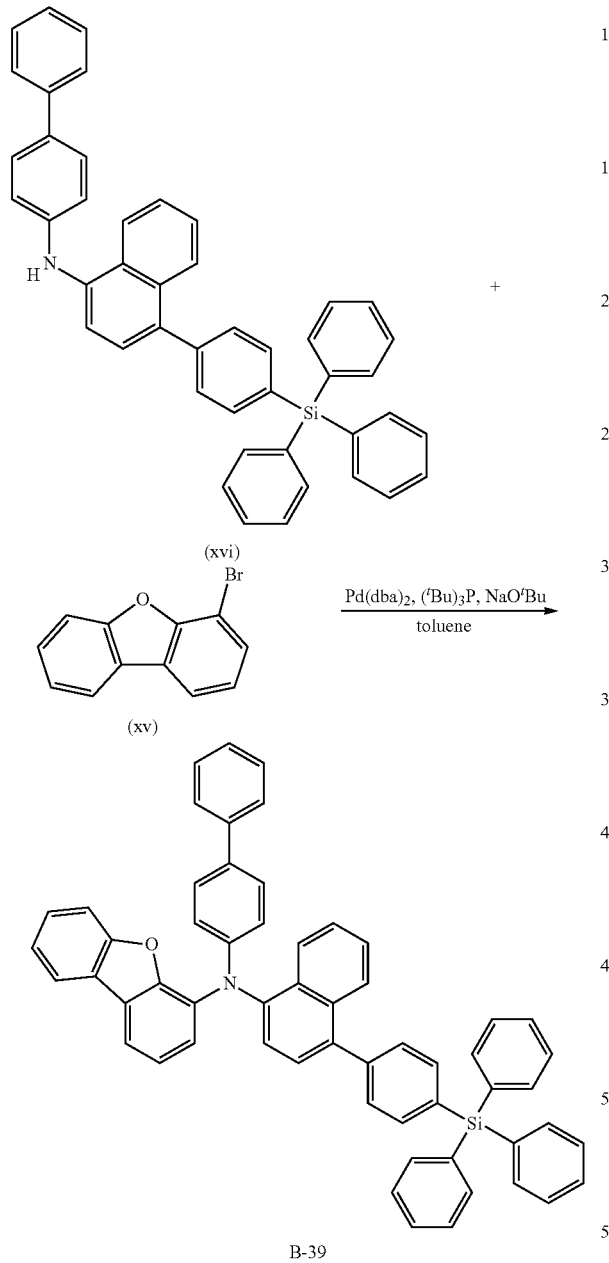

The chemical shift values of Compound B-39 measured by $^1$H NMR were 8.49 (d, 2H), 8.16 (d, 2H), 7.81 (d, 2H), 7.78-7.55 (m, 12H), 749-7.33 (m, 16H), 7.32-7.25 (m, 5H), 7.13 (d, 2H). In addition, the molecular weight of Compound B-39 measured by FAB-MS was 795.

Hereinafter, organic electroluminescent devices using the above described Compounds B-1, B-16, B-21, B-34 and B-39 as the materials for the organic electroluminescent device according to an embodiment in a hole transport layer will be explained. An organic electroluminescent device using Compound B-1 in the hole transport layer corresponds to Example 10, an organic electroluminescent device using Compound B-16 in the hole transport layer corresponds to Example 11, an organic electroluminescent device using Compound B-21 in the hole transport layer corresponds to Example 12, an organic electroluminescent device using Compound B-34 in the hole transport layer corresponds to Example 13 and an organic electroluminescent device using Compound B-39 in the hole transport layer corresponds to Example 14.

The manufacture of the organic electroluminescent device according to Example 10 according to an embodiment was conducted by a vacuum deposition as for the organic electroluminescent device of Example 1 and the following procedure. First, with respect to an ITO-glass substrate patterned and washed in advance, surface treatment using ozone was conducted. In addition, the layer thickness of an ITO layer was about 150 nm. Immediately after the ozone treatment, a layer was formed using 2-TNATA as a hole injection material (thickness of about 60 nm) on the ITO layer.

Then, a layer was formed using Compound B-1 according to an embodiment as a hole transport material (about 30 nm), and a layer of ADN doped with TBP in a ratio of about 3% was formed by a co-deposition (about 25 nm).

After that, a layer was formed using Alq$_3$ as an electron transport material (about 25 nm), and LiF (about 1.0 nm) as an electron injection layer and aluminum (about 100 nm) as a cathode were laminated one by one to manufacture the organic electroluminescent device 200 shown in FIG. 2.

As Examples 11, 12, 13 and 14, organic electroluminescent devices were manufactured by performing the same procedure described in Example 10 except for using Compound B-16, Compound B-21, Compound B-34 and Compound B-39 instead of Compound B-1 used in Example 10.

As Comparative Examples 6 and 7, organic electroluminescent devices were manufactured by performing the same procedure described in Example 10 except for using Comparative Compounds 6 and 7 represented in the following as compounds constituting hole transport materials of organic electroluminescent devices.

[Formula 97]

Comparative Compound 6

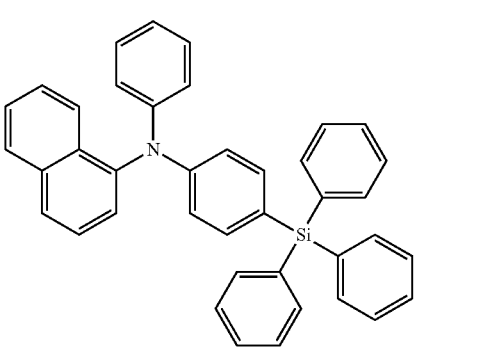

-continued

Comparative Compound 7

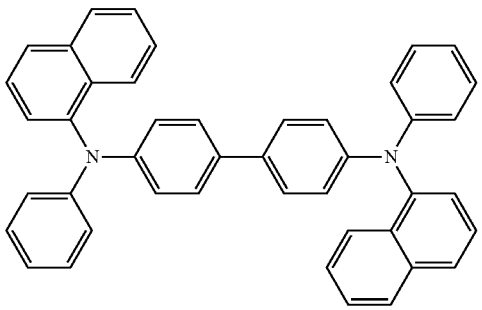

The driving voltage, the emission efficiency and the half life of the organic electroluminescent devices 200 manufactured in Examples 10 to 14 and Comparative Examples 6 and 7 were evaluated. In addition, emission efficiency means values at about 10 mA/cm$^2$, and half life means luminance decrease time to half from an initial luminance of about 1,000 cd/m$^2$. The evaluation results are shown in Table 3.

TABLE 3

| | Hole transport material | Voltage (V) | Current efficiency (cd/A) | Half life (hr) |
|---|---|---|---|---|
| Example 10 | Compound B-1 | 6.5 | 6.6 | 2,000 |
| Example 11 | Compound B-16 | 6.4 | 6.9 | 2,100 |
| Example 12 | Compound B-21 | 6.3 | 6.9 | 3,300 |
| Example 13 | Compound B-34 | 6.3 | 6.8 | 2,900 |
| Example 14 | Compound B-39 | 6.6 | 6.8 | 1,800 |
| Comparative Example 6 | Comparative Compound 6 | 8.1 | 6.3 | 1,200 |
| Comparative Example 7 | Comparative Compound 7 | 8.1 | 5.3 | 1,200 |

According to Table 3, the organic electroluminescent devices of Examples 10 to 14 have decreased driving voltage, improved emission efficiency and longer life than the organic electroluminescent devices of Comparative Examples 6 and 7. For example, it can be seen that the decrease of the driving voltage and the improvement of the emission efficiency and the life of Example 12 using Compound B-21 having the configuration of combining the substituted or unsubstituted dibenzofuryl group for Ar$^3$ with the nitrogen atom (N) at the amine part at position 3 in an example amine derivative according to an embodiment, were marked.

In the above-described Examples 10 to 14, an example amine derivative according to an embodiment, in which the substituted or unsubstituted dibenzofuryl group for Ar$^3$ was combined with L of the single bond in General Formula (1), was used as the hole transport material of the organic electroluminescent device as an embodiment, however, the use of the amine derivative according to an embodiment is not limited to the organic electroluminescent device, and is expanded to other luminescent devices or luminescent apparatus. In addition, the organic electroluminescent device using an example amine derivative according to an embodiment, in which the substituted or unsubstituted dibenzofuryl group for Ar$^3$ is combined with the single bond of L in General Formula (1) may be used in an organic electroluminescent display of a passive-matrix driving type, and they may be also used in an organic electroluminescent display of an active-matrix driving type.

Remarkable improvement of the emission efficiency, the driving voltage and the life of an organic electroluminescent device may be obtained by disposing the amine derivative represented by General Formula (1), particularly, an amine derivative having the following structure as a material for an organic electroluminescent device between an emission layer and an anode.

In an example structure of the amine derivative represented by General Formula (1), Ar$^1$ and Ar$^2$ are independently a substituted or unsubstituted aryl group or a substituted or unsubstituted heteroaryl group, at least one of Ar$^1$ and Ar$^2$ is substituted with a substituted or unsubstituted silyl group, Ar$^3$ is a substituted or unsubstituted fluorenyl group, and L is a substituted or unsubstituted arylene group or a substituted or unsubstituted heteroarylene group.

Here, as the aryl group and the heteroaryl group of "the substituted or unsubstituted aryl group" or "the substituted or unsubstituted heteroaryl group" of Ar$^1$ and Ar$^2$, as described above, a phenyl group, a naphthyl group, an anthracenyl group, a phenanthryl group, a biphenyl group, a terphenyl group, a fluorenyl group, a triphenylene group, a biphenylene group, a pyrenyl group, a benzothiazolyl group, a thiophenyl group, a thienothiophenyl group, a thienothienothiophenyl group, a benzothiophenyl group, a dibenzothiophenyl group, a dibenzofuryl group, a N-arylcarbazolyl group, a N-heteroarylcarbazolyl group, a N-alkylcarbazolyl group, a phenoxazyl group, a phenothiazyl group, a pyridyl group, a pyrimidyl group, a triazinyl group, a quinolinyl group, and a quinoxalyl group are examples. The phenyl group, the naphthyl group, the biphenyl group, the terphenyl group, the fluorenyl group, the triphenylene group, the dibenzothiophenyl group, the dibenzofuryl group and the N-phenylcarbazolyl group may be used. As the aryl group, an aryl group having 6 to 18 carbon atoms for forming a ring may be used, and as the heteroaryl group, a heteroaryl group having 5 to 18 carbon atoms for forming a ring may be used.

As the substituent of the aryl group or the heteroaryl group of Ar$^1$ and Ar$^2$, an alkyl group, an alkoxy group, an aryl group and a heteroaryl group are examples. Examples of the aryl group and the heteroaryl group are the same as the above exemplified aryl group and the heteroaryl group of Ar$^1$ and Ar$^2$. The alkyl group of the substituent of the aryl group or the heteroaryl group of Ar$^1$ and Ar$^2$ is not specifically limited and may include a methyl group, an ethyl group, a propyl group, an isopropyl group, a cyclopropyl group, a butyl group, an isobutyl group, a t-butyl group, a cyclobutyl group, a pentyl group, an isopentyl group, a neopentyl group, a cyclopentyl group, a hexyl group, a cyclohexyl group, a heptyl group, a cycloheptyl group, an octyl group, a nonyl group, a decyl group, etc. In addition, the alkoxy group of the substituent of the aryl group or the heteroaryl group of Ar$^1$ and Ar$^2$ is not specifically limited and may include a methoxy group, an ethoxy group, a n-propoxy group, an isopropoxy group, a n-butoxy group, an isobutoxy group, a t-butoxy group, a n-pentyloxy group, a neopentyloxy group, a n-hexyloxy group, a n-heptyloxy group, a n-octyloxy group, a 2-ethylhexyloxy group, a nonyloxy group, a decyloxy group, a 3,7-dimethyloctyloxy group, etc.

As the substituent of the silyl group for at least one of Ar$^1$ and Ar$^2$, an alkyl group, an alkoxy group, an aryl group and a heteroaryl group are examples. For example, the same alkyl group, alkoxy group, aryl group and heteroaryl group explained as the substituent of the aryl group or the heteroaryl group of Ar$^1$ and Ar$^2$ may be used, and, for example, a phenyl group and a methyl group may be used. In addition, as the silyl group substituted for at least one of Ar$^1$ and Ar$^2$ may be a triarylsilyl group where an aryl substituent at the silyl group has 6 to 18 carbon atoms for forming a ring or a trialkylsilyl group where an alkyl substituent at the silyl group has 1 to 6 carbon atoms.

In addition, in an example amine derivative according to an embodiment, only one of $Ar^1$ and $Ar^2$ may be substituted with the substituted or unsubstituted silyl group. Since only one of $Ar^1$ and $Ar^2$ may be substituted with the substituted or unsubstituted silyl group, the localization of the lowest unoccupied molecular orbital (LUMO) around amine may be restrained, and the decrease of energy gap may be prevented.

In an example structure of the amine derivative according to an embodiment, $Ar^3$ is a substituted or unsubstituted fluorenyl group. Each substituent of the fluorenyl group is independently a hydrogen atom, a substituted or unsubstituted aryl group having 6 to 18 carbon atoms for forming a ring, a substituted or unsubstituted heteroaryl group having 5 to 18 carbon atoms for forming a ring, or a substituted or unsubstituted alkyl group having 1 to 10 carbon atoms. The substituent of the fluorenyl group may be the substituted or unsubstituted aryl group and may for example be a phenyl group at position 9.

In an example structure of the amine derivative, L is a substituted or unsubstituted arylene group or a substituted or unsubstituted heteroarylene group. Here, as the aryl group and the heteroarylene group of "the substituted or unsubstituted arylene group" and "the substituted or unsubstituted heteroarylene group" of L may be the same aryl group and the heteroaryl group of "the substituted or unsubstituted aryl group" or "the substituted or unsubstituted heteroaryl group" exemplified for $Ar^1$ and $Ar^2$. As the arylene group and the heteroarylene group of "the substituted or unsubstituted arylene group" and "the substituted or unsubstituted heteroarylene group" of L, an aryl group having 6 to 18 carbon atoms for forming a ring and a heteroarylene group having 5 to 18 carbon atoms for forming a ring may be used. A phenylene group and a biphenylene group may be used. In addition, the substituted or unsubstituted fluorenyl group for $Ar^3$ may be combined at position 2 with L at para position with respect to the nitrogen atom (N) around an amine part. Through the combination of the fluorenyl group with L at position 2, appropriate levels of HOMO and LUMO may be realized.

In an example amine derivative according to an embodiment, $Ar^3$ is the substituted or unsubstituted fluorenyl group, and L is the substituted or unsubstituted arylene group or the substituted or unsubstituted heteroarylene group. Through the bonding of the substituted or unsubstituted fluorenyl group for $Ar^3$ with the nitrogen atom (N) at the amine part combined with $Ar^1$ and $Ar^2$, at least one of which is substituted with a silyl group, via the substituted or unsubstituted arylene group or the substituted or unsubstituted heteroarylene group of L, the conjugation system of π electrons may be enlarged, and hole transport properties and the stability of a molecule may be improved. In addition, by introducing the fluorenyl group, the substituted or unsubstituted arylene group or the substituted or unsubstituted heteroarylene group of the connecting group L may be planarized, thereby improving the hole transport properties of the amine derivative. Through using the amine derivative according to an embodiment as the material of a hole transport layer disposed between an emission layer and an anode, the improvement of the emission efficiency, the decrease of the driving voltage and the increase of the life of the organic electroluminescent device may be realized. For example, the improvement of the emission efficiency, the decrease of the driving voltage and the increase of the life of the organic electroluminescent device may be realized in a blue-bluish green region.

As an example amine derivative according to an embodiment, in which the substituted or unsubstituted fluorenyl group for $Ar^3$ is combined with the substituted or unsubstituted arylene group or the substituted or unsubstituted heteroarylene group of L in General Formula (1), the following compounds are examples, without limitation.

[Formula 98]

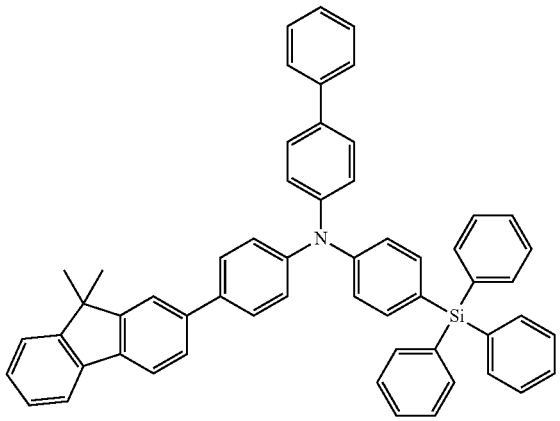

C-1

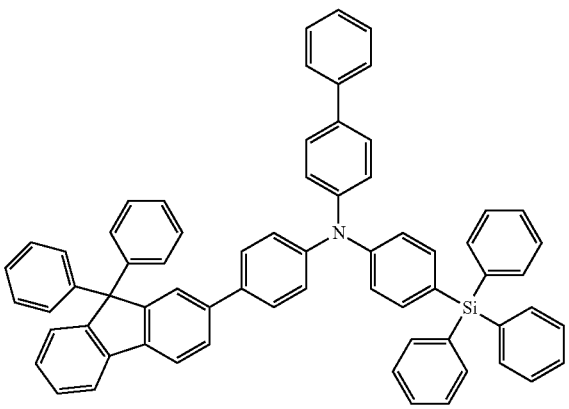

C-2

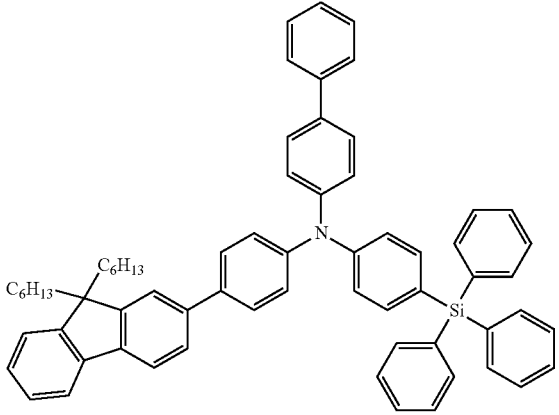

C-3

C-4
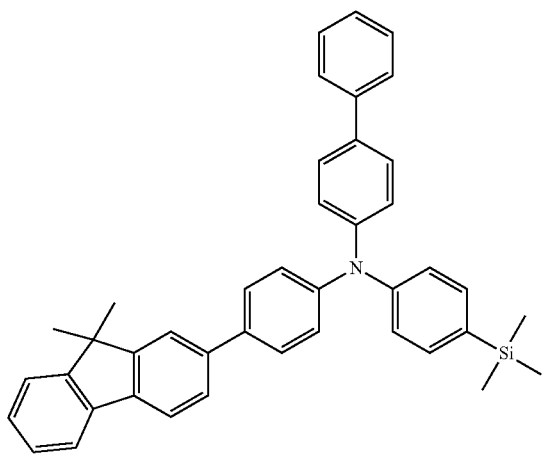
[Formula 99]
C-5
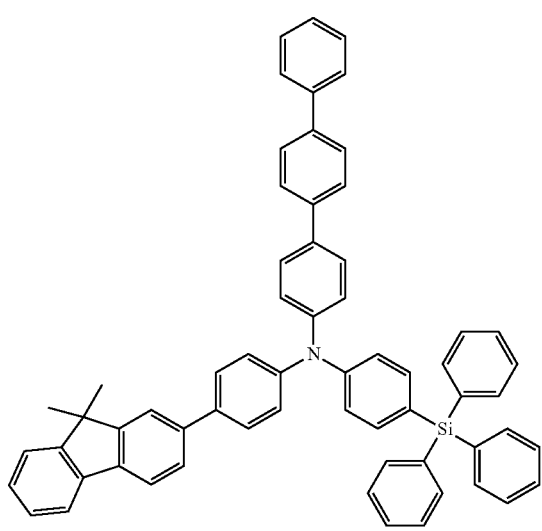
C-6
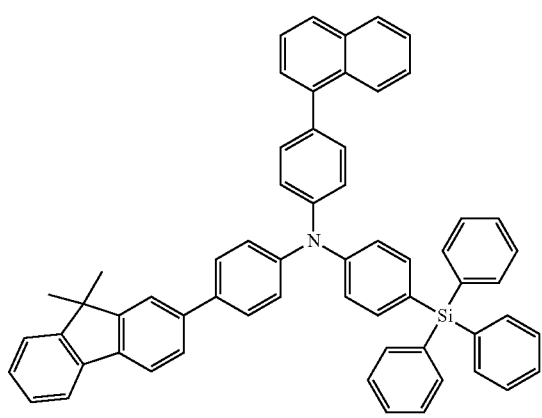
C-7
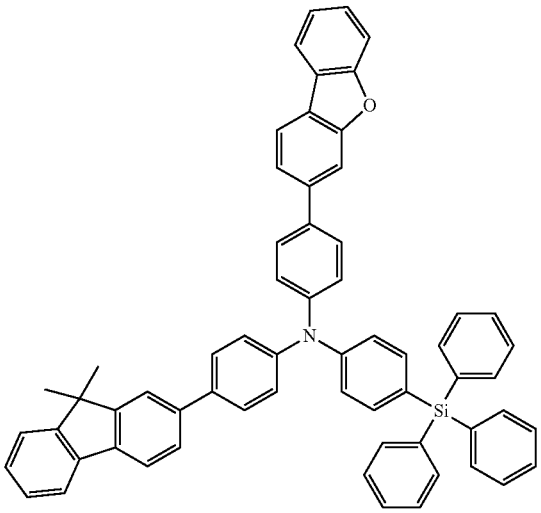
C-8
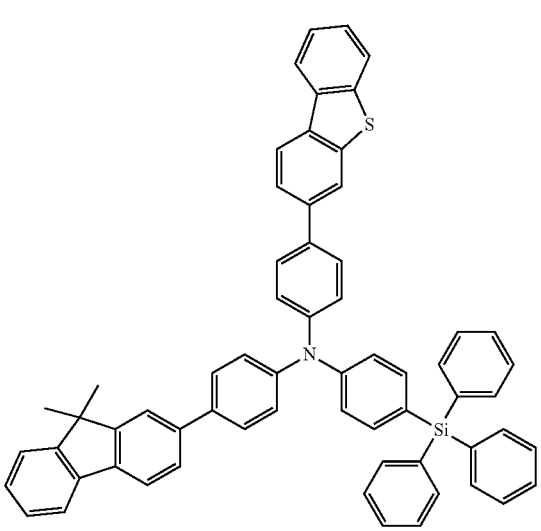
[Formula 100]
C-9
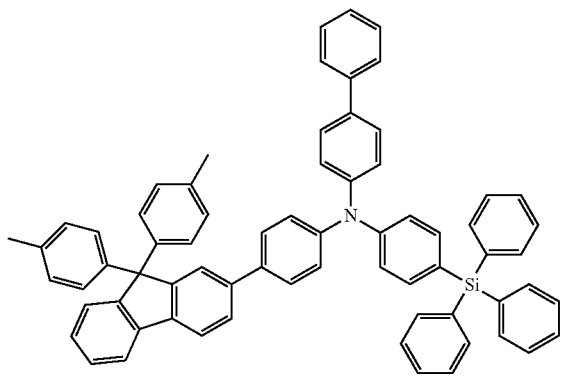

C-10
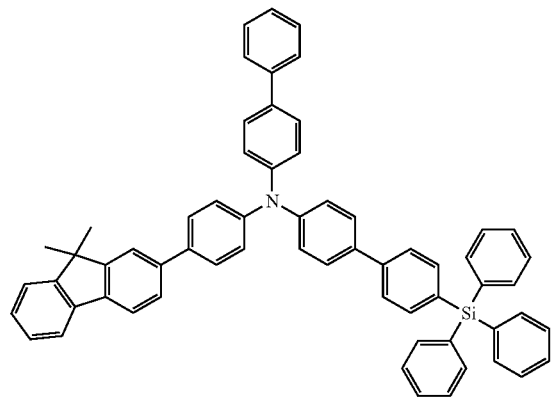
C-11
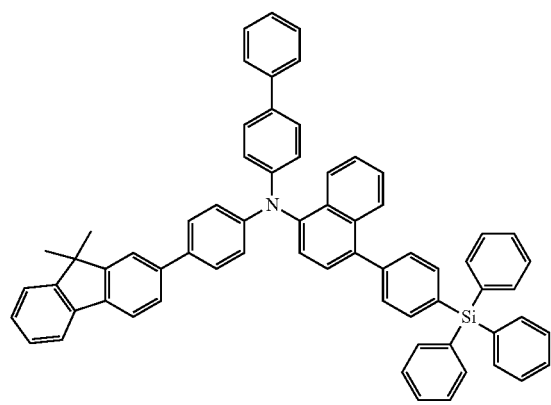
C-12
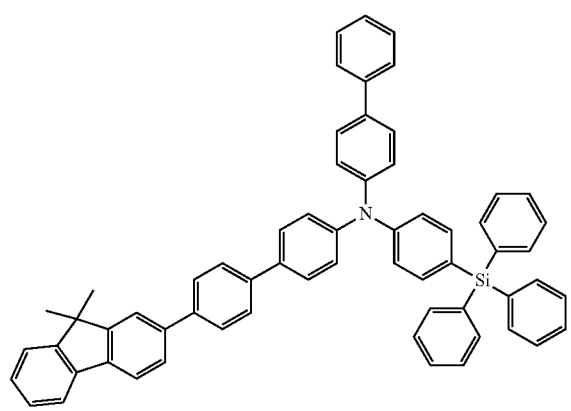
[Formula 101]
C-13
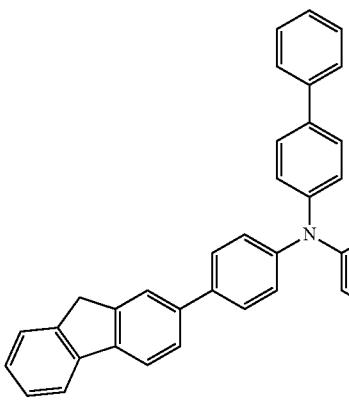
C-14
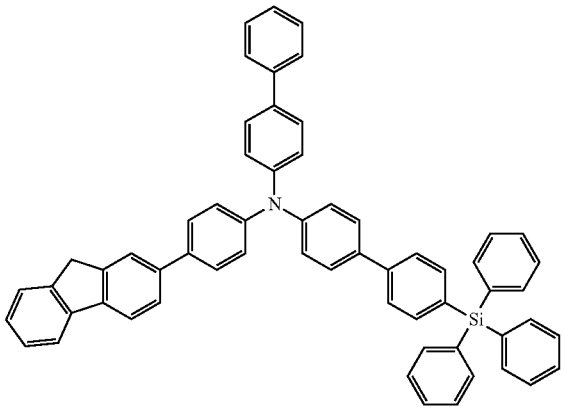
C-15
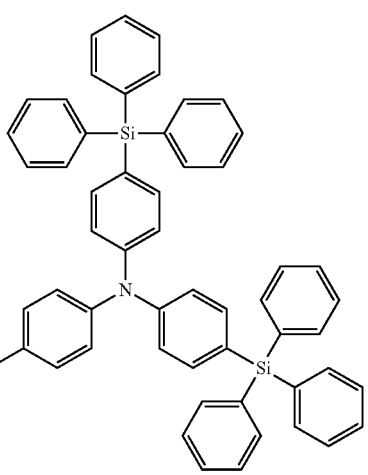

C-16

[Formula 102]

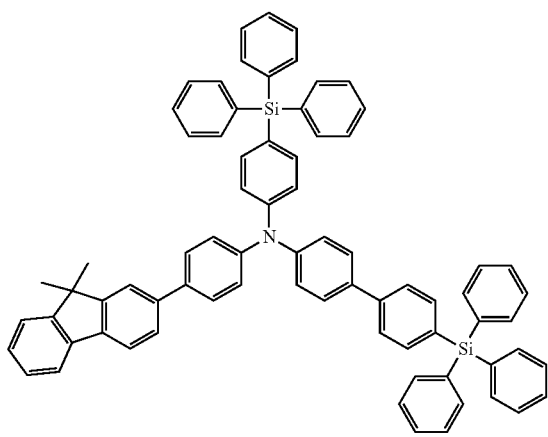

C-17

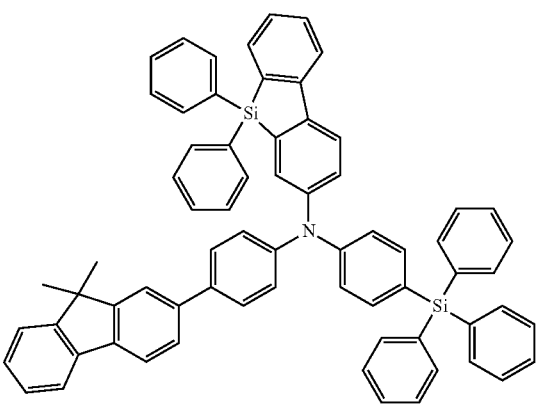

An example amine derivative according to an embodiment, which is an amine derivative in which the substituted or unsubstituted fluorenyl group for $Ar^3$ is combined with the substituted or unsubstituted arylene group or the substituted or unsubstituted heteroarylene group of L in General Formula (1), may be used as the material of the hole transport layer of the organic electroluminescent device 100 shown in FIG. 1. In addition, the configuration of the organic electroluminescent device 100 shown in FIG. 1 is an illustration of the organic electroluminescent device according to an embodiment without limitation, and may be variously modified.

In addition, the use of an example amine derivative according to an example embodiment, which is an amine derivative in which the fluorenyl group for $Ar^3$ is combined with the substituted or unsubstituted arylene group or the substituted or unsubstituted heteroarylene group of L in General Formula (1), is not limited to the hole transport material of the organic electroluminescent device; it may be used as the material of the hole injection layer or the material of the emission layer. In the case that the amine derivative is used as the material of the hole injection layer or the material of the emission layer, the emission efficiency of the organic electroluminescent device may be improved, and the long life of the organic electroluminescent device may be realized as the case using the amine derivative as the material of the hole transport layer.

Example IV

With respect to an example amine derivative according to an embodiment, represented by General Formula (1), in which the fluorenyl group for $Ar^3$ is combined with the substituted or unsubstituted arylene group or the substituted or unsubstituted heteroarylene group of L, examples of synthesizing Compound C-1, Compound C-2, Compound C-4 and Compound C-6 will be explained hereinafter. However, the following synthetic methods are only examples, and embodiments are not limited thereto.

(Synthesis of Compound C-1)

First, under an argon atmosphere, 7.0 g of 4-bromotetraphenylsilane, 0.241 g of copper(I) oxide, 34.16 mL of N-methylpyrrolidone and 11.40 mL of a 28% aqueous ammonia solution were added to a 300 mL Schlenk flask, followed by heating and stirring at about 40° C. for about 10 minutes. Then, the temperature was elevated to about 80° C., followed by heating and stirring for 12 hours. Water was added to the reaction mixture, and extraction with ethyl acetate was conducted. The solvent was distilled under a reduced pressure, and the residue thus obtained was separated by silica gel column chromatography to produce 5.8 g of Compound (xvii).

[Formula 103]

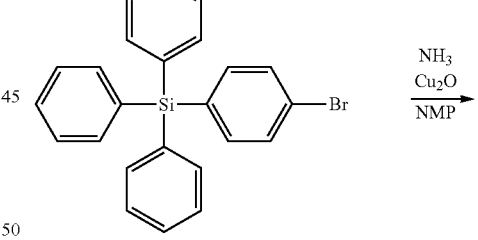

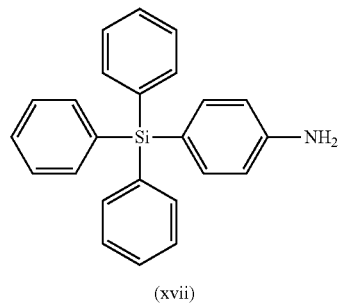

(xvii)

Then, under an argon atmosphere, 4.0 g of Compound (xvii), 2.65 g of 4-bromobiphenyl, 0.59 g of Pd$_2$(dba)$_3$·CHCl$_3$, 0.46 g of (t-Bu)$_3$P and 2.19 g of sodium t-butoxide were added to a 200 mL three-necked flask, followed by heating and stirring in 120 mL of a toluene solvent at about 80° C. for about 3 hours. The reaction mixture was extracted with toluene, and an organic layer was distilled under a reduced pressure. The residue thus obtained was separated by silica gel column chromatography to produce 5.34 g of Compound (x).

[Formula 104]

In addition, under an argon atmosphere, 2.65 g of 9,9-dimethylfluorene-2-boronic acid, 3.0 g of 4-bromoiodobenzene, 21.6 mL of toluene, 10.6 mL of ethanol, 10.6 mL of a 2 M sodium carbonate aqueous solution and 0.193 g of tetrakis(triphenylphosphine)palladium(0) were added to a 100 mL four-necked flask, followed by heating and stirring at about 80° C. for about 3 hours. The reaction mixture was extracted with toluene, and an organic layer was distilled under a reduced pressure. The residue thus obtained was separated by silica gel column chromatography to produce 3.3 g of Compound (xviii).

[Formula 105]

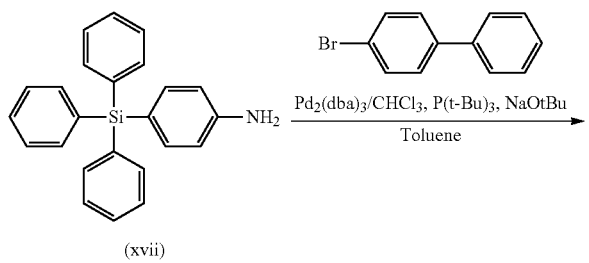

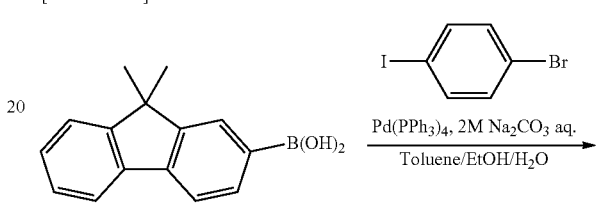

After that, under an argon atmosphere, 1.04 g of Compound (xviii), 1.50 g of Compound (x), 0.15 g of Pd$_2$(dba)$_3$·CHCl$_3$, 0.12 g of (t-Bu)$_3$P and 0.57 g of sodium t-butoxide were added to a 100 mL three-necked flask, followed by heating and stirring in 30 mL of a toluene solvent at about 80° C. for about 3 hours. The reaction mixture was extracted with toluene, and an organic layer was distilled under a reduced pressure. The residue thus obtained was separated by silica gel column chromatography to produce 2.10 g of Compound C-1.

[Formula 106]

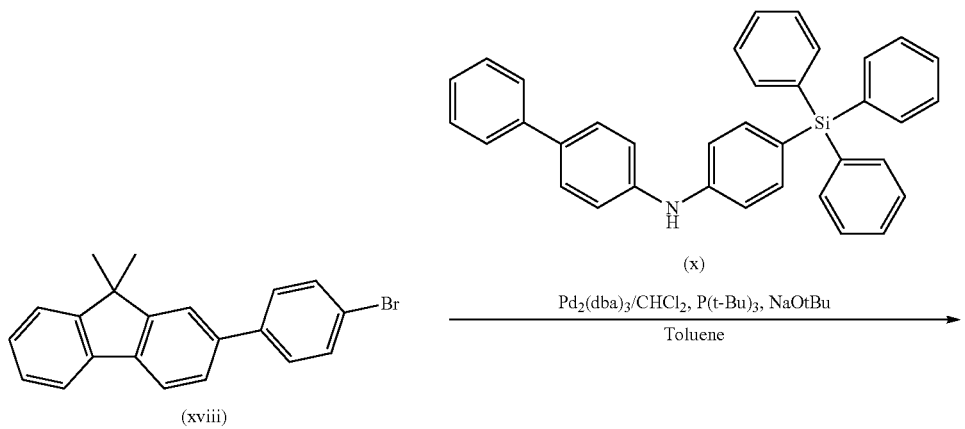

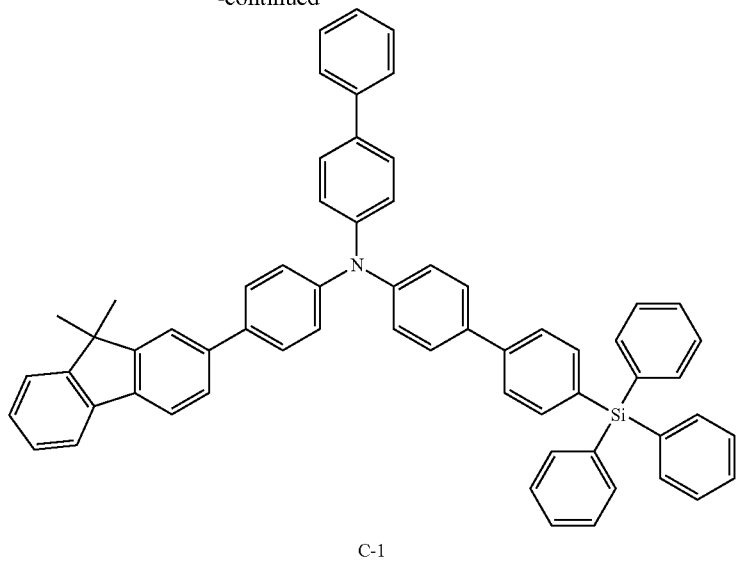

C-1

(Synthesis of Compound C-2)

First, under an argon atmosphere, 4.03 g of 9,9-biphenyl-fluorene-2-boronic acid, 3.0 g of 4-bromoiodobenzene, 21.6 mL of toluene, 10.6 mL of ethanol, 10.6 mL of a 2 M sodium carbonate aqueous solution, and 0.193 g of tetrakis(triphenylphosphine)palladium(0) were added to a 100 mL four-necked flask, followed by heating and stirring at about 80° C. for about 3 hours. The reaction mixture was extracted with toluene, and an organic layer was distilled under a reduced pressure. The residue thus obtained was separated by silica gel column chromatography to produce 3.5 g of Compound (xix).

[Formula 107]

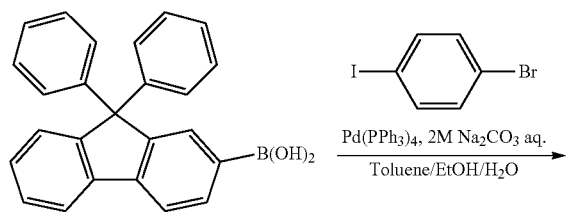

[Formula 108]

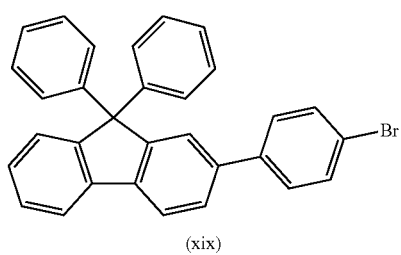

(xix)

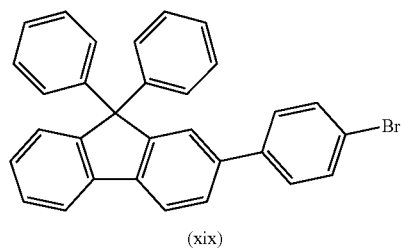

(xix)

Then, under an argon atmosphere, 1.17 g of Compound (xix), 1.50 g of Compound (x), 0.15 g of $Pd_2(dba)_3 \cdot CHCl_3$, 0.12 g of $(t-Bu)_3P$ and 0.57 g of sodium t-butoxide were added to a 100 mL four-necked flask, followed by heating and stirring in 30 mL of a toluene solvent at about 80° C. for about 3 hours. The reaction mixture was extracted with toluene, and an organic layer was distilled under a reduced pressure. The residue thus obtained was separated by silica gel column chromatography to produce 2.30 g of Compound C-2.

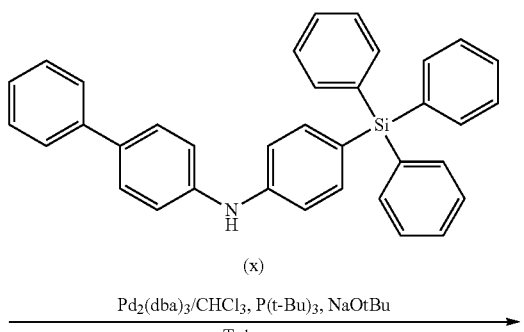

(x)

$Pd_2(dba)_3/CHCl_3$, $P(t-Bu)_3$, NaOtBu
Toluene

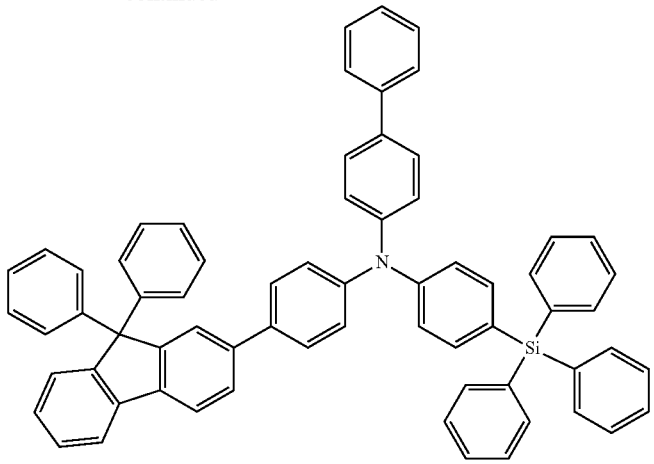

C-2

(Synthesis of Compound C-4)

First, under an argon atmosphere, 2.00 g of 2-bromo-9,9-dimethylfluorene, 1.76 g of 4-(4,4,5,5-tetramethyl-1,3,2-dioxaborolan-2-yl)aniline, 14.7 mL of toluene, 7.3 mL of ethanol, 3.6 mL of a 2 M sodium phosphate aqueous solution and 0.254 g of tetrakis(triphenylphosphine)palladium(0) were added to a 100 mL four-necked flask, followed by heating and stirring at about 80° C. for about 3 hours. The reaction mixture was extracted with toluene, and an organic layer was distilled under a reduced pressure. The residue thus obtained was separated by silica gel column chromatography to produce 1.25 g of Compound

[Formula 109]

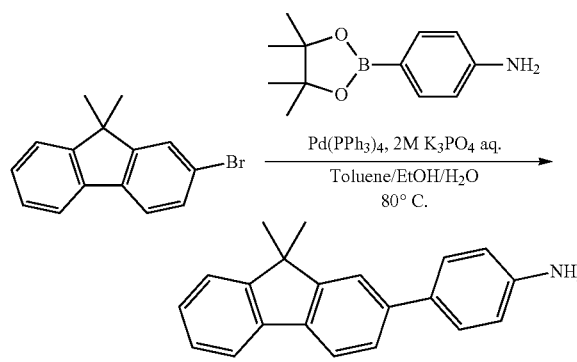

[Formula 110]

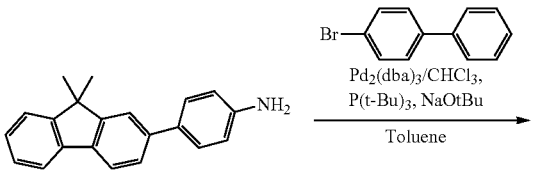

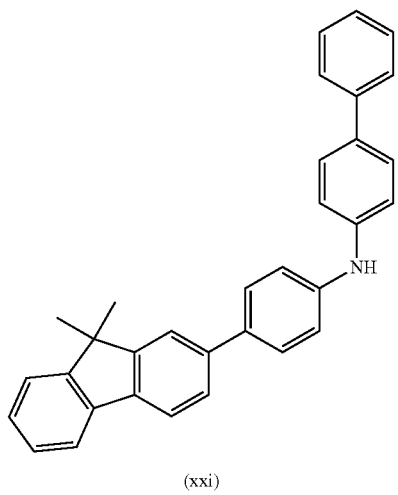

Then, under an argon atmosphere, 1.25 g of Compound (xx), 1.02 g of 4-bromobiphenyl, 0.13 g of $Pd_2(dba)_3 \cdot CHCl_3$, 0.18 g of $(t\text{-Bu})_3P$ and 0.84 g of sodium t-butoxide were added to a 200 mL four-necked flask, followed by heating and stirring in 43.8 mL of a toluene solvent at about 80° C. for about 3 hours. The reaction mixture was extracted with toluene, and an organic layer was distilled under a reduced pressure. The residue thus obtained was separated by silica gel column chromatography to produce 1.63 g of Compound (xxi).

After that, under an argon atmosphere, 1.63 g of Compound (xxi), 0.85 g of (4-bromophenyl)trimethylsilane, 0.11 g of $Pd_2(dba)_3 \cdot CHCl_3$, 0.15 g of $(t\text{-Bu})_3P$ and 0.72 g of sodium t-butoxide were added to a 100 mL four-necked flask, followed by heating and stirring at about 80° C. for about 3 hours. The reaction mixture was extracted with toluene, and an organic layer was distilled under a reduced pressure. The residue thus obtained was separated by silica gel column chromatography to produce 2.00 g of Compound C-4.

[Formula 111]

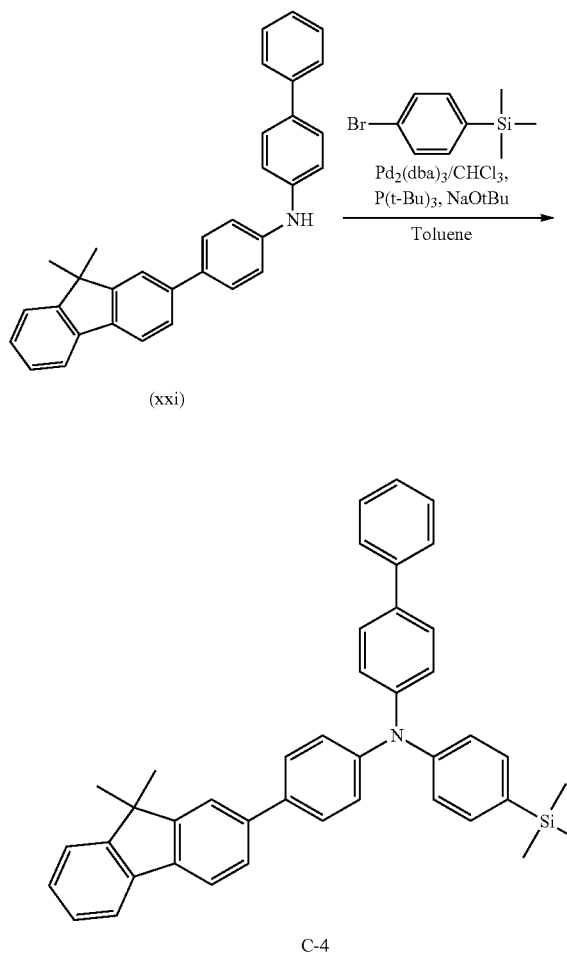

(xxi)

C-4

(Synthesis of Compound C-6)

First, under an argon atmosphere, 1.00 g of Compound (xx), 1.46 g of (4-bromotetraphenylsilane, 0.1 g of Pd$_2$(dba)$_3$·CHCl$_3$, 0.14 g of (t-Bu)$_3$P and 0.67 g of sodium t-butoxide were added to a 200 mL four-necked flask, followed by heating and stirring in 35.0 mL of a toluene solvent at about 80° C. for about 3 hours. The reaction mixture was extracted with toluene, and an organic layer was distilled under a reduced pressure. The residue thus obtained was separated by silica gel column chromatography to produce 2.05 g of Compound (xxii).

[Formula 112]

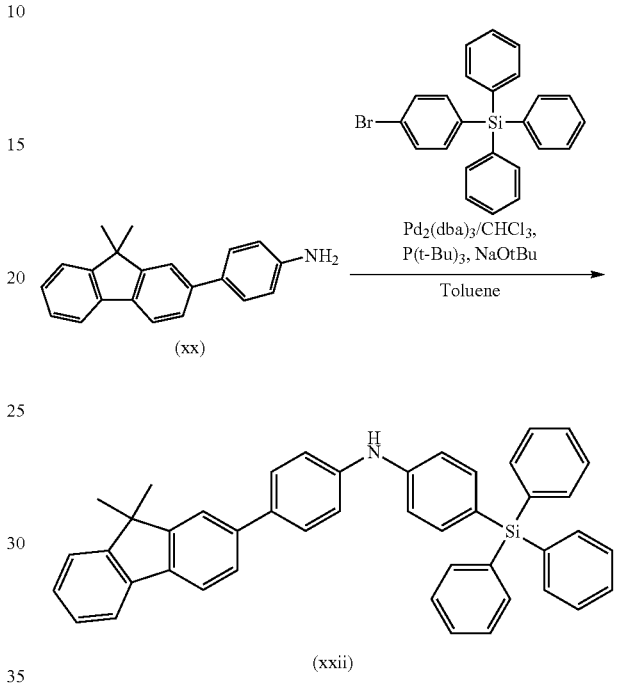

(xx)

(xxii)

After that, under an argon atmosphere, 2.05 g of Compound (xxii), 0.94 g of 1-(4-bromophenyl)naphthalene, 0.10 g of Pd$_2$(dba)$_3$·CHCl$_3$, 0.13 g of (t-Bu)$_3$P and 0.64 g of sodium t-butoxide were added to a 100 mL four-necked flask, followed by heating and stirring in 33 mL of a toluene solvent at about 80° C. for about 3 hours. The reaction mixture was extracted with toluene, and an organic layer was distilled under a reduced pressure. The residue thus obtained was separated by silica gel column chromatography to produce 2.52 g of Compound C-6.

[Formula 113]

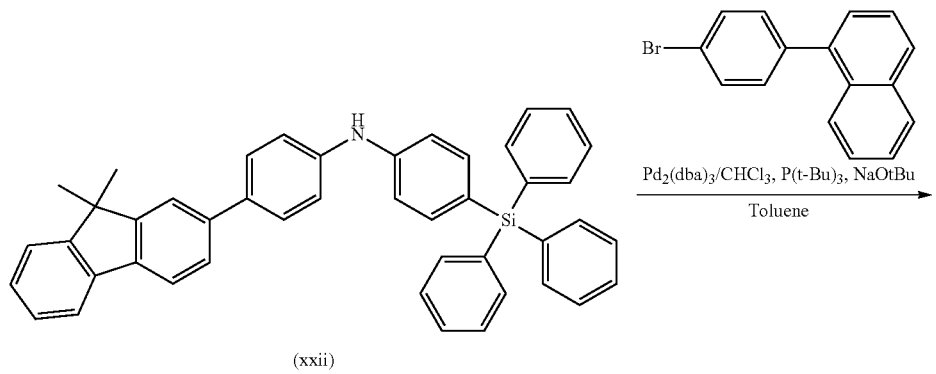

(xxii)

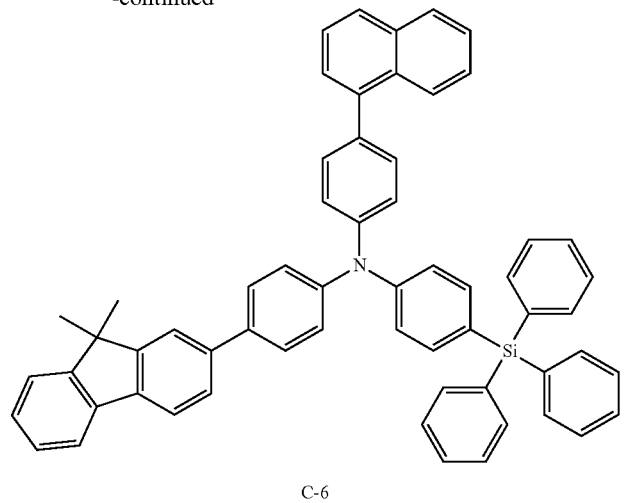

C-6

Hereinafter, organic electroluminescent devices using the above described Compound C-1, Compound C-2, Compound C-4 and Compound C-6 as the material for the organic electroluminescent device according to an embodiment in a hole transport layer will be explained. An organic electroluminescent device using Compound C-1 in the hole transport layer corresponds to Example 15, an organic electroluminescent device using Compound C-2 in the hole transport layer corresponds to Example 16, an organic electroluminescent device using Compound C-4 in the hole transport layer corresponds to Example 17 and an organic electroluminescent device using Compound C-6 in the hole transport layer corresponds to Example 18.

The manufacture of the organic electroluminescent device according to Example 15 according to an embodiment was conducted by a vacuum deposition as for the organic electroluminescent device of Example 1 and the following procedure. First, with respect to an ITO-glass substrate patterned and washed in advance, surface treatment using ozone was conducted. In addition, the layer thickness of an ITO layer was about 150 nm. Immediately after the ozone treatment, a layer was formed using 2-TNATA as a hole injection material (thickness of about 60 nm) on the ITO layer.

Then, a layer was formed using Compound C-1 according to an embodiment as a hole transport material (about 30 nm), and a layer of ADN doped with TBP in a ratio of about 3% was formed by a co-deposition (about 25 nm).

After that, a layer was formed using $Alq_3$ as an electron transport material (about 25 nm), and LiF (about 1.0 nm) as an electron injection layer and aluminum (about 100 nm) as a cathode were laminated one by one to manufacture the organic electroluminescent device 200 shown in FIG. 2.

As Examples 16, 17 and 18, organic electroluminescent devices were manufactured by performing the same procedure described in Example 15 except for using Compound C-2, Compound C-4 and Compound C-6 instead of Compound C-1 used in Example 15.

As Comparative Example 8, an organic electroluminescent device was manufactured by performing the same procedure described in Example 15 except for using Comparative Compound 8 represented in the following as a compound constituting a hole transport material of an organic electroluminescent device.

[Formula 114]

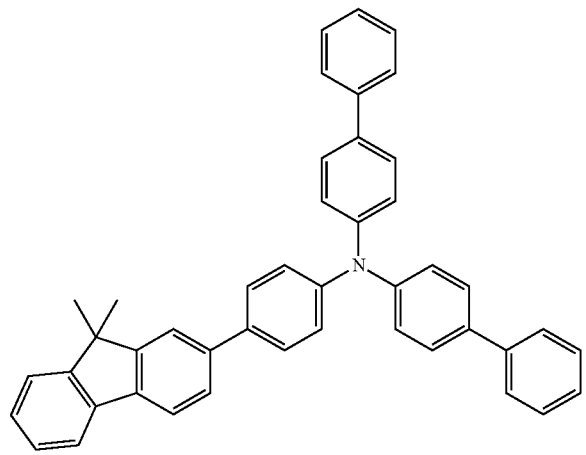

Comparative Compound 8

The driving voltage, the emission efficiency and the half life of the organic electroluminescent devices 200 manufactured in Examples 15 to 18 and Comparative Example 8 were evaluated. In addition, emission efficiency means values at about 10 $mA/cm^2$, and half life means luminance decrease time to half from an initial luminance of about 1,000 $cd/m^2$. The evaluation results are shown in Table 4.

TABLE 4

| | Hole transport material | Voltage (V) | Current efficiency (cd/A) | Half life (hr) |
|---|---|---|---|---|
| Example 15 | Compound C-1 | 6.2 | 7.4 | 2,500 |
| Example 16 | Compound C-2 | 6.1 | 7.5 | 2,600 |
| Example 17 | Compound C-4 | 6.2 | 7.0 | 2,300 |
| Example 18 | Compound C-6 | 6.2 | 7.1 | 2,500 |
| Comparative Example 9 | Comparative Compound 8 | 6.8 | 6.8 | 1,900 |

According to Table 4, the organic electroluminescent devices of Examples 15 to 18 have decreased driving voltage, improved emission efficiency and longer life than the organic electroluminescent device of Comparative Example 8. For example, it can be seen that the decrease of the driving voltage and the improvement of the emission efficiency and the life of Example 16 using Compound C-2 in which a phenyl group is substituted at position 9 of the substituted or unsubstituted fluorenyl group for $Ar^3$ in an example structure of the amine derivative, were marked.

In the above-described Examples 15 to 18, an example amine derivative according to an embodiment, in which the substituted or unsubstituted fluorenyl group for $Ar^3$ is combined with the substituted or unsubstituted arylene group or the substituted or unsubstituted heteroarylene group of L in General Formula (1), was used as the hole transport material of the organic electroluminescent device as an embodiment; however, the use of the amine derivative according to an embodiment is not limited to the organic electroluminescent device, and may be expanded to other luminescent devices or luminescent apparatus. In addition, the organic electroluminescent device using an example amine derivative according to an embodiment may be used in an organic electroluminescent display of a passive-matrix driving type, and they may be also used in an organic electroluminescent display of an active-matrix driving type.

Remarkable improvement of the emission efficiency, the driving voltage and the life of an organic electroluminescent device may be obtained by disposing the amine derivative represented by General Formula (1), for example, an amine derivative having the following structure as a material for an organic electroluminescent device between an emission layer and an anode.

In an example structure of the amine derivative represented by General Formula (1), $Ar^1$ and $Ar^2$ are independently a substituted or unsubstituted aryl group or a substituted or unsubstituted heteroaryl group, at least one of $Ar^1$ and $Ar^2$ is substituted with a substituted or unsubstituted silyl group, $Ar^3$ is a substituted or unsubstituted fluorenyl group, and L is a single bond. An example structure of the amine derivative represented by General Formula (1) is represented by the following General Formula (3).

[Formula 115]

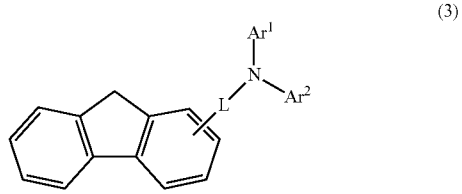

(3)

Here, as the aryl group and the heteroaryl group of "the substituted or unsubstituted aryl group" or "the substituted or unsubstituted heteroaryl group" of $Ar^1$ and $Ar^2$, as described above, a phenyl group, a naphthyl group, an anthracenyl group, a phenanthryl group, a biphenyl group, a terphenyl group, a fluorenyl group, a triphenylene group, a biphenylene group, a pyrenyl group, a benzothiazolyl group, a thiophenyl group, a thienothiophenyl group, a thienothienothiophenyl group, a benzothiophenyl group, a dibenzothiophenyl group, a dibenzofuryl group, a N-arylcarbazolyl group, a N-heteroarylcarbazolyl group, a N-alkylcarbazolyl group, a phenoxazyl group, a phenothiazyl group, a pyridyl group, a pyrimidyl group, a triazinyl group, a quinolinyl group and a quinoxalyl group are examples. The phenyl group, the naphthyl group, the biphenyl group, the terphenyl group, the fluorenyl group, the triphenylene group, the dibenzothiophenyl group, the dibenzofuryl group and the N-phenylcarbazolyl group may be used. As the aryl group, an aryl group having 6 to 18 carbon atoms for forming a ring may be used, and the phenyl group and the triphenylene group are examples. As the heteroaryl group, a heteroaryl group having 5 to 18 carbon atoms for forming a ring may be used, and the dibenzofuryl group and the N-phenylcarbazolyl group are examples.

$Ar^1$ and $Ar^2$ may be independently a substituted or unsubstituted aryl group. In addition, $Ar^1$ may be the substituted or unsubstituted aryl group and $Ar^2$ may be the substituted or unsubstituted dibenzoheterole group.

As the substituent of the aryl group or the heteroaryl group of $Ar^1$ and $Ar^2$, a halogen atom, an alkyl group, an alkoxy group, an aryl group and a heteroaryl group are examples. Examples of the aryl group and the heteroaryl group are the same as the above exemplified aryl group and the heteroaryl group of $Ar^1$ and $Ar^2$. As the halogen atom, a fluorine atom may be used, without specific limitation. The alkyl group is not specifically limited and may include a methyl group, an ethyl group, a propyl group, an isopropyl group, a cyclopropyl group, a butyl group, an isobutyl group, a t-butyl group, a cyclobutyl group, a pentyl group, an isopentyl group, a neopentyl group, a cyclopentyl group, a hexyl group, a cyclohexyl group, a heptyl group, a cycloheptyl group, an octyl group, a nonyl group, a decyl group, etc. The alkoxy group is not specifically limited and may include a methoxy group, an ethoxy group, a n-propoxy group, an isopropoxy group, a n-butoxy group, an isobutoxy group, a t-butoxy group, a n-pentyloxy group, a neopentyloxy group, a n-hexyloxy group, a n-heptyloxy group, a n-octyloxy group, a 2-ethylhexyloxy group, a nonyloxy group, a decyloxy group, a 3,7-dimethyloctyloxy group, etc.

In an example amine derivative according to an embodiment represented by General Formula (3), $Ar^3$ is a substituted or unsubstituted fluorenyl group in General Formula (1). By introducing the fluorenyl group, the hole transport properties of the amine derivative according to an embodiment may be improved. By using an example amine derivative according to an embodiment introducing the fluorenyl group as the material for a hole transport layer disposed between an anode and an emission layer, the improvement of the emission efficiency and the increase of the life of the organic electroluminescent device may be realized. For the substituted fluorenyl group, each substituent is independently a substituted or unsubstituted aryl group or a substituted or unsubstituted heteroaryl group. As the alkyl group for the substitution in the fluorenyl group for $Ar^3$, an alkyl group having 1 to 10 carbon atoms may be used. For example, a methyl group may be used. As the aryl group for substitution in the fluorenyl group for $Ar^3$, an aryl group having 6 to 12 carbon atoms for forming a ring may be used. For example, a phenyl group or a naphthyl group may be used. As the heteroaryl group for the substitution in the fluorenyl group for $Ar^3$, a heteroaryl group having 4 to 12 carbon atoms for forming a ring may be used. For example, a dibenzofuryl group may be used.

As the substituent of the alkyl group, the aryl group or the heteroaryl group substituted in the fluorenyl group, an aryl group, an alkoxy group, a heteroaryl group, a halogen atom may be used. Examples of the aryl group and the heteroaryl group may be the same as the aryl group and the heteroaryl group exemplified for $Ar^1$ and $Ar^2$. The halogen atom may be a fluorine atom, without specific limitation. Examples of the alkyl group may be the same as the alkyl group explained as the substituent of the aryl group or the heteroaryl group of Ar¹ and Ar².

As described above, in the amine derivative represented by General Formula (3), which is an example amine derivative according to an embodiment, L is a single bond. The bonding position of the substituted or unsubstituted fluorenyl group for Ar³ with L, that is, the bonding position of the fluorenyl group with a nitrogen atom (N), is not specifically limited, however, position 2 may be used. In an example amine derivative according to an embodiment represented by General Formula (3), the substituted or unsubstituted fluorenyl group for Ar³ is combined with the nitrogen atom (N) of an amine part at position 2. Thus, the conjugation system of the π electrons of a whole molecule may be enlarged, and hole transport properties and the stability of the molecule may be improved. Accordingly, the improvement of the emission efficiency and the increase of the life of the organic electroluminescent device may be realized.

As the substituent of the silyl group substituted for at least one of Ar¹ and Ar², an alkyl group, an alkoxy group, an aryl group and a heteroaryl group are examples. For example, the substituent is the same as the alkyl group, the alkoxy group, the aryl group and the heteroaryl group explained as the substituent of the aryl group or the heteroaryl group of Ar¹ and Ar². For example, as the silyl group substituted for at least one of Ar¹ and Ar², a triarylsilyl group where an aryl substituent at the silyl group has 6 to 18 carbon atoms for forming a ring or a trialkylsilyl group where an alkyl substituent at the silyl group has 1 to 6 carbon atoms may be used.

In the amine derivative represented by General Formula (3), which is an example amine derivative according to an embodiment, only at least one of Ar¹ and Ar² may be substituted with a substituted or unsubstituted silyl group.

As the amine derivative represented by General Formula (3), which is an example amine derivative according to an embodiment, the following compounds are examples, without limitation.

[Formula 116]

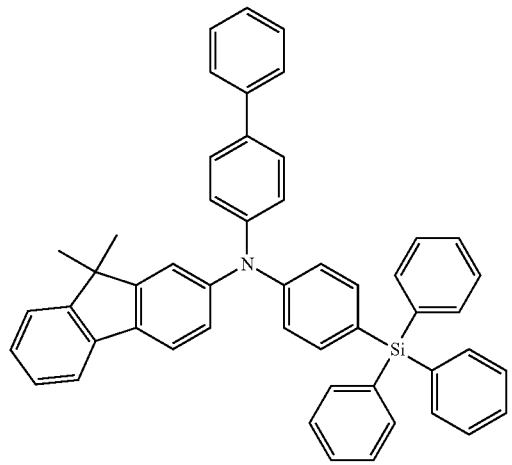
D-1

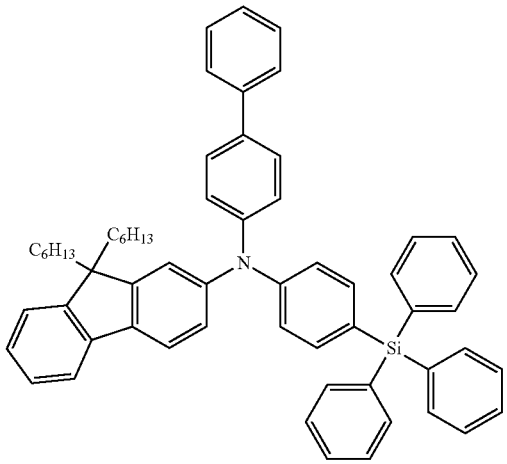
D-2

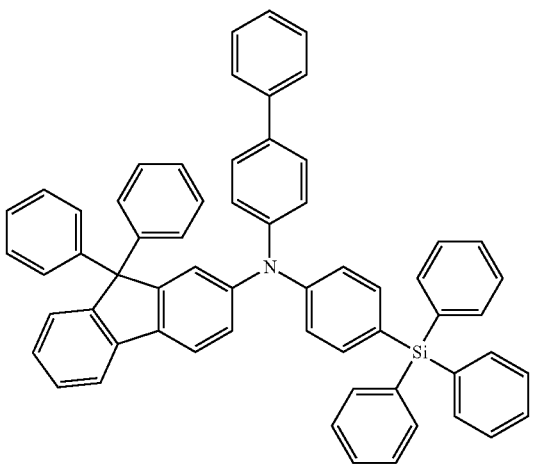
D-3

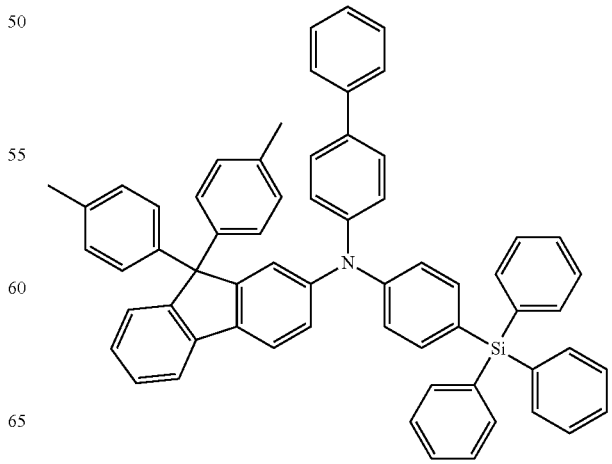
D-4

[Formula 117]
D-5
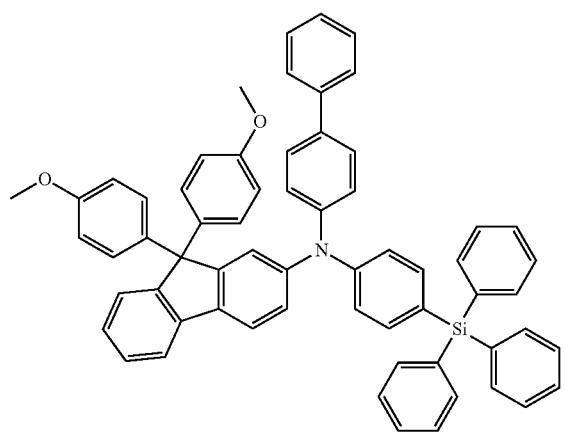
D-6
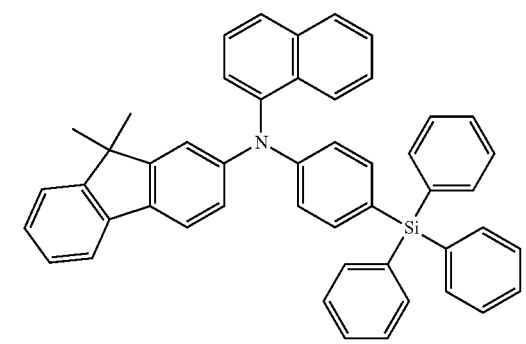
D-7
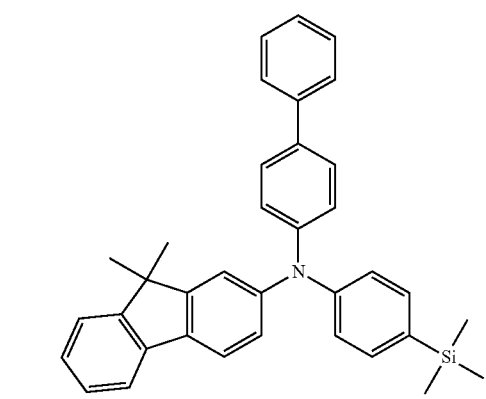
D-8
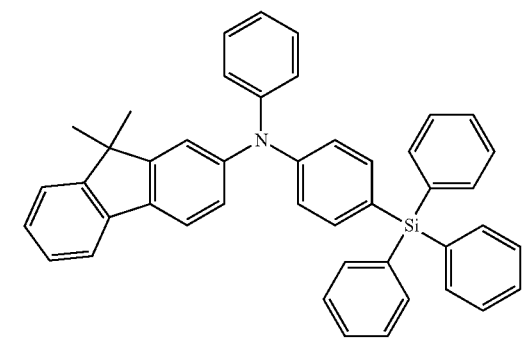
[Formula 118]
D-9
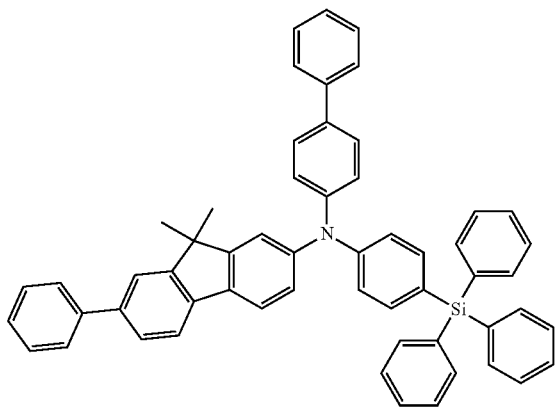
D-10
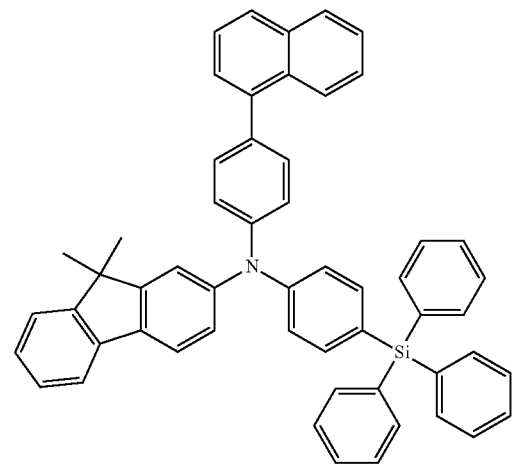
D-11
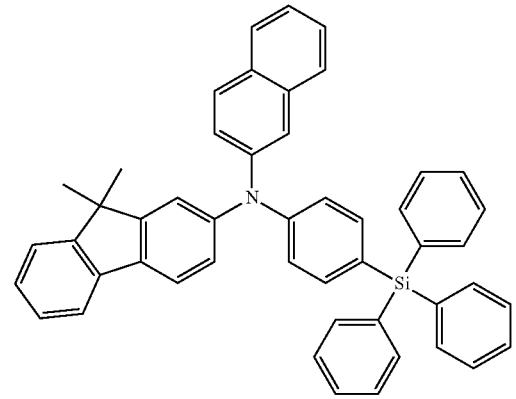

D-12
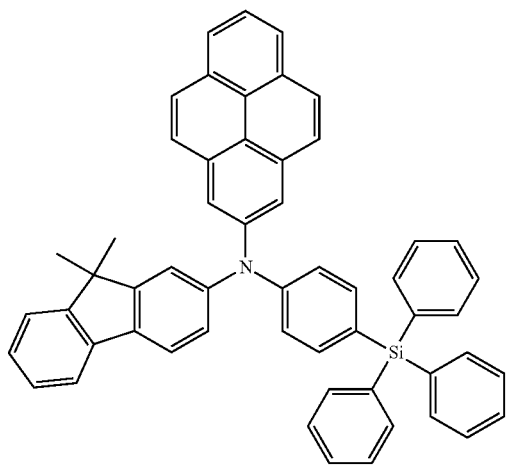
[Formula 119]
D-13
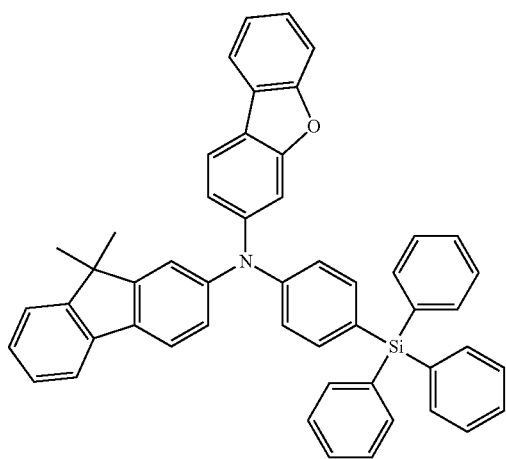
D-14
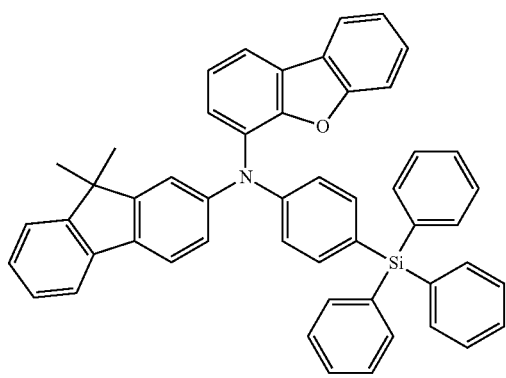
D-15
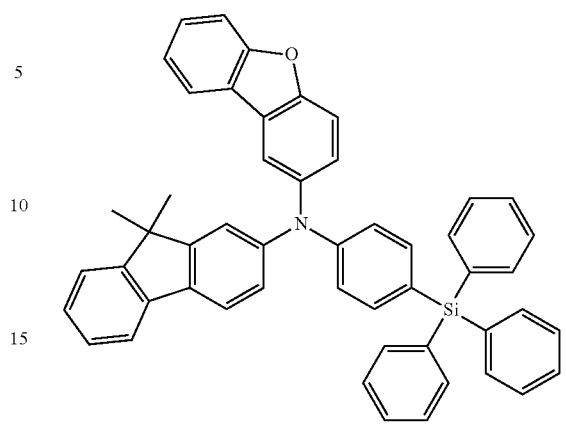
D-16
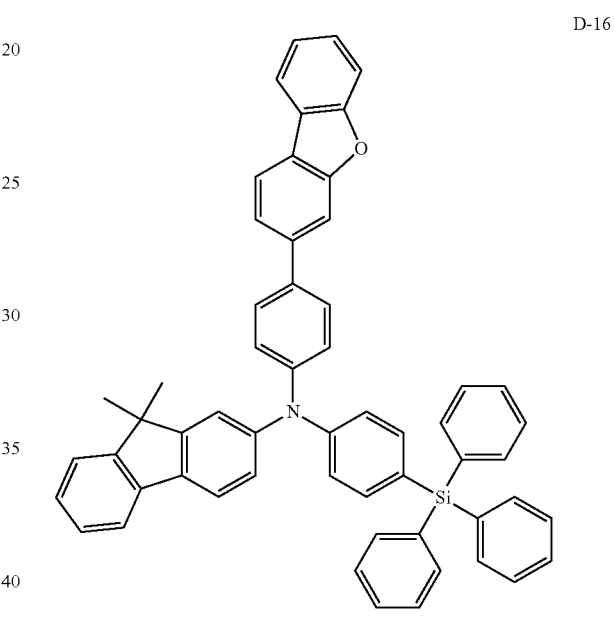
[Formula 120]
D-17
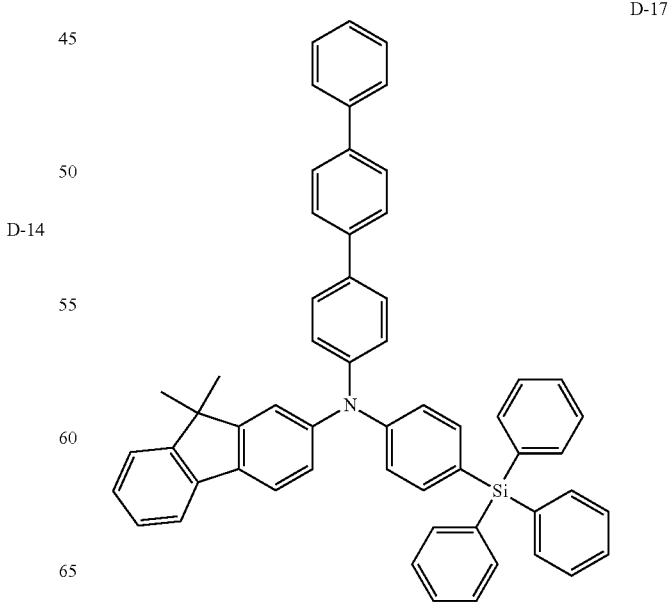

D-18
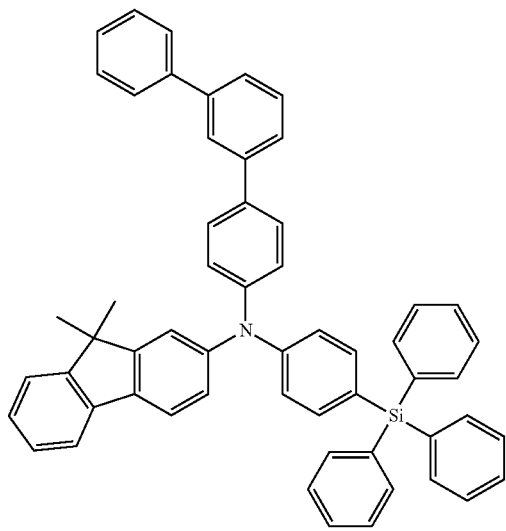
D-19
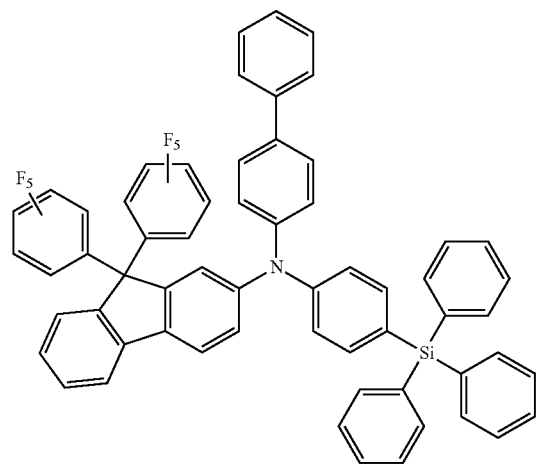
D-20
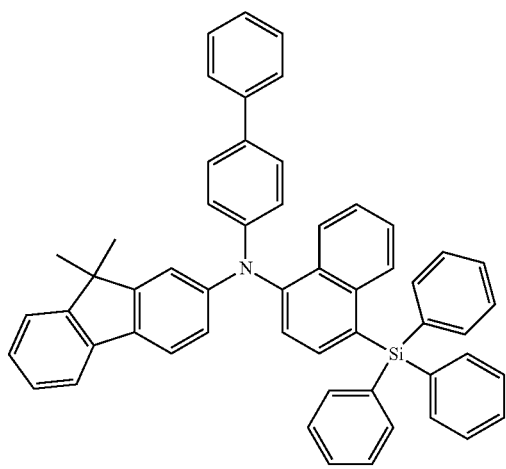
[Formula 121]
D-21
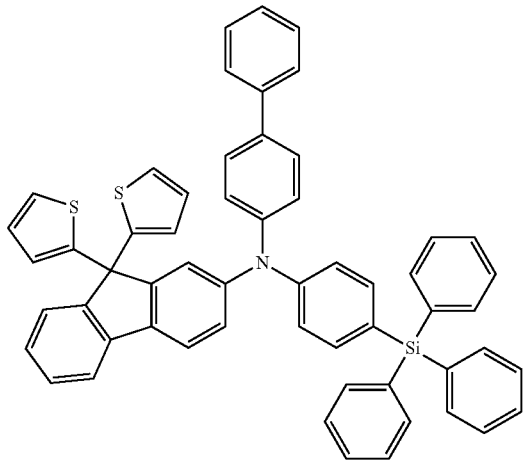
D-22
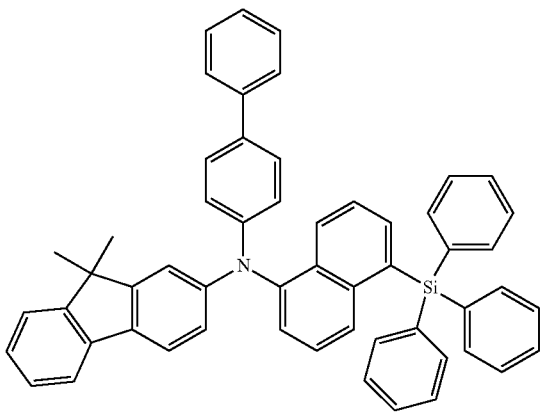
D-23
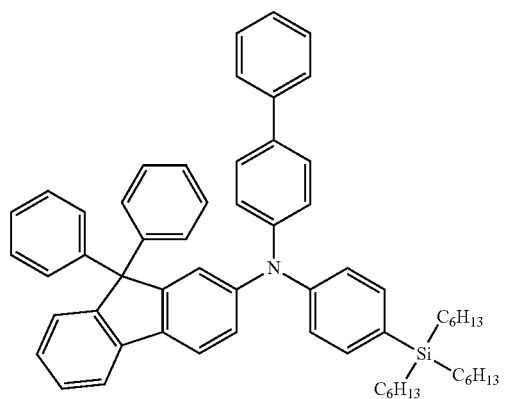

D-24
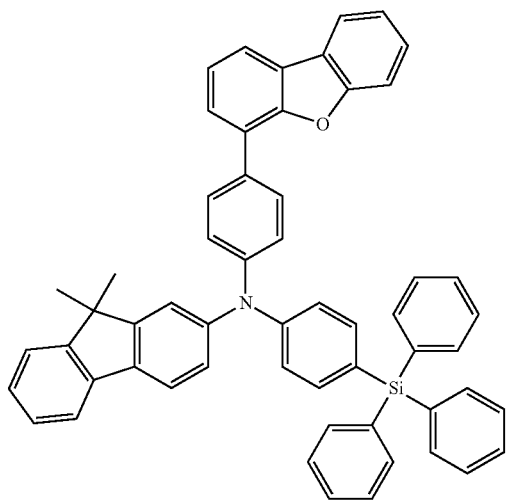
[Formula 122]
D-25
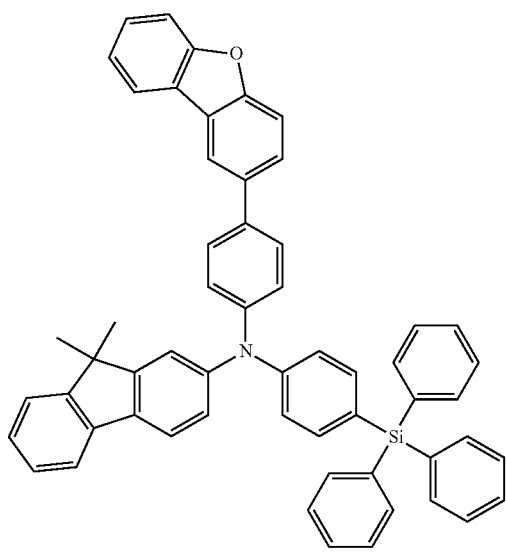
D-26
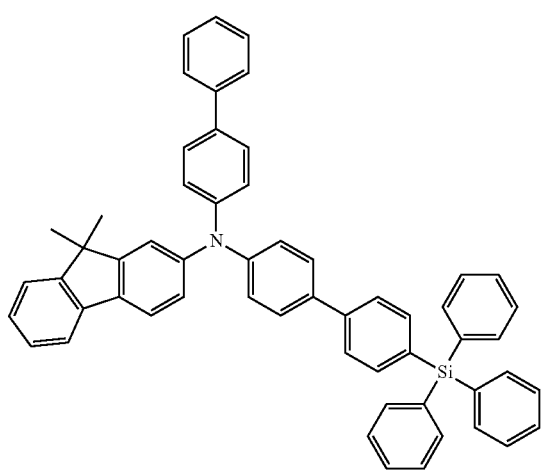
D-27
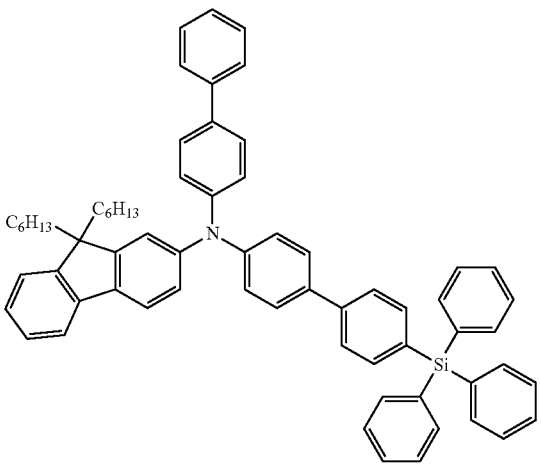
D-28
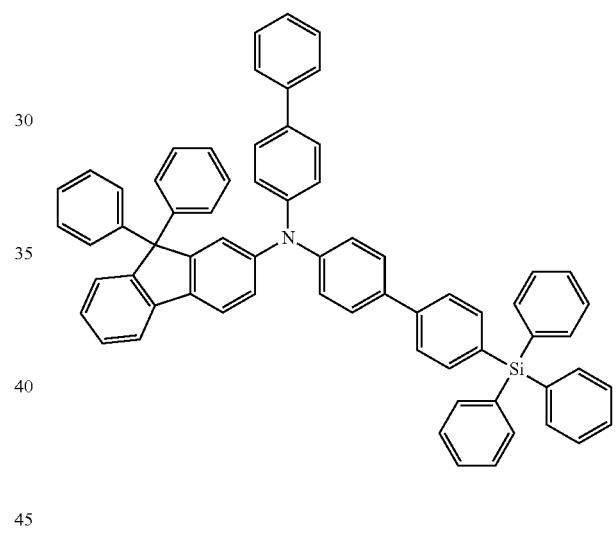
[Formula 123]
D-29
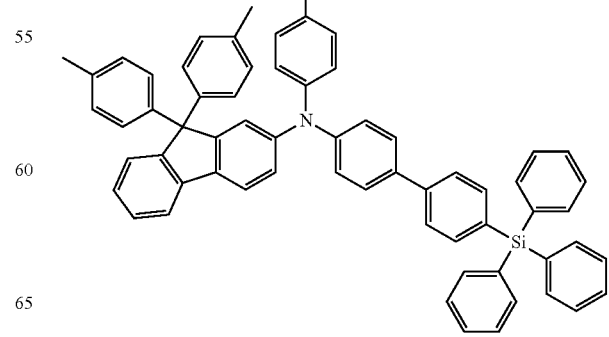

[Formula 124]
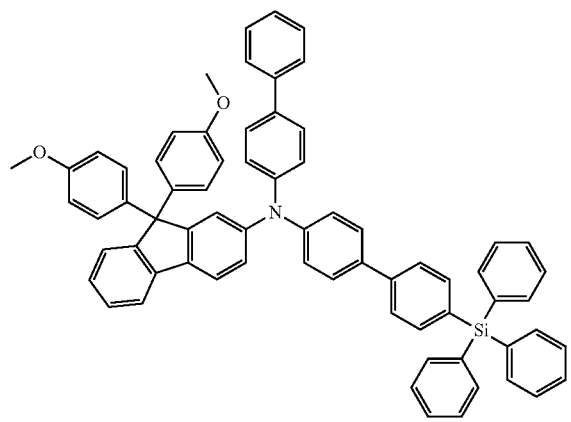
D-30
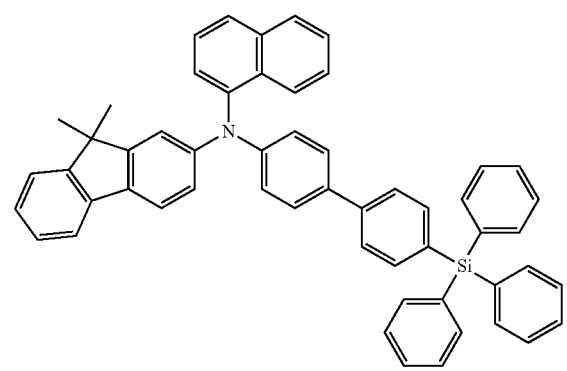
D-31
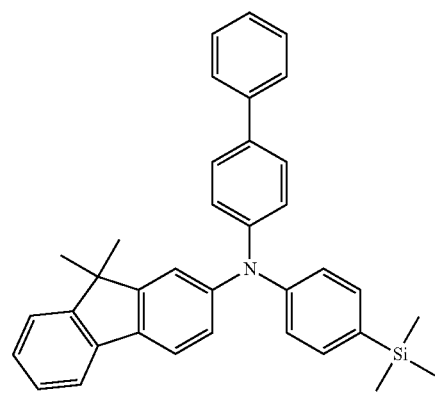
D-32
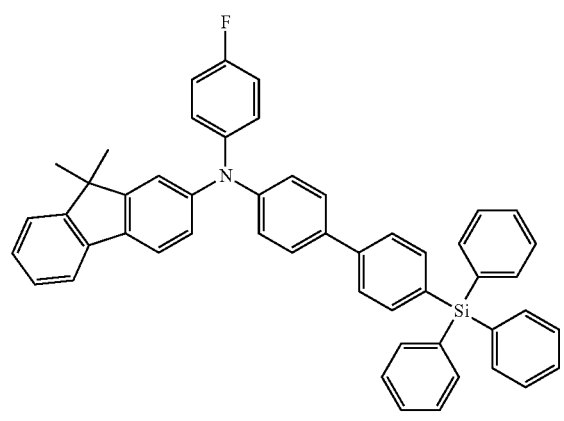
D-33
D-34
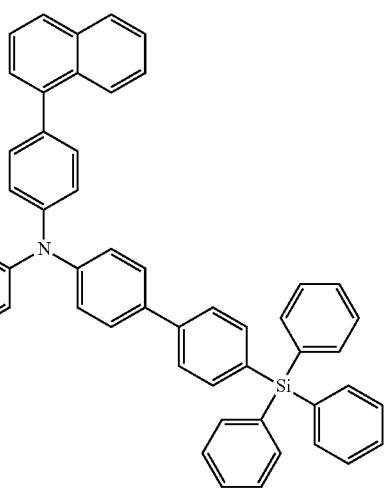
D-35

-continued
D-36
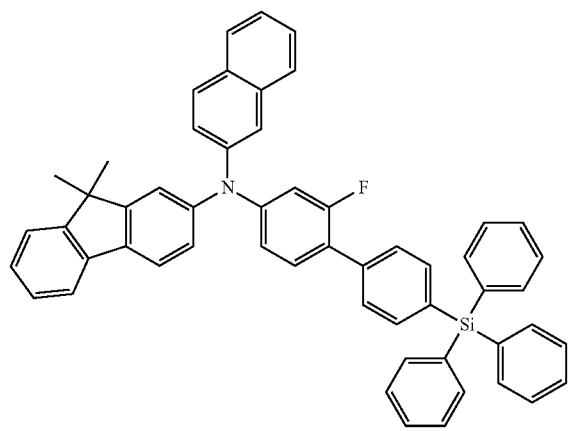
[Formula 125]
D-37
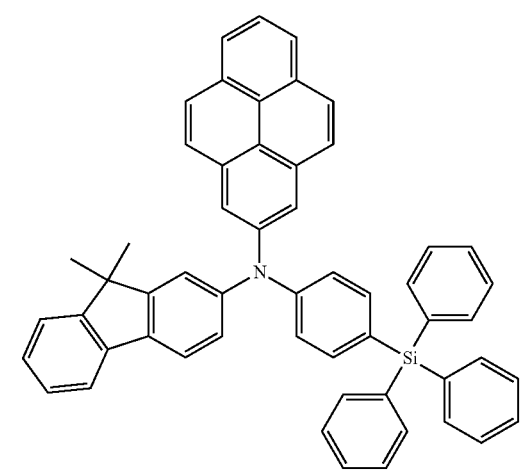
D-38
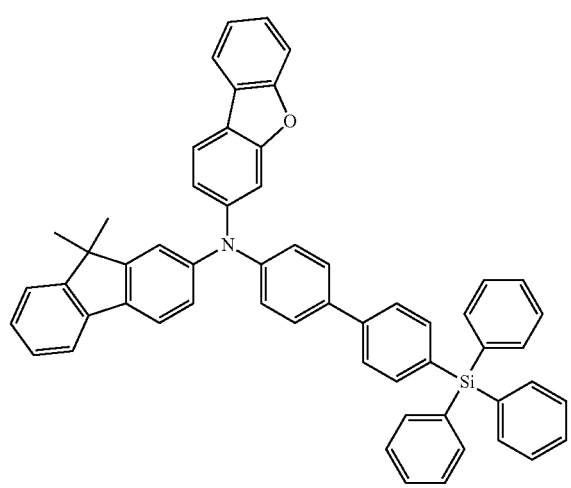
-continued
D-39
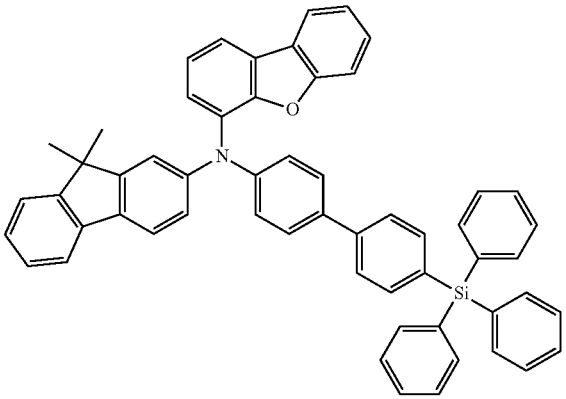
D-40
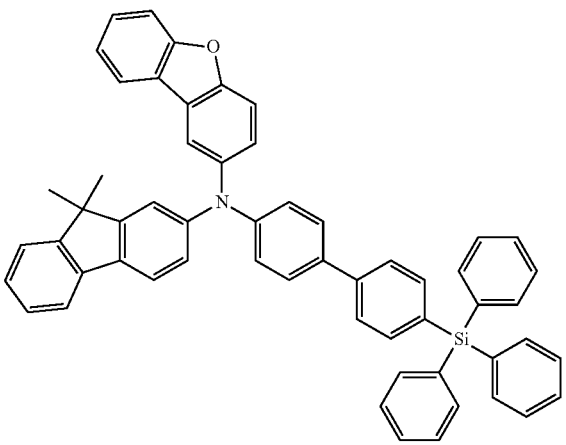
[Formula 126]
D-41
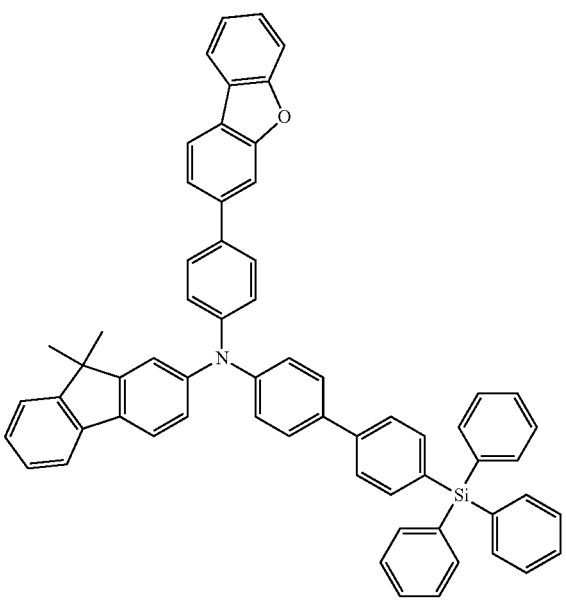

D-42
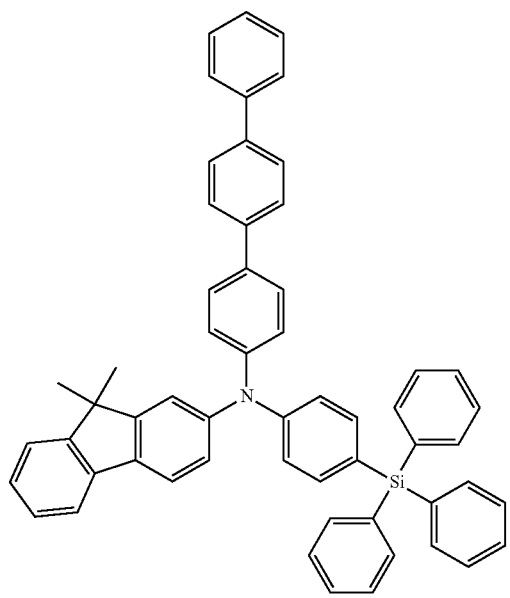
D-43
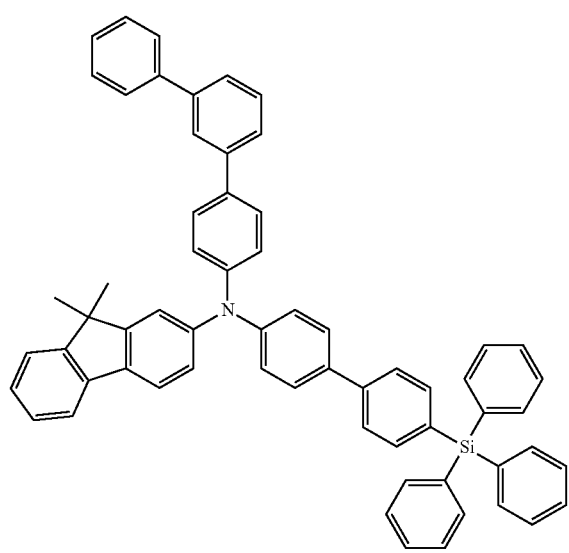
[Formula 127]
D-44
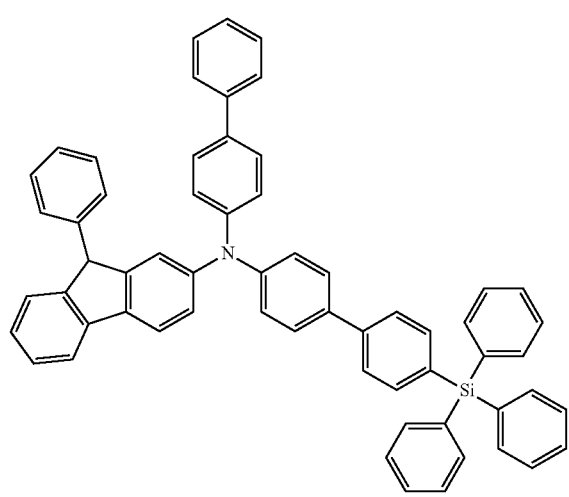
D-45
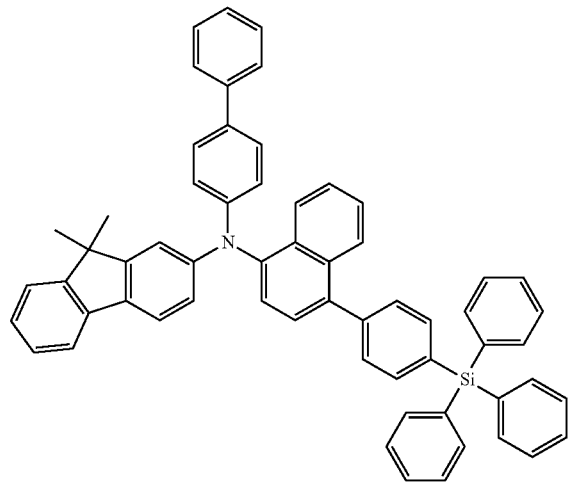
D-46
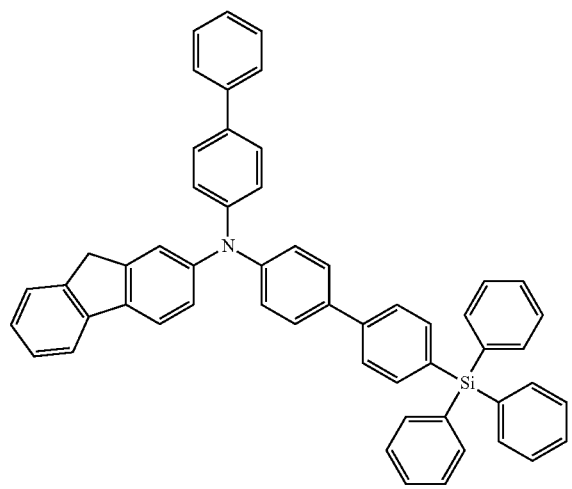
[Formula 128]
D-47
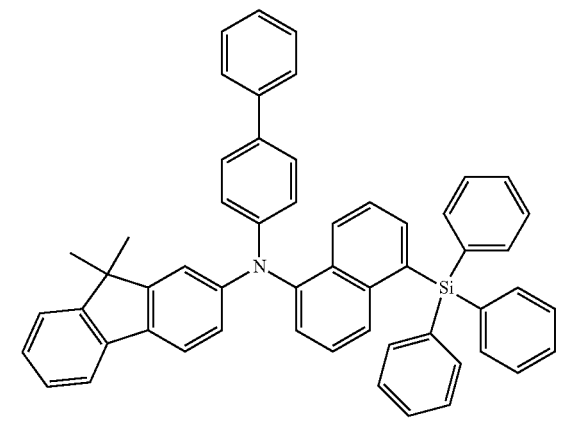

D-48
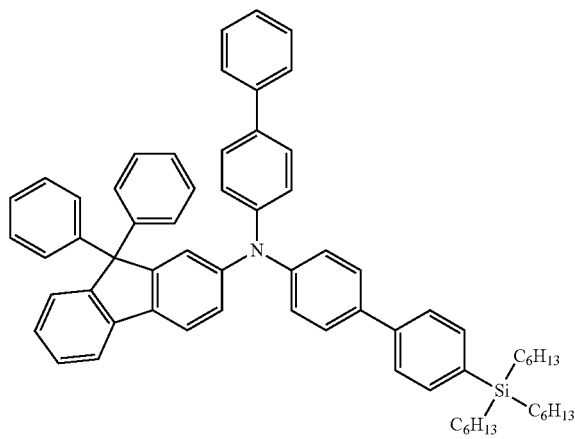
D-49
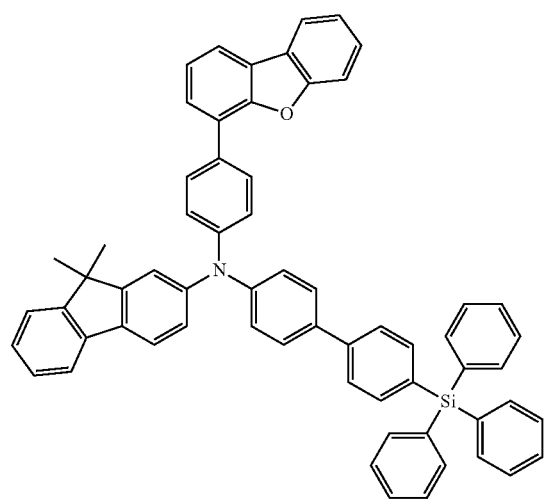
[Formula 129]
D-50
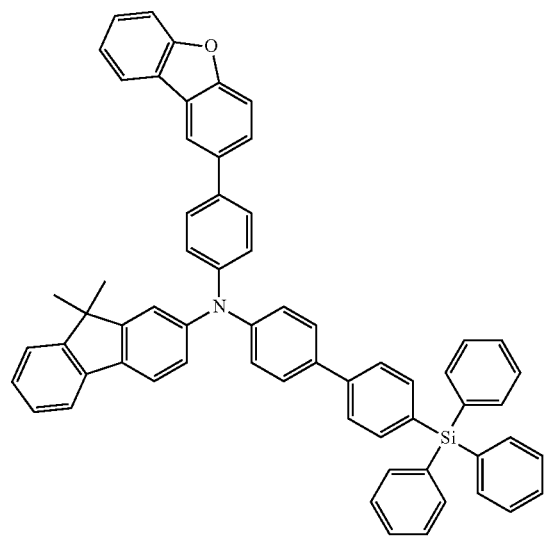
D-51
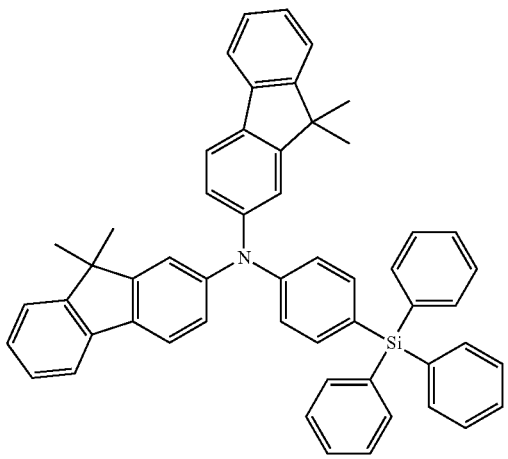
D-52
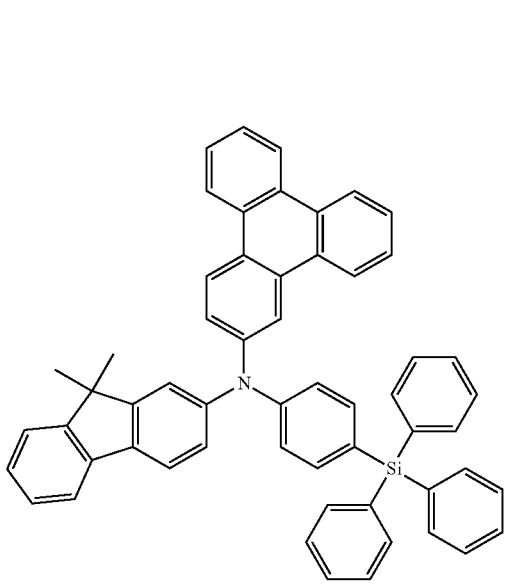
D-53
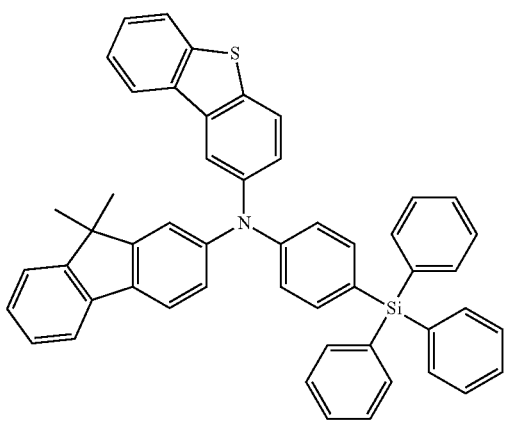

[Formula 130]
D-54
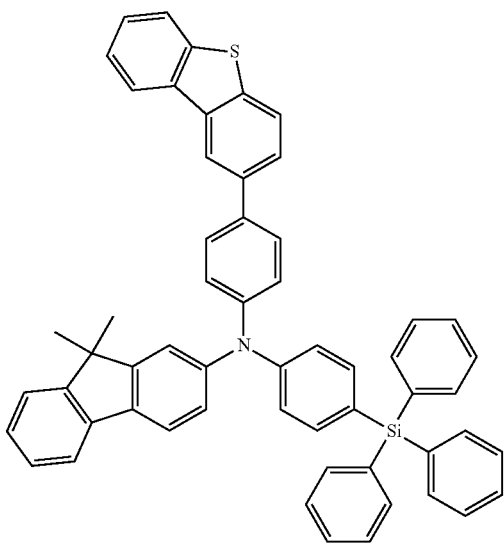
D-55
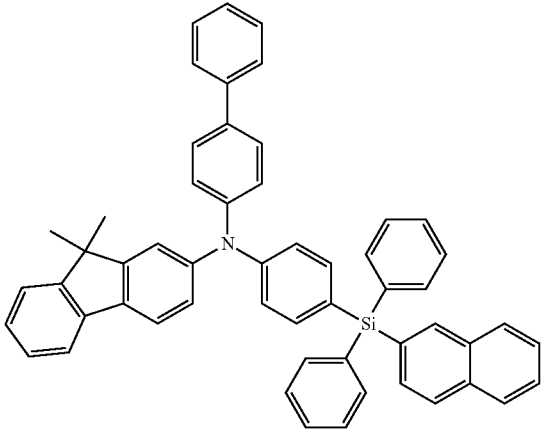
D-56
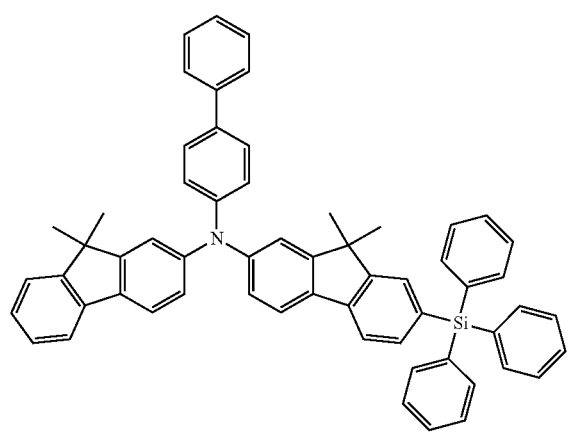
D-57
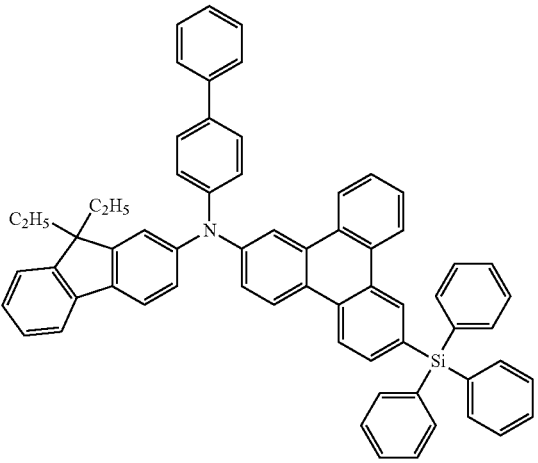
[Formula 131]
D-58
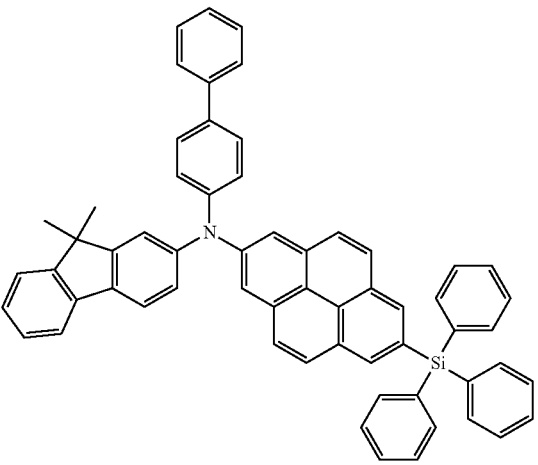
D-59
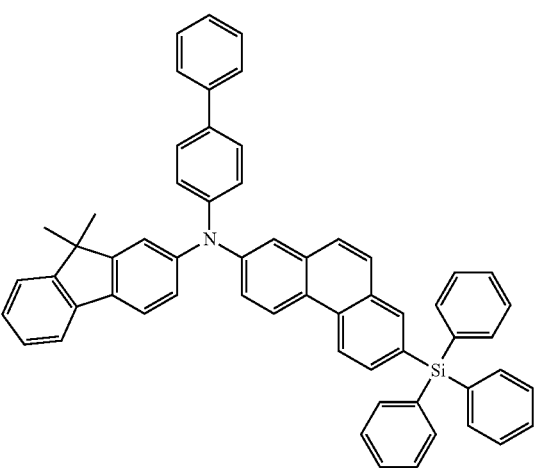

D-60
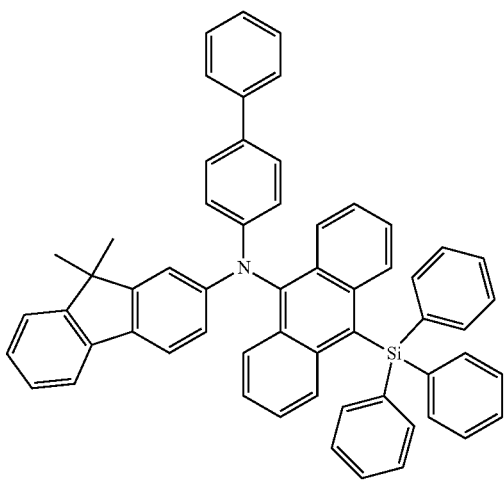
[Formula 132]
D-61
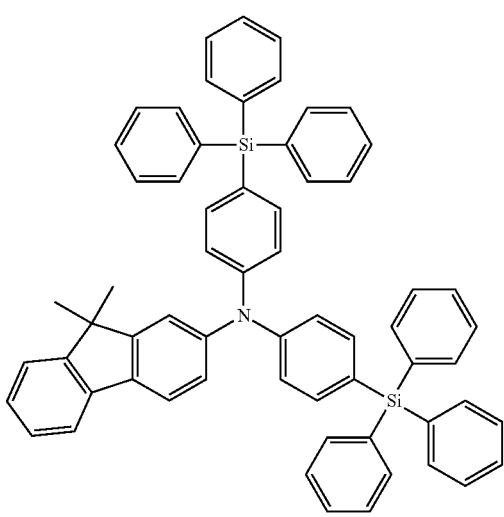
D-62
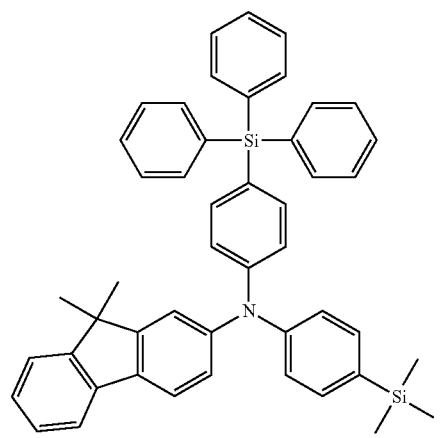
D-63
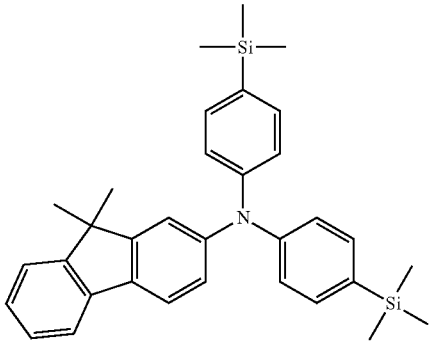
D-64
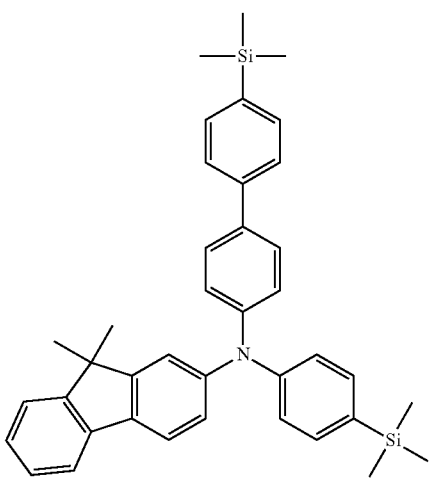
D-65
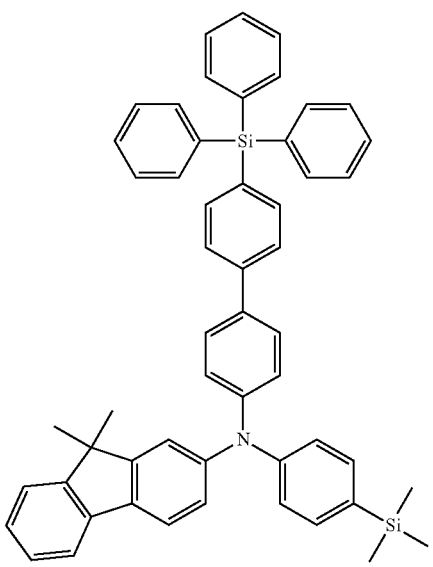

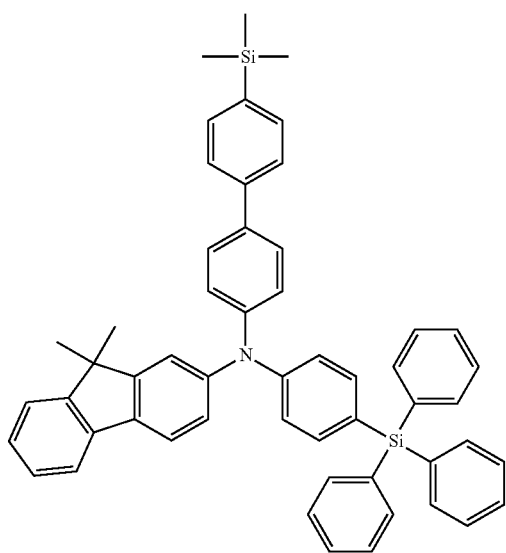

D-66

[Formula 133]

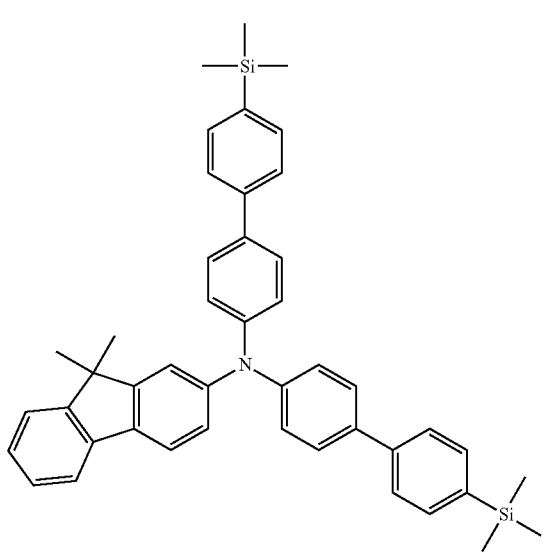

D-67

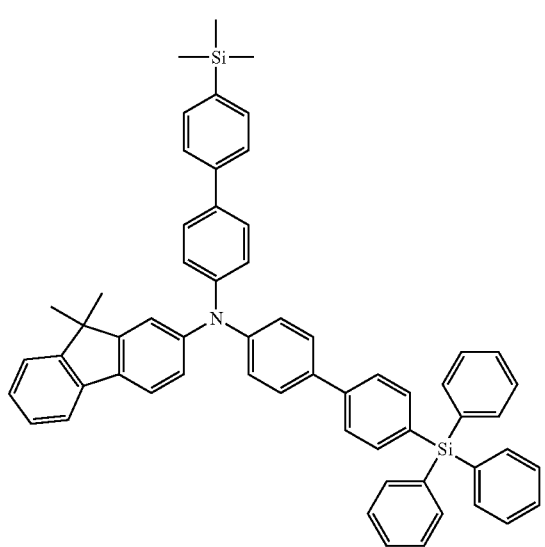

D-68

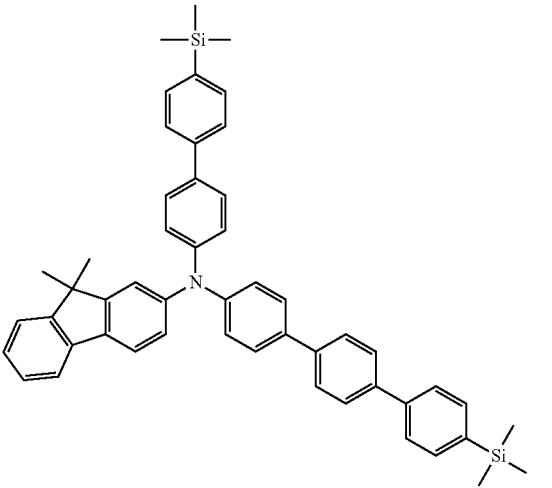

D-69

D-70

As described above, in an example structure of the amine derivative according to an embodiment, $Ar^3$ is the substituted or unsubstituted fluorenyl group in General Formula (1). Through the combination of the fluorenyl group with the single bond of L, that is, through the combination of the substituted or unsubstituted fluorenyl group for $Ar^3$ with the nitrogen atom (N) of an amine part, hole transport properties may be improved. Thus, the emission efficiency may be improved, and the long life may be realized for the organic electroluminescent device by disposing the amine derivative as the material of the organic electroluminescent device between an emission layer and an anode. For example, the emission efficiency may be improved, and the long life may be realized for the organic electroluminescent device by using the amine derivative in a blue-bluish green region.

An example structure of the amine derivative according to an embodiment represented by General Formula (3) may be used as the material of the hole transport layer of the organic electroluminescent device 100 shown in FIG. 1. In addition, the configuration of the organic electroluminescent device 100 shown in FIG. 1 is an illustration of the organic electroluminescent device according to an embodiment without limitation, and may be variously modified.

In addition, the use of the amine derivative according to an embodiment represented by General Formula (3), which has the structure of the amine derivative according to an embodiment, is not limited to the hole transport material of the organic electroluminescent device; it may be used as the material of the hole injection layer or the material of the emission layer. In the case that the amine derivative is used as the material of the hole injection layer or the material of the emission layer, the emission efficiency of the organic electroluminescent device may be improved, and the long life of the organic electroluminescent device may be realized as the case using the amine derivative as the material of the hole transport layer.

Example V

With respect to the amine derivative according to an embodiment represented by General Formula (3), examples of synthesizing Compound D-1, Compound D-3 and Compound D-26 will be explained hereinafter. However, the following synthetic methods are only examples, and embodiments are not limited thereto. In addition, Compound D-1 is the same as Compound 1 in the above-described Example 1.

(Synthesis of Compound D-1)

Compound (i) (1.57 g, 4.33 mmol), Compound (ii) (1.50 g, 3.61 mmol), $Pd_2(dba)_3 \cdot CHCl_3$ (0.37 g, 0.36 mmol) and toluene (36 mL) were added to a reaction vessel. Then, tri(t-butyl)phosphine (0.93 mL, 1.44 mmol, 1.56 M) and sodium t-butoxide (1.04 g, 10.8 mmol) were added thereto, and the inner part of the vessel was purged with a nitrogen gas, followed by stirring at about 80° C. for about 4 hours. After cooling in the air, water was added to the reaction mixture, and an organic layer was extracted. The organic layer thus obtained was dried with anhydrous magnesium sulfate and filtered. The filtrate was concentrated by a rotary evaporator. The crude product thus obtained was separated by silica gel column chromatography (developing solvent: dichloromethane/hexane), and the solid thus obtained was recrystallized using toluene/hexane to produce 2.26 g of a target product, Compound D-1, as a white powder solid with the yield of 90% (FAB-MS: C51H41NSi, measured value 695).

[Formula 134]

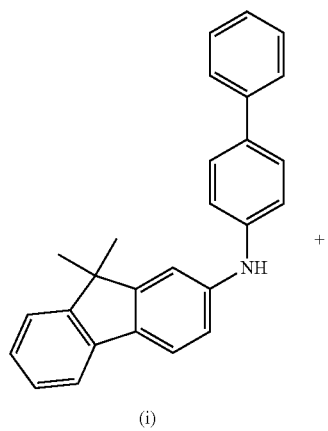

(i)

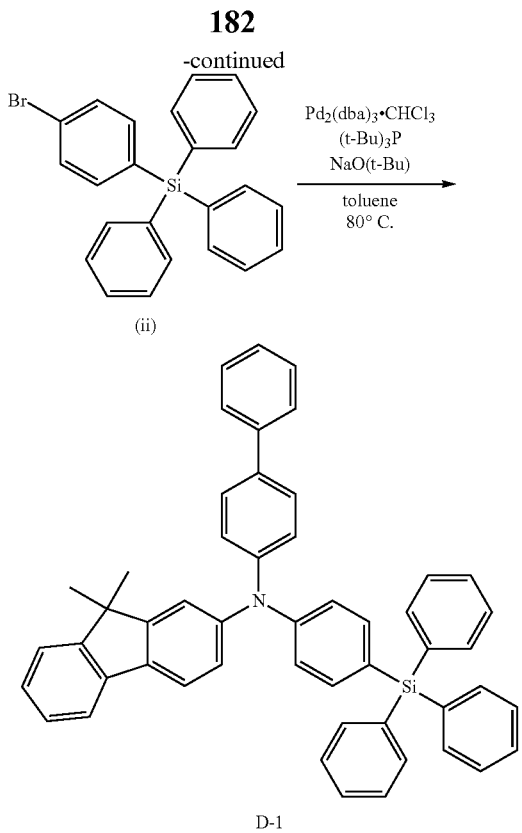

(Synthesis of Compound D-3)

Compound (xxii) (1.40 g, 2.89 mmol), Compound (ii) (1.00 g, 2.41 mmol), $Pd_2(dba)_3 \cdot CHCl_3$ (0.25 g, 0.24 mmol) and toluene (28 mL) were added to a reaction vessel. Then, tri(t-butyl)phosphine (0.62 mL, 0.96 mmol, 1.56 M) and sodium t-butoxide (0.69 g, 7.22 mmol) were added thereto, and the inner part of the vessel was purged with a nitrogen gas, followed by stirring at about 100° C. for about 8 hours. After cooling in the air, water was added to the reaction mixture, and an organic layer was extracted. The organic layer thus obtained was dried with anhydrous magnesium sulfate and filtered. The filtrate was concentrated by a rotary evaporator. The crude product thus obtained was separated by silica gel column chromatography (developing solvent: dichloromethane/hexane), and the solid thus obtained was recrystallized using toluene/hexane to produce 1.38 g of a target product, Compound D-3, as a white powder solid with the yield of 70% (FAB-MS: C61H45NSi, measured value 819).

[Formula 135]

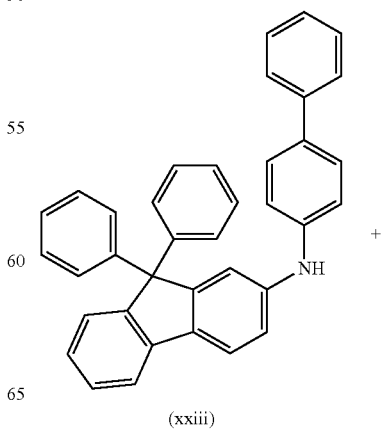

(xxiii)

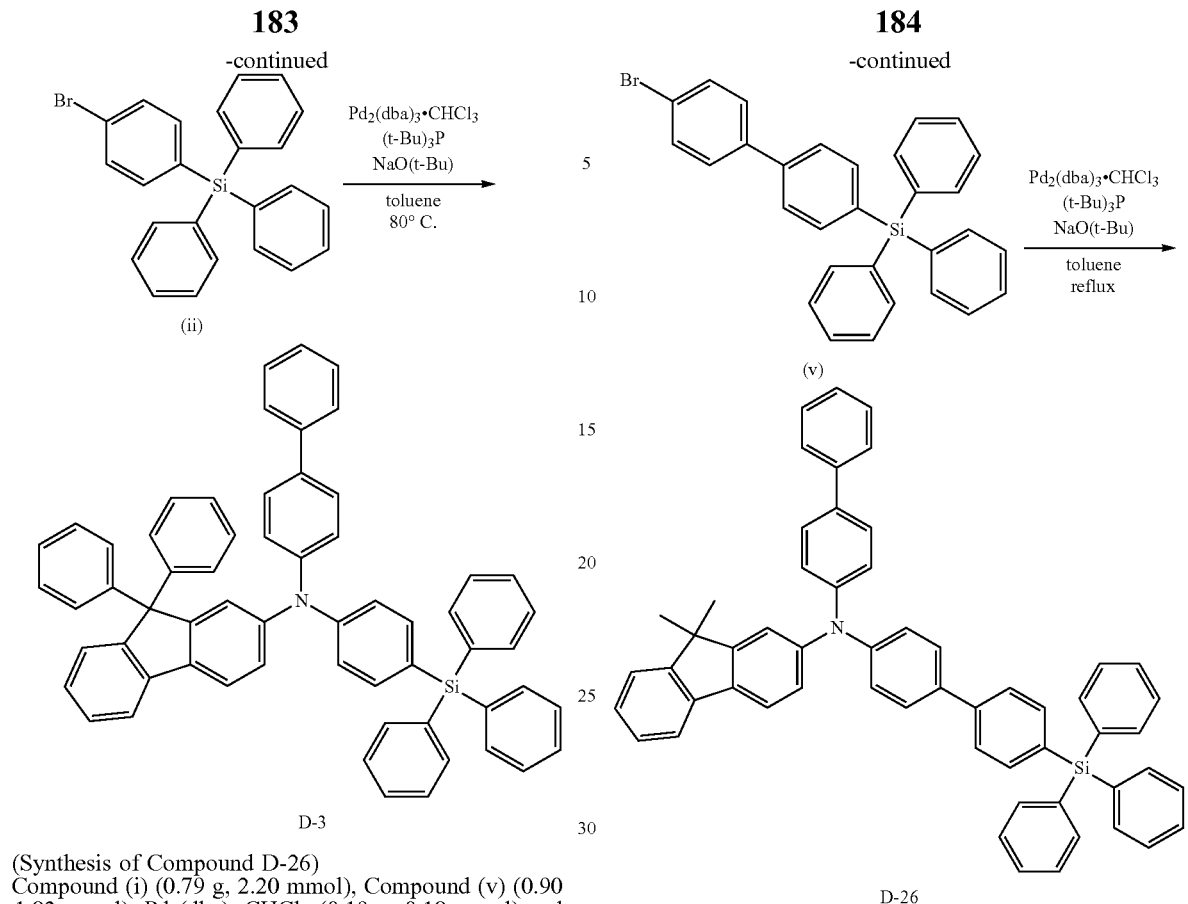

D-3

D-26

(Synthesis of Compound D-26)

Compound (i) (0.79 g, 2.20 mmol), Compound (v) (0.90 g, 1.83 mmol), Pd$_2$(dba)$_3$·CHCl$_3$ (0.19 g, 0.18 mmol) and toluene (18 mL) were added to a reaction vessel. Then, tri(t-butyl)phosphine (0.47 mL, 0.73 mmol, 1.56 M) and sodium t-butoxide (0.53 g, 5.49 mmol) were added thereto, and the inner part of the vessel was purged with a nitrogen gas, followed by stirring at about 100° C. for about 12 hours. After cooling in the air, water was added to the reaction mixture, and an organic layer was extracted. The organic layer thus obtained was dried with anhydrous magnesium sulfate and filtered. The filtrate was concentrated by a rotary evaporator. The crude product thus obtained was separated by silica gel column chromatography (developing solvent: dichloromethane/hexane), and the solid thus obtained was recrystallized using toluene/hexane to produce 1.06 g of a target product, Compound D-26, as a white powder solid with the yield of 75% (FAB-MS: C57H45NSi, measured value 771).

[Formula 136]

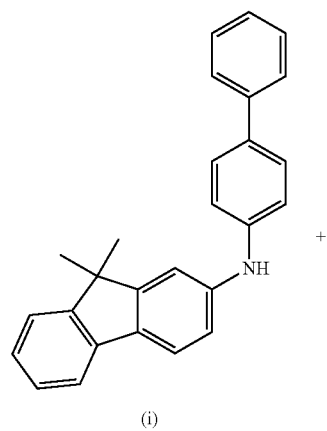

(i)

Hereinafter, organic electroluminescent devices using the above described Compound D-1, Compound D-3 and Compound C-26 as the materials for the organic electroluminescent devices according to an embodiment in hole transport layers will be explained. An organic electroluminescent device using Compound D-1 in the hole transport layer corresponds to Example 19, an organic electroluminescent device using Compound D-3 in the hole transport layer corresponds to Example 20 and an organic electroluminescent device using Compound D-26 in the hole transport layer corresponds to Example 21. As described above, Compound D-1 is the same as Compound 1 in Example 1.

The manufacture of the organic electroluminescent device according to Example 19 according to an embodiment was conducted by a vacuum deposition as for the organic electroluminescent device of Example 1 and the following procedure. First, with respect to an ITO-glass substrate patterned and washed in advance, surface treatment using ozone was conducted. In addition, the layer thickness of an ITO layer was about 150 nm. Immediately after the ozone treatment, a layer was formed using 2-TNATA as a hole injection material (thickness of about 60 nm) on the ITO layer.

Then, a layer was formed using Compound D-1 according to an embodiment as a hole transport material (about 30 nm), and a layer of ADN doped with TBP in a ratio of about 3% was formed by a co-deposition (about 25 nm).

After that, a layer was formed using Alq$_3$ as an electron transport material (about 25 nm), and LiF (about 1.0 nm) as an electron injection layer and aluminum (about 100 nm) as a cathode were laminated one by one to manufacture the organic electroluminescent device 200 shown in FIG. 2.

As Examples 20 and 21, organic electroluminescent devices were manufactured by performing the same procedure described in Example 19 except for using Compound D-3 and Compound D-26 instead of Compound D-1 used in Example 19.

As Comparative Examples 9 and 10, organic electroluminescent devices were manufactured by performing the same procedure described in Example 19 except for using Comparative Compound 9 and Comparative Compound 10 represented in the following as compounds constituting hole transport materials of the organic electroluminescent devices, like in the above Example 1.

[Formula 137]

Comparative Compound 9

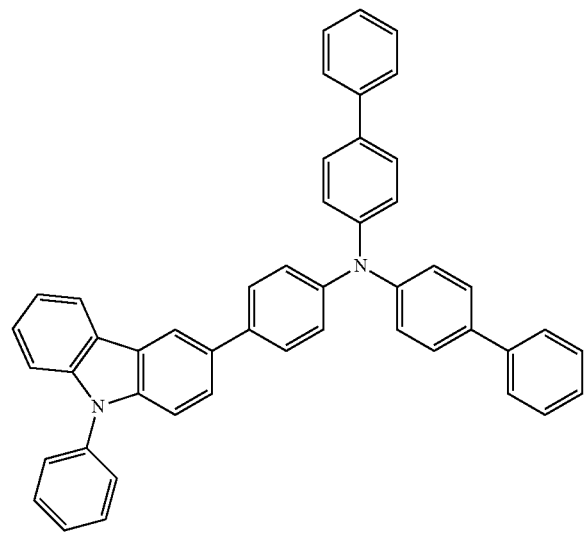

Comparative Compound 10

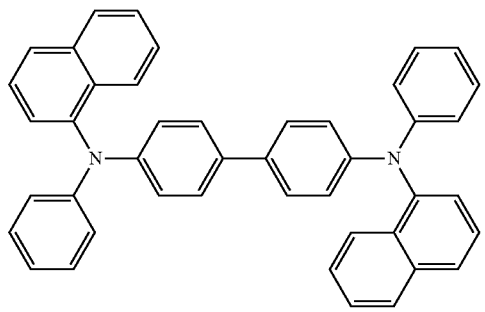

The driving voltage, the current efficiency and the half life of the organic electroluminescent devices 200 manufactured in Examples 19 to 21 and Comparative Examples 9 and 10 were evaluated. In addition, current efficiency means values at about 10 mA/cm$^2$, and half life means luminance decrease time to half from an initial luminance of about 1,000 cd/m$^2$. The evaluation results are shown in Table 5.

TABLE 5

| | Hole transport material | Voltage (V) | Current efficiency (cd/A) | Half life (hr) |
| --- | --- | --- | --- | --- |
| Example 19 | Compound D-1 | 7.1 | 6.4 | 1,700 |
| Example 20 | Compound D-3 | 7.3 | 6.7 | 1,900 |
| Example 21 | Compound D-26 | 6.7 | 6.9 | 2,100 |
| Comparative Example 9 | Comparative Compound 9 | 7.5 | 6.2 | 1,500 |
| Comparative Example 10 | Comparative Compound 10 | 8.1 | 5.3 | 1,200 |

According to Table 5, the organic electroluminescent devices of Examples 19 to 21 have improved emission efficiency and longer life than the organic electroluminescent devices of Comparative Examples 9 and 10. In addition, the organic electroluminescent devices of Examples 19 to 21 have a decreased driving voltage than the organic electroluminescent devices of Comparative Examples 9 and 10.

In the above-described Examples 19 to 21, an example amine derivative according to an embodiment represented by General Formula (3), was used as the hole transport material of the organic electroluminescent device as an embodiment; however, the use of the amine derivative according to an embodiment is not limited to the organic electroluminescent device and may be expanded to other luminescent devices or luminescent apparatus. In addition, the organic electroluminescent device using the amine derivative according to an embodiment represented by General Formula (3) may be used in an organic electroluminescent display of a passive-matrix driving type, and they may be also used in an organic electroluminescent display of an active-matrix driving type.

Remarkable improvement of the emission efficiency, the driving voltage and the life of an organic electroluminescent device may be obtained by disposing the amine derivative represented by General Formula (1), particularly, an amine derivative having the following structure as a material for an organic electroluminescent device between an emission layer and an anode.

In an example structure of the amine derivative represented by the above General Formula (1), Ar$^1$ and Ar$^2$ are independently a substituted or unsubstituted aryl group or a substituted or unsubstituted heteroaryl group, at least one of Ar$^1$ and Ar$^2$ is substituted with a substituted or unsubstituted silyl group, Ar$^3$ is a substituted or unsubstituted carbazole group, and L is a substituted or unsubstituted arylene group or a substituted or unsubstituted heteroarylene group.

Here, as the aryl group and the heteroaryl group of "the substituted or unsubstituted aryl group" or "the substituted or unsubstituted heteroaryl group" of Ar$^1$ and Ar$^2$, as described above, a phenyl group, a naphthyl group, an anthracenyl group, a phenanthryl group, a biphenyl group, a terphenyl group, a fluorenyl group, a triphenylene group, a biphenylene group, a pyrenyl group, a benzothiazolyl group, a thiophenyl group, a thienothiophenyl group, a thienothienothiophenyl group, a benzothiophenyl group, a dibenzothiophenyl group, a dibenzofuryl group, a N-arylcarbazolyl group, a N-heteroarylcarbazolyl group, a N-alkylcarbazolyl group, a phenoxazyl group, a phenothiazyl group, a pyridyl group, a pyrimidyl group, a triazinyl group, a quinolinyl group and a quinoxalyl group are examples. The phenyl group, the naphthyl group, the biphenyl group, the terphenyl group, the fluorenyl group, the triphenylene group, the dibenzothiophenyl group, the dibenzofuryl group and the N-phenylcarbazolyl group may be used. As the aryl group, an aryl group having 6 to 18 carbon atoms for forming a ring may be used, and as the heteroaryl group, a heteroaryl group having 5 to 18 carbon atoms for forming a ring may be used.

As the substituent of the aryl group or the heteroaryl group of $Ar^1$ and $Ar^2$, an alkyl group, an alkoxy group, an aryl group and a heteroaryl group are examples. Examples of the aryl group and the heteroaryl group are the same as the above exemplified aryl group and the heteroaryl group of $Ar^1$ and $Ar^2$. The alkyl group as the substituent of the aryl group or the heteroaryl group of $Ar^1$ and $Ar^2$ is not specifically limited and may include a methyl group, an ethyl group, a propyl group, an isopropyl group, a cyclopropyl group, a butyl group, an isobutyl group, a t-butyl group, a cyclobutyl group, a pentyl group, an isopentyl group, a neopentyl group, a cyclopentyl group, a hexyl group, a cyclohexyl group, a heptyl group, a cycloheptyl group, an octyl group, a nonyl group, a decyl group, etc. In addition, the alkoxy group as the substituent of the aryl group or the heteroaryl group of $Ar^1$ and $Ar^2$ is not specifically limited and may include a methoxy group, an ethoxy group, a n-propoxy group, an isopropoxy group, a n-butoxy group, an isobutoxy group, a t-butoxy group, a n-pentyloxy group, a neopentyloxy group, a n-hexyloxy group, a n-heptyloxy group, a n-octyloxy group, a 2-ethylhexyloxy group, a nonyloxy group, a decyloxy group, a 3,7-dimethyloctyloxy group, etc.

As the substituent of the silyl group substituted for at least one of $Ar^1$ and $Ar^2$, an alkyl group, an alkoxy group, an aryl group and a heteroaryl group are examples. For example, the substituent is the same as the alkyl group, the alkoxy group, the aryl group and the heteroaryl group explained as the substituent of the aryl group or the heteroaryl group of $Ar^1$ and $Ar^2$. For example, a phenyl group and a methyl group may be used. In addition, as the silyl group substituted for at least one of $Ar^1$ and $Ar^2$, a triarylsilyl group where an aryl substituent at the silyl group has 6 to 18 carbon atoms and a trialkylsilyl group where an alkyl substituent at the silyl group has 1 to 6 carbon atoms may be used.

In an example structure of the amine derivative according to an embodiment, $Ar^3$ is a substituted or unsubstituted carbazolyl group in General Formula (1). The substituent of the carbazolyl group is independently a hydrogen atom, a substituted or unsubstituted aryl group having 6 to 18 carbon atoms for forming a ring, a substituted or unsubstituted heteroaryl group having 5 to 18 carbon atoms for forming a ring or a substituted or unsubstituted alkyl group having 1 to 10 carbon atoms. As the substituent of the carbazolyl group, the substituted or unsubstituted aryl group may be used and, for example, a carbazolyl group substituted with a phenyl group at position 9 may be used. By substituting the phenyl group at position 9 of the carbazolyl group, ionization potential may be controlled, and hole transport properties may be improved. In addition, by positioning a tertiary amine at position 9 of the carbazolyl group, the durability of the amine derivative may be improved, and the long life of the organic electroluminescent device may be attained.

In an example structure of the amine derivative, L is a substituted or unsubstituted arylene group or a substituted or unsubstituted heteroarylene group. In General Formula (1), by combining the carbazolyl group for $Ar^3$ with an amine part via a connecting group of L, the conjugation system of the π electrons of a whole molecule may be enlarged, and hole transport properties and the stability of the molecule may be improved.

Here, as the aryl group and the heteroarylene group of "the substituted or unsubstituted arylene group" and "the substituted or unsubstituted heteroarylene group" of L may be the same aryl group and the heteroaryl group of "the substituted or unsubstituted aryl group" or "the substituted or unsubstituted heteroaryl group" exemplified for $Ar^1$ and $Ar^2$. As the arylene group and the heteroarylene group of "the substituted or unsubstituted arylene group" and "the substituted or unsubstituted heteroarylene group" of L, an aryl group having 6 to 18 carbon atoms for forming a ring and a heteroarylene group having 5 to 18 carbon atoms for forming a ring may be used. A phenylene group may be used. Since L is the phenylene group, an appropriate energy level may be realized.

In an example structure of the amine derivative according to an embodiment, the substituted or unsubstituted carbazolyl group for $Ar^3$ is connected to the substituted or unsubstituted arylene group or the substituted or unsubstituted heteroarylene group of the connecting group L at position 1 to position 4. In an implementation, the substituted or unsubstituted carbazolyl group for $Ar^3$ is connected to L at position 2 or position 3, and, for example, is connected to L at position 3. Through the combination of the substituted or unsubstituted carbazolyl group for $Ar^3$ with L at position 2 or position 3, HOMO may be enlarged, and hole transport properties may be improved. For example, in the case that the bonding position with L is position 3 of the carbazolyl group, the long life of the organic electroluminescent device may be attained because LUMO is not present in the carbazolyl group.

In an example amine derivative according to an embodiment, $Ar^3$ is the substituted or unsubstituted carbazolyl group, and L is the substituted or unsubstituted arylene group or the substituted or unsubstituted heteroarylene group. Through introducing the substituted or unsubstituted carbazolyl group for $Ar^3$, the hole transport properties of the amine derivative may be improved. In addition, through the combination of the substituted or unsubstituted carbazolyl group with the nitrogen atom (N) at the amine part combined with $Ar^1$ and $Ar^2$, at least one of which is substituted with a silyl group, via the substituted or unsubstituted arylene group or the substituted or unsubstituted heteroarylene group of L, the conjugation system of π electrons may be enlarged, and hole transport properties may be improved, and the level of HOMO may be controlled, thereby improving the emission efficiency of the organic electroluminescent device and realizing the decrease of the driving voltage and the long life thereof. For example, the improvement of the emission efficiency, the decrease of the driving voltage and the increase of the life of the organic electroluminescent device may be realized in a blue-bluish green region.

As an example amine derivative in which the substituted or unsubstituted carbazolyl group for $Ar^3$ is combined with the substituted or unsubstituted arylene group or the substituted or unsubstituted heteroarylene group of L in General Formula (1), the following compounds are examples, without limitation.

[Formula 138]

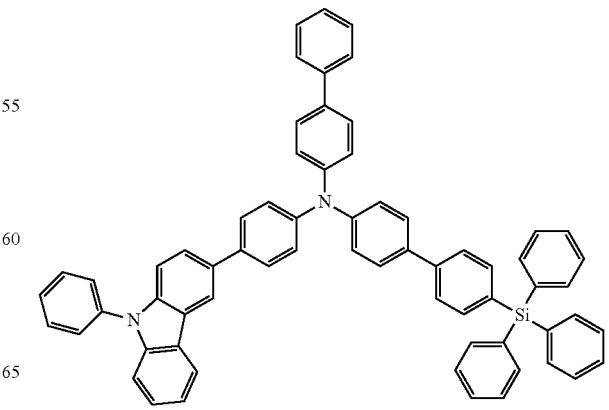

E-1

[Formula 139]
E-2
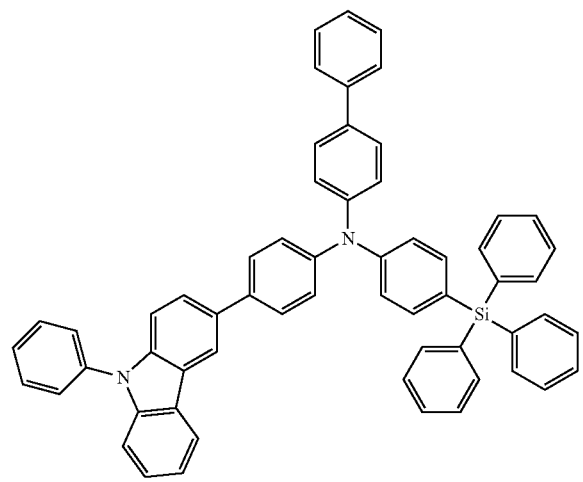
E-5
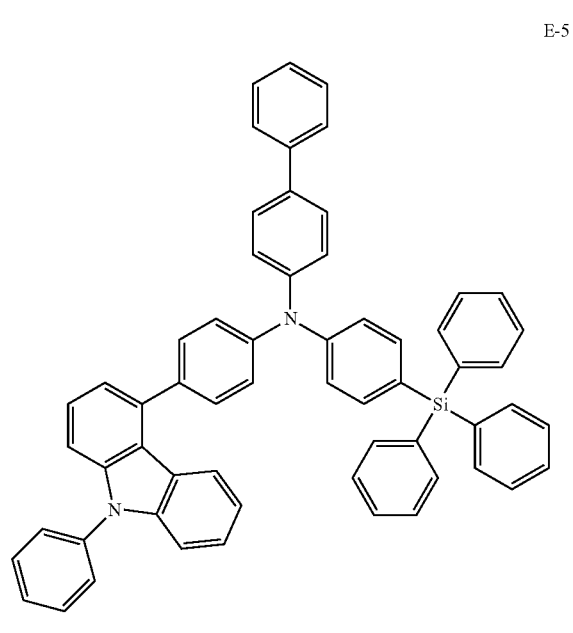
E-3
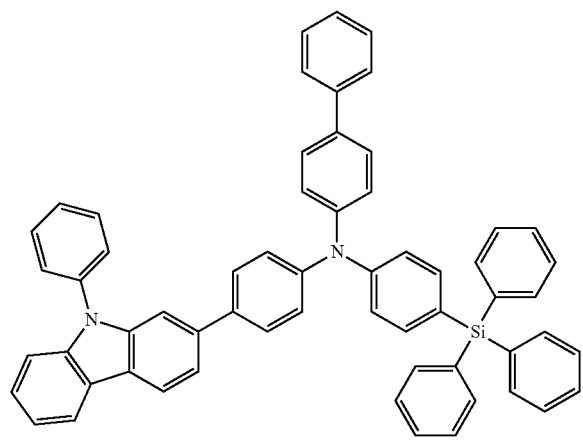
E-6
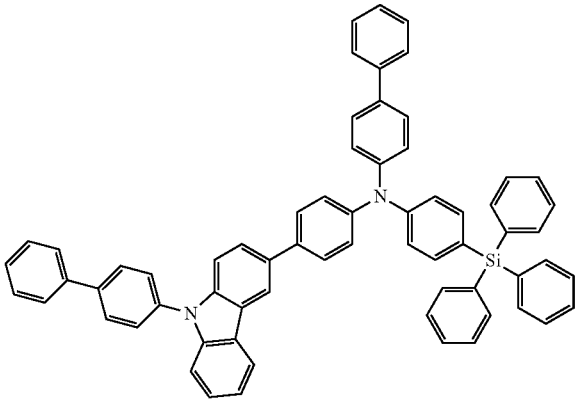
E-4
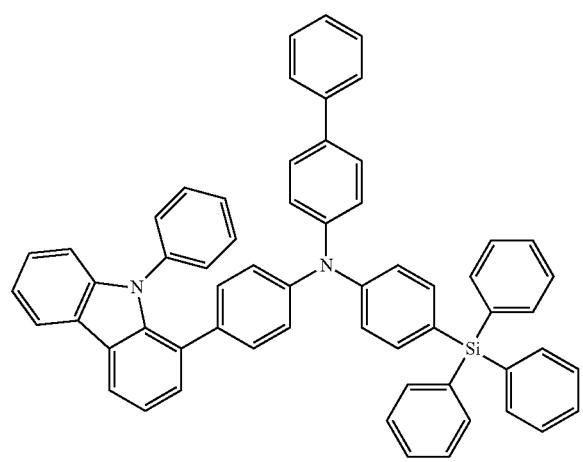
E-7
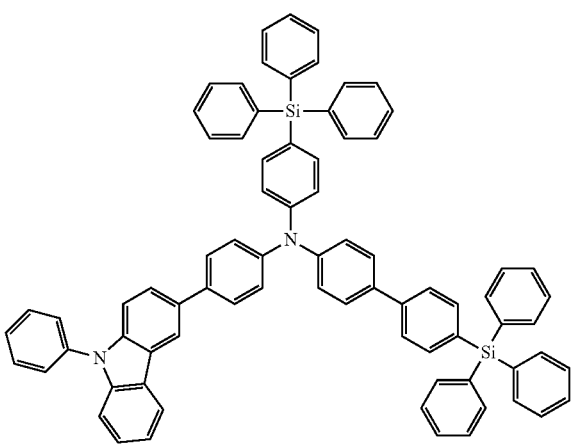

E-8
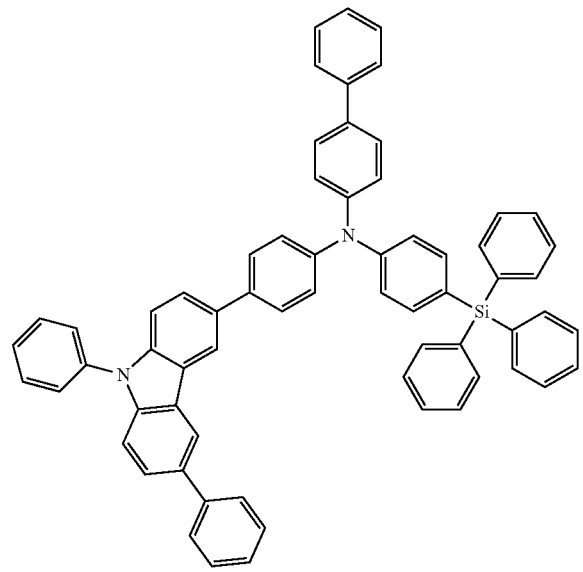
[Formula 140]
E-9
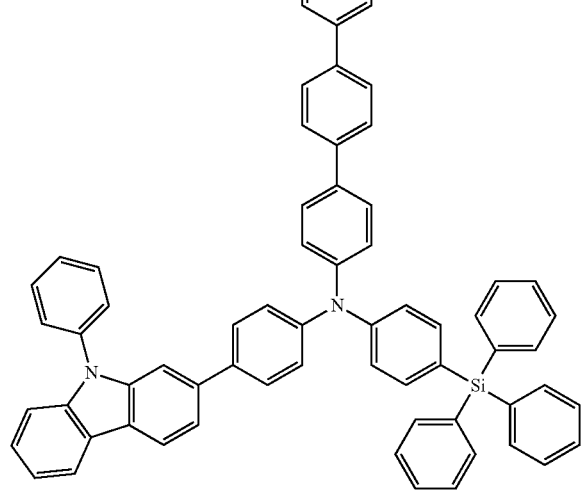
E-10
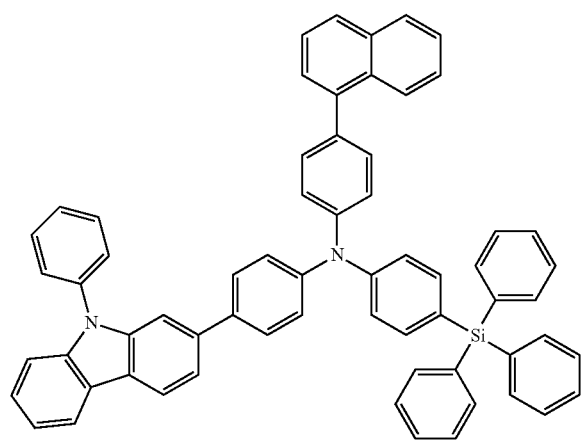
E-11
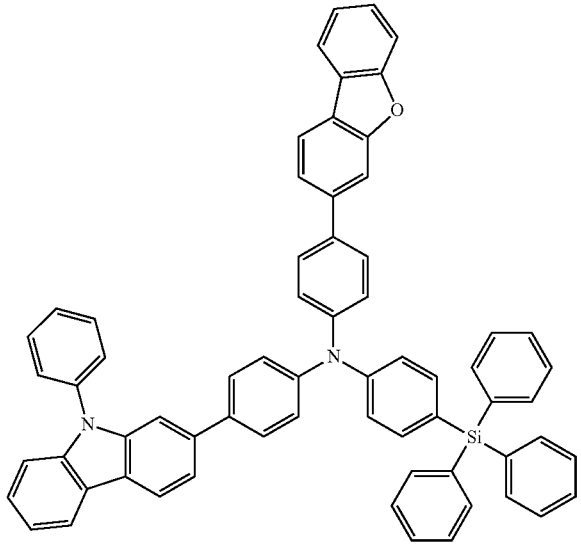
E-12
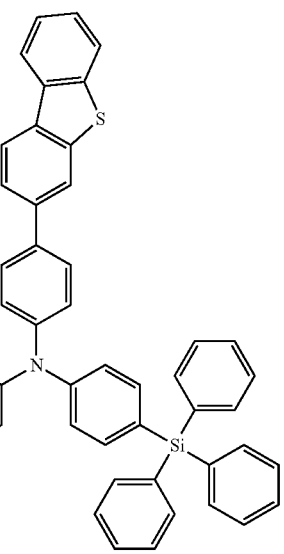
[Formula 141]
E-13
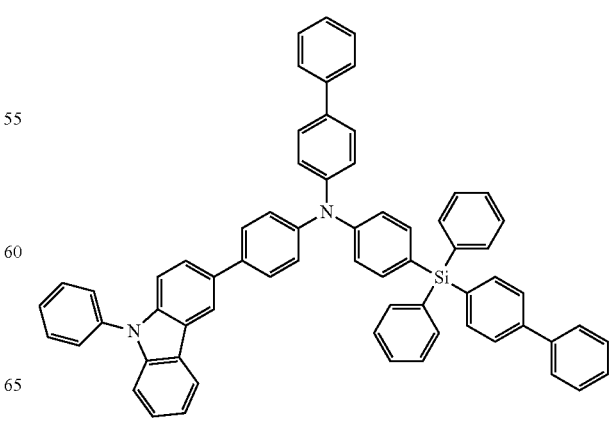

E-14

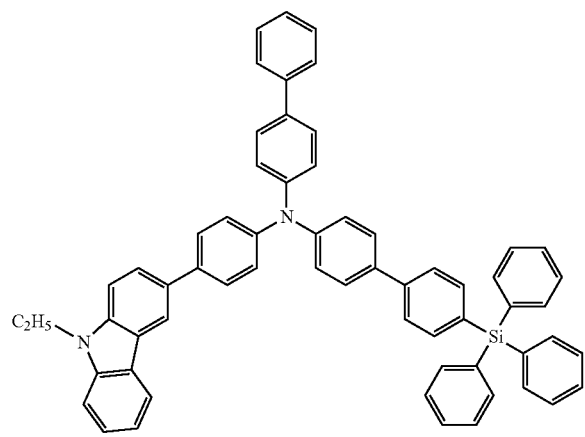

E-15

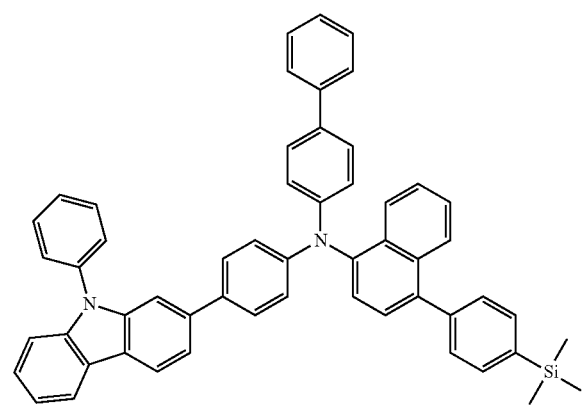

E-16

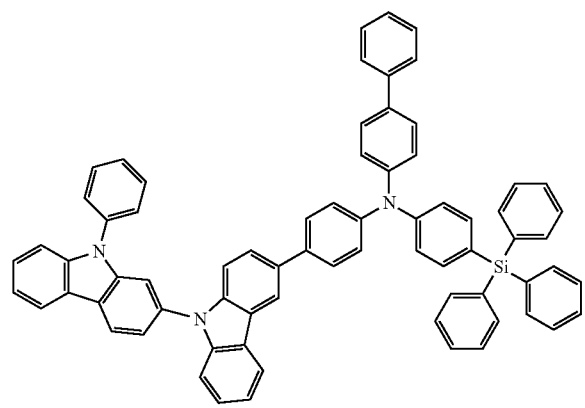

[Formula 142]

E-17

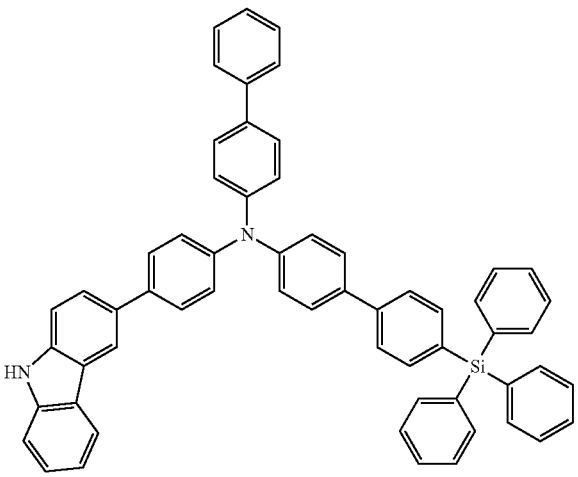

E-18

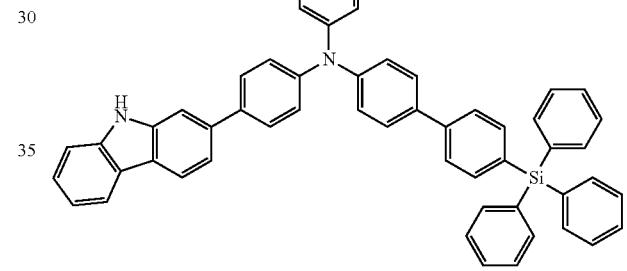

An example amine derivative according to an embodiment, which is an amine derivative in which the substituted or unsubstituted carbazolyl group for Ar³ is combined with the substituted or unsubstituted arylene group or the substituted or unsubstituted heteroarylene group of L in General Formula (1), may be used as the material of the hole transport layer of the organic electroluminescent device 100 shown in FIG. 1. In addition, the configuration of the organic electroluminescent device 100 shown in FIG. 1 is an illustration of the organic electroluminescent device according to an embodiment without limitation, and may be variously modified.

In addition, the use of an example amine derivative according to an embodiment, the amine derivative in which the substituted or unsubstituted carbazolyl group for Ar³ is combined with the substituted or unsubstituted arylene group or the substituted or unsubstituted heteroarylene group of L in General Formula (1), is not limited to the hole transport material of the organic electroluminescent device; it may be used as the material of the hole injection layer or the material of the emission layer. In the case that the amine derivative is used as the material of the hole injection layer or the material of the emission layer, the emission efficiency of the organic electroluminescent device may be improved, and the long life of the organic electroluminescent device may be realized as the case using the amine derivative as the material of the hole transport layer.

Example VI

With respect to an example amine derivative according to an embodiment, which is the amine derivative in which the substituted or unsubstituted carbazolyl group for Ar3 is combined with the substituted or unsubstituted arylene group or the substituted or unsubstituted heteroarylene group of L in General Formula (1), examples of synthesizing Compound E-1, Compound E-2 and Compound E-3 will be explained hereinafter. However, the following synthetic methods are only examples, and embodiments are not limited thereto. In addition, Compound E-1 is the same as Compound 61 in the above-described Example 3, and Compound E-2 is the same as Compound 63 in the above-described Example 4.

(Synthesis of Compound E-1)

Compound (iv) (0.70 g, 1.44 mmol), Compound (v) (0.71 g, 1.44 mmol), Pd$_2$(dba)$_3$ (0.04 g, 0.07 mmol) and toluene (30 mL) were added to a reaction vessel. Then, tri(t-butyl) phosphine (0.14 mL, 0.28 mmol, 2.00 M) and sodium t-butoxide (0.21 g, 2.16 mmol) were added thereto, and the inner part of the vessel was purged with a nitrogen gas, followed by refluxing for about 6 hours. After cooling in the air, water was added to the reaction mixture, and an organic layer was extracted. The organic layer thus obtained was dried with anhydrous magnesium sulfate and filtered. The filtrate was concentrated by a rotary evaporator. The crude product thus obtained was separated by silica gel column chromatography (developing solvent: toluene/hexane), and the solid thus obtained was recrystallized using dichloromethane/hexane to produce 1.15 g of a target product, Compound E-1, as a white powder solid with the yield of 89% (FAB-MS: C66H48N2Si, measured value 897).

[Formula 143]

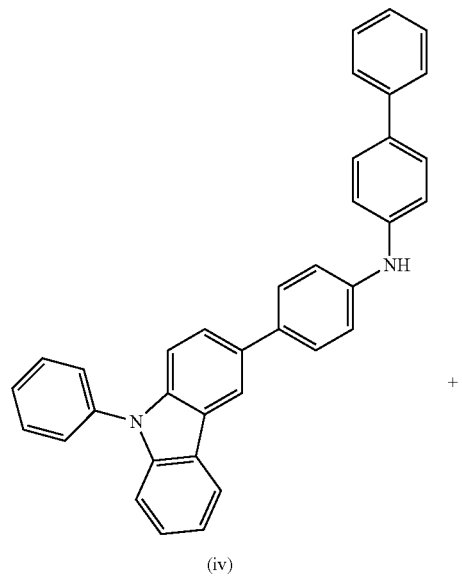

(iv)

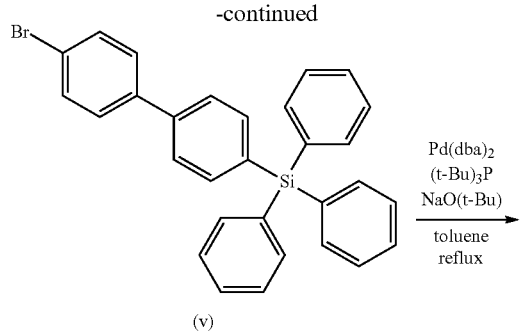

(v)

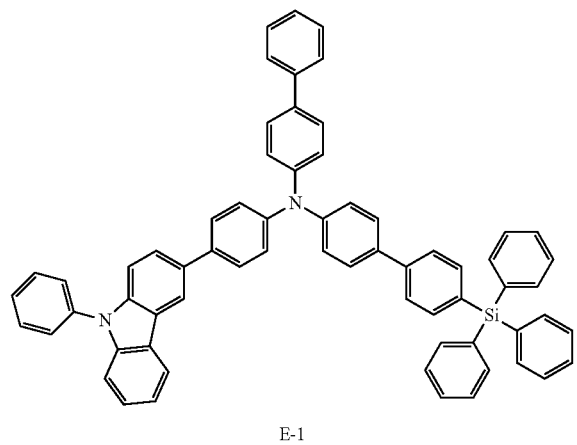

E-1

(Synthesis of Compound E-2)

Compound (iv) (1.00 g, 2.06 mmol), Compound (ii) (0.85 g, 2.06 mmol), Pd(dba)$_2$ (0.06 g, 0.10 mmol) and toluene (10 mL) were added to a reaction vessel. Then, tri(t-butyl) phosphine (0.03 mL, 0.06 mmol, 2.00 M) and sodium t-butoxide (0.30 g, 3.08 mmol) were added thereto, and the inner part of the vessel was purged with a nitrogen gas, followed by stirring while refluxing for about 4 hours. After cooling in the air, water was added to the reaction mixture, and an organic layer was extracted. The organic layer thus obtained was dried with anhydrous magnesium sulfate and filtered. The filtrate was concentrated by a rotary evaporator. The crude product thus obtained was separated by silica gel column chromatography (developing solvent: toluene/hexane), and the solid thus obtained was recrystallized using dichloromethane/hexane to produce 1.59 g of a target product, Compound E-2, as a white powder solid with the yield of 94% (FAB-MS: C60H44N2Si, measured value 821)

[Formula 144]

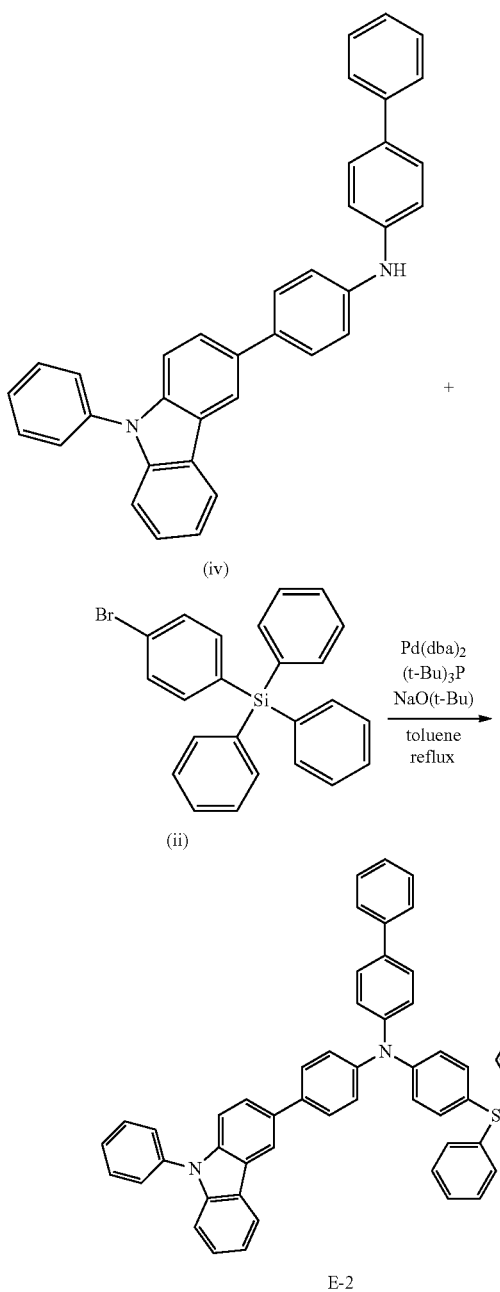

E-2

[Formula 145]

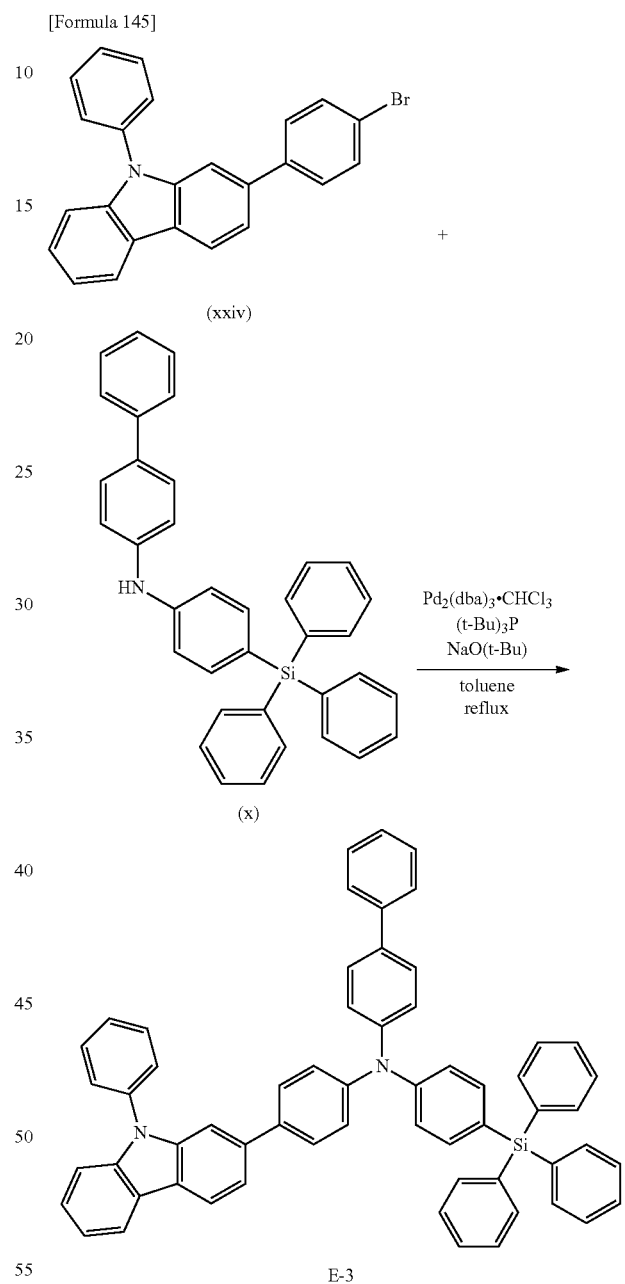

E-3 toluene/hexane), and the solid thus obtained was recrystallized using dichloromethane/hexane to produce 2.00 g of a target product, Compound E-3, as a white powder solid with the yield of 97% (FAB-MS: C60H44N2Si, measured value 821).

(Synthesis of Compound E-3)

Compound (xxiv) (1.00 g, 2.51 mmol), Compound (x) (1.26 g, 2.51 mmol), $Pd_2(dba)_3 \cdot CHCl_3$ (0.13 g, 0.13 mmol) and toluene (25 mL) were added to a reaction vessel. Then, tri(t-butyl)phosphine (0.33 mL, 0.50 mmol, 1.5 M) and sodium t-butoxide (0.48 g, 5.02 mmol) were added thereto, and the inner part of the vessel was purged with a nitrogen gas, followed by stirring while refluxing for about 3 hours. After cooling in the air, water was added to the reaction mixture, and an organic layer was extracted. The organic layer thus obtained was dried with anhydrous magnesium sulfate and filtered. The filtrate was concentrated by a rotary evaporator. The crude product thus obtained was separated by silica gel column chromatography (developing solvent:

Hereinafter, organic electroluminescent devices using the above described Compound E-1, Compound E-2 and Compound E-3 as the materials for the organic electroluminescent devices according to an embodiment in hole transport layers will be explained. An organic electroluminescent device using Compound E-1 in the hole transport layer corresponds to Example 22, an organic electroluminescent device using Compound E-2 in the hole transport layer corresponds to Example 23 and an organic electroluminescent device using Compound E-3 in the hole transport layer corresponds to Example 24. In addition, as described above, Compound E-1 is the same as Compound 61 in Example 3, and Compound E-2 is the same as Compound 63 in Example 4.

The manufacture of the organic electroluminescent device according to Example 22 according to an embodiment was conducted by a vacuum deposition as for the organic electroluminescent device of Example 1 and the following procedure. First, with respect to an ITO-glass substrate patterned and washed in advance, surface treatment using ozone was conducted. In addition, the layer thickness of an ITO layer was about 150 nm. Immediately after the ozone treatment, a layer was formed using 2-TNATA as a hole injection material (thickness of about 60 nm) on the ITO layer.

Then, a layer was formed using Compound E-1 according to an embodiment as a hole transport material (about 30 nm), and a layer of ADN doped with TBP in a ratio of about 3% was formed by a co-deposition (about 25 nm).

After that, a layer was formed using $Alq_3$ as an electron transport material (about 25 nm), and LiF (about 1.0 nm) as an electron injection layer and aluminum (about 100 nm) as a cathode were laminated one by one to manufacture the organic electroluminescent device 200 shown in FIG. 2.

As Examples 23 and 24, organic electroluminescent devices were manufactured by performing the same procedure described in Example 22 except for using Compound E-2 and Compound E-3 instead of Compound E-1 used in Example 22.

As Comparative Examples 11, 12 and 13, organic electroluminescent devices were manufactured by performing the same procedure described in Example 22 except for using Comparative Compounds 11, 12 and 13 represented in the following as compounds constituting hole transport materials of the organic electroluminescent devices.

[Formula 146]

Comparative Compound 11

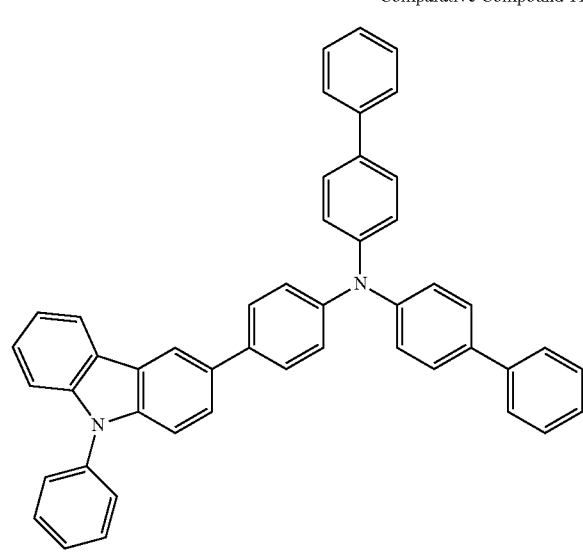

Comparative Compound 12

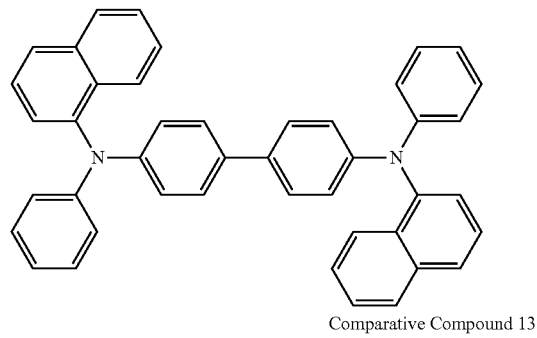

Comparative Compound 13

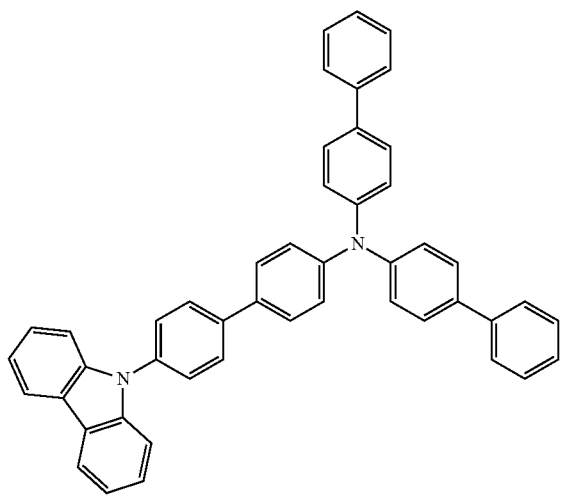

The driving voltage, the current efficiency and the half life of the organic electroluminescent devices 200 manufactured in Examples 22 to 24 and Comparative Examples 11 to 13 were evaluated. In addition, emission efficiency means values at about 10 $mA/cm^2$, and half life means luminance decrease time to half from an initial luminance of about 1,000 $cd/m^2$. The evaluation results are shown in Table 6.

TABLE 6

| | Hole transport material | Current Voltage (V) | efficiency (cd/A) | Half life (hr) |
|---|---|---|---|---|
| Example 22 | Compound E-1 | 6.7 | 6.9 | 2,000 |
| Example 23 | Compound E-2 | 6.8 | 6.7 | 1,900 |
| Example 24 | Compound E-3 | 6.9 | 6.6 | 1,800 |
| Comparative Example 11 | Comparative Compound 11 | 7.5 | 6.2 | 1,500 |
| Comparative Example 12 | Comparative Compound 12 | 8.1 | 5.3 | 1,200 |
| Comparative Example 13 | Comparative Compound 13 | 7.2 | 6.0 | 1,500 |

According to Table 6, the organic electroluminescent devices of Examples 22 to 24 have decreased driving voltage, improved emission efficiency and longer life than the organic electroluminescent devices of Comparative Examples 11 to 13.

In the above-described Examples 22 to 24, an example amine derivative according to an embodiment, in which the substituted or unsubstituted carbazolyl group for $Ar^3$ is combined with the substituted or unsubstituted arylene group or the substituted or unsubstituted heteroarylene group of L in General Formula (1), was used as the hole transport material of the organic electroluminescent device as an embodiment; however, the use of the amine derivative according to an embodiment is not limited to the organic electroluminescent device, and is expanded to other luminescent devices or luminescent apparatus. In addition, the organic electroluminescent device using an example amine derivative according to an embodiment may be used in an organic electroluminescent display of a passive-matrix driving type, and they may be also used in an organic electroluminescent display of an active-matrix driving type.

Remarkable improvement of the emission efficiency, the driving voltage and the life of an organic electroluminescent device may be obtained by disposing the amine derivative represented by General Formula (1), for example, an amine derivative having the following structure as a material for an organic electroluminescent device between an emission layer and an anode.

In an example structure of the amine derivative represented by General Formula (1), $Ar^1$ and $Ar^2$ are independently a substituted or unsubstituted aryl group or a substituted or unsubstituted heteroaryl group, at least one of $Ar^1$ and $Ar^2$ is substituted with a substituted or unsubstituted silyl group, $Ar^3$ is a substituted or unsubstituted carbazolyl group, and L is a divalent connecting group including a substituted or unsubstituted arylene group or a substituted or unsubstituted heteroarylene group. An example structure of the amine derivative represented by General Formula (1) is represented by the following General Formula (4).

[Formula 147]

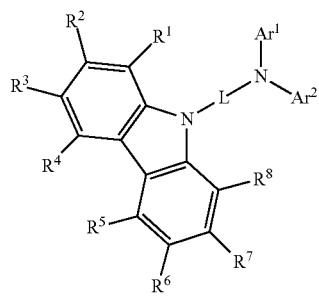

(4)

Here, as the aryl group and the heteroaryl group of "the substituted or unsubstituted aryl group" or "the substituted or unsubstituted heteroaryl group" of $Ar^1$ and $Ar^2$, as described above, a phenyl group, a naphthyl group, an anthracenyl group, a phenanthryl group, a biphenyl group, a terphenyl group, a fluorenyl group, a triphenylene group, a biphenylene group, a pyrenyl group, a benzothiazolyl group, a thiophenyl group, a thienothiophenyl group, a thienothienothiophenyl group, a benzothiophenyl group, a dibenzothiophenyl group, a dibenzofuryl group, a N-arylcarbazolyl group, a N-heteroarylcarbazolyl group, a N-alkylcarbazolyl group, a phenoxazyl group, a phenothiazyl group, a pyridyl group, a pyrimidyl group, a triazinyl group, a quinolinyl group, and a quinoxalyl group are examples. The phenyl group, the naphthyl group, the biphenyl group, the terphenyl group, the fluorenyl group, the triphenylene group, the dibenzothiophenyl group, the dibenzofuryl group and the N-phenylcarbazolyl group may be used. As the aryl group, an aryl group having 6 to 18 carbon atoms for forming a ring may be used, and as the heteroaryl group, a heteroaryl group having 5 to 18 carbon atoms for forming a ring may be used.

As the substituent of the aryl group or the heteroaryl group of $Ar^1$ and $Ar^2$, a halogen atom, an alkyl group, an alkoxy group, an aryl group and a heteroaryl group are examples. Examples of the aryl group and the heteroaryl group are the same as the above exemplified aryl group and the heteroaryl group of $Ar^1$ and $Ar^2$. As the halogen atom, a fluorine atom may be used, without specific limitation. The alkyl group is not specifically limited and may include a methyl group, an ethyl group, a propyl group, an isopropyl group, a cyclopropyl group, a butyl group, an isobutyl group, a t-butyl group, a cyclobutyl group, a pentyl group, an isopentyl group, a neopentyl group, a cyclopentyl group, a hexyl group, a cyclohexyl group, a heptyl group, a cycloheptyl group, an octyl group, a nonyl group, a decyl group, etc. The alkoxy group is not specifically limited and may include a methoxy group, an ethoxy group, a n-propoxy group, an isopropoxy group, a n-butoxy group, an isobutoxy group, a t-butoxy group, a n-pentyloxy group, a neopentyloxy group, a n-hexyloxy group, a n-heptyloxy group, a n-octyloxy group, a 2-ethylhexyloxy group, a nonyloxy group, a decyloxy group, a 3,7-dimethyloctyloxy group, etc.

$Ar^3$ is a substituted or unsubstituted carbazolyl group, and the carbazolyl group is combined with L at position 9. $R^1$ to $R^8$ in General Formula (4) are independently a hydrogen atom, a substituted or unsubstituted aryl group having 6 to 30 carbon atoms for forming a ring, a substituted or unsubstituted heteroaryl group having 5 to 30 carbon atoms for forming a ring, a substituted or unsubstituted alkyl group having 1 to 15 carbon atoms, a substituted or unsubstituted silyl group, a cyano group, a halogen atom or a deuterium atom. Examples of the aryl group and the heteroaryl group substituted for $R^1$ to $R^8$ of the carbazolyl group may be the same as the substitute or unsubstituted aryl group and the heteroaryl group of $Ar^1$ and $Ar^2$. Examples of the alkyl group substituted for $R^1$ to $R^8$ of the carbazolyl group may be the same as the alkyl group substituted at the aryl group and the heteroaryl group of $Ar^1$ and $Ar^2$. The substituent of $R^1$ to $R^8$ of the carbazolyl group may be the same as the above-described substituent of the aryl group or the heteroaryl group of $Ar^1$ and $Ar^2$. In addition, $R^1$ to $R^8$ in General Formula (4) may be combined to each other to form a saturated or unsaturated ring.

L is a divalent connecting group and preferably, a substituted or unsubstituted arylene group or a substituted or unsubstituted heteroarylene group. The substituted or unsubstituted arylene group of L preferably has 6 to 18 carbon atoms for forming a ring. The substituted or unsubstituted heteroarylene group of L has preferably 6 to 18 carbon atoms for forming a ring. The arylene group and the heteroarylene group of "the substituted or unsubstituted arylene group" or "the substituted or unsubstituted heteroarylene group" of L may be a phenylene group, a naphthylene group, a biphenylene group, an anthracenyl group, a triphenylene group, a fluorenylene group, etc., and the phenylene group, the biphenylene group and the fluorenylene group may be used.

In addition, in the case that L is the fluorenylene group, $Ar^1$ and $Ar^2$ in General Formula (4) may be the aryl group having 6 to 12 carbon atoms for forming a ring.

As the substituent of the silyl group substituted for at least one of $Ar^1$ and $Ar^2$, an alkyl group, an alkoxy group, an aryl group and a heteroaryl group are examples. For example, the substituent is the same as the alkyl group, the alkoxy group, the aryl group and the heteroaryl group explained as the substituent of the aryl group or the heteroaryl group of $Ar^1$ and $Ar^2$. For example, as the silyl group substituted in at least one of $Ar^1$ and $Ar^2$, a triarylsilyl group where an aryl substituent at the silyl group has 6 to 18 carbon atoms for forming a ring and a trialkylsilyl group where an alkyl substituent at the silyl group has 1 to 6 carbon atoms may be used.
As amine derivative represented by General Formula (4), which is an example amine derivative according to an embodiment, the following compounds are examples, without limitation.
[Formula 148]
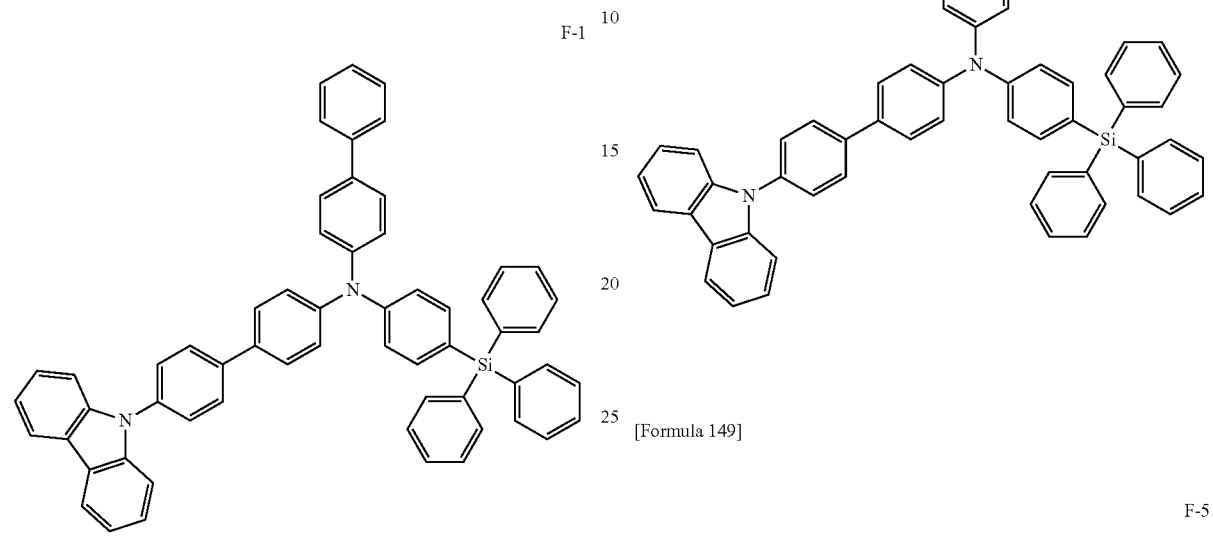
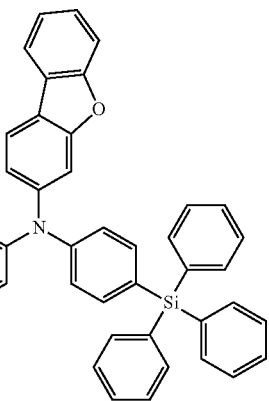
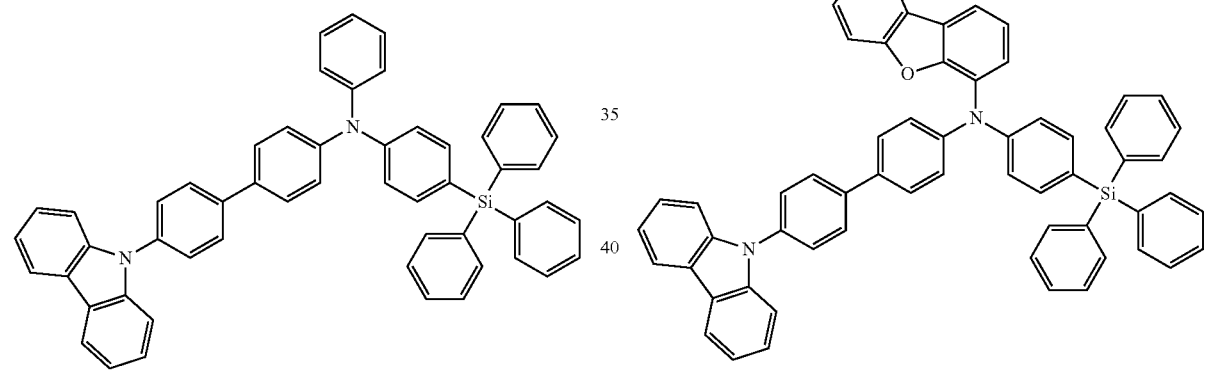
[Formula 149]
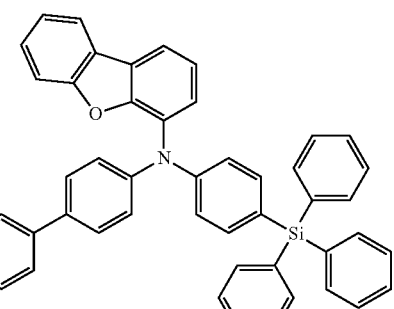
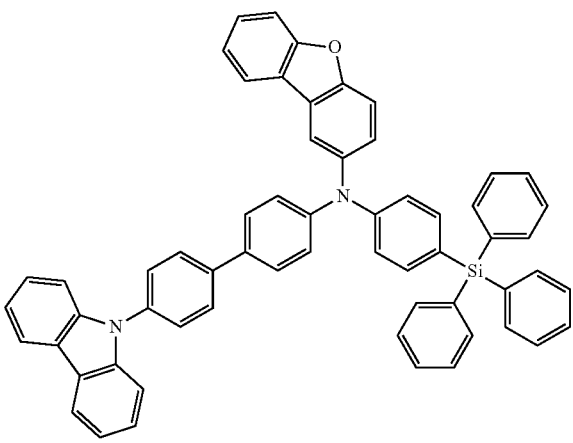

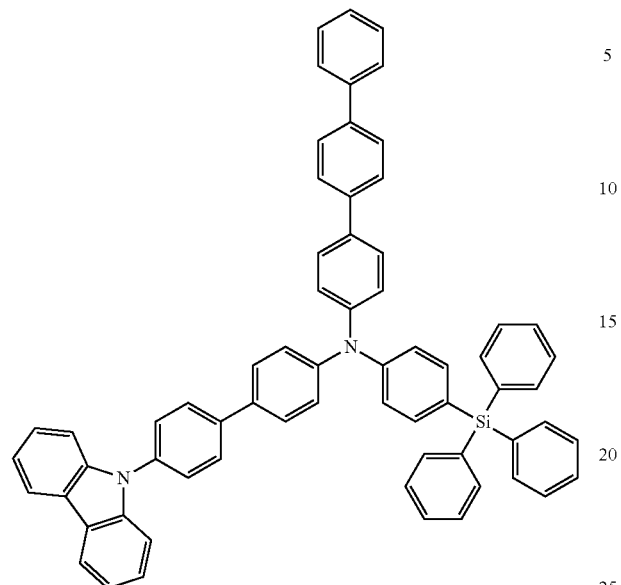
F-7
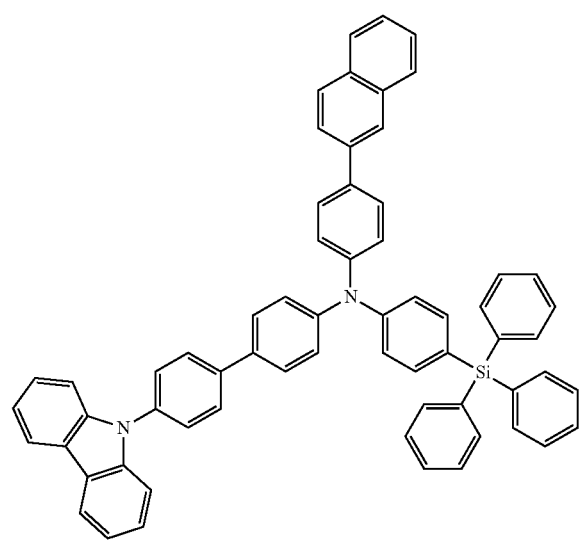
F-8
F-9
[Formula 150]
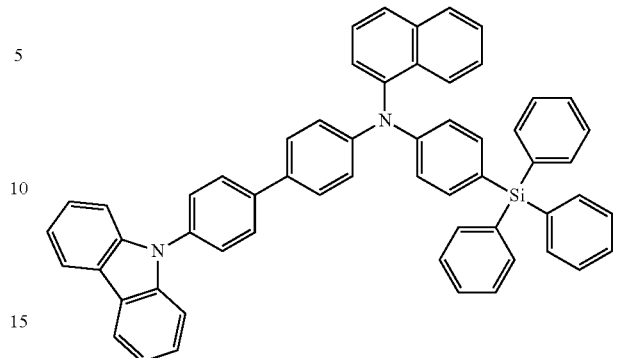
F-10
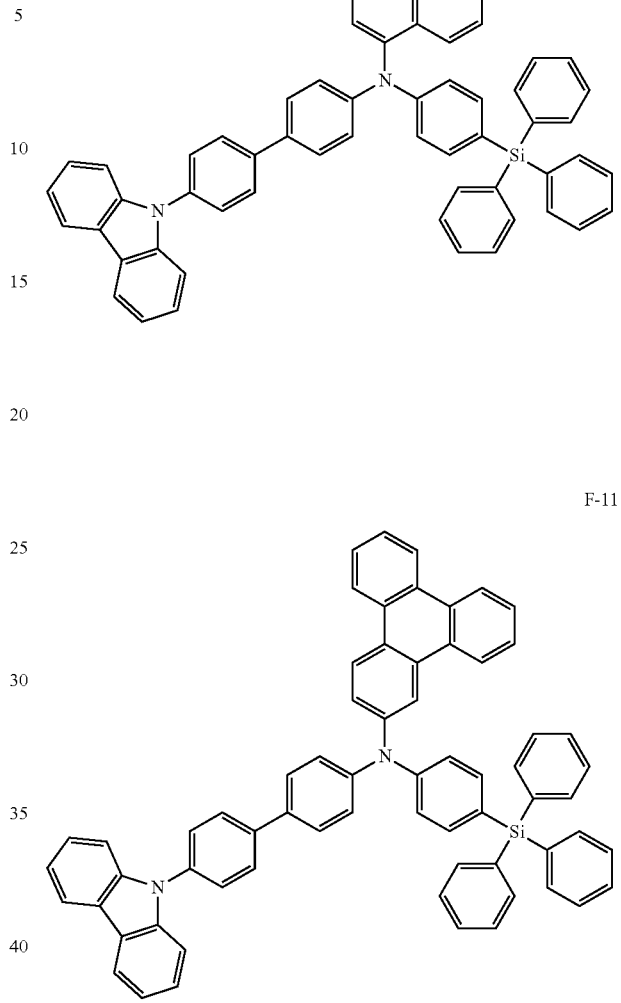
F-11
F-12

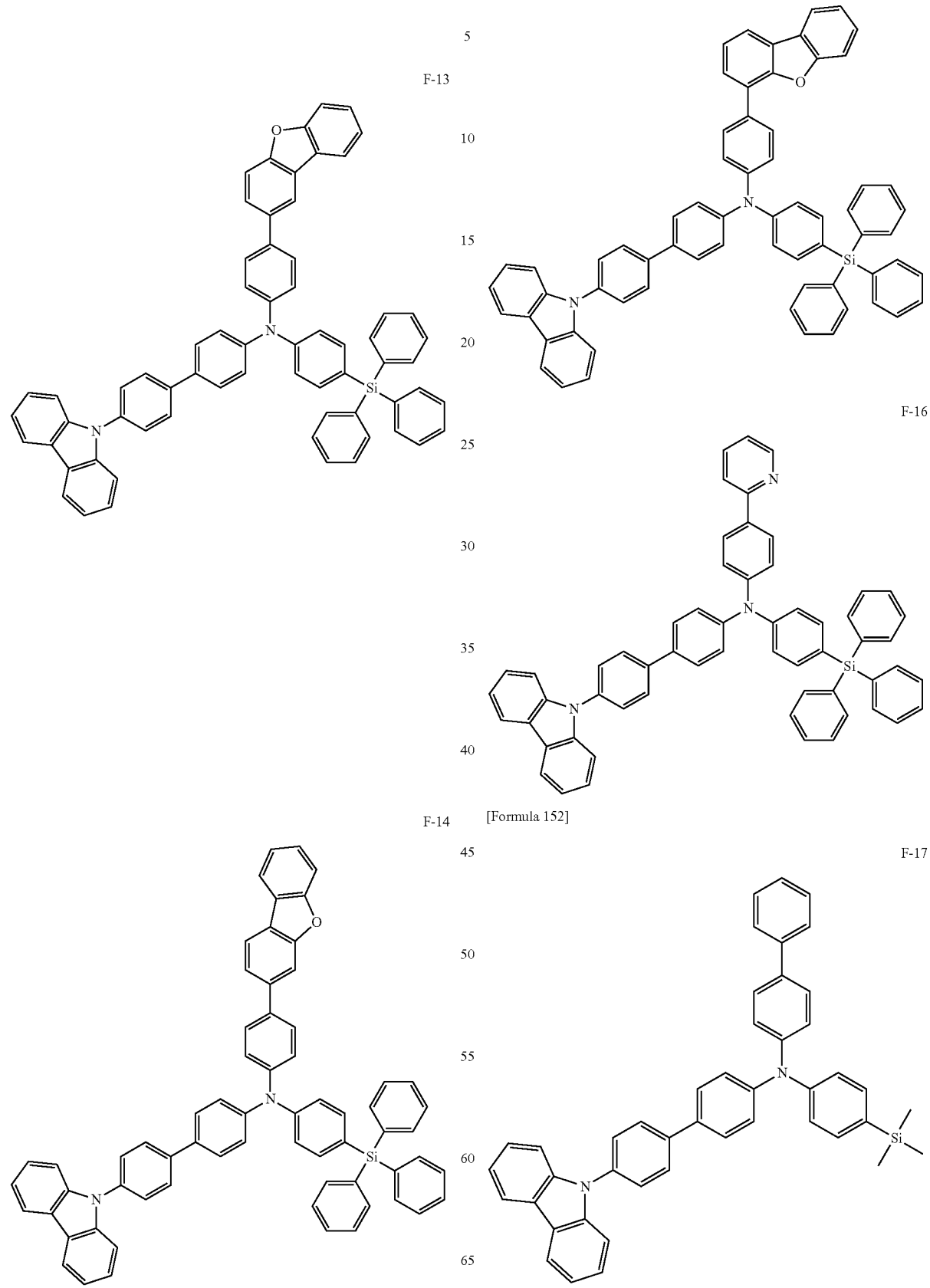

F-18
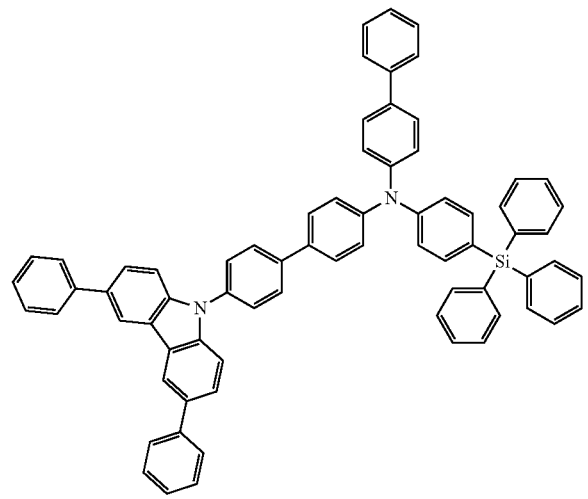
F-19
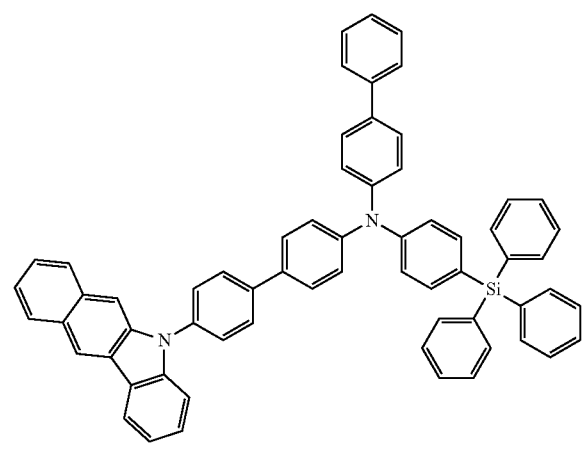
F-20
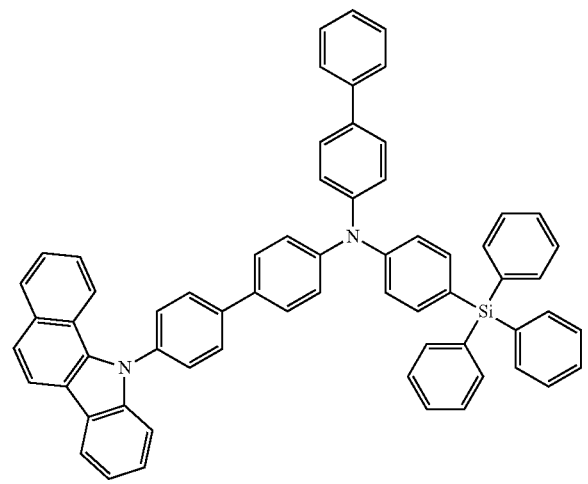
[Formula 153]
F-21
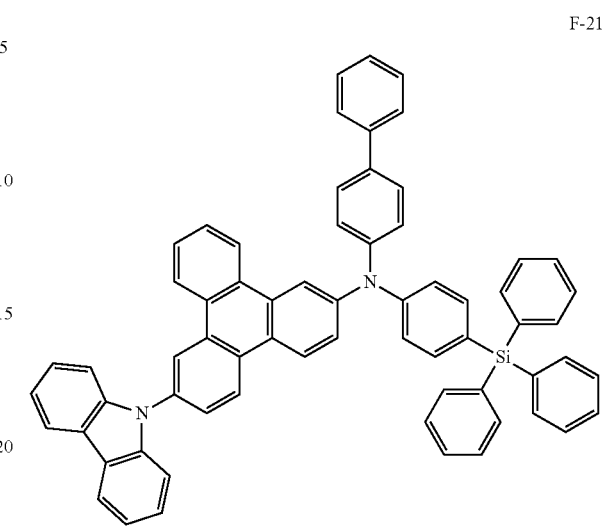
F-22
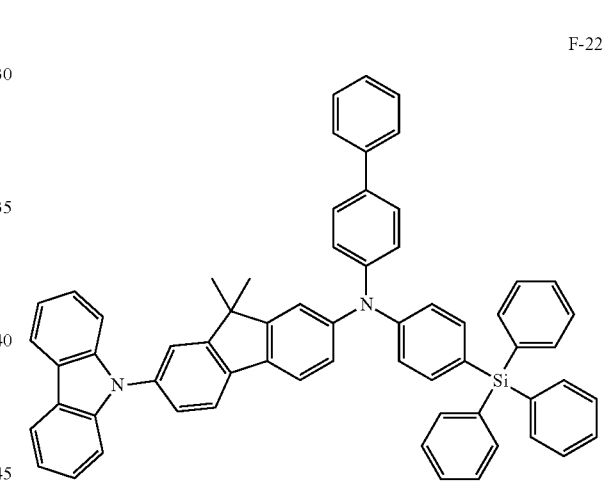
F-23
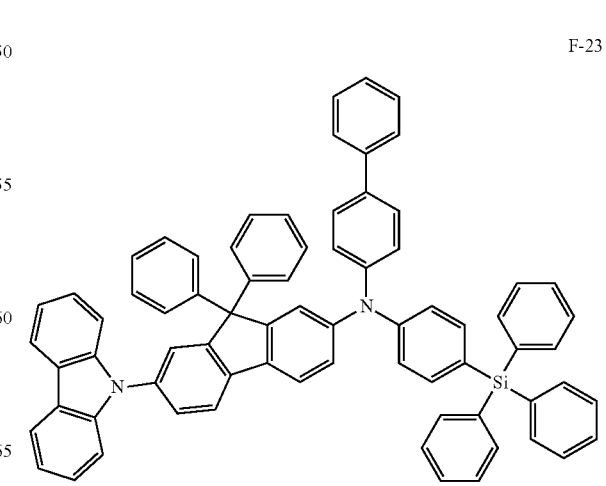

F-24
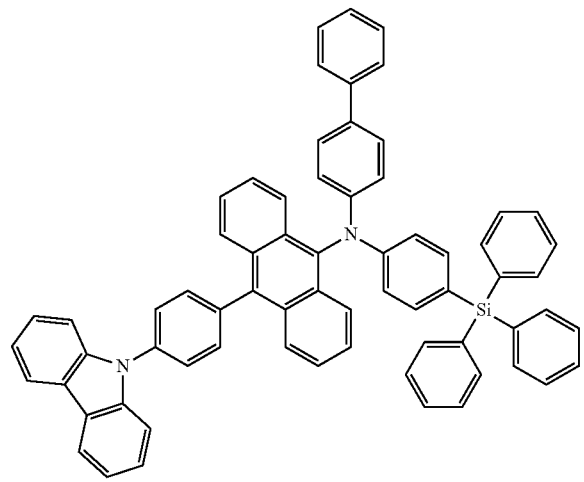
[Formula 154]
F-25
F-27
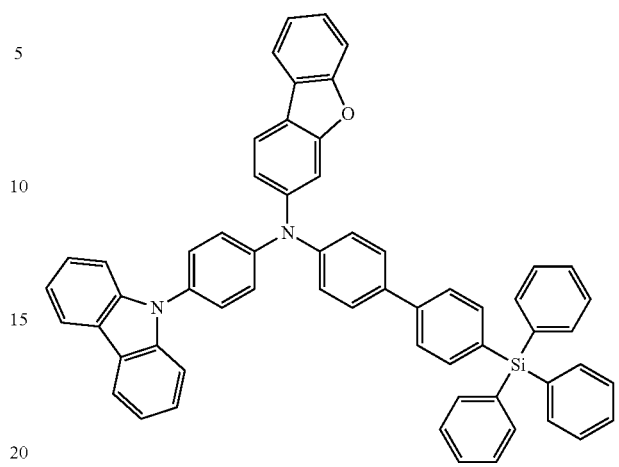
[Formula 155]
F-28
F-26
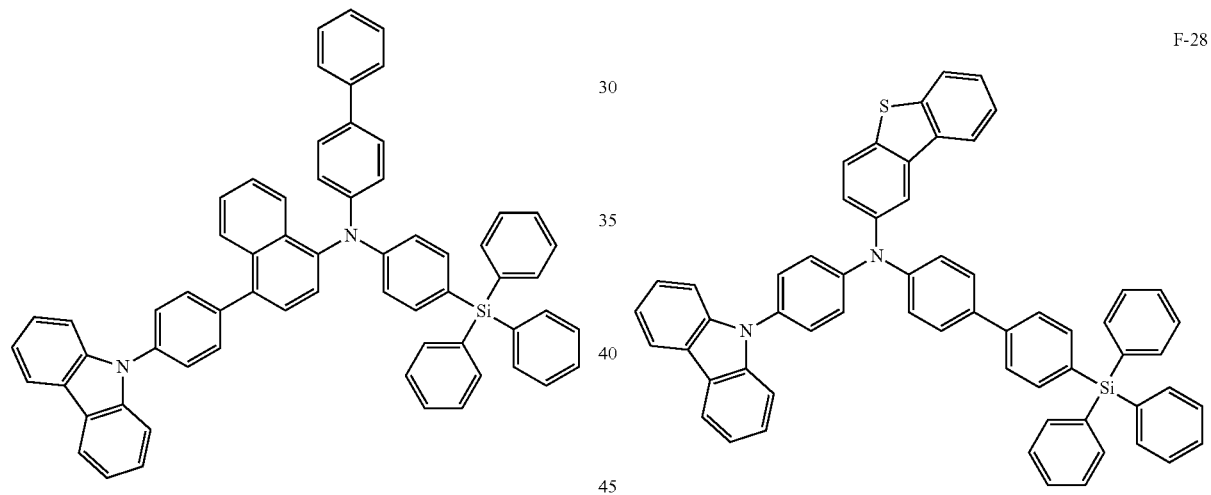
F-29
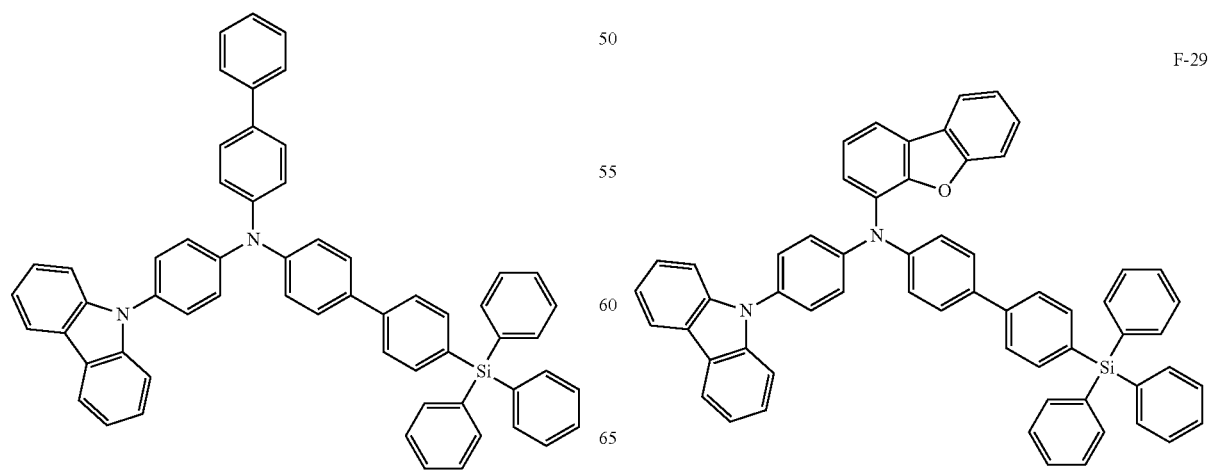

F-30
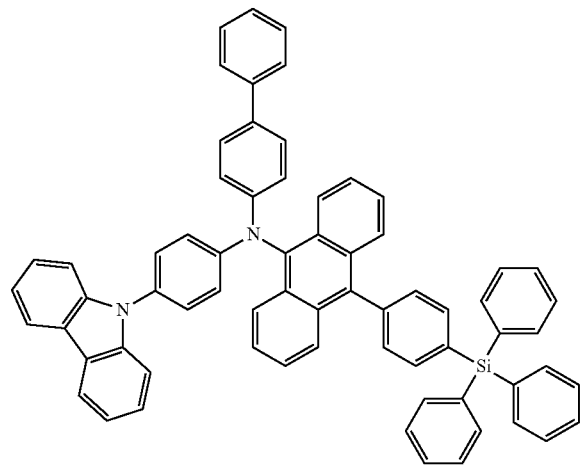
F-31
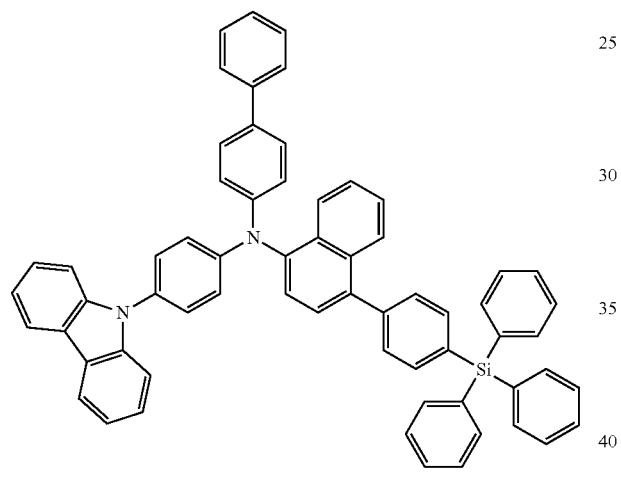
[Formula 156]
F-32
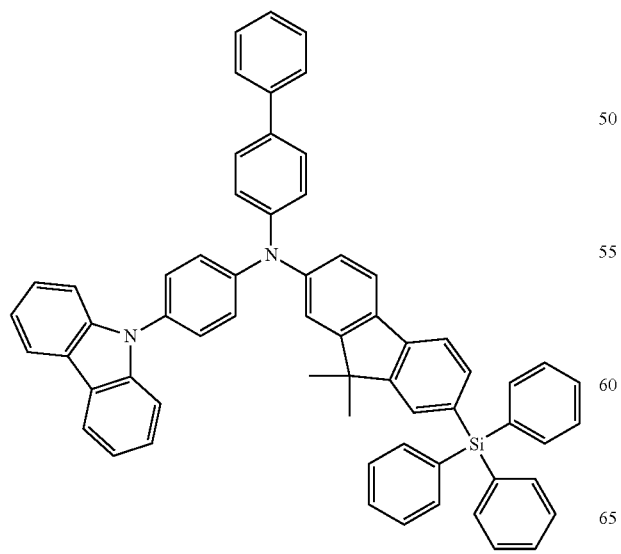
F-33
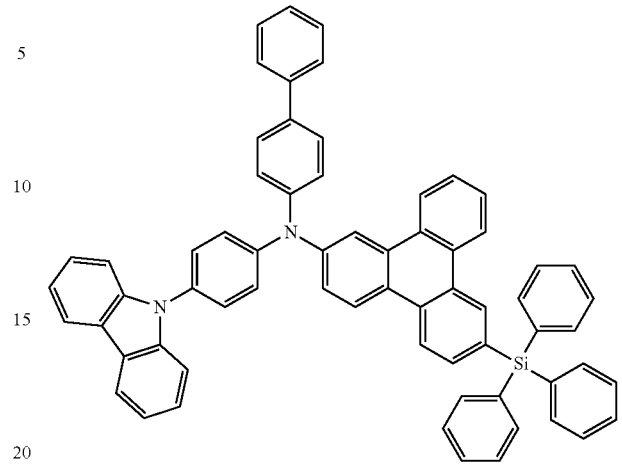
F-34
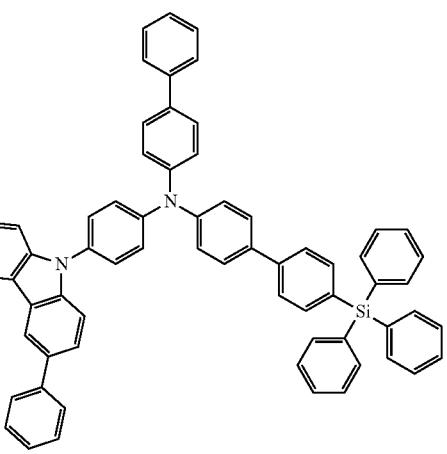
F-35
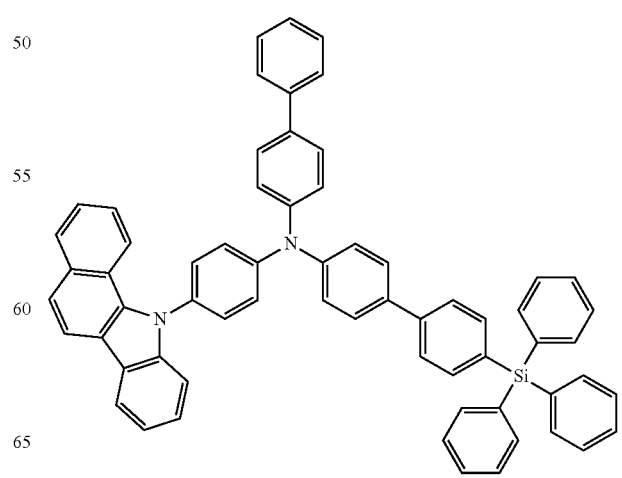

-continued
[Formula 157]
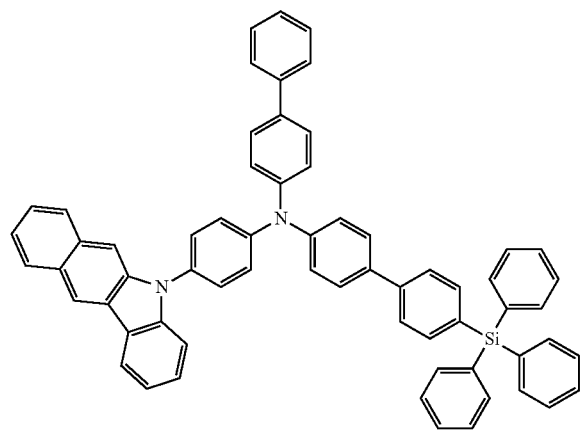
F-36
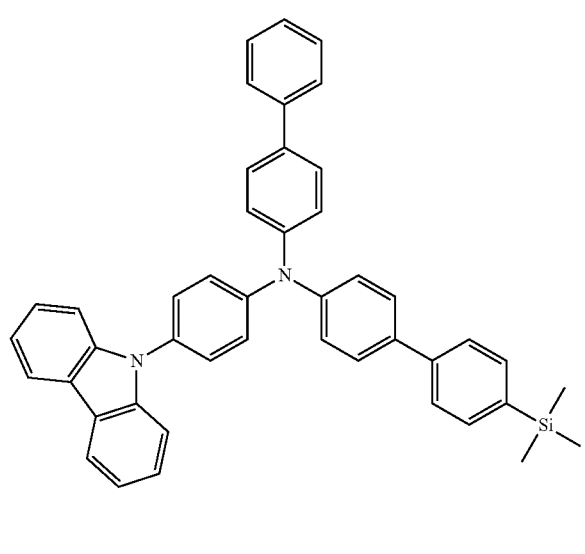
F-37
F-38
-continued
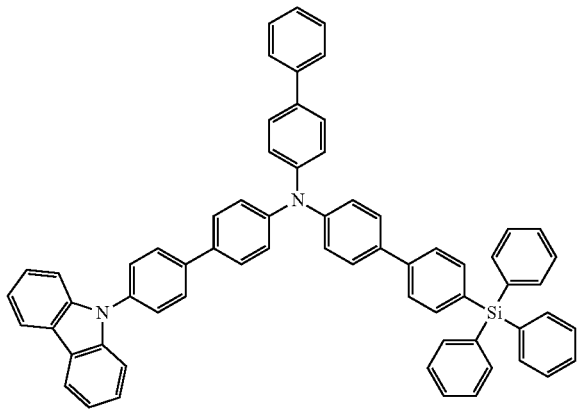
F-39
[Formula 158]
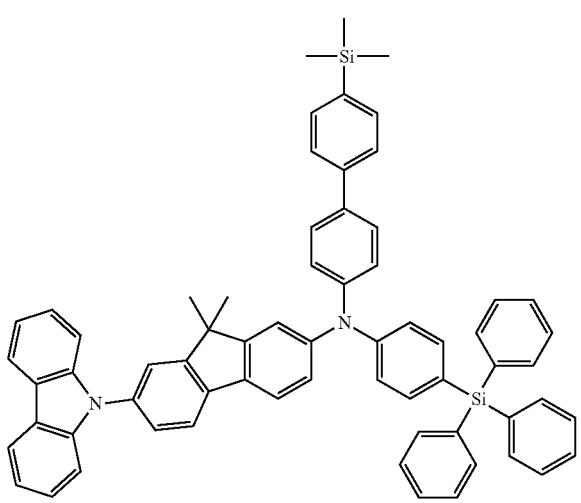
F-40
F-41

F-42
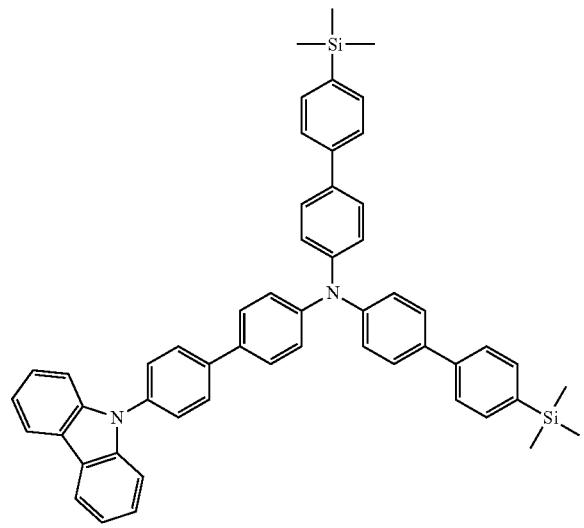
F-43
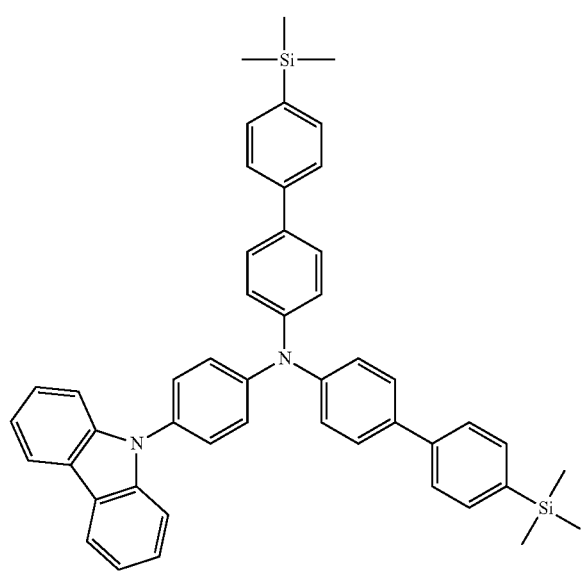
[Formula 159]
F-44
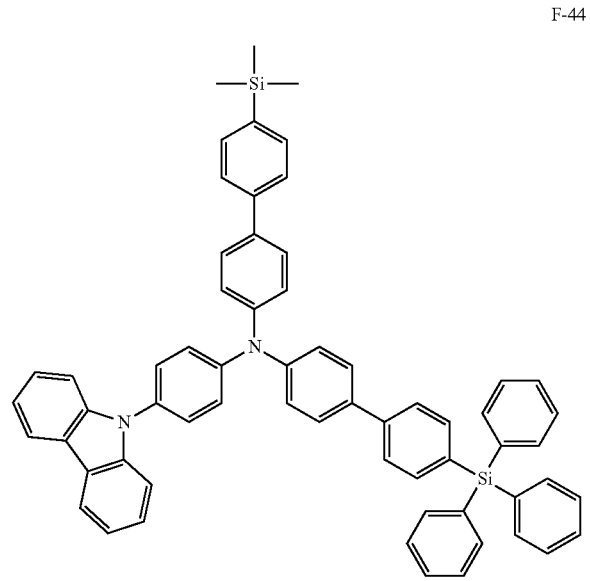
F-45
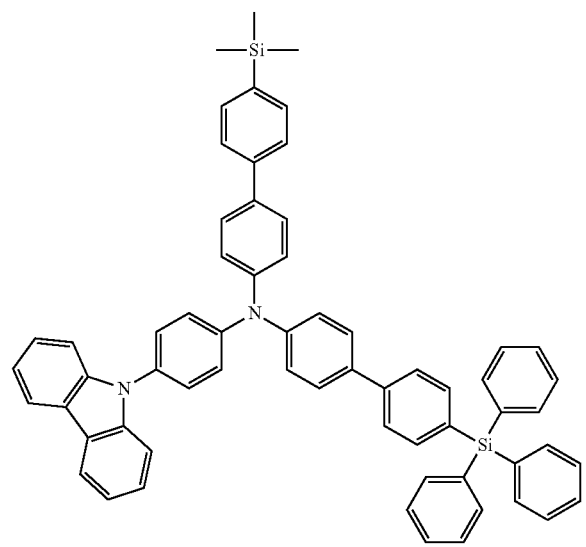
F-46
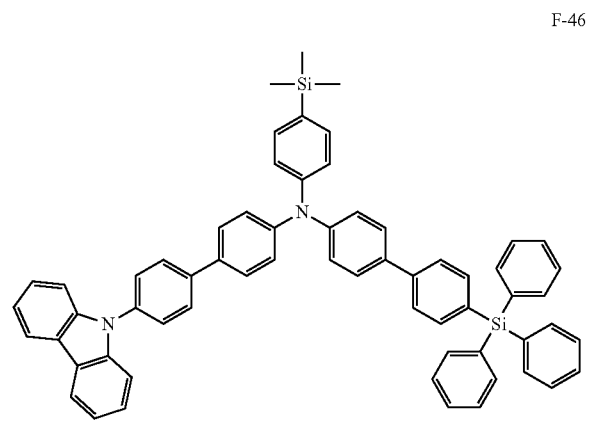

F-47
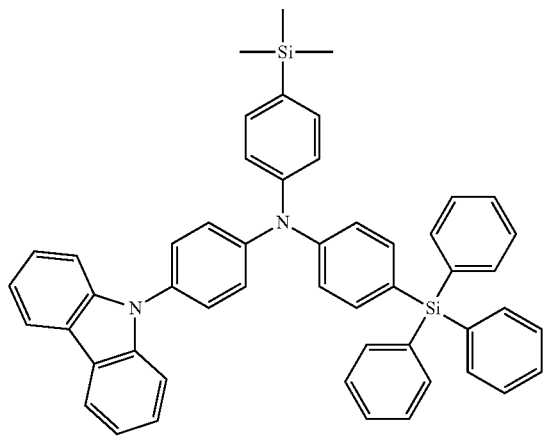
F-50
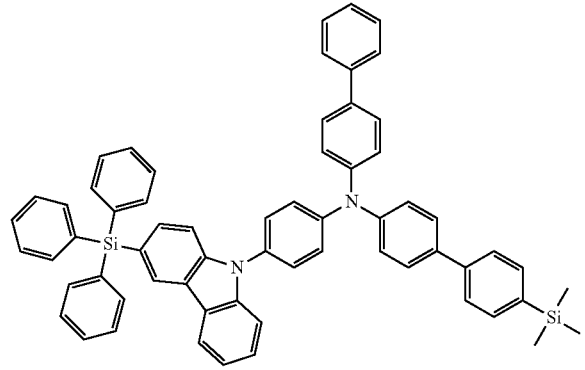
[Formula 160]
F-48
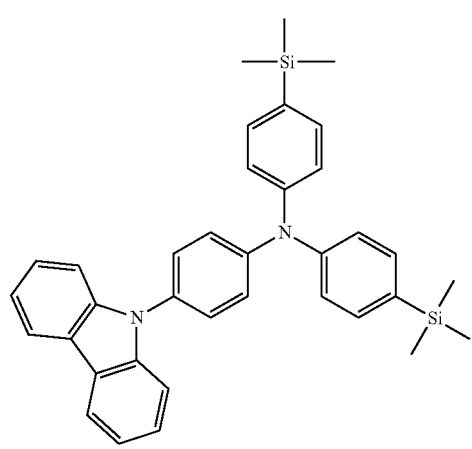
F-51
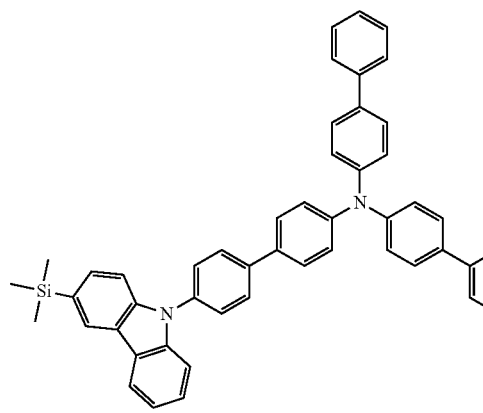
[Formula 161]
F-49
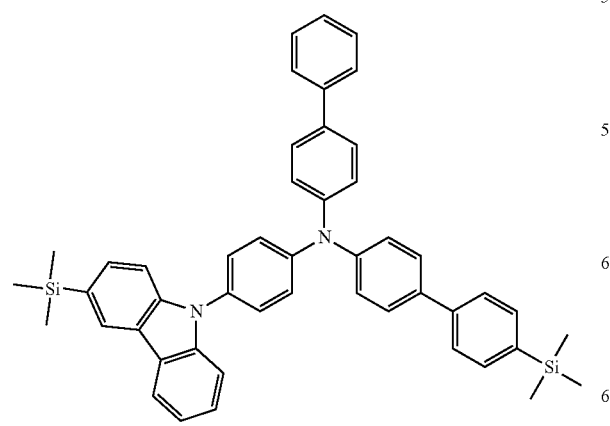
F-52
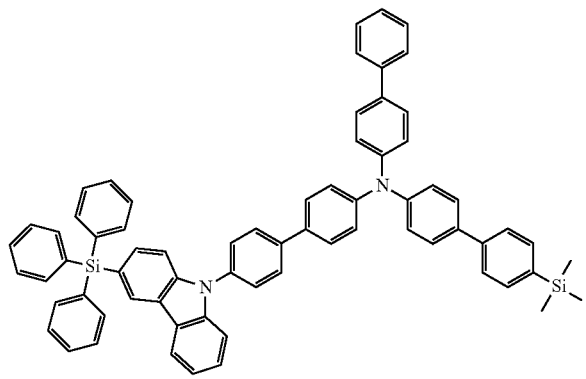

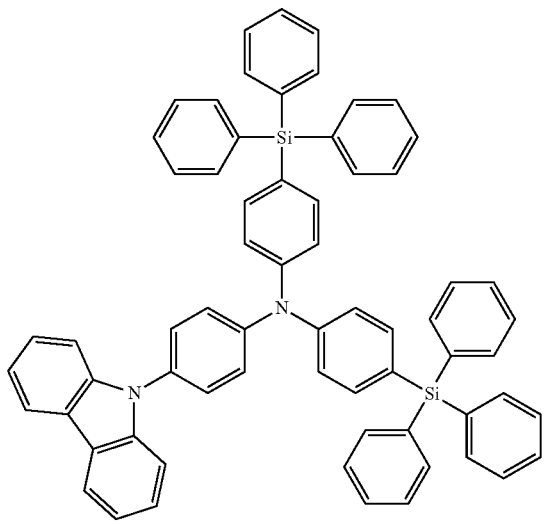

F-53

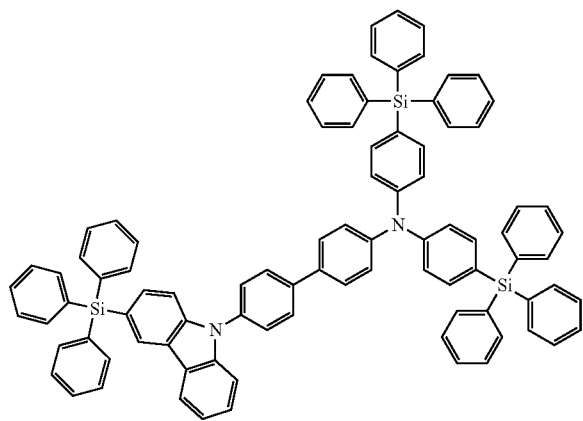

F-54

In an example amine derivative according to an embodiment, $Ar^3$ is the substituted or unsubstituted carbazolyl group in General Formula (1). By introducing the carbazolyl group in the amine derivative according to an embodiment, hole transport properties may be improved. In addition, by introducing the carbazolyl group in the amine derivative according to an embodiment having a silyl group substituted for at least one of $Ar^1$ and $Ar^2$, more appropriate level of HOMO may be realized. In addition, by combining the carbazolyl group with the amine part via the connecting group L, the level of HOMO may be controlled further. Thus, by disposing the amine derivative as a material for an organic electroluminescent device between an emission layer and an anode, the emission efficiency of the organic electroluminescent device may be improved and the driving at a low voltage and the long life thereof may be realized. For example, the amine derivative according to an embodiment may contribute to the improvement of the emission efficiency of the organic electroluminescent device and the realization of the driving at a low voltage and the long life thereof in a blue-bluish green region.

The amine derivative of the invention represented by General Formula (4), which shows an example structure of the amine derivative according to an embodiment, may be used as the material of the hole transport layer of the organic electroluminescent device 100 shown in FIG. 1. In addition, the configuration of the organic electroluminescent device 100 shown in FIG. 1 is an illustration of the organic electroluminescent device according to an embodiment without limitation, and may be variously modified.

In addition, the use of the amine derivative according to an embodiment, which shows an example structure of the amine derivative according to an embodiment, is not limited to the hole transport material of the organic electroluminescent device; it may be used as the material of the hole injection layer or the material of the emission layer. In the case that the amine derivative is used as the material of the hole injection layer or the material of the emission layer, the emission efficiency of the organic electroluminescent device may be improved, and the long life of the organic electroluminescent device may be realized as the case using the amine derivative as the material of the hole transport layer.

Example VII

With respect to the amine derivative according to an embodiment represented by General Formula (4), examples of synthesizing Compound F-10, Compound F-26 and Compound F-38 will be explained hereinafter. However, the following synthetic methods are only examples, and embodiments are not limited thereto.

(Synthesis of Compound F-1)

Under an argon atmosphere, 1.50 g of Compound (xxv), 1.90 g of Compound (x), 0.11 g of $Pd(dba)_2$, 0.15 g of $(t-Bu)_3P$ and 0.54 g of sodium t-butoxide were added to a 100 mL three-necked flask, followed by heating and refluxing in 45 mL of a toluene solvent for about 6 hours. After cooling in the air, water was added to the reaction mixture to separate an organic layer, and solvents were distilled. The crude product thus obtained was separated by silica gel column chromatography (using a mixture solvent of dichloromethane and hexane) and was recrystallized using a mixture solvent of toluene/hexane to produce 2.50 g (yield 81%) of Compound F-1 as a white solid.

[Formula 162]

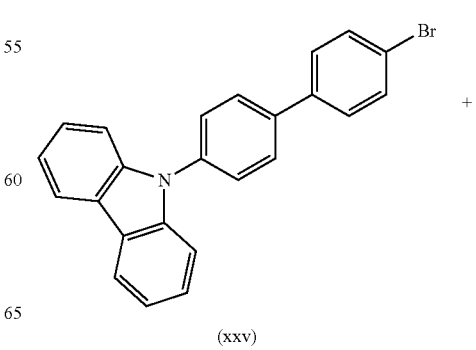

(xxv)

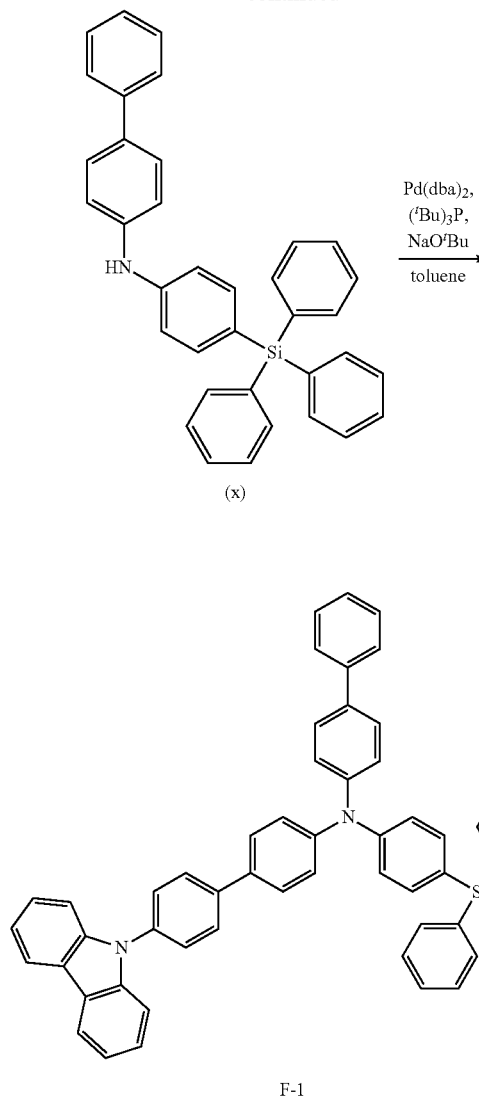

F-1

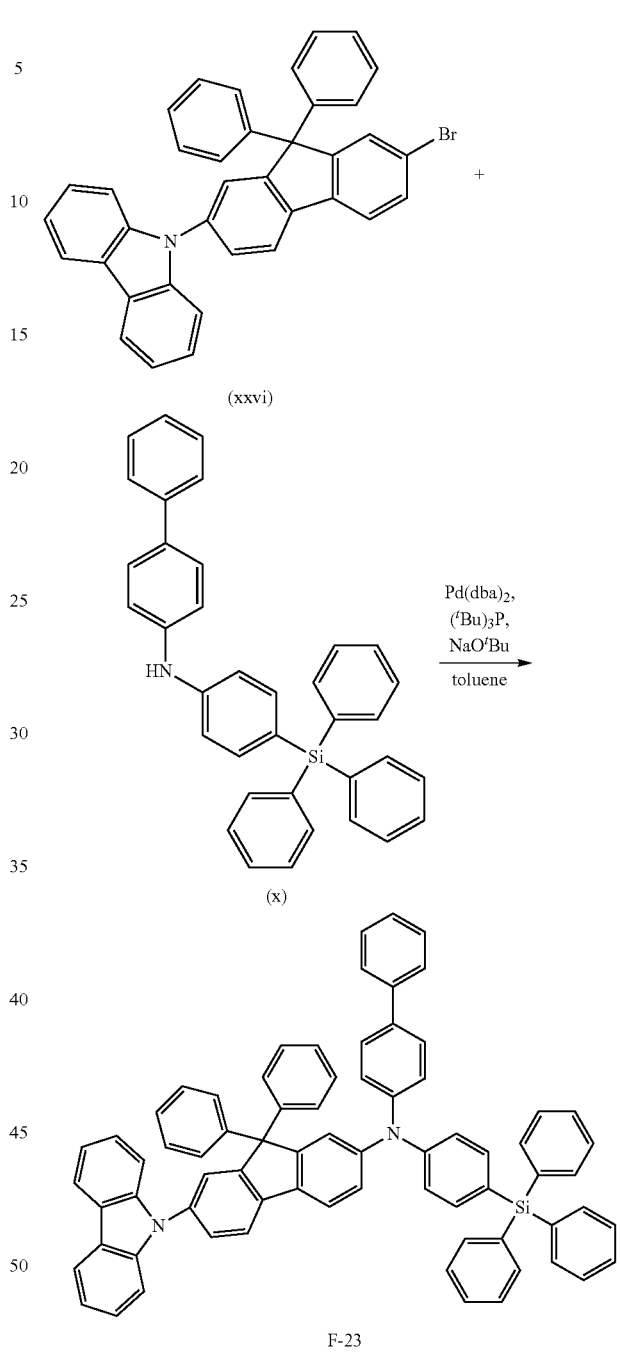

F-23

The chemical shift values of Compound F-1 measured by ¹H NMR were 8.15 (d, 2H), 7.81 (d, 2H), 7.66-7.51 (m, 14H), 7.51-7.34 (m, 18H), 7.34-7.26 (m, 6H), 7.17 (d, 2H). In addition, the molecular weight of Compound F-1 measured by FAB-MS was 821.

(Synthesis of Compound F-23)

Under an argon atmosphere, 1.20 g of Compound (xxvi), 1.07 g of Compound (x), 0.06 g of Pd(dba)$_2$, 0.09 g of (t-Bu)$_3$P and 0.31 g of sodium t-butoxide were added to a 100 mL three-necked flask, followed by heating and refluxing in 36 mL of a toluene solvent for about 8 hours. After cooling in the air, water was added to the reaction mixture to separate an organic layer, and solvents were distilled. The crude product thus obtained was separated by silica gel column chromatography (using a mixture solvent of dichloromethane and hexane) and was recrystallized using a mixture solvent of toluene/hexane to produce 1.60 g (yield 76%) of Compound F-23 as a white solid.

The chemical shift values of Compound F-23 measured by ¹H NMR were 8.30 (d, 2H), 7.98 (d, 2H), 7.82 (d, 1H), 7.75-7.18 (m, 39H), 7.37-7.23 (m, 6H), 7.15 (d, 2H). In addition, the molecular weight of Compound F-23 measured by FAB-MS was 984.

(Synthesis of Compound F-26)

Under an argon atmosphere, 1.50 g of Compound (xxvii), 2.70 g of Compound (vii), 0.13 g of Pd(dba)$_2$, 0.19 g of (t-Bu)$_3$P and 0.67 g of sodium t-butoxide were added to a 100 mL three-necked flask, followed by heating and refluxing in 45 mL of a toluene solvent for about 7 hours. After cooling in the air, water was added to the reaction mixture to separate an organic layer, and solvents were distilled. The crude product thus obtained was separated by silica gel column chromatography (using a mixture solvent of dichloromethane and hexane) and was recrystallized using a mixture solvent of toluene/hexane to produce 3.29 g (yield 86%) of Compound F-26 as a white solid.

[Formula 164]

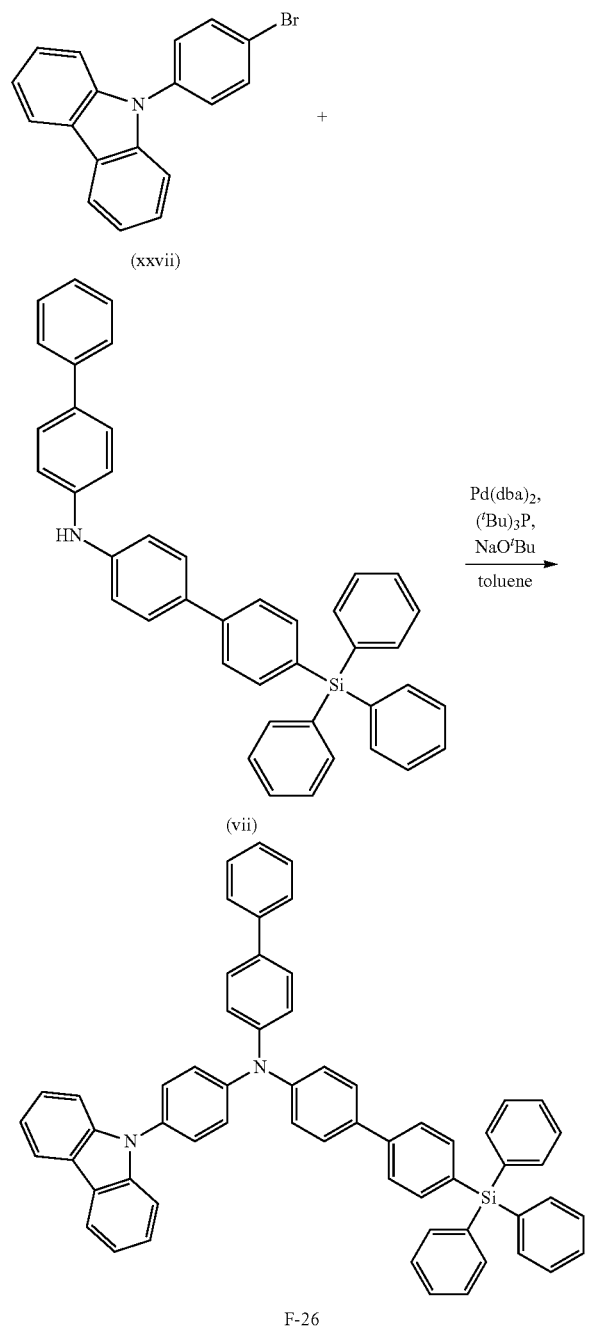

(Synthesis of Compound F-38)

Under an argon atmosphere, 1.50 g of Compound (xxvii), 2.35 g of Compound (x), 0.13 g of Pd(dba)$_2$, 0.19 g of (t-Bu)$_3$P and 0.67 g of sodium t-butoxide were added to a 100 mL three-necked flask, followed by heating and refluxing in 45 mL of a toluene solvent for about 7 hours. After cooling in the air, water was added to the reaction mixture to separate an organic layer, and solvents were distilled. The crude product thus obtained was separated by silica gel column chromatography (using a mixture solvent of dichloromethane and hexane) and was recrystallized using a mixture solvent of toluene/hexane to produce 2.74 g (yield 79%) of Compound F-38 as a white solid.

[Formula 165]

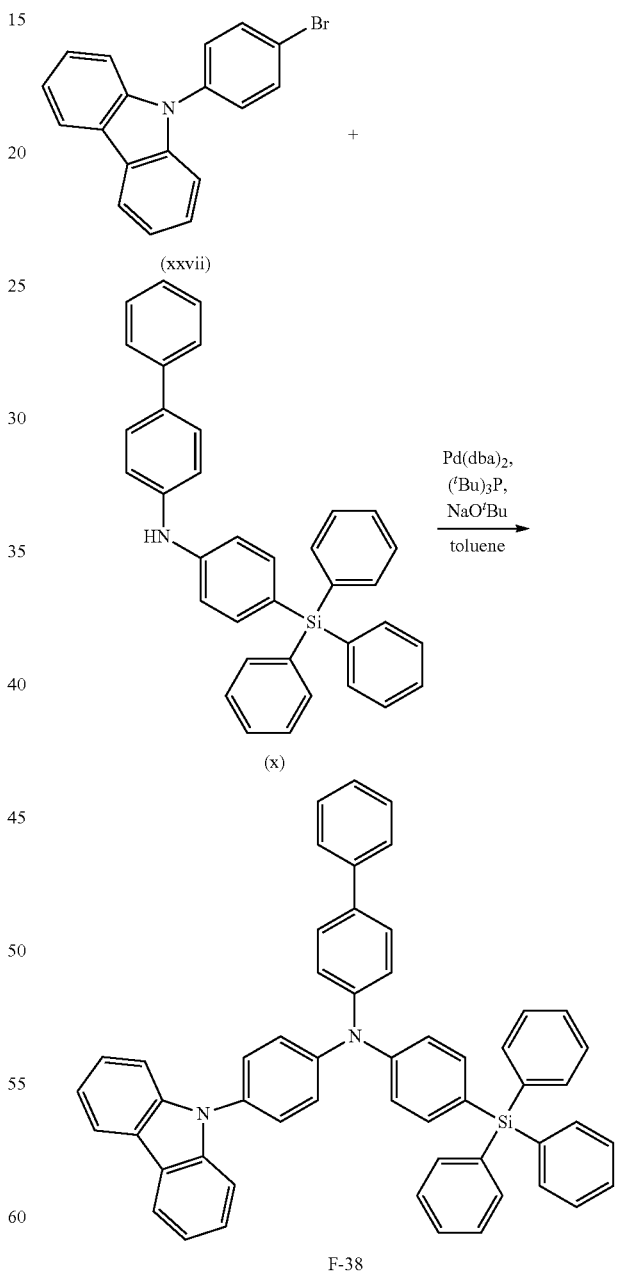

The chemical shift values of Compound F-26 measured by $^1$H NMR were 8.07 (d, 2H), 7.75 (d, 2H), 7.67-7.52 (m, 12H), 7.51-7.33 (m, 18H), 7.33-7.20 (m, 8H), 7.16 (d, 2H). In addition, the molecular weight of Compound F-26 measured by FAB-MS was 821.

The chemical shift values of Compound F-38 measured by $^1$H NMR were 8.09 (d, 2H), 7.76 (d, 2H), 7.65-7.51 (m, 10H), 7.51-7.35 (m, 18H), 7.32-7.21 (m, 6H), 7.18 (d, 2H). In addition, the molecular weight of Compound F-38 measured by FAB-MS was 744.

(Synthesis of Compound F-39)

Under an argon atmosphere, 1.50 g of Compound (xxv), 2.18 g of Compound (vii), 0.11 g of Pd(dba)$_2$, 0.15 g of (t-Bu)$_3$P and 0.54 g of sodium t-butoxide were added to a 100 mL three-necked flask, followed by heating and refluxing in 45 mL of a toluene solvent for about 7 hours. After cooling in the air, water was added to the reaction mixture to separate an organic layer, and solvents were distilled. The crude product thus obtained was separated by silica gel column chromatography (using a mixture solvent of dichloromethane and hexane) and was recrystallized using a mixture solvent of toluene/hexane to produce 2.97 g (yield 88%) of Compound F-39 as a white solid.

[Formula 166]

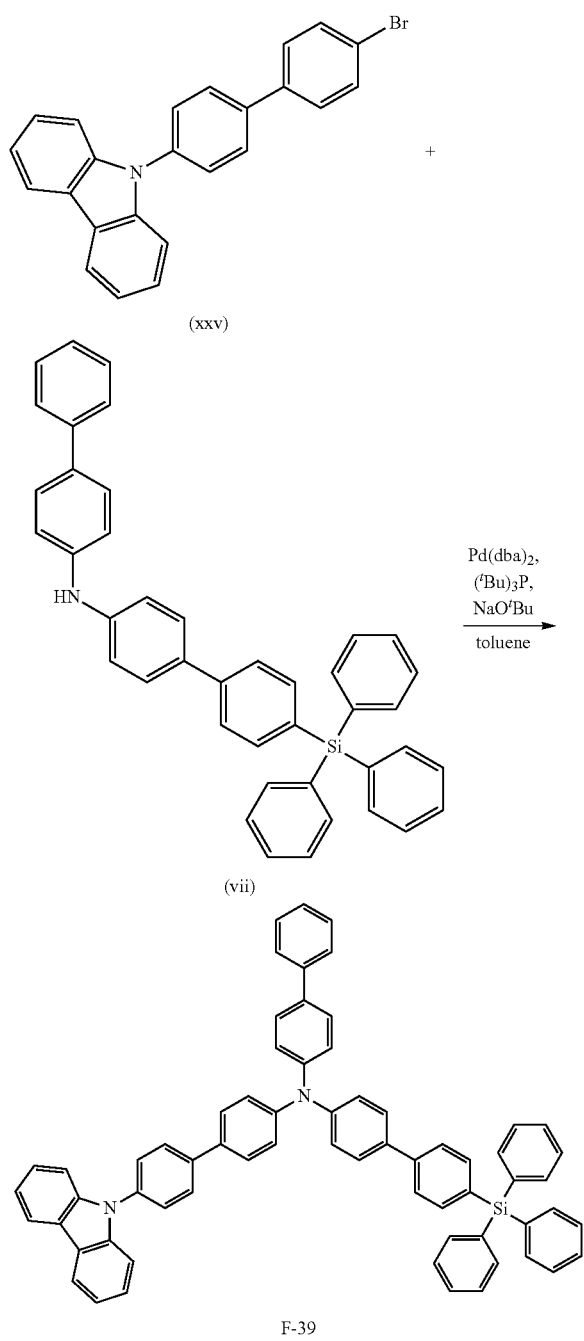

The chemical shift values of Compound F-39 measured by $^1$H NMR were 8.18 (d, 2H), 7.82 (d, 2H), 7.68-7.51 (m, 14H), 7.51-7.35 (m, 20H), 7.35-7.28 (m, 8H), 7.16 (d, 2H). In addition, the molecular weight of Compound F-39 measured by FAB-MS was 896.

Hereinafter, organic electroluminescent devices using the above described Compound F-1, Compound F-23 Compound F-26, Compound F-38 and Compound F-39 as the materials for the organic electroluminescent devices according to an embodiment in hole transport layers will be explained. An organic electroluminescent device using Compound F-1 in the hole transport layer corresponds to Example 25, an organic electroluminescent device using Compound F-23 in the hole transport layer corresponds to Example 26, an organic electroluminescent device using Compound F-26 in the hole transport layer corresponds to Example 27, an organic electroluminescent device using Compound F-38 in the hole transport layer corresponds to Example 28 and an organic electroluminescent device using Compound F-39 in the hole transport layer corresponds to Example 29.

The manufacture of the organic electroluminescent device according to Example 25 according to an embodiment was conducted by a vacuum deposition as for the organic electroluminescent device of Example 1 and the following procedure. First, with respect to an ITO-glass substrate patterned and washed in advance, surface treatment using ozone was conducted. In addition, the layer thickness of an ITO layer was about 150 nm. Immediately after the ozone treatment, a layer was formed using 2-TNATA as a hole injection material (thickness of about 60 nm) on the ITO layer.

Then, a layer was formed using Compound F-1 according to an embodiment as a hole transport material (about 30 nm), and a layer of ADN doped with TBP in a ratio of about 3% was formed by a co-deposition (about 25 nm).

After that, a layer was formed using Alq$_3$ as an electron transport material (about 25 nm), and LiF (about 1.0 nm) as an electron injection layer and aluminum (about 100 nm) as a cathode were laminated one by one to manufacture the organic electroluminescent device 200 shown in FIG. 2.

As Examples 26, 27, 28 and 29, organic electroluminescent devices were manufactured by performing the same procedure described in Example 25 except for using Compound F-23, Compound F-26, Compound F-38 and Compound F-39 instead of Compound F-1 used in Example 25.

As Comparative Examples 14 and 15, organic electroluminescent devices were manufactured by performing the same procedure described in Example 25 except for using Comparative Compounds 14 and 15 represented in the following as compounds constituting hole transport materials of the organic electroluminescent devices.

[Formula 167]

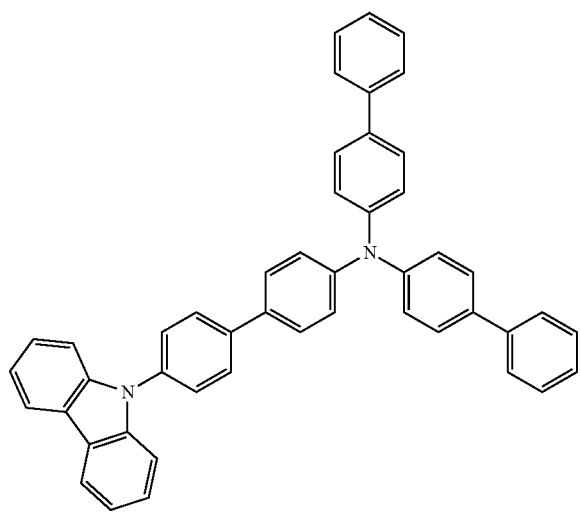

Comparative Compound 14

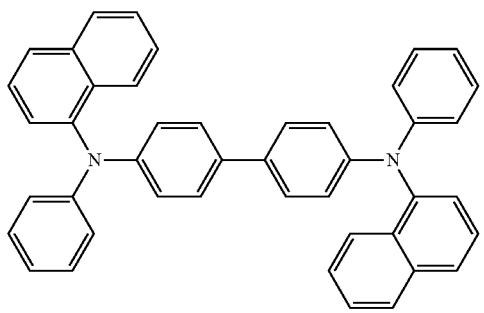

Comparative Compound 15

The driving voltage, the current efficiency and the half life of the organic electroluminescent devices 200 manufactured in Examples 25 to 29 and Comparative Examples 14 and 15 were evaluated. In addition, emission efficiency means values at about 10 mA/cm$^2$, and half life means luminance decrease time to half from an initial luminance of about 1,000 cd/m$^2$. The evaluation results are shown in Table 7.

TABLE 7

| | Hole transport material | Voltage (V) | Current efficiency (cd/A) | Half life (hr) |
|---|---|---|---|---|
| Example 25 | Compound F-1 | 6.4 | 6.6 | 2,000 |
| Example 26 | Compound F-23 | 6.9 | 6.7 | 2,000 |
| Example 27 | Compound F-26 | 6.3 | 6.8 | 2,100 |
| Example 28 | Compound F-38 | 6.3 | 6.9 | 1,800 |
| Example 29 | Compound F-39 | 6.5 | 6.6 | 2,300 |
| Comparative Example 14 | Comparative Compound 14 | 7.2 | 6.0 | 1,500 |
| Comparative Example 15 | Comparative Compound 15 | 8.1 | 5.3 | 1,500 |

According to Table 7, the organic electroluminescent devices of Examples 25 to 29 have improved emission efficiency and longer life than the organic electroluminescent devices of Comparative Examples 14 and 15. In addition, the organic electroluminescent devices of Examples 25 to 29 have a decreased driving voltage when compared to that of the organic electroluminescent devices of Comparative Examples 14 and 15.

In the above-described Examples 25 to 29, an example amine derivative according to an embodiment represented by General Formula (4), was used as the hole transport material of the organic electroluminescent device as an embodiment; however, the use of the amine derivative according to an embodiment is not limited to the organic electroluminescent device, and is expanded to other luminescent devices or luminescent apparatus. In addition, the organic electroluminescent device using the amine derivative having a silyl group according to an embodiment represented by General Formula (4) may be used in an organic electroluminescent display of a passive-matrix driving type, and they may be also used in an organic electroluminescent display of an active-matrix driving type.

Remarkable improvement of the emission efficiency, the driving voltage and the life of an organic electroluminescent device may be obtained by disposing the amine derivative represented by General Formula (1), particularly, an amine derivative having the following structure as a material for an organic electroluminescent device between an emission layer and an anode.

An example structure of the amine derivative having a silyl group, represented by the above General Formula (1) is represented by the following General Formula (8).

[Formula 168]

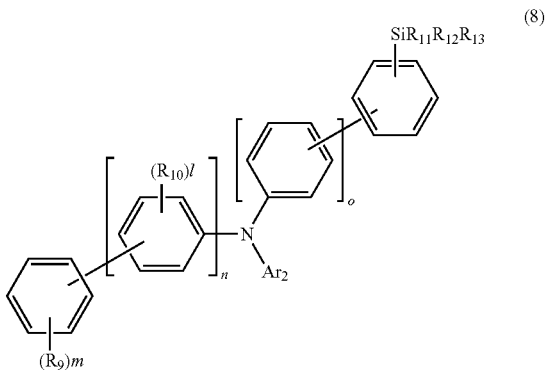

(8)

That is, in the amine derivative represented by the above General Formula (1), Ar$^1$ is an aryl group substituted with a silyl group represented by the following General Formula (5).

[Formula 169]

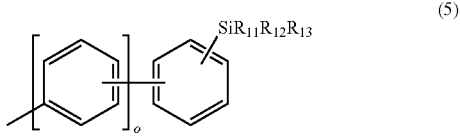

(5)

In General Formula (5), o is an integer satisfying the relation of 0≤o≤2, R$_{11}$, R$_{12}$ and R$_{13}$ are independently an alkyl group having 1 to 15 carbon atoms, a substituted or unsubstituted aryl group having 6 to 30 carbon atoms for forming a ring or a heteroaryl group having 1 to 30 carbon atoms for forming a ring. R$_{11}$, R$_{12}$ and R$_{13}$ may be connected to each other to form a ring.

In General Formula (5), o may be 0 or 1. Since o is 0 or 1, the blocking capability of the amine derivative according to an embodiment from the intrusion of electrons into a hole transport layer may be increased, the deterioration may be restrained, and the long life of the organic electroluminescent device may be realized. In addition, in General Formula (5), $R_{11}$, $R_{12}$ and $R_{13}$ are independently a methyl group, a normal alkyl group having 6 or less carbon atoms, a phenyl group, a biphenylyl group, a terphenyl group, a quaterphenyl group, a naphthyl group, a carbazolyl group and a dibenzofuran group. For example, when $R_{11}$, $R_{12}$ and $R_{13}$ are independently the phenyl group, the glass transition temperature (Tg) may be increased, and layer forming properties may be improved.

In addition, an example amine derivative having a silyl group according to an embodiment represented by General Formula (8) is an amine derivative represented by General Formula (1), in which $Ar^2$ is a substituted or unsubstituted aryl group having 6 to 30 carbon atoms for forming a ring. In addition, $Ar^2$ in the amine derivative represented by General Formula (1) is also represented by $Ar^2$ in the amine derivative represented by General Formula (8).

The aryl group of $Ar^2$ may include, for example, a phenyl group, a naphthyl group, an anthracenyl group, a phenanthryl group, a biphenyl group, a terphenyl group, a quaterphenyl group, etc.

In addition, an example amine derivative having a silyl group according to an embodiment represented by General Formula (8) is an amine derivative represented by General Formula (1), in which $Ar^3$ is an aryl group represented by the following General Formula (6).

[Formula 170]

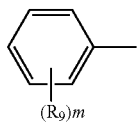

(6)

In General Formula (6), each $R_9$ is independently a hydrogen atom, a halogen atom, an alkyl group having 1 to 15 carbon atoms or a substituted or unsubstituted aryl group having 6 to 30 carbon atoms for forming a ring, and m is an integer satisfying the relation of $0 \leq m \leq 5$.

In addition, an example amine derivative having a silyl group according to an embodiment represented by General Formula (8) is an amine derivative represented by General Formula (1), in which L is an arylene group represented by the following General Formula (7).

[Formula 171]

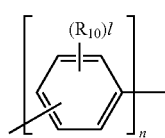

(7)

In General Formula (7), each $R_{10}$ is independently a hydrogen atom, a halogen atom, an alkyl group having 1 to 15 carbon atoms or a substituted or unsubstituted aryl group having 6 to 30 carbon atoms for forming a ring. l is an integer satisfying the relation of $0 \leq l \leq 4$, and n is an integer satisfying the relation of $2 \leq n \leq 5$. Here, the kind and number (1) of $R_{10}$ substituted in the arylene group represented by General Formula (7) may be different for each arylene group. In General Formula (7), n may be 2 or 3. Since n is 2 or 3, the electron tolerance of the amine derivative may be improved further. In addition, through the increase of a molecular weight, the attainment of high glass transition temperature may be easy.

The amine derivative having a silyl group according to an embodiment represented by General Formula (8) may include the following compounds, without limitation. In the following exemplified compounds, Ph represents a phenyl group, and Me represents a methyl group.

[Formula 172]

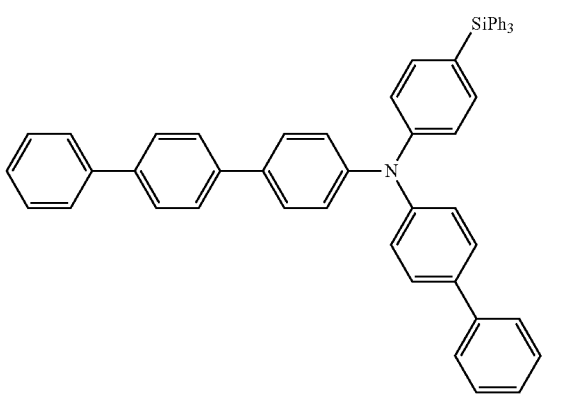

G-1

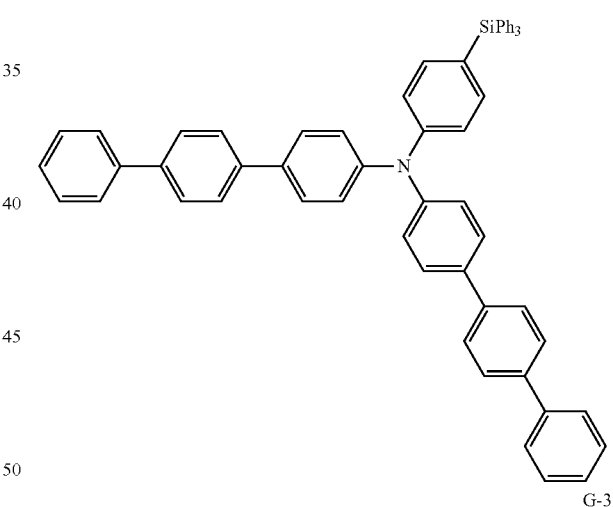

G-2

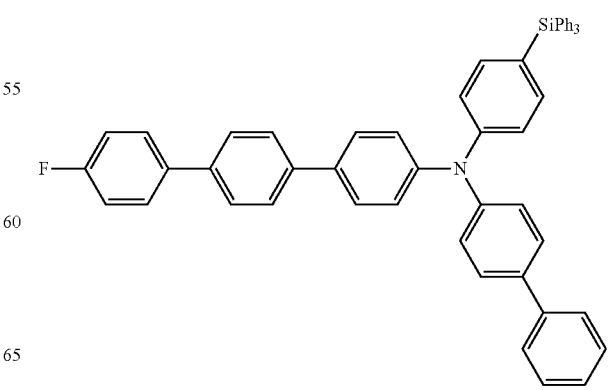

G-3

G-4
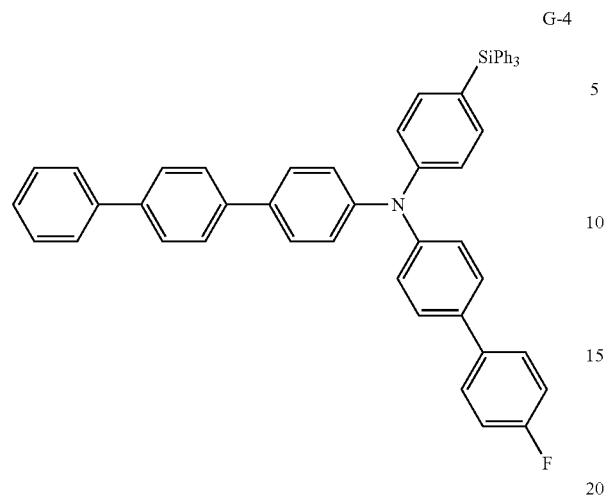
[Formula 173]
G-5
G-6
G-7
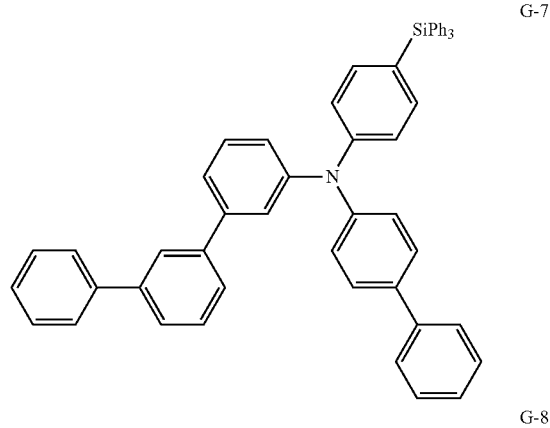
G-8
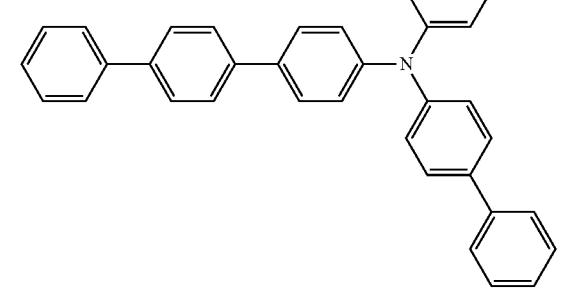
[Formula 174]
G-9
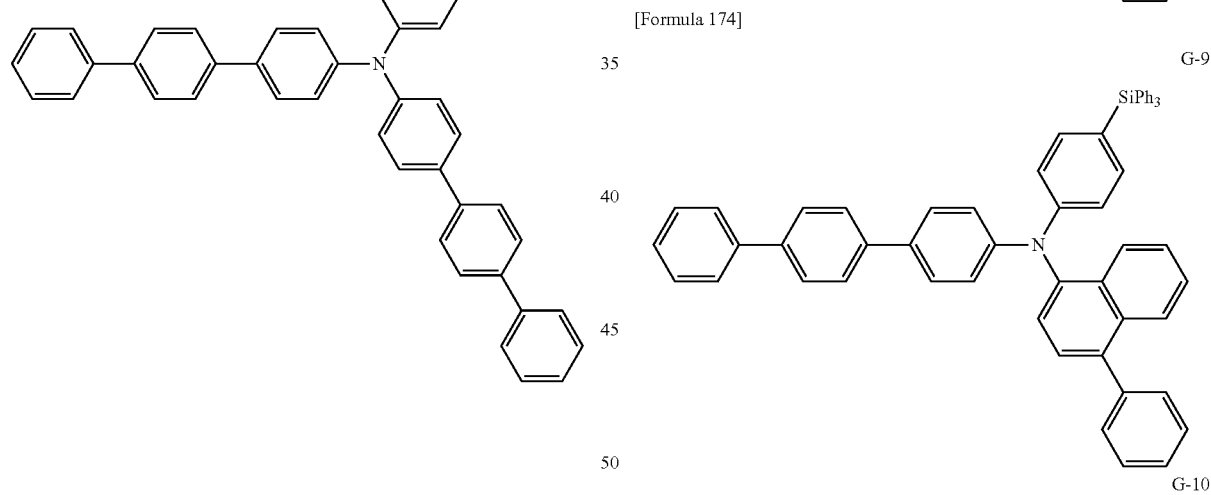
G-10
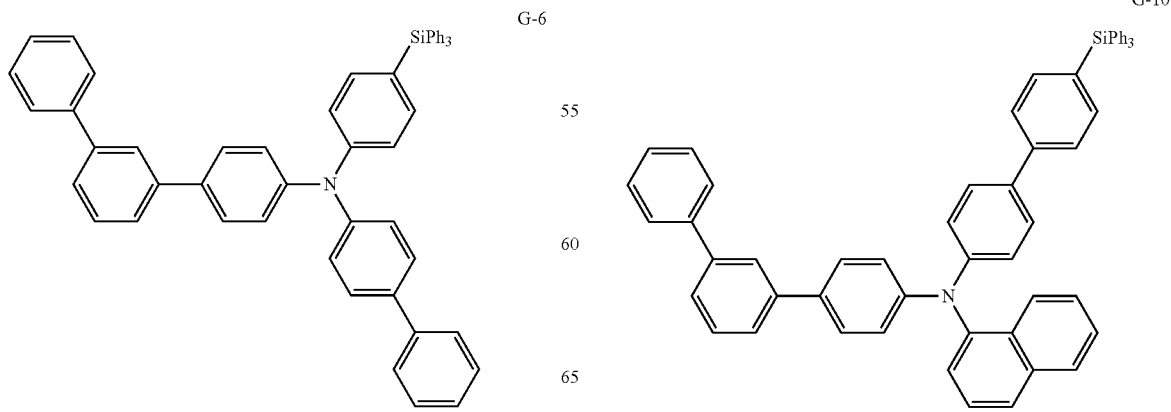

-continued
G-11
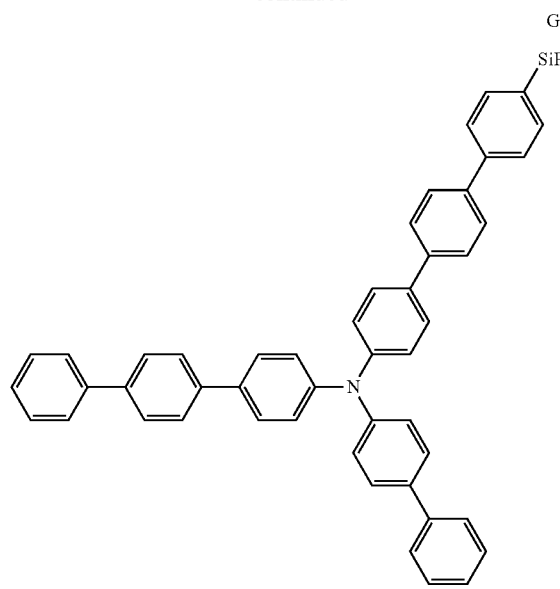
[Formula 175]
G-12
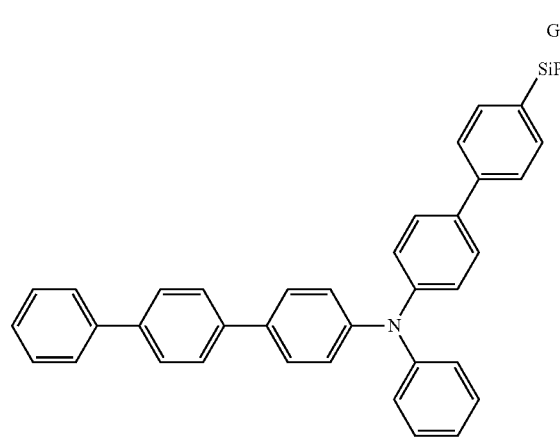
G-13
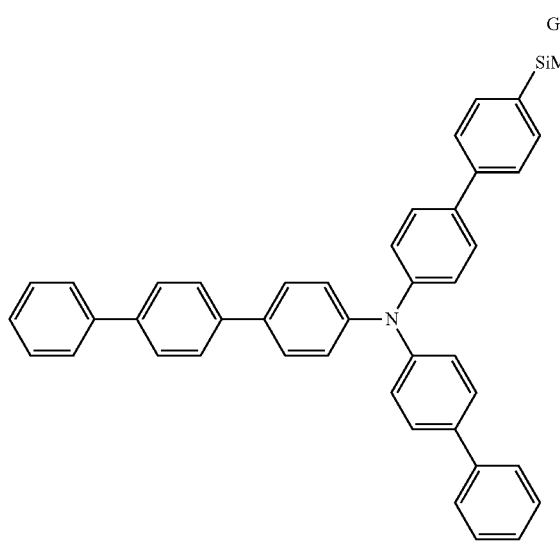
-continued
G-14
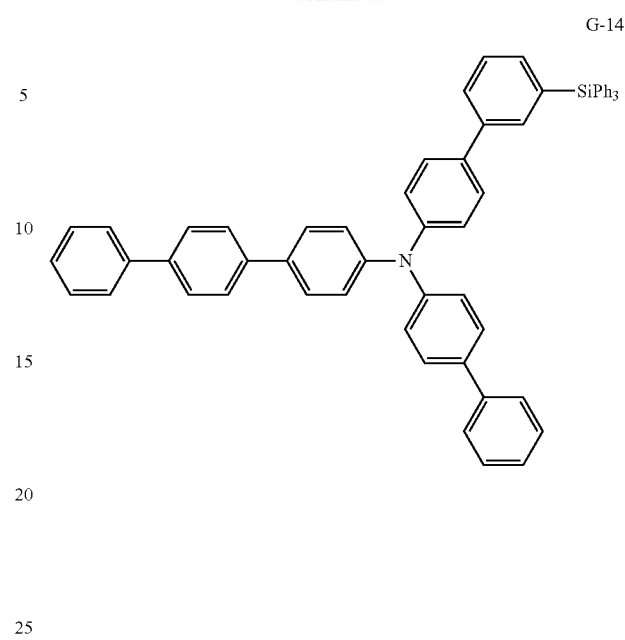
[Formula 176]
G-15
G-16
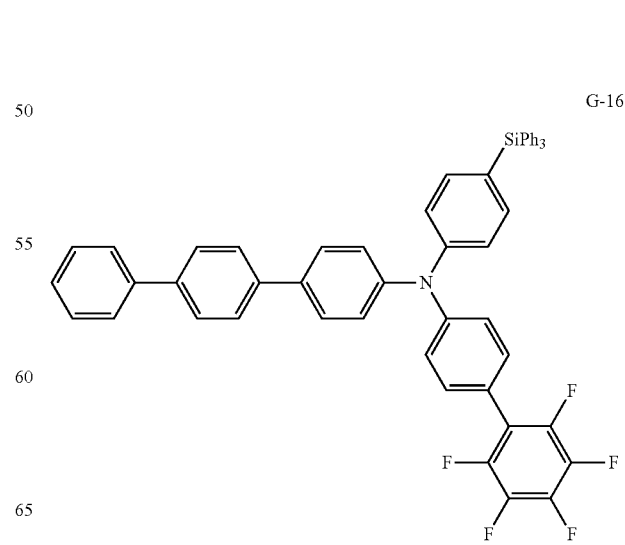

-continued
[Formula 177]
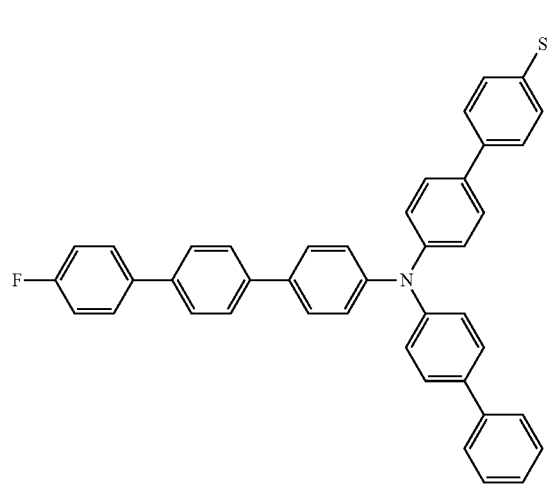
G-17
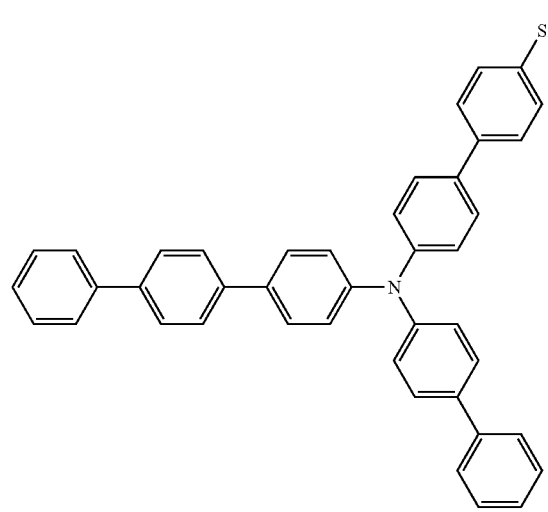
G-18
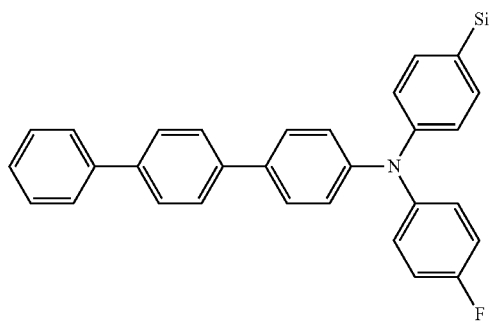
G-19
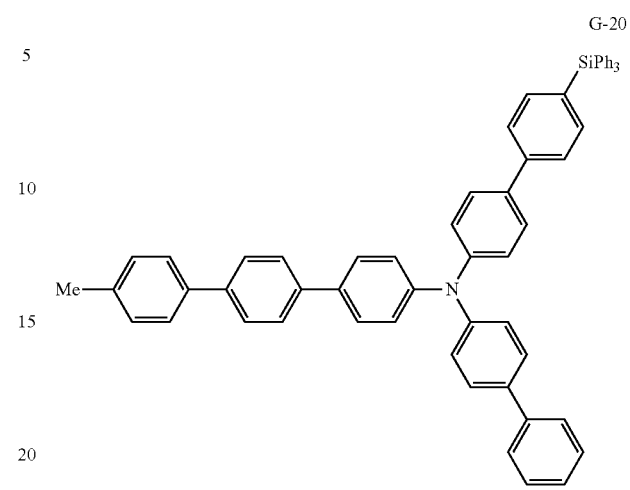
G-20
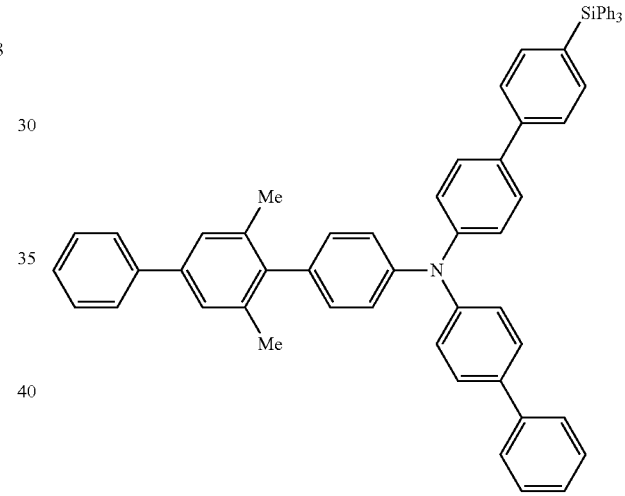
G-21
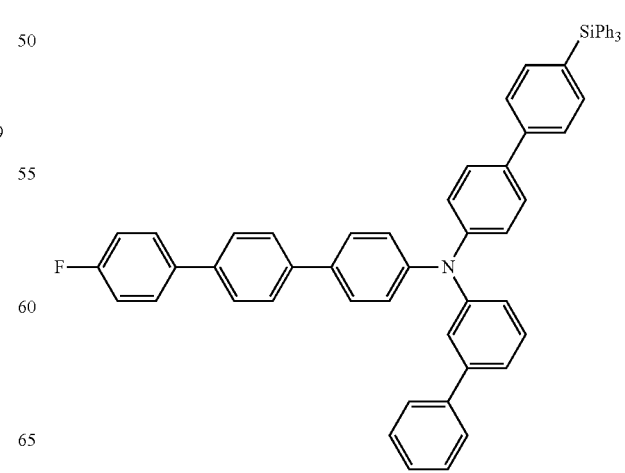
G-22

G-23

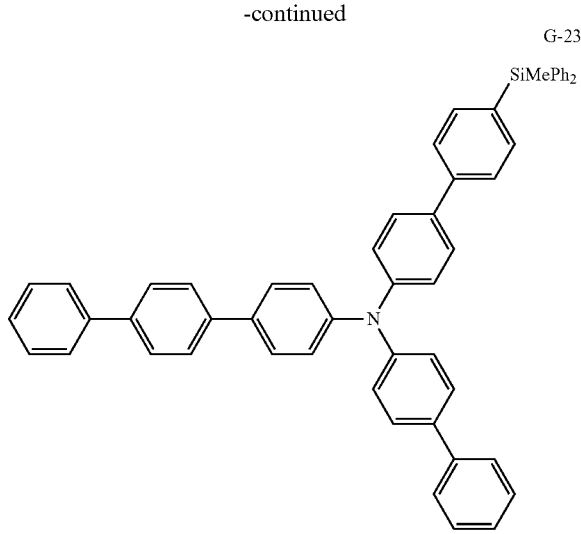

The amine derivative having a silyl group according to an embodiment represented by General Formula (8) is an amine derivative according to an embodiment, in which Ar¹ is an aryl group substituted with a silyl group having strong electron tolerance. Thus, the amine derivative having a silyl group according to an embodiment represented by General Formula (8) is stable to electrons. When the amine derivative is used as a material for an organic electroluminescent device, particularly, as the material of a hole transport layer adjacent to an emission layer, the electron tolerance of the hole transport layer may be improved, the deterioration of the hole transport material due to electrons intruded into the hole transport layer may be restrained, and the increase of the life of the organic electroluminescent device may be realized.

In addition, since the amine derivative having a silyl group according to an embodiment represented by General Formula (8) has an arylene group in which n is at least 2 in General Formula (7), it electrons may be enlarged, hole transport properties may be improved, and the improvement of the emission efficiency and the increase of the life of the organic electroluminescent device may be realized. In addition, since the amine derivative having a silyl group according to an embodiment represented by General Formula (8) has an arylene group of which n is at least 2 in General Formula (7), glass transition temperature (Tg) may be increased, and layer forming properties may be improved.

In addition, in the amine derivative having a silyl group according to an embodiment represented by General Formula (8), the arylene group in which n is 2 in General Formula (7) includes an aryl group represented by General Formula (6), and at least one terphenyl group is combined with the N atom of amine. A compound having a terphenylamine skeleton has very high hole tolerance and electron tolerance. Thus, when n is 2 in General Formula (7), by using the amine derivative having a silyl group according to an embodiment as the material for the organic electroluminescent device, particularly, as the material of a hole transport layer adjacent to an emission layer, the tolerance with respect to electrons inflowing from the emission layer to the hole transport layer may be improved further, the emission efficiency of the organic electroluminescent device may be improved, and the life of the organic electroluminescent device may be increased further.

The amine derivative having a silyl group of the invention represented by General Formula (8) may be used as the material of the hole transport layer of the organic electroluminescent device 100 shown in FIG. 1. In addition, the configuration of the organic electroluminescent device 100 shown in FIG. 1 is an illustration of the organic electroluminescent device according to an embodiment without limitation, and may be variously modified.

In addition, the use of the amine derivative having a silyl group according to an embodiment represented by General Formula (8), is not limited to the hole transport material of the organic electroluminescent device; it may be used as the material of the hole injection layer or the material of the emission layer like the amine derivative having a silyl group represented by General Formula (1). In the case that the amine derivative having a silyl group represented by General Formula (8) is used as the material of the hole injection layer, the emission efficiency of the organic electroluminescent device may be improved, and the long life of the organic electroluminescent device may be realized as the case using the amine derivative having a silyl group as the material of the hole transport layer.

Example VIII

With respect to the amine derivative having a silyl group according to an embodiment represented by General Formula (8), examples of synthesizing Compound G-8, Compound G-9, Compound G-13 and Compound G-18 will be explained hereinafter. However, the following synthetic methods are only examples, and embodiments are not limited thereto.

(Synthesis of Compound G-8)

Compound G-8 according to an embodiment was synthesized by the following procedure.

Under an argon atmosphere, 3 g of 4-aminoterphenyl, 5.08 g of 4-bromotetraphenylsilane, 0.34 g of Pd₂(dba)₃, 2.34 g of sodium t-butoxide and 120 mL of toluene were added to a 300 mL three-necked flask, and 0.5 mL of a 2M toluene solution of (t-Bu)₃P was added thereto, followed by stirring at room temperature for about 24 hours. After cooling in the air, an organic layer was separated, and solvents were distilled. The solid thus obtained was separated by silica gel column chromatography to produce 5.0 g (yield 73%) of Precursor G-8a as a white solid.

[Formula 178]

Precursor G-8a

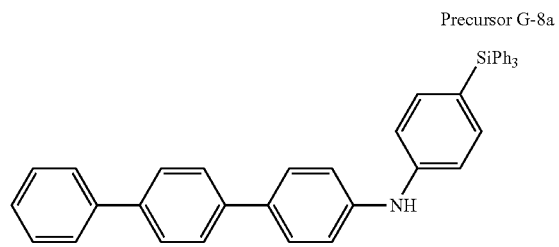

Under an argon atmosphere, 5.0 g of Precursor A-8a, 2.0 g of 4-bromobiphenyl, 0.23 g of Pd₂(dba)₃, 1.65 g of sodium t-butoxide and 100 mL of toluene were added to a 300 mL three-necked flask, and 0.5 mL of a 2M toluene solution of (t-Bu)$_3$P was added thereto, followed by heating and stirring at about 80° C. for about 12 hours. After cooling in the air, water was added, an organic layer was separated, and solvents were distilled. The solid thus obtained was separated by column chromatography to produce 2.5 g (yield 73%) of Compound G-8 as a white solid (FAB-MS measured value: 731.3).

[Formula 179]

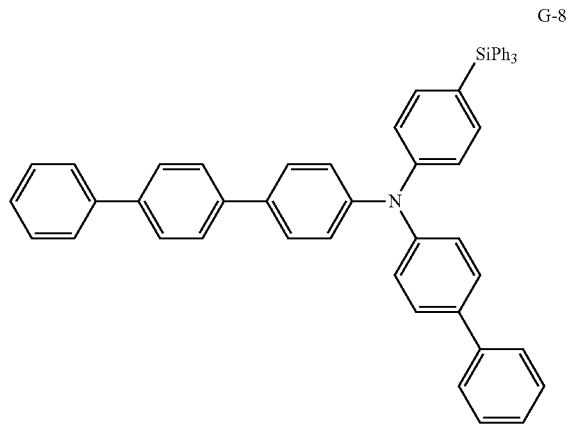

G-8

(Synthesis of Compound G-9)

Compound G-9 according to an embodiment was synthesized by the following procedure.

Under an argon atmosphere, 5.0 g of Precursor A-8a, 2.4 g of 1-bromo-4-phenylanthracene, 0.23 g of Pd$_2$(dba)$_3$, 1.65 g of sodium t-butoxide and 100 mL of toluene were added to a 300 mL three-necked flask, and 0.35 ml of a 2 M toluene solution of (t-Bu)$_3$P was added thereto, followed by heating and stirring at about 80° C. for about 12 hours. After cooling in the air, water was added, an organic layer was separated, and solvents were distilled. The solid thus obtained was separated by column chromatography to produce 4.4 g (yield 60%) of Compound G-9 as a white solid (FAB-MS measured value: 781.3).

[Formula 180]

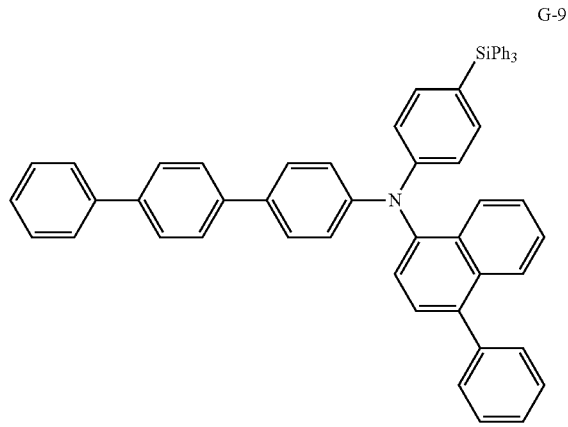

G-9

(Synthesis of Compound G-13)

Compound G-13 according to an embodiment was synthesized by the following procedure.

Under an argon atmosphere, 2.5 g of 4-aminoterphenyl, 2.3 g of 4-bromobiphenyl, 0.34 g of Pd$_2$(dba)$_3$, 2.34 g of sodium t-butoxide and 120 mL of toluene were added to a 300 mL three-necked flask, and 0.5 ml of a 2 M toluene solution of (t-Bu)$_3$P was added thereto, followed by stirring at room temperature for about 24 hours. After cooling in the air, water was added, an organic layer was separated, and solvents were distilled. The solid thus obtained was separated by column chromatography to produce 3.0 g (yield 76%) of Precursor G-13a as a white solid.

[Formula 181]

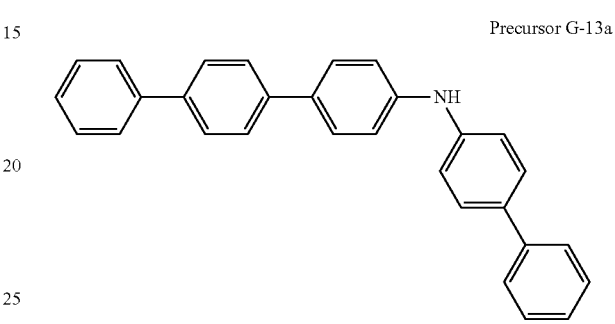

Precursor G-13a

Under an argon atmosphere, 3.0 g of Precursor G-13a, 2.3 g of 4-bromo(4'-trimethylsilyl)biphenyl, 0.23 g of Pd$_2$(dba)$_3$, 1.65 g of sodium t-butoxide and 100 mL of toluene were added to a 300 mL three-necked flask, and 0.35 ml of a 2 M toluene solution of (t-Bu)$_3$P was added thereto, followed by heating and stirring at about 80° C. for about 12 hours. After cooling in the air, water was added, an organic layer was separated, and solvents were distilled. The solid thus obtained was separated by column chromatography to produce 4.3 g (yield 91%) of Compound G-13 as a white solid (FAB-MS measured value: 621.3).

[Formula 182]

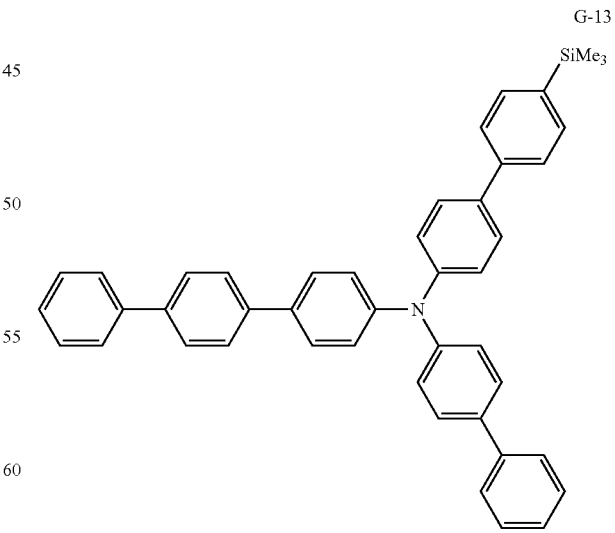

G-13

(Synthesis of Compound G-18)

Compound G-18 according to an embodiment was synthesized by the following procedure.

Under an argon atmosphere, 3.0 g of Precursor G-13a, 3.7 g of 4-bromo(4'-triphenylsilyl)biphenyl, 0.23 g of Pd$_2$(dba)$_3$, 1.65 g of sodium t-butoxide and 100 mL of toluene were added to a 300 mL three-necked flask, and 0.35 ml of a 2 M toluene solution of (t-Bu)$_3$P was added thereto, followed by stirring at about 80° C. for about 12 hours. After cooling in the air, water was added, an organic layer was separated, and solvents were distilled. The solid thus obtained was separated by column chromatography to produce 6.1 g (yield 90%) of the following Compound G-18 as a white solid.

[Formula 183]

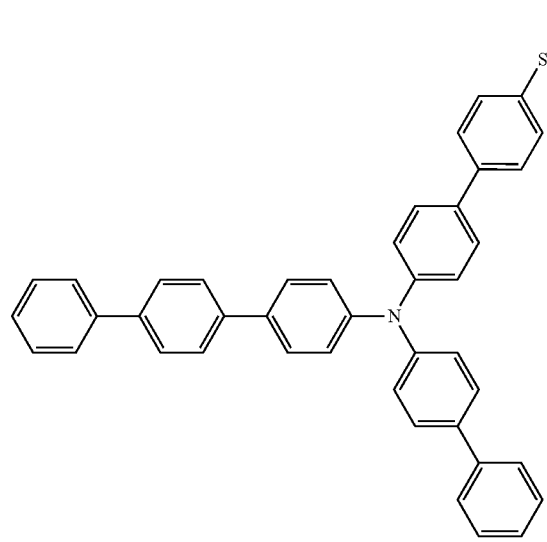

G-18

Hereinafter, an organic electroluminescent device manufactured using the above described Compound G-8 in a hole transport layer according to Example 30 will be explained.

The manufacture of the organic electroluminescent device according to Example 30 according to an embodiment was conducted by a vacuum deposition as for the organic electroluminescent device of Example 1 and the following procedure. First, with respect to an ITO-glass substrate patterned and washed in advance, surface treatment using ozone was conducted. In addition, the layer thickness of an ITO layer was about 150 nm. Immediately after the ozone treatment, a layer was formed using 2-TNATA as a hole injection material (thickness of about 60 nm) on the ITO layer.

Then, a layer was formed using Compound G-8 according to an embodiment as a hole transport material (about 30 nm), and a layer of ADN doped with TBP in a ratio of about 3% was formed by a co-deposition (about 25 nm).

After that, a layer was formed using Alq$_3$ as an electron transport material (about 25 nm), and LiF (about 1.0 nm) as an electron injection layer and aluminum (about 100 nm) as a cathode were laminated one by one to manufacture the organic electroluminescent device 200 shown in FIG. 2.

As Example 31, an organic electroluminescent device was manufactured by performing the same procedure described in Example 30 except for using Compound G-9 instead of Compound G-8 used in Example 30.

[Formula 184]

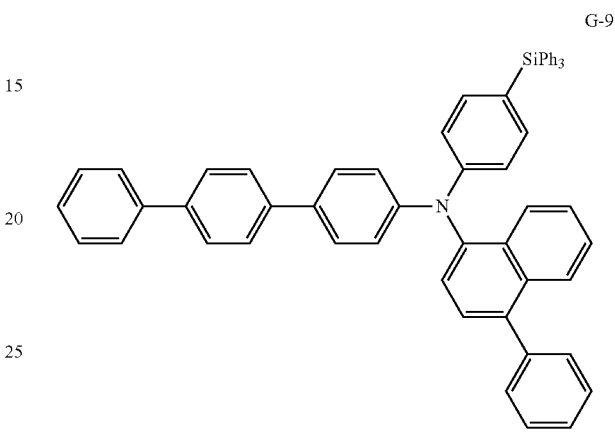

G-9

As Example 32, an organic electroluminescent device was manufactured by performing the same procedure described in Example 30 except for using Compound G-13 instead of Compound G-8 used in Example 30.

[Formula 185]

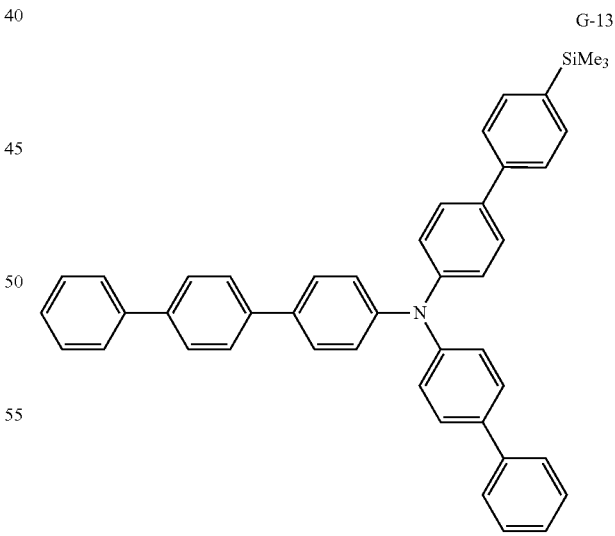

G-13

As Example 33, an organic electroluminescent device was manufactured by performing the same procedure described in Example 30 except for using Compound G-18 instead of Compound G-8 used in Example 30.

[Formula 186]

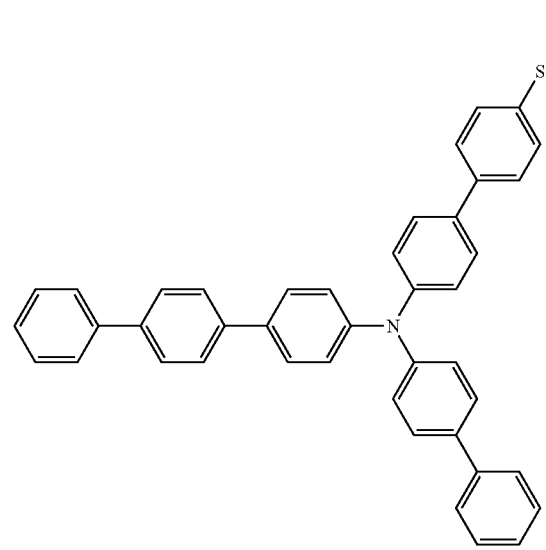

G-18

As Comparative Examples 16, 17 and 18, organic electroluminescent devices were manufactured by performing the same procedure described in Example 30 except for using Comparative Compounds 16, 17 and 18 represented in the following as compounds constituting hole transport materials of the organic electroluminescent devices.

[Formula 187]

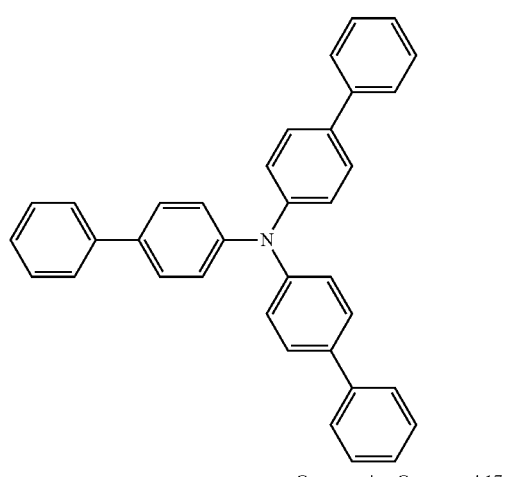

Comparative Compound 16

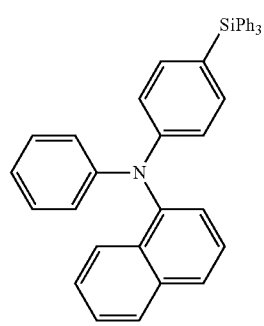

Comparative Compound 17

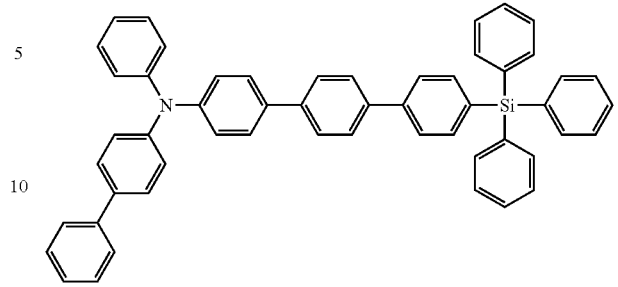

Comparative Compound 18

The driving voltage, the emission efficiency and the half life of the organic electroluminescent devices 200 manufactured in Examples 30 to 33 and Comparative Examples 16 to 18 were evaluated. In addition, emission efficiency means values at about 10 mA/cm², and half life means luminance decrease time to half from an initial luminance of about 1,000 cd/m². The evaluation results are shown in Table 8.

TABLE 8

| | Hole transport material | Voltage (V) | Current efficiency (cd/A) | Life (hr) | Tg (° C.) |
|---|---|---|---|---|---|
| Example 30 | Compound G-8 | 7.5 | 8.9 | 4,900 | 112 |
| Example 31 | Compound G-9 | 8.1 | 7.2 | 2,500 | 119 |
| Example 32 | Compound G-13 | 6.9 | 9.2 | 2,200 | 134 |
| Example 33 | Compound G-18 | 7.5 | 9.2 | 4,900 | 127 |
| Comparative Example 16 | Comparative Compound 16 | 7.5 | 5.2 | 1,800 | 77 |
| Comparative Example 17 | Comparative Compound 17 | 8.1 | 6.3 | 1,200 | 66 |
| Comparative Example 18 | Comparative Compound 18 | 7.7 | 8.5 | 2,100 | 110 |

According to Table 8, the organic electroluminescent devices of Examples 30 to 33 have improved emission efficiency and longer life than the organic electroluminescent devices of Comparative Examples 16, 17 and 18.

The amine derivative having a silyl group according to an embodiment represented by General Formula (8) is provided with a silyl group having electron tolerance and has strong electron tolerance. In addition, since the amine derivative having a silyl group according to an embodiment has an arylene group in which n is at least 2 in General Formula (7), electron tolerance may be improved and hole transport properties may be improved, thereby realizing the improvement of the emission efficiency and the long life of the organic electroluminescent device. By using the amine derivative having a silyl group according to an embodiment represented by General Formula (8), the deterioration of the device due to electrons intruded in the hole transport layer may be restrained, hole transport properties may be improved, and the improvement of the emission efficiency and the increase of the life of the organic electroluminescent device may be realized.

In the above-described Examples 30 to 33, the amine derivative having a silyl group according to an embodiment represented by General Formula (8), was used as the hole transport material of the organic electroluminescent device as an embodiment; however, the use of the amine derivative according to an embodiment is not limited to the organic electroluminescent device, and may be expanded to other luminescent devices or luminescent apparatus. In addition, the organic electroluminescent device using the amine derivative having a silyl group according to an embodiment represented by General Formula (8) may be used in an organic electroluminescent display of a passive-matrix driving type, and they may be also used in an organic electroluminescent display of an active-matrix driving type.

By way of summation and review, an organic electroluminescent device including a plurality of layers having different properties, such as an emission layer and a layer for transporting carriers (holes and electrons) to the emission layer, has been considered. To realize the improvement of the emission properties and the long life of the organic electroluminescent device, a hole transport layer having good hole transporting capability and carrier tolerance is desired. From this point of view, various hole transport materials have been considered.

As materials used in each layer of an organic electroluminescent device, various compounds such as an aromatic amine compound, etc. have been considered. For example, a carbazole derivative has been considered as a hole transport material or a hole injection material. In addition, an amine compound having a terphenyl group has been considered as a hole transport material and a host material in an emission layer. An amine compound having a fluorenyl group has been considered as a hole transport material or a hole injection material. An amine derivative having a dibenzofuryl group has been considered as a hole transport material or a host material of an emission layer. An amine derivative having a silyl group has been considered as a hole transport material. A carbazole derivative substituted with a condensed ring has been considered. A triarylamine derivative has been considered as a material of an emission layer or a hole injection transport material. A tri(p-terphenyl-4-yl)amine compound has been considered as a hole transport material. A diamine compound has been considered as a hole transport material. An amine compound having a silyl group has been considered as a material of an emission layer. An amine compound having a silyl group has been considered as a material of an electron inhibiting layer or a material of an emission layer. However, the organic electroluminescent devices using the above-described materials may not have sufficient emission life, and an organic electroluminescent device having higher efficiency, driven at a low voltage and having long emission life is desired. Thus, the increase of life is desired for an organic luminescent material for the application of an organic electroluminescent device in a display device. However, devices using the materials discussed here in a hole injection layer or a hole transport layer may not provide a desired level of tolerance, and the improvement of the device life is desired.

As described above, an amine derivative according to an embodiment may realize the improvement of the emission efficiency and the increase of the life of the organic electroluminescent device, and may be used in various uses such as an organic electroluminescent display, lighting, etc.

Restraints on the device life of the organic electroluminescent device may be due to, during the recombination of holes and electrons near the interface of an emission layer and a hole transport layer and emitting light, the intrusion of electrons that have not participated in the recombination into the hole transport layer and the damage to a hole transport material, which may deteriorate the device. As set forth in the present disclosure, embodiments may provide an organic electroluminescent device having improved life and an organic luminescent material for realizing thereof by restraining the deterioration of the device due to electrons intruded into a hole transport layer.

According to an embodiment, hole transport properties may be improved. Thus, the high efficiency, the low driving voltage and the long life of an organic electroluminescent device may be realized.

According to an embodiment, the high efficiency and the long life of an organic electroluminescent device may be realized.

According to an embodiment, the amine derivative is the compound of General Formula (1), in which $Ar^1$ is an aryl group substituted with a silyl group exhibiting high electron tolerance, and electron tolerance may be improved, and the improvement of the emission efficiency and the long life of an organic electroluminescent device may be realized.

The amine derivative according to an embodiment may introduce a dibenzofuryl group, and the electron tolerance thereof may be improved further, and the transition temperature thereof may be elevated. Thus, the high efficiency and the long life of an organic electroluminescent device may be realized.

In the amine derivative according to an embodiment, L is not the single bond but a divalent connecting group, and the conjugation system of it electrons of a whole molecule may be enlarged. Thus, hole transport properties may be improved, and the stability of the molecule may be further improved. In addition, the high efficiency, the low driving voltage and the long life of an organic electroluminescent device may be realized.

According to an embodiment, the improvement of the emission efficiency, the decrease of the driving voltage and the increase of the life of an organic electroluminescent device may be realized.

According to an embodiment, an organic electroluminescent device realizing the improvement of high efficiency, the decrease of a driving voltage and the increase of long life may be provided.

According to an embodiment, the high efficiency and the long life of an organic electroluminescent device may be realized. The dibenzofuryl group exhibits strong electron tolerance and high planarity, and high glass transition temperature thereof may be shown. Thus, the improvement of the emission efficiency, the driving at a low voltage and the long life of an organic electroluminescent device may be realized. In addition, the improvement of layer forming properties may be enhanced when manufacturing the organic electroluminescent device.

According to an embodiment, the dibenzofuryl group is combined with L at position 3, that is, with a nitrogen atom (N) around an amine part, and the conjugation system of it electrons in a whole molecule may be enlarged. Thus, the improvement of hole transport properties may be enhanced, and the improvement of the high efficiency and the long life of an organic electroluminescent device may be realized.

According to an embodiment, the fluorenyl group may be combined with the amine part via the connecting group L, and the conjugation system of it electrons may be enlarged, and the hole transport properties and the stability of a molecule may be improved. In addition, by introducing the fluorenyl group, the connecting group L of a substituted or unsubstituted arylene group or a substituted or unsubstituted heteroarylene group may be planarized, and the hole transport properties of the amine derivative may be improved. Thus, the improvement of the emission efficiency and the long life of an organic electroluminescent device may be realized.

According to an embodiment, the fluorenyl group is combined with a nitrogen atom (N) around an amine part at position 2, and the conjugation system of it electrons in a whole molecule may be enlarged. Thus, hole transport properties may be improved and the stability of the molecule may be improved, and the high efficiency and the long life of an organic electroluminescent device may be realized.

The amine derivative according to an embodiment introduces a carbazolyl group, and hole transport properties may be improved. By the combination of the carbazolyl group with an amine part via the substituted or unsubstituted arylene group or the substituted or unsubstituted heteroarylene group of L, the level of the highest occupied molecular orbital (HOMO) may be controlled. Thus, the improvement of the emission efficiency and the long life of an organic electroluminescent device may be realized.

According to an embodiment, the carbazolyl group is combined with L at position 2 or position 3, and the conjugation system of π electrons of a whole molecule may be enlarged. Thus, hole transport properties may be improved, and the stability of the molecule may be improved at the same time. In addition, the improvement of the emission efficiency and the long life of an organic electroluminescent device may be realized.

The amine derivative according to an embodiment introduces a carbazolyl group, and hole transport properties may be improved. The carbazolyl group is combined with an amine part via a connecting group L, and the level of HOMO may be controlled. Thus, the improvement of the emission efficiency and the long life of an organic electroluminescent device may be realized.

In the amine derivative according to an embodiment, $Ar^1$ in General Formula (1) is an aryl group substituted with a silyl group exhibiting strong electron tolerance, and electron tolerance of the amine derivative may be improved. In addition, since General Formula (7) includes an arylene group having n greater than or equal to 2, it electrons may be enlarged, and good hole transport properties may be exhibited. Thus, the amine derivative according to an embodiment may realize an organic electroluminescent device having improved emission efficiency and long life. In addition, since the amine derivative according to an embodiment includes an arylene group having n greater than or equal to 2 in General Formula (7), the glass transition temperature (Tg) thereof may be improved, and layer forming properties may be improved. The preferable glass transition temperature of the amine derivative may be greater than or equal to about 120° C. in consideration of a manufacturing process.

$R_{11}$, $R_{12}$ and $R_{13}$ in General Formula (5) are a phenyl group in the amine derivative according to an embodiment, and the glass transition temperature (Tg) thereof may be improved, and layer forming properties may be improved.

Since o may be 0 or 1 in General Formula (5) in the amine derivative according to an embodiment, the blocking capability of electrons from the intrusion into a hole transport layer may be increased, the deterioration of a hole transport material may be restrained, and the long life of an organic electroluminescent device may be realized.

Since n may be 2 in General Formula (7) in the amine derivative according to an embodiment, the electron tolerance of the amine derivative may be improved further.

According to an embodiment, a material for an organic electroluminescent device exhibiting strong electron tolerance and good hole transport properties may be provided.

According to an embodiment, an organic electroluminescence device having improved emission efficiency and increased device life, and a material for an organic electroluminescent device realizing thereof may be provided.

In the amine derivative according to an embodiment, the connecting group L is the phenylene group, the biphenylene group or the fluorenylene group, and the conjugation system of the π electrons of a whole molecule may be enlarged and hole transport properties and the stability of the molecule may be improved. The improvement of the emission efficiency and the long life of an organic electroluminescent device may be realized.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A monoamine derivative represented by the following General Formula (1):

[Formula 1]

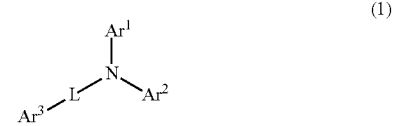

(1)

wherein, in General Formula (1), $Ar^1$, $Ar^2$ and $Ar^3$ are independently a substituted with at least one of an alkyl group or an aryl group or unsubstituted aryl group, a substituted or unsubstituted heteroaryl group including at least one of O, P or S as a hetero atom, or a substituted or unsubstituted benzocarbazole group, at least one of $Ar^1$, $Ar^2$ and $Ar^3$ being substituted with one substituted or unsubstituted silyl group, L is a single bond, a substituted or unsubstituted arylene group or a substituted or unsubstituted heteroarylene group, when all of Ar1, Ar2, and Ar3 are substituted or unsubstituted aryl groups, the case where all of Ar1, Ar2, and Ar3 are substituted with a silyl group is excluded, and wherein at least one of $Ar^1$, $Ar^2$ and $Ar^3$ is represented by the following Formula 8:

[Formula 8]

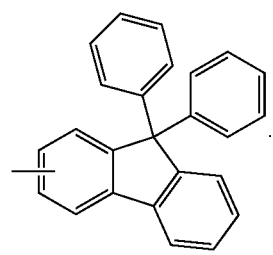

2. The monoamine derivative as claimed in claim 1, wherein at least one of $Ar^1$, $Ar^2$ and $Ar^3$ is the substituted or unsubstituted dibenzoheterole group.

3. The monoamine derivative as claimed in claim 1, wherein Ar¹ and Ar² are independently the substituted with at least one of an alkyl group or an aryl group or unsubstituted aryl group.

4. The monoamine derivative as claimed in claim 2, wherein Ar¹ and Ar² are independently a substituted with at least one of an alkyl group or an aryl group or unsubstituted aryl group having 6 to 18 carbon atoms for forming a ring, and Ar³ is a substituted or unsubstituted dibenzoheterole group.

5. The monoamine derivative as claimed in claim 1, wherein the silyl group is:
a triarylsilyl group where an aryl substituent at the silyl group has 6 to 18 carbon atoms for forming a ring, or
a trialkylsilyl group where an alkyl substituent at the silyl group has 1 to 6 carbon atoms.

6. The monoamine derivative as claimed in claim 1, wherein each of Ar¹ and Ar² is substituted with one silyl group.

7. The monoamine derivative as claimed in claim 1, wherein each of Ar³ is substituted with one silyl group.

8. The monoamine derivative having a silyl group as claimed in claim 1, wherein L is a single bond or an arylene group having 6 to 14 carbon atoms for forming a ring.

9. The monoamine derivative as claimed in claim 4, wherein Ar³ is a substituted or unsubstituted dibenzofuryl group.

10. The monoamine derivative as claimed in claim 9, wherein L is not the single bond.

11. The monoamine derivative as claimed in claim 10, wherein L is a phenylene group, and the dibenzofuryl group is combined with L at position 3 of the dibenzofuryl group.

12. The monoamine derivative as claimed in claim 1, wherein at least one of Ar¹ and Ar² is substituted with one substituted or unsubstituted silyl group, Ar³ is a substituted or unsubstituted benzocarbazolyl group, and L is a substituted or unsubstituted arylene group or a substituted or unsubstituted heteroarylene group.

13. The monoamine derivative as claimed in claim 1, wherein Ar² is a substituted or unsubstituted fluorenyl group represented by the Formula 8.

14. The monoamine derivative as claimed in claim 13, wherein the fluorenyl group is combined with L at position 2 of the fluorenyl group.

15. The monoamine derivative as claimed in claim 13, wherein Ar¹ and Ar³ are independently a substituted with at least one of an alkyl group or an aryl group or unsubstituted aryl group.

16. The monoamine derivative as claimed in claim 13, wherein Ar¹ is a substituted with at least one of an alkyl group or an aryl group or unsubstituted aryl group and Ar³ is a substituted or unsubstituted dibenzoheterole group.

17. The monoamine derivative as claimed in claim 13, wherein one of Ar¹ and Ar² is substituted with a substituted or unsubstituted silyl group.

18. The monoamine derivative as claimed in claim 13, wherein the silyl group is:
a triarylsilyl group where an aryl substituent at the silyl group has 6 to 18 carbon atoms for forming a ring, or
a trialkylsilyl group where an alkyl substituent at the silyl group has 1 to 6 carbon atoms.

19. The monoamine derivative as claimed in claim 1, wherein L is a phenylene group, a biphenylene group or a fluorenylene group.

20. The monoamine derivative as claimed in claim 19, wherein Ar¹ and Ar² are an aryl group having 6 to 12 carbon atoms for forming a ring when L is the fluorenylene group.

21. The monoamine derivative as claimed in claim 1, wherein Ar¹ is an aryl group substituted with a silyl group and represented by the following General Formula (5), Ar² is a substituted or unsubstituted aryl group having 6 to 30 carbon atoms for forming a ring, Ar³ is an aryl group represented by the following General Formula (6), and L is an arylene group represented by the following General Formula (7):

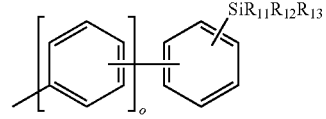

(5)

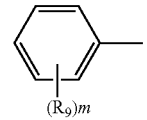

(6)

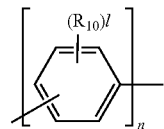

(7)

wherein,
in the above General Formula (5), o is an integer satisfying the relation of 0≤o≤2, $R_{11}$, $R_{12}$ and $R_{13}$ are independently an alkyl group having 1 to 15 carbon atoms, a substituted or unsubstituted aryl group having 6 to 30 carbon atoms for forming a ring, or a heteroaryl group having 1 to 30 carbon atoms for forming a ring,
in the above General Formula (6), each $R_9$ is independently a hydrogen atom, a halogen atom, an alkyl group having 1 to 15 carbon atoms, a substituted or unsubstituted aryl group having 6 to 30 carbon atoms for forming a ring, and m is an integer satisfying the relation of 0≤m≤5, and
in the above General Formula (7), each $R_{10}$ is independently a hydrogen atom, a halogen atom, an alkyl group having 1 to 15 carbon atoms, a substituted or unsubstituted aryl group having 6 to 30 carbon atoms for forming a ring, l is an integer satisfying the relation of 0≤l≤4, and n is an integer satisfying the relation of 2≤n≤5.

22. The monoamine derivative as claimed in claim 21, wherein $R_{11}$, $R_{12}$ and $R_{13}$ are each a phenyl group.

23. The monoamine derivative as claimed in claim 22, wherein o is 0 or 1.

24. The monoamine derivative as claimed in claim 23, wherein n is 2.

25. A material for an organic electroluminescent device, the material comprising an monoamine derivative represented by the following General Formula (1):

[Formula 1]

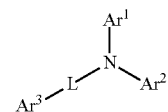

(1)

wherein, in General Formula (1),
Ar¹, Ar² and Ar³ are independently a substituted with at least one of an alkyl group or an aryl group or unsubstituted aryl group, a substituted or unsubstituted heteroaryl group including at least one of O, P or S as a hetero atom, or a substituted or unsubstituted benzocarbazole group, at least one of Ar¹, Ar² and Ar³ being substituted with one substituted or unsubstituted silyl group, L is a single bond, a substituted or unsubstituted arylene group or a substituted or unsubstituted heteroarylene group, and when all of Ar1, Ar2, and Ar3 are substituted or unsubstituted aryl groups, the case where all of Ar1, Ar2, and Ar3 are substituted with a silyl group is excluded, and wherein at least one of Ar¹, Ar² and Ar³ is represented by the following Formula 8:

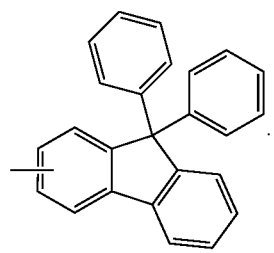

[Formula 8]

26. The material for an organic electroluminescent device as claimed in claim 25, wherein the material for an organic electroluminescent device is a hole transport material.

27. An organic electroluminescent device comprising a monoamine derivative at least in an emission layer and in one layer of laminated layers between the emission layer and an anode, wherein the amine derivative represented by the following General Formula (1):

[Formula 1]

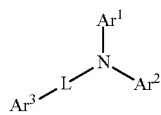

(1)

wherein, in General Formula (1),

Ar¹, Ar² and Ar³ are independently a substituted with at least one of an alkyl group or an aryl group or unsubstituted aryl group, a substituted or unsubstituted heteroaryl group including at least one of O, P or S as a hetero atom, or a substituted or unsubstituted benzocarbazole group, at least one of Ar¹, Ar² and Ar³ being substituted with one substituted or unsubstituted silyl group, L is a single bond, a substituted or unsubstituted arylene group or a substituted or unsubstituted heteroarylene group, and when all of Ar1, Ar2, and Ar3 are substituted or unsubstituted aryl groups, the case where all of Ar1, Ar2, and Ar3 are substituted with a silyl group is excluded, and wherein at least one of Ar¹, Ar² and Ar³ is represented by the following Formula 8:

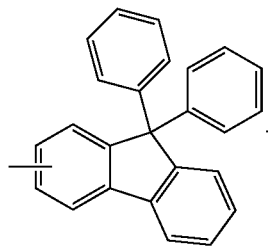

[Formula 8]

28. The monoamine derivative as claimed in claim 5, wherein the silyl group is a triphenylsilyl group.

29. The monoamine derivative as claimed in claim 1, wherein Ar² is represented by the Formula 8.

30. The monoamine derivative as claimed in claim 29, wherein Ar³ is substituted with one substituted or unsubstituted silyl group.

31. The monoamine derivative as claimed in claim 30, wherein Ar³ is substituted with a triphenyl silyl group.

32. The material for an organic electroluminescent device as claimed in claim 25, wherein the silyl group is a triphenylsilyl group.

33. The material for an organic electroluminescent device as claimed in claim 25, wherein Ar² is represented by the Formula 8.

34. The material for an organic electroluminescent device as claimed in claim 33, wherein Ar³ is substituted with one substituted or unsubstituted silyl group.

35. The organic electroluminescent device comprising the monoamine derivative as claimed in claim 34, wherein the silyl group is a triphenylsilyl group.

36. The organic electroluminescent device comprising the monoamine derivative as claimed in claim 27, wherein Ar² is represented by the Formula 8.

37. The organic electroluminescent device comprising the monoamine derivative as claimed in claim 36, wherein Ar³ is substituted with one substituted or unsubstituted silyl group.

38. The organic electroluminescent device comprising the monoamine derivative as claimed in claim 37, wherein the silyl group is a triphenylsilyl group.

* * * * *